United States Patent
Jung et al.

(10) Patent No.: US 10,062,853 B2
(45) Date of Patent: Aug. 28, 2018

(54) CONDENSED CYCLIC COMPOUND AND ORGANIC LIGHT-EMITTING DEVICE INCLUDING THE SAME

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Yongsik Jung, Yongin-si (KR); Miyoung Chae, Suwon-si (KR); Jhunmo Son, Yongin-si (KR); Dalho Huh, Suwon-si (KR); Eunsuk Kwon, Suwon-si (KR); Sangmo Kim, Hwaseong-si (KR); Saeyoun Lee, Suwon-si (KR); Soonok Jeon, Seoul (KR); Yeonsook Chung, Seoul (KR); Hosuk Kang, Suwon-si (KR); Jongsoo Kim, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/346,090

(22) Filed: Nov. 8, 2016

(65) Prior Publication Data
US 2017/0358755 A1    Dec. 14, 2017

(30) Foreign Application Priority Data
Jun. 9, 2016   (KR) .................. 10-2016-0071733

(51) Int. Cl.
| | | |
|---|---|---|
| H01L 51/50 | (2006.01) | |
| H01L 51/00 | (2006.01) | |
| C07D 209/86 | (2006.01) | |
| C09K 11/02 | (2006.01) | |

(52) U.S. Cl.
CPC ........ *H01L 51/0072* (2013.01); *C07D 209/86* (2013.01); *C09K 11/025* (2013.01); *H01L 51/5012* (2013.01); *H01L 51/5096* (2013.01)

(58) Field of Classification Search
CPC ...... C09D 209/86; C07D 209/86; H01L 51/50
See application file for complete search history.

(56) References Cited

U.S. PATENT DOCUMENTS

| | | |
|---|---|---|
| 8,361,637 B2 | 1/2013 | Kinoshita |
| 9,273,000 B2 | 3/2016 | Hayashi et al. |
| 2017/0365796 A1 | 12/2017 | Kim et al. |

FOREIGN PATENT DOCUMENTS

| | | | |
|---|---|---|---|
| JP | 2010-245063 A | 10/2010 | |
| JP | 2011-044365 | * 3/2011 | ............ H01L 51/50 |
| JP | 2011-044365 A | 3/2011 | |
| JP | 2011-192524 A | 9/2011 | |
| JP | 2011-256143 A | 12/2011 | |

* cited by examiner

*Primary Examiner* — Gregory D Clark
(74) *Attorney, Agent, or Firm* — Cantor Colburn LLP

(57) ABSTRACT

A condensed cyclic compound represented by Formula 1:

$$Ar_1\text{-}L_1\text{-}L_2\text{-}Ar_2 \quad \text{Formula 1}$$

wherein in Formula 1, $Ar_1$, $Ar_2$, $L_1$, and $L_2$ are the same as described in the specification.

20 Claims, 1 Drawing Sheet

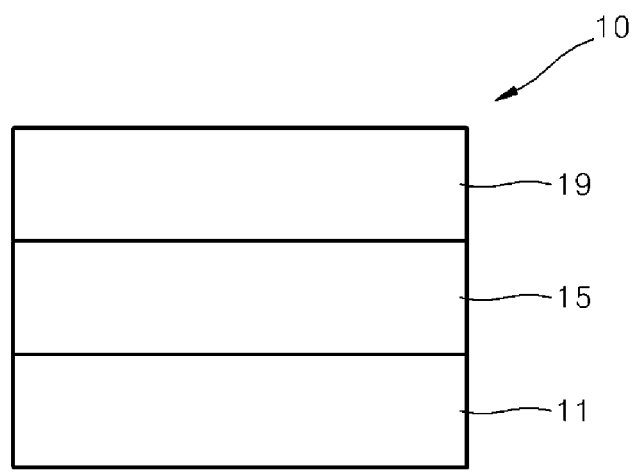

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0071733, filed on Jun. 9, 2016, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emission devices that have wide viewing angles, high contrast ratios, and short response times. In addition, OLEDs display excellent brightness, driving voltage, and response speed characteristics, and produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state, thereby generating light.

Various types of organic light emitting devices are known. However, there still remains a need in OLEDs having low driving voltage, high efficiency, high brightness, and long lifespan.

SUMMARY

One or more embodiments include a novel condensed cyclic compound and an organic light-emitting device including the same.

Additional aspects will be set forth in part in the description which follows and, in part, will be apparent from the description, or may be learned by practice of the presented embodiments.

According to one or more embodiments, a condensed cyclic compound is represented by Formula 1:

Formula 1

$Ar_1-L_1-L_2-Ar_2$

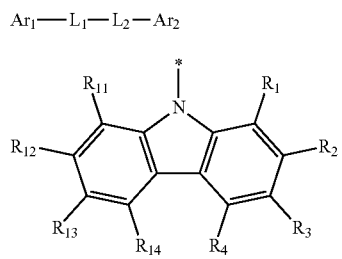

Formula 2

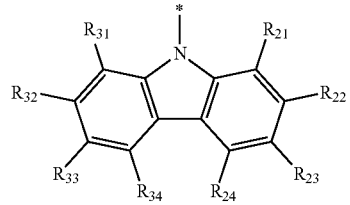

Formula 3

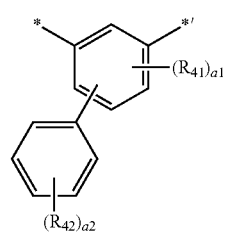

Formula 4A

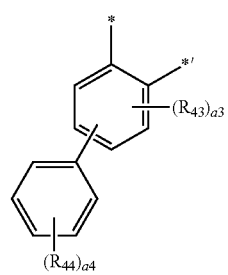

Formula 4B

Formula 4C

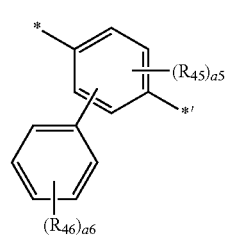

Formula 4D

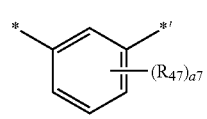

Formula 4E

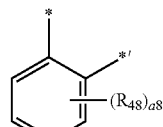

Formula 4F

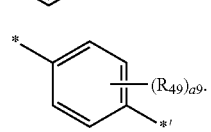

In Formula 1, $Ar_1$ may be a group represented by Formula 2, $Ar_2$ may be a group represented by Formula 3, $L_1$ may be selected from a group represented by Formula 4A, a group represented by Formula 4B, and a group represented by Formula 4C, and $L_2$ may be selected from a group represented by Formula 4D, a group represented by Formula 4E, and a group represented by Formula 4F, wherein a case in which $L_1$ is a group represented by Formula 4C and $L_2$ is a group represented by Formula 4F is excluded, $R_1$ to $R_4$, $R_{11}$ to $R_{14}$, $R_{21}$ to $R_{24}$, $R_{31}$ to $R_{34}$, and $R_{41}$ to $R_{49}$ may each independently be selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group (provided that the substituted or unsubstituted monovalent non-aromatic condensed heteropolycyclic group is not a substituted or unsubstituted carbazolyl group), —N($Q_4$)($Q_5$), and —B($Q_6$)($Q_7$), the number of cyano group(s) (CN) included in a group represented by *-$L_1$-$L_2$-*' in Formula 1 may be 1, 2, 3, or 4, a1 to a9 may each independently an integer selected from 0 to 5,

* and *' may each be a binding site to a neighboring atom, at least one of substituents of the substituted carbazolyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —CD$_3$, —CD$_2$H, —CDH$_2$, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group (provided that the non-aromatic condensed heteropolycyclic group is not a carbazolyl group);

a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group (provided that the non-aromatic condensed heteropolycyclic group is not a carbazolyl group), each substituted with at least one selected from deuterium, —CD$_3$, —CD$_2$H, —CDH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group (provided that the non-aromatic condensed heteropolycyclic group is not a carbazolyl group), —N($Q_{24}$)($Q_{25}$), and —B($Q_{26}$)($Q_{27}$); and —N($Q_{34}$)($Q_{35}$) and —B($Q_{36}$)($Q_{37}$), wherein $Q_4$ to $Q_7$, $Q_{24}$ to $Q_{27}$, and $Q_{34}$ to $Q_{37}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (provided that the substituted or unsubstituted monovalent non-aromatic condensed heteropolycyclic group is not a substituted or unsubstituted carbazolyl group).

According to one or more embodiments, an organic light-emitting device includes:

a first electrode, a second electrode, and an organic layer disposed between the first electrode and the second electrode, wherein the organic layer includes an emission layer and at least one condensed cyclic compound represented by Formula 1.

BRIEF DESCRIPTION OF THE DRAWING

These and/or other aspects will become apparent and more readily appreciated from the following description of the embodiments, taken in conjunction with FIG. 1 which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An aspect provides a condensed cyclic compound represented by Formula 1 below:

Ar$_1$-L$_1$-L$_2$-Ar$_2$     Formula 1

In Formula 1,

Ar$_1$ may be selected from a group represented by Formula 2,

Ar$_2$ may be a group represented by Formula 3,

L$_1$ may be selected from a group represented by Formula 4A, a group represented by Formula 4B, and a group represented by Formula 4C, L$_2$ may be selected from a group represented by Formula 4D, a group represented by Formula 4E, and a group represented by Formula 4F, wherein a case in which L$_1$ is a group represented by Formula 4C and L$_2$ is a group represented by Formula 4F is excluded:

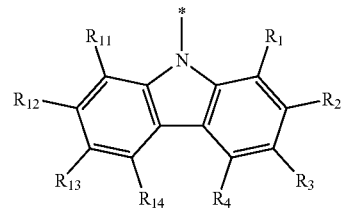

Formula 2

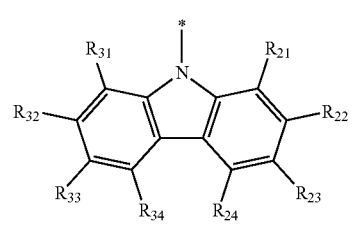

Formula 3

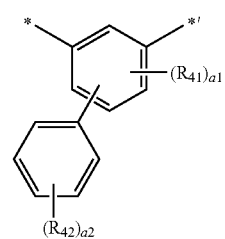

Formula 4A

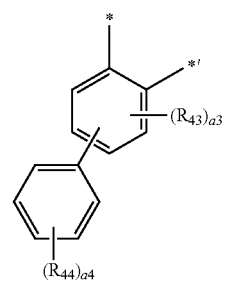

Formula 4B

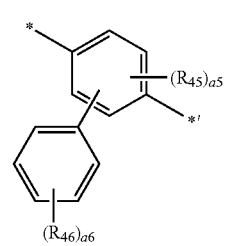

Formula 4C

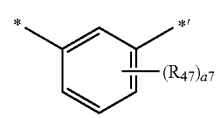

Formula 4D

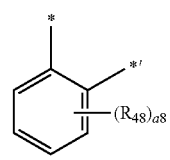

Formula 4E

Formula 4F

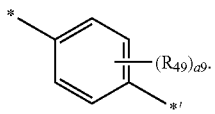

In Formulae 1 to 3 and 4A to 4F, $R_1$ to $R_4$, $R_{11}$ to $R_{14}$, $R_{21}$ to $R_{24}$, $R_{31}$ to $R_{34}$, and $R_{41}$ to $R_{49}$ may each independently be selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group (provided that the substituted or unsubstituted monovalent non-aromatic condensed heteropolycyclic group is not a substituted or unsubstituted carbazolyl group), —N($Q_4$)($Q_5$), and —B($Q_6$)($Q_7$), wherein $Q_4$ to $Q_7$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (provided that the substituted or unsubstituted non-aromatic condensed heteropolycyclic group is not a substituted or unsubstituted carbazolyl group).

In an embodiment, $R_1$ to $R_4$, $R_{11}$ to $R_{14}$, $R_{21}$ to $R_{24}$, $R_{31}$ to $R_{34}$, and $R_{41}$ to $R_{49}$ may each independently be selected from:

hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzooxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and pyridobenzothiazinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzooxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{34}$)($Q_{35}$), and —B($Q_{36}$)($Q_{37}$); and —N($Q_4$)($Q_5$) and —B($Q_6$)($Q_7$), wherein $Q_4$ to $Q_7$ and $Q_{34}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, and a dibenzothiophenyl group.

In one or more embodiments, $R_1$ to $R_4$, $R_{11}$ to $R_{14}$, $R_{21}$ to $R_{24}$, $R_{31}$ to $R_{34}$, and $R_{41}$ to $R_{49}$ may each independently be selected from:

hydrogen, deuterium, and a cyano group (CN);

a phenyl group, a biphenyl group, a terphenyl group, a naphthyl group, a fluorenyl group, a dibenzofuranyl group, and a dibenzothiophenyl group; and a phenyl group, a biphenyl group, a terphenyl group, a naphthyl group, a fluorenyl group, a dibenzofuranyl group, and a dibenzothiophenyl group, each substituted with at least one selected from deuterium, a cyano group, a phenyl group, a biphenyl group, a terphenyl group, and a naphthyl group.

In one or more embodiments, $R_1$ to $R_4$, $R_{11}$ to $R_{14}$, $R_{21}$ to $R_{24}$ and $R_{31}$ to $R_{34}$, and $R_{41}$ to $R_{49}$ may each independently be selected from hydrogen and a cyano group (CN), but embodiments of the present disclosure are not limited thereto.

a1 in Formula 4A indicates the number of groups $R_{41}$, and may be an integer selected from 0 to 5, wherein, when a1 is two or more, two or more groups $R_{41}$ may be identical to or different from each other. a2 to a9 may be understood by using the description of a1 and the structures of Formulae 4A to 4F.

For example, a1 to a9 may each independently be 0, 1, or 2, but embodiments of the present disclosure are not limited thereto.

In one or more embodiments, at least one selected from $R_3$, $R_{13}$, $R_{23}$, and $R_{33}$ in Formulae 2 and 3 may be a cyano group. In an embodiment, one, two, or three selected from $R_3$, $R_{13}$, $R_{23}$, and $R_{33}$ in Formulae 2 and 3 may be a cyano group. In one or more embodiments, one or two selected from $R_3$ and $R_{13}$ in Formula 2 may be a cyano group, or one or two selected from $R_{23}$ and $R_{33}$ in Formula 3 may be a cyano group.

In one or more embodiments, in Formula 1, i) when $L_1$ is a group represented by Formula 4A, $L_2$ may be selected from a group represented by Formula 4D, a group represented by Formula 4E, and a group represented by Formula 4F;

ii) when $L_1$ is a group represented by Formula 4B, $L_2$ may be selected from a group represented by Formula 4D, a group represented by Formula 4E, and a group represented by Formula 4F; and iii) when $L_1$ is a group represented by Formula 4C, $L_2$ may be selected from a group represented by Formula 4D and a group represented by Formula 4E.

A case in which, in Formula 1, $L_1$ is a group represented by Formula 4C and $L_2$ is a group represented by Formula 4F is excluded. That is, a group represented by *-$L_1$-$L_2$-*' in Formula 1 may be a substituted terphenylene group (for example, a terphenylene group substituted with at least one cyano group).

The number of cyano group(s) included in the group represented by *-$L_1$-$L_2$-*' in Formula 1 may be 1, 2, 3, or 4, and the number of cyano group(s) included in the condensed cyclic compound represented by Formula 1 may be 1, 2, 3, or 4. In other words, the number of cyano group(s) included in the condensed cyclic compound represented by Formula 1 is 1, 2, 3, or 4, provided that the group represented by *-$L_1$-$L_2$-*' in Formula 1 necessarily includes a cyano group.

In an embodiment, when the number of cyano group(s) included in the condensed cyclic compound represented by Formula 1 is 1, the number of cyano group(s) included in the group represented by *-$L_1$-$L_2$-*' in Formula 1 may be 1; when the number of cyano group(s) included in the condensed cyclic compound represented by Formula 1 is 2, the number of cyano group(s) included in the group represented by *-$L_1$-$L_2$-*' in Formula 1 may be 1 or 2; when the number of cyano group(s) included in the condensed cyclic compound represented by Formula 1 is 3, the number of cyano group(s) included in the group represented by *-$L_1$-$L_2$-*' in Formula 1 may be 1, 2, or 3; and when the number of cyano group(s) included in the condensed cyclic compound represented by Formula 1 is 4, the number of cyano group(s) included in the group represented by *-$L_1$-$L_2$-*' in Formula 1 may be 1, 2, 3, or 4.

In an embodiment, one, two, three, or four substituents of *-$L_1$-$L_2$-*' in Formula 1 may each independently be selected from:

a cyano group; and a phenyl group, a biphenyl group, and a terphenyl group, each substituted with at least one cyano group.

In an embodiment, the number of carbazole rings in the condensed cyclic compound represented by Formula 1 may be 2. That is, the condensed cyclic compound represented by Formula 1 may not further include, in its molecular structure, a substituted or unsubstituted carbazolyl group, except for the group represented by Formula 2 and the group represented by Formula 3.

In an embodiment, the condensed cyclic compound may be represented by one of Formulae 1-1 to 1-28:

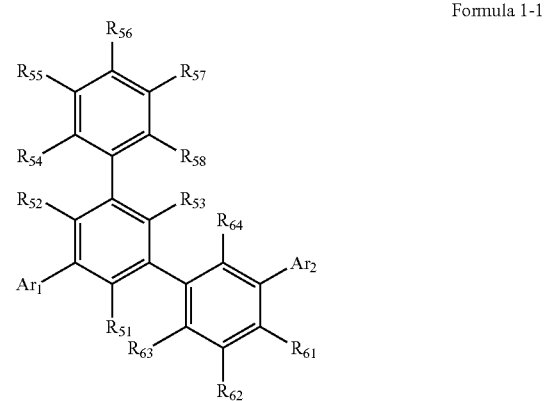

Formula 1-1

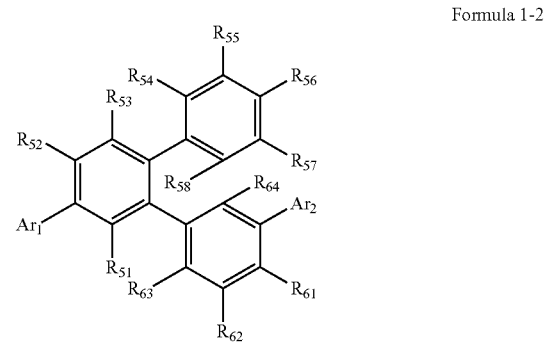

Formula 1-2

Formula 1-3
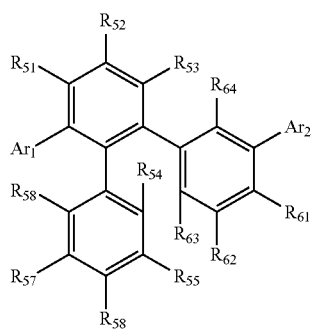
Formula 1-4
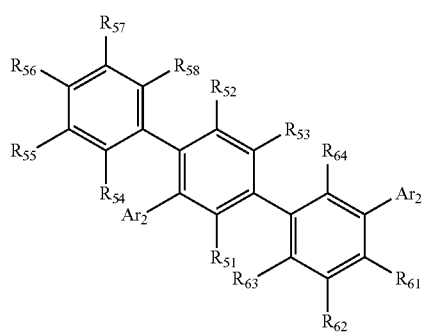
Formula 1-5
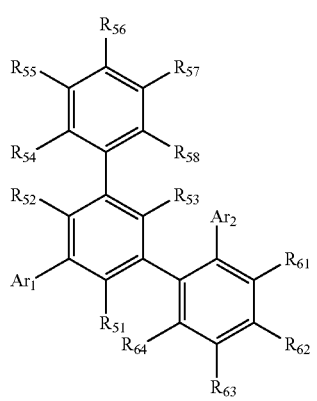
Formula 1-6
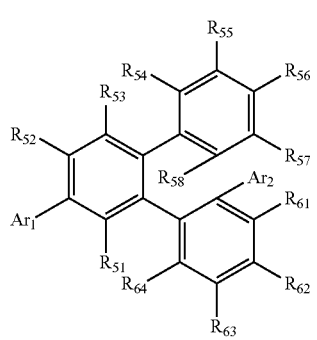
Formula 1-7
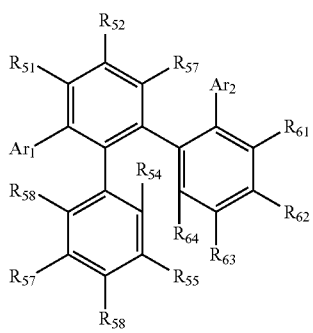
Formula 1-8
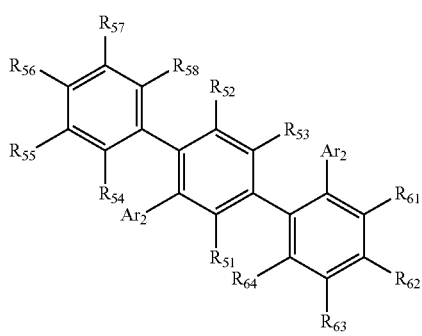
Formula 1-9
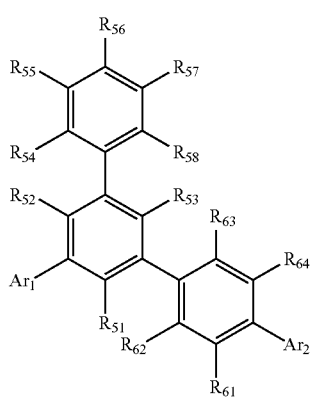
Formula 1-10
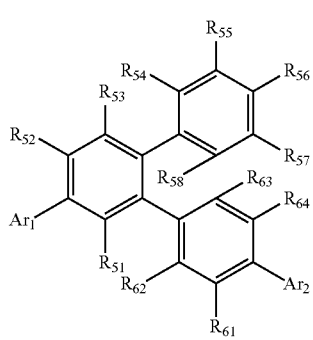

Formula 1-11
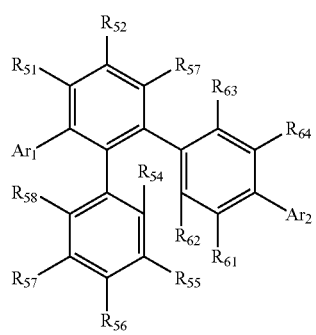
Formula 1-12
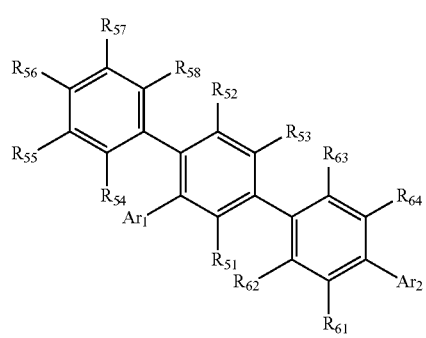
Formula 1-13
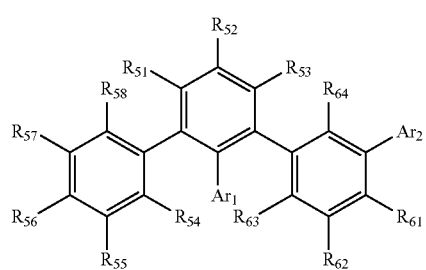
Formula 1-14
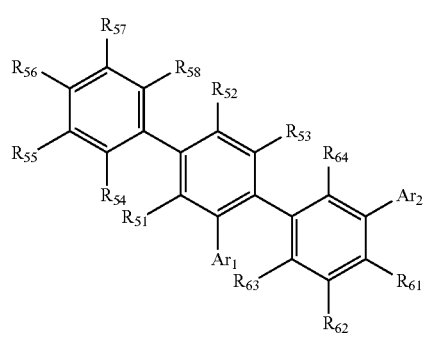
Formula 1-15
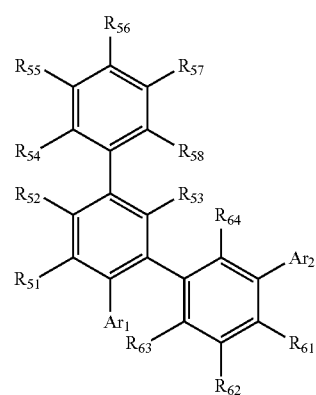
Formula 1-16
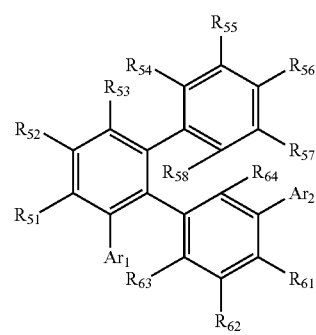
Formula 1-17
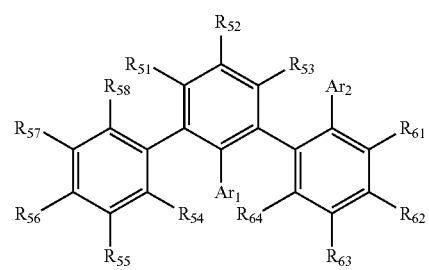
Formula 1-18
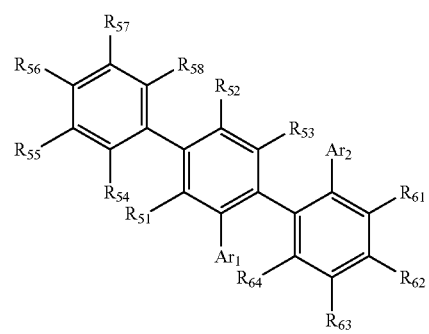

Formula 1-19
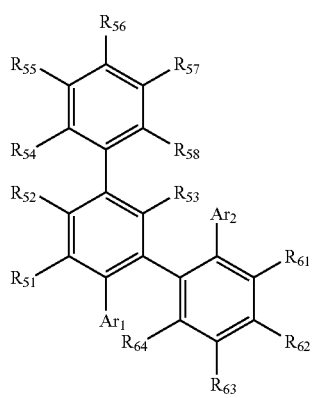
Formula 1-20
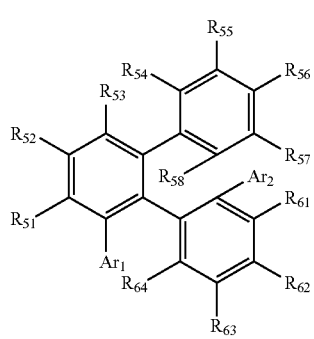
Formula 1-21
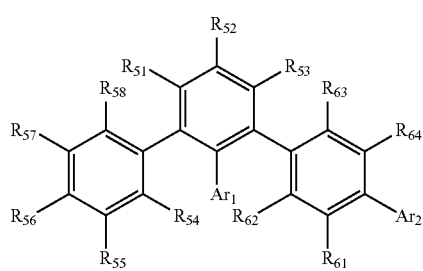
Formula 1-22
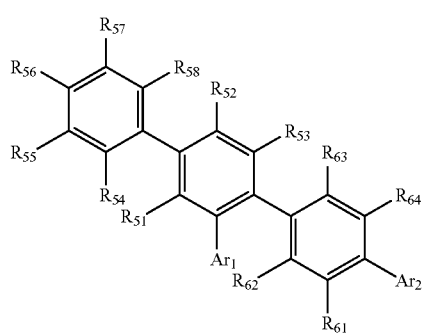
Formula 1-23
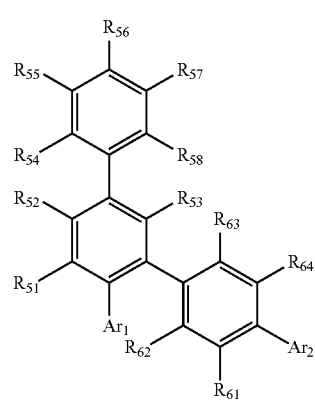
Formula 1-24
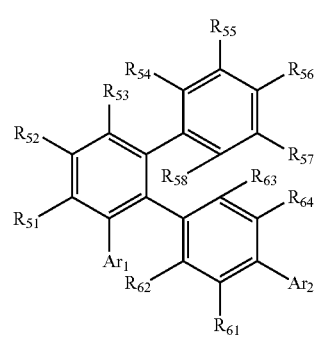
Formula 1-25
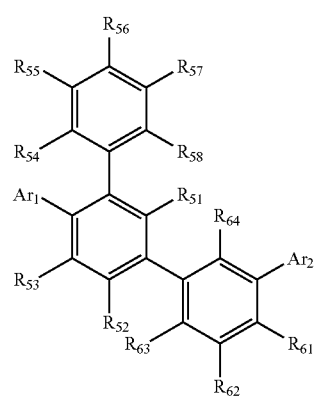
Formula 1-26
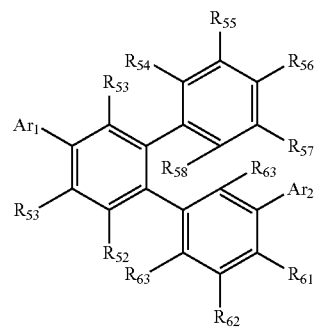

-continued

Formula 1-27

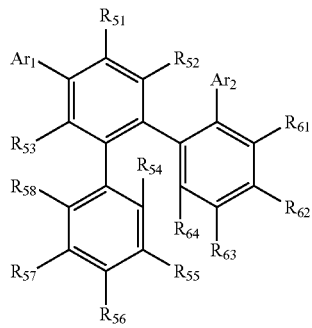

Formula 1-28

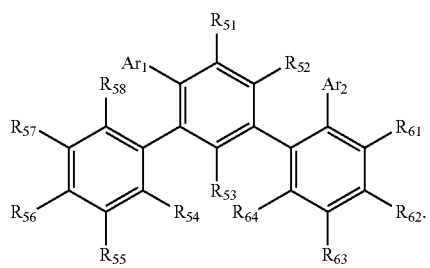

In Formulae 1-1 to 1-28,

Ar$_1$ and Ar$_2$ are the same as described above,

R$_{51}$ to R$_{58}$ and R$_{61}$ to R$_{64}$ are each independently the same as described in connection with R$_{41}$, and the number of cyano group(s) in R$_{51}$ to R$_{58}$ and R$_{61}$ to R$_{64}$ may be 1, 2, 3, or 4.

For example, R$_{51}$ to R$_{58}$ and R$_{61}$ to R$_{64}$ in Formulae 1-1 to 1-28 may each independently be selected from:

hydrogen, deuterium, and a cyano group;

a phenyl group, a biphenyl group, a terphenyl group, a naphthyl group, a fluorenyl group, a dibenzofuranyl group, and a dibenzothiophenyl group; and a phenyl group, a biphenyl group, a terphenyl group, a naphthyl group, a fluorenyl group, a dibenzofuranyl group, and a dibenzothiophenyl group, each substituted with at least one selected from deuterium, a cyano group, a phenyl group, a biphenyl group, a terphenyl group, and a naphthyl group.

One, two, three, or four selected from R$_{51}$ to R$_{58}$ and R$_{61}$ to R$_{64}$ in Formulae 1-1 to 1-28 may each independently be selected from:

a cyano group; and a phenyl group, a biphenyl group, and a terphenyl group, each substituted with at least one cyano group.

One, two, three, or four selected from R$_{51}$ to R$_{58}$ and R$_{61}$ to R$_{64}$ in Formulae 1-1 to 1-28 may be a cyano group.

The condensed cyclic compound may be selected from Compounds 1 to 260, but embodiments of the present disclosure are not limited thereto:

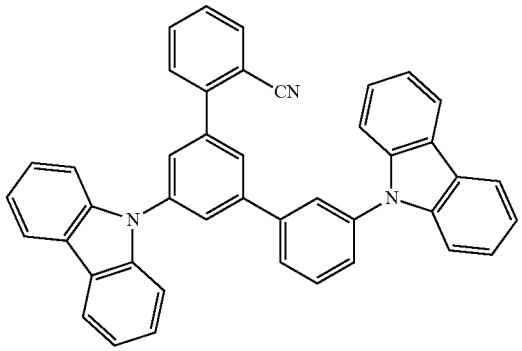

1

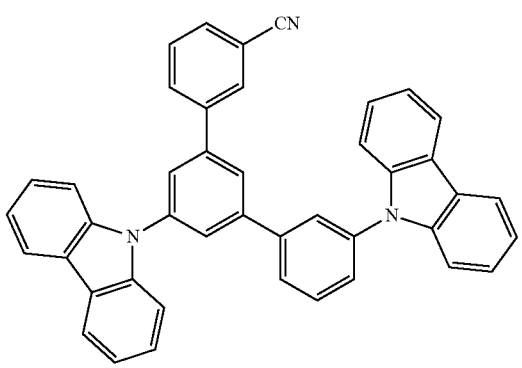

2

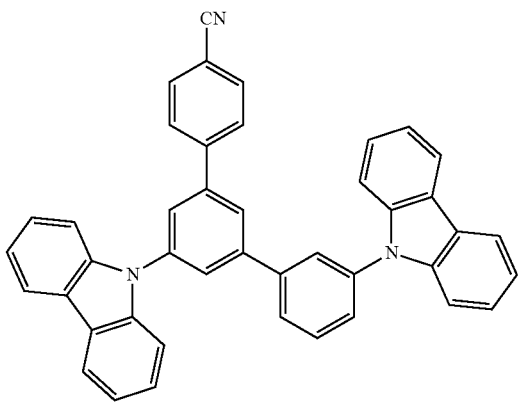

3

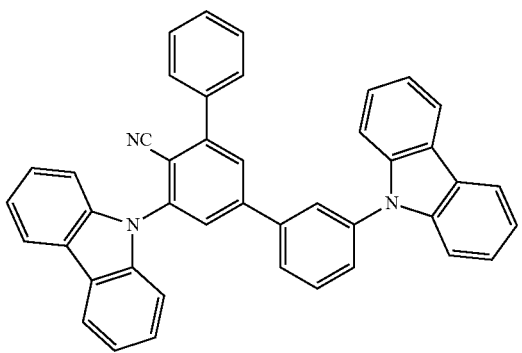

4

5
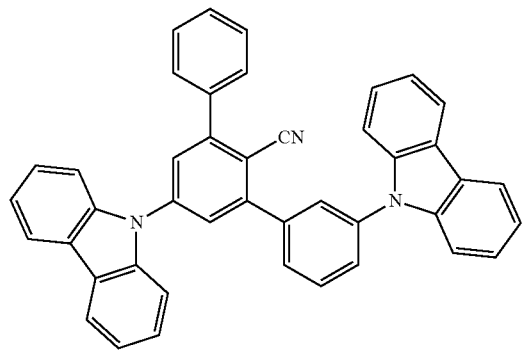
6
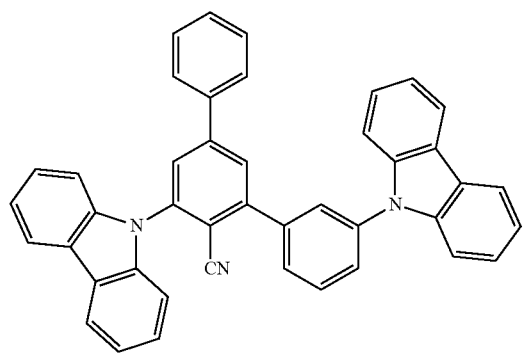
7
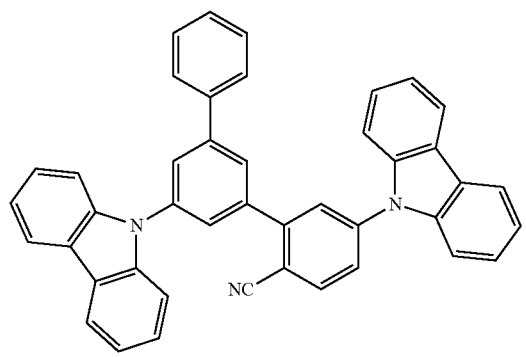
8
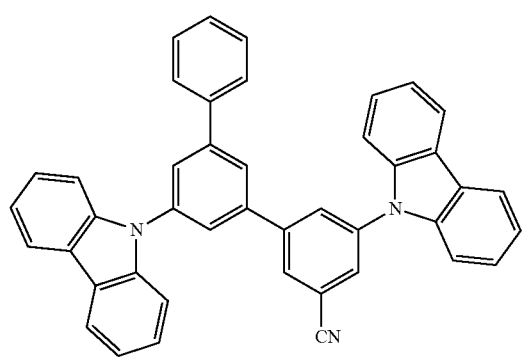
9
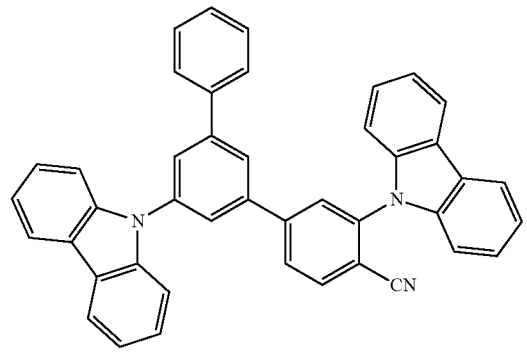
10
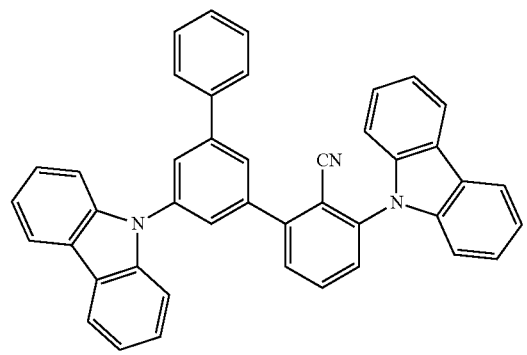
11
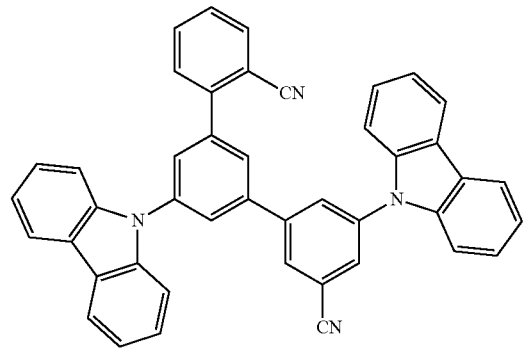
12
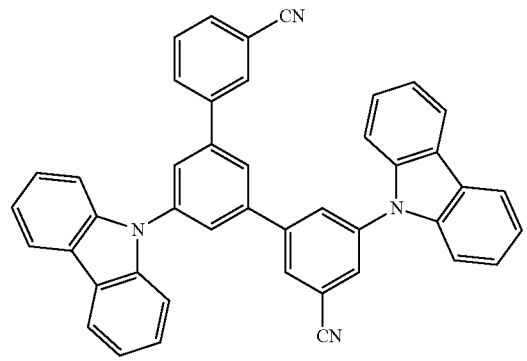

13
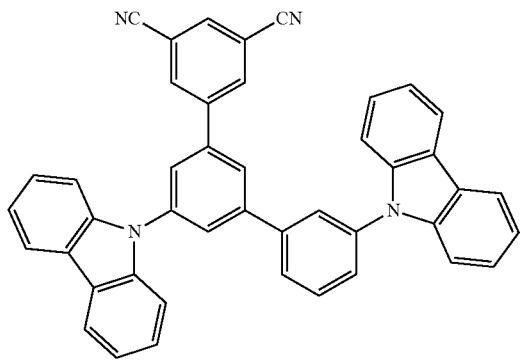
14

15
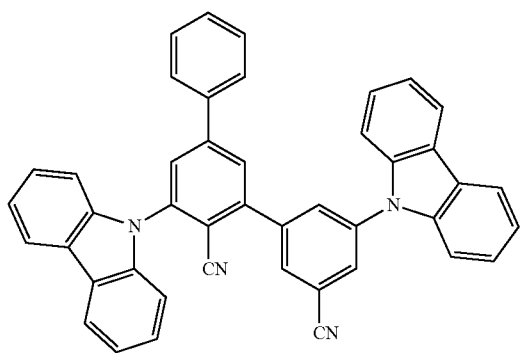
16
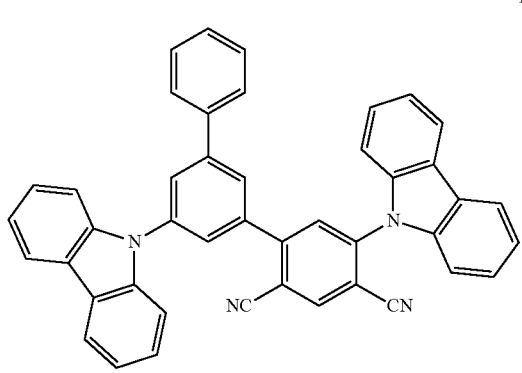
17
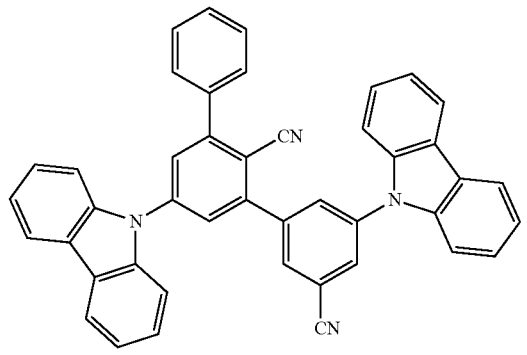
18
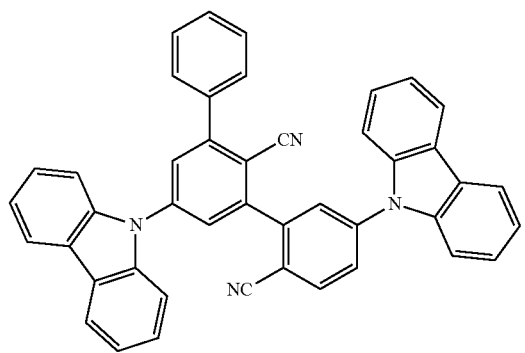
19
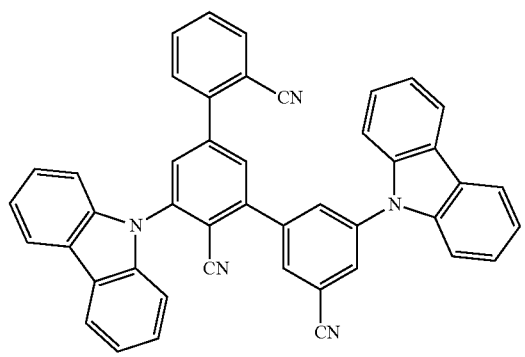
20
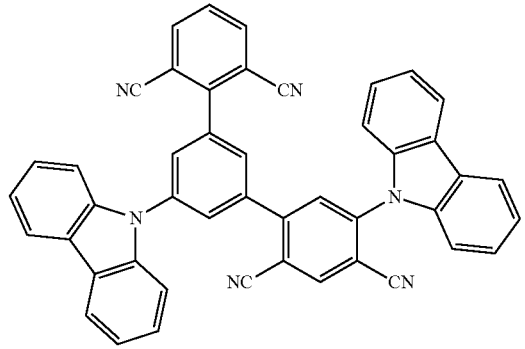

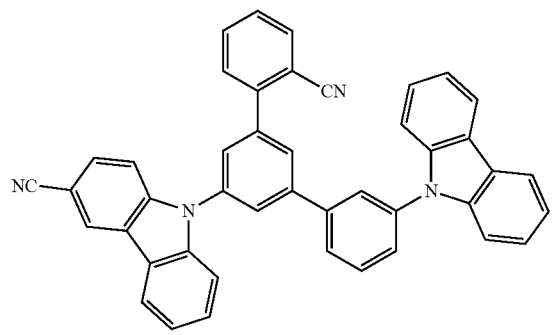
21
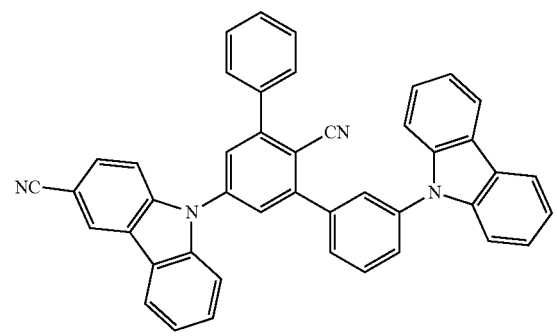
25
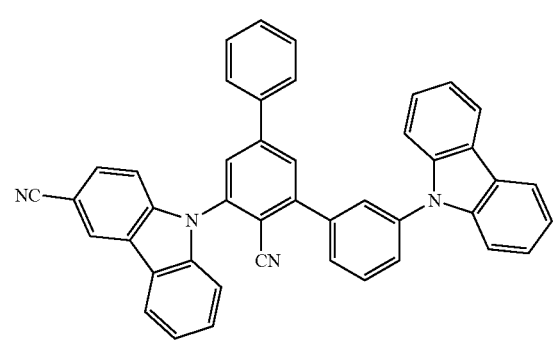
26
22
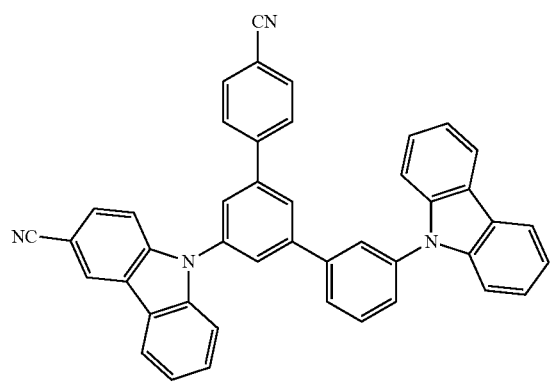
23
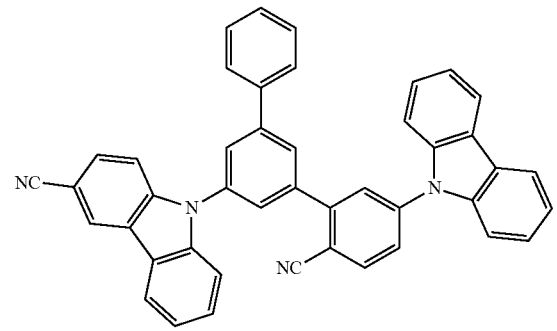
27
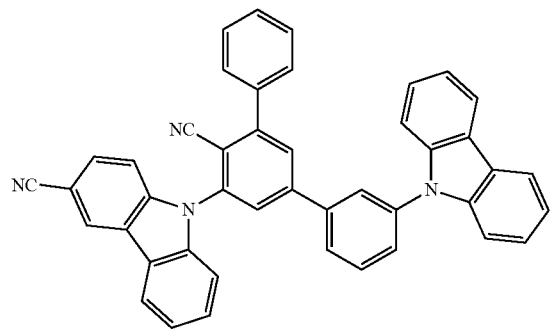
24
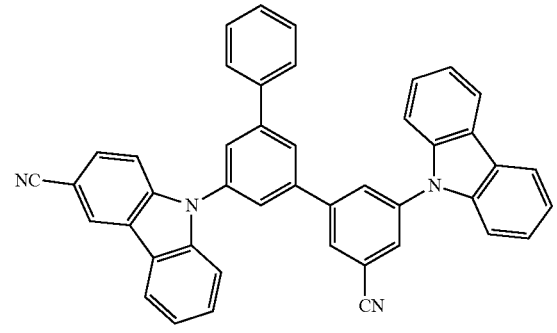
28

-continued
29
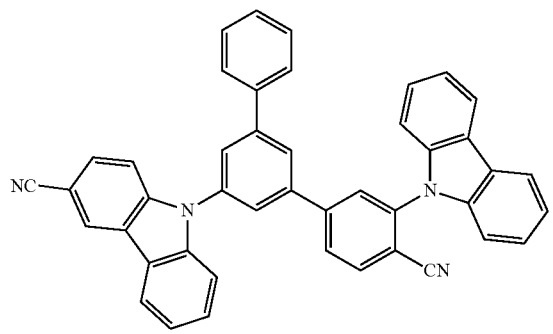
30
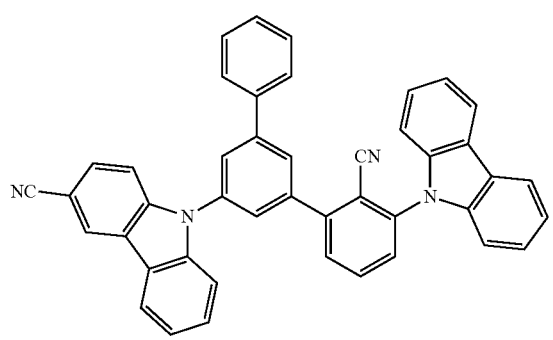
31
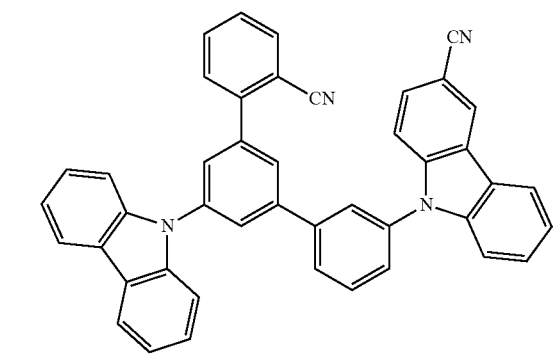
32
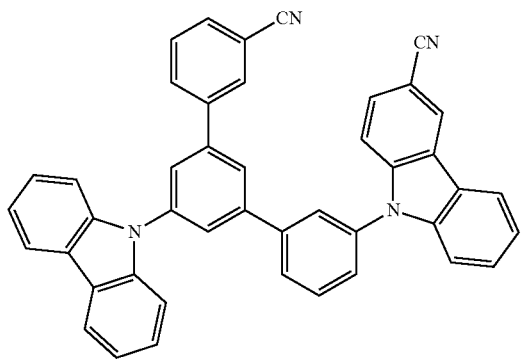
-continued
33
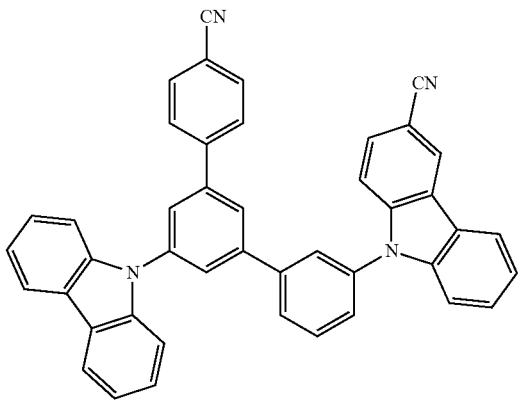
34
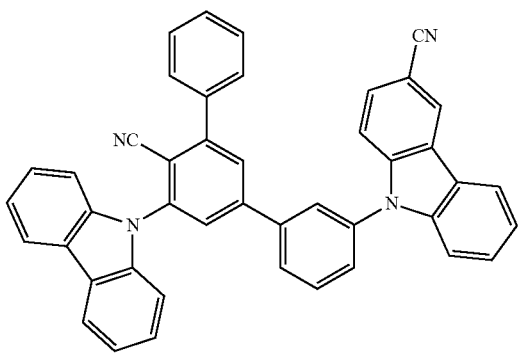
35
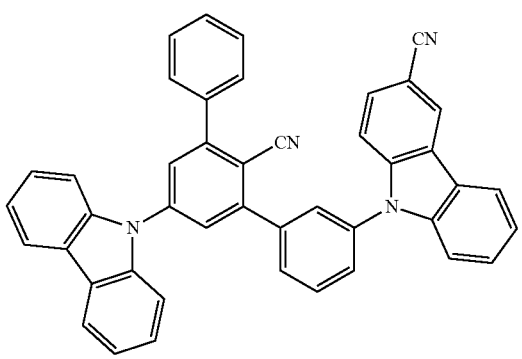
36
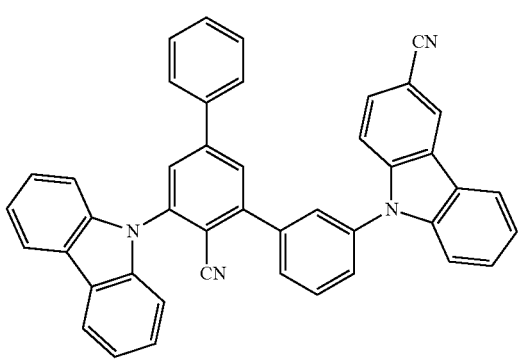

-continued
37
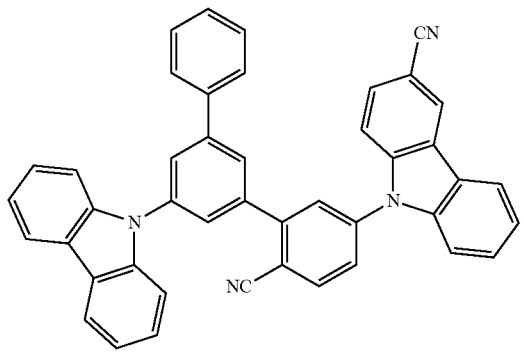
38
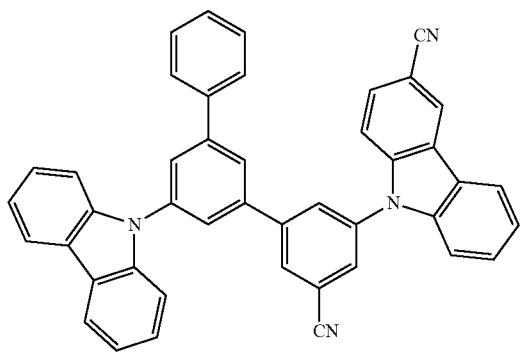
39
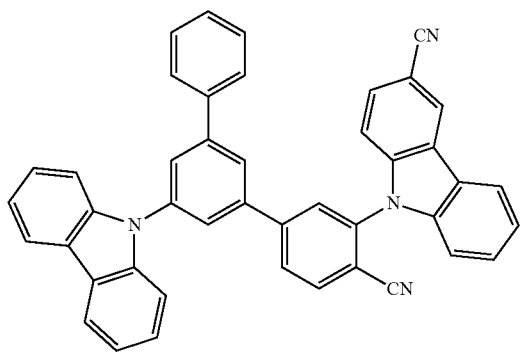
40
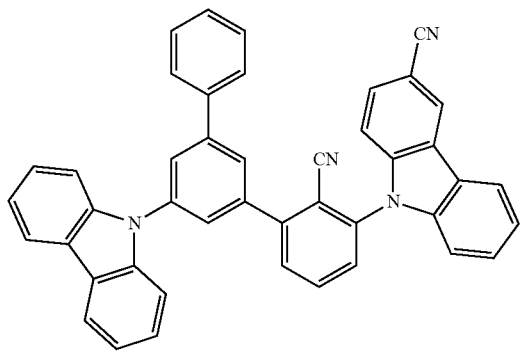
-continued
41
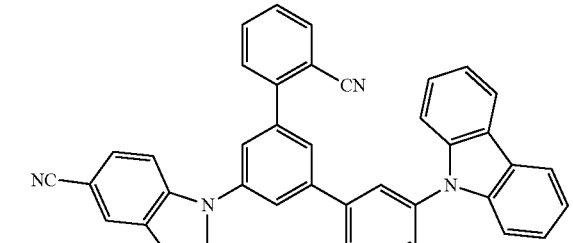
42
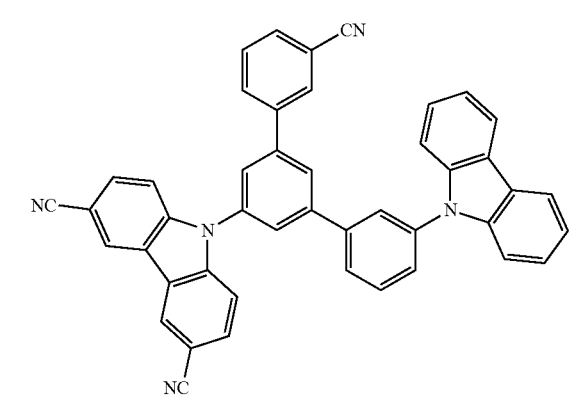
43
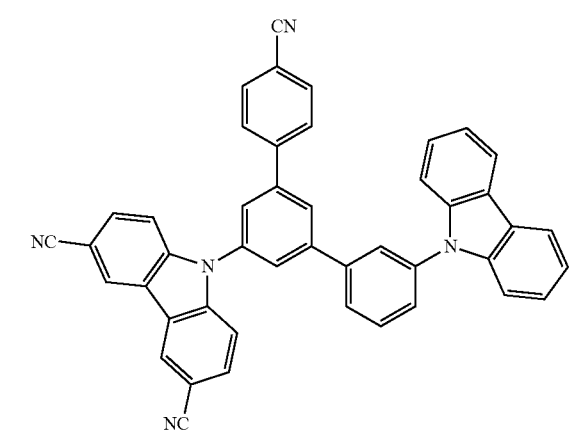
44
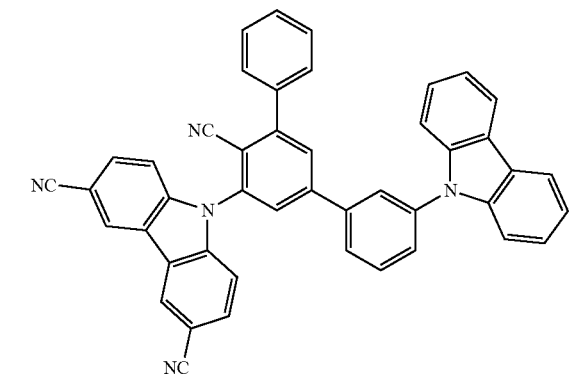

45
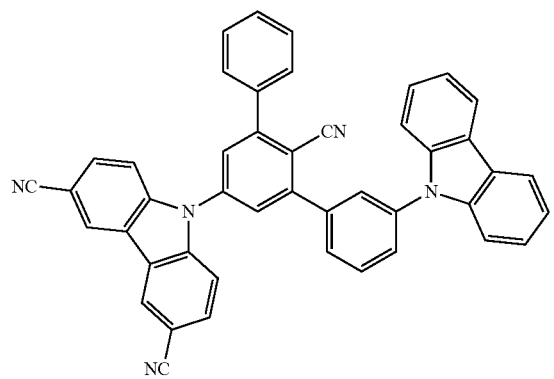
46
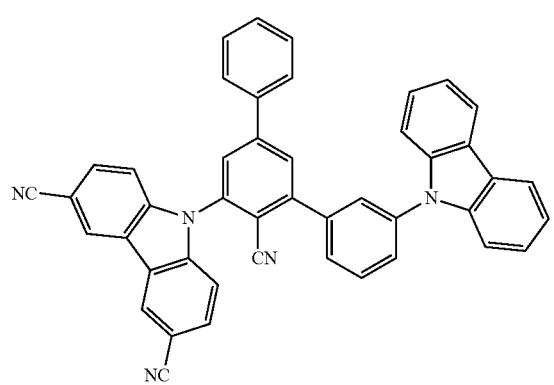
47
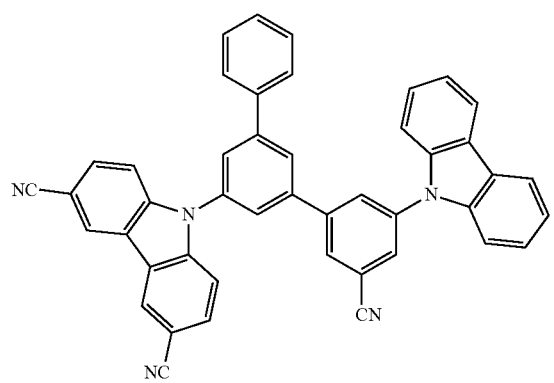
48
49
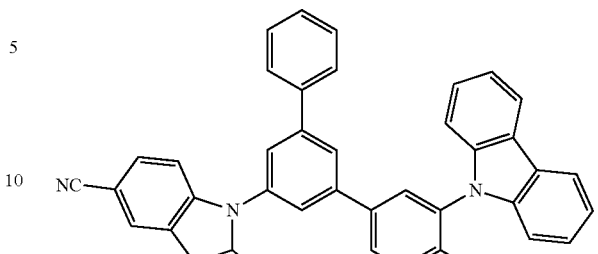
50
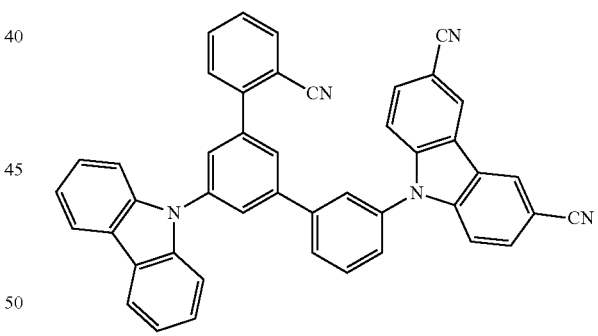
51
52
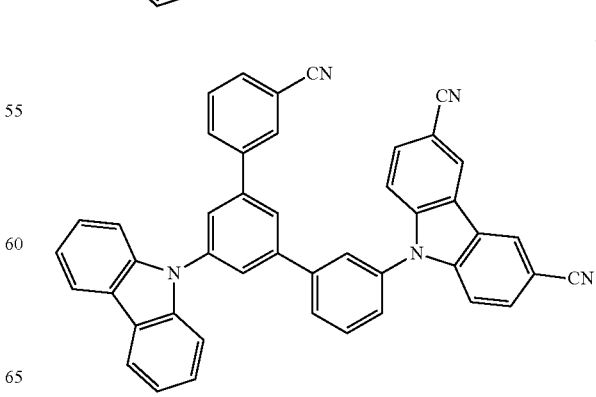

53
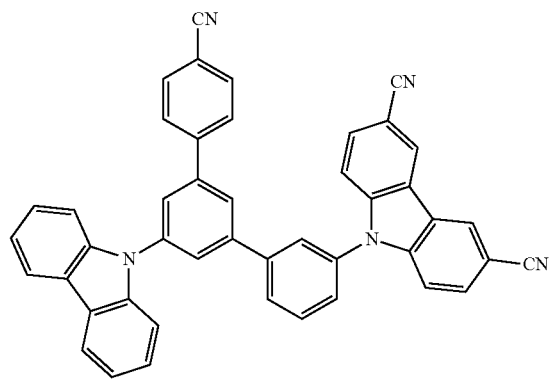
54
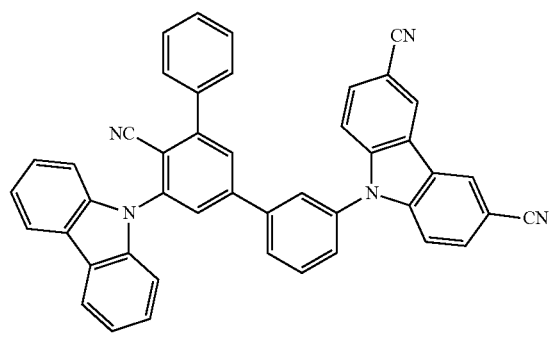
55
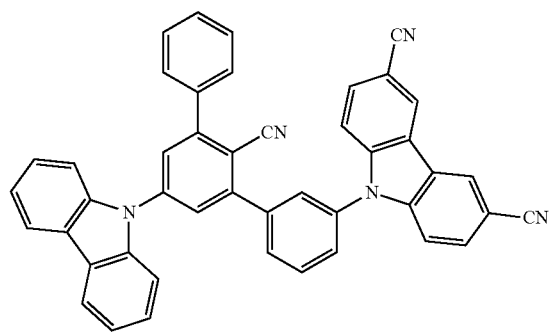
56
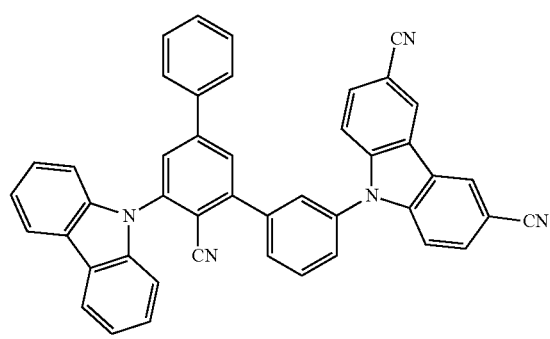
57
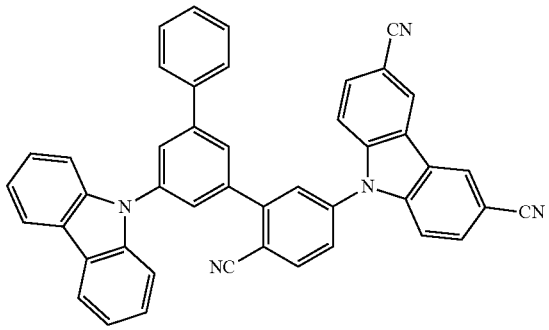
58
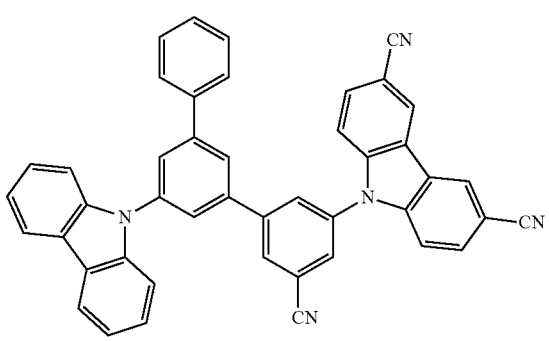
59
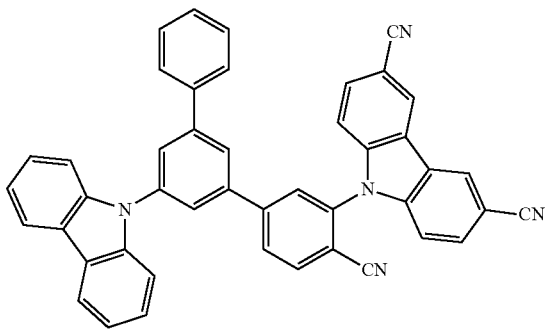
60
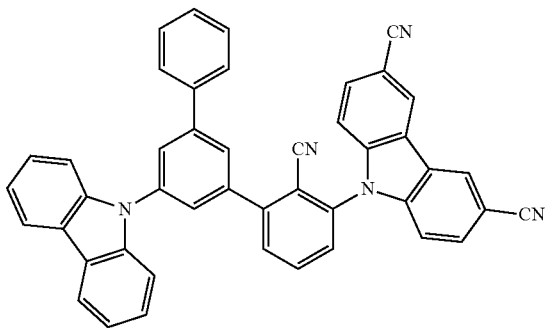

-continued
61
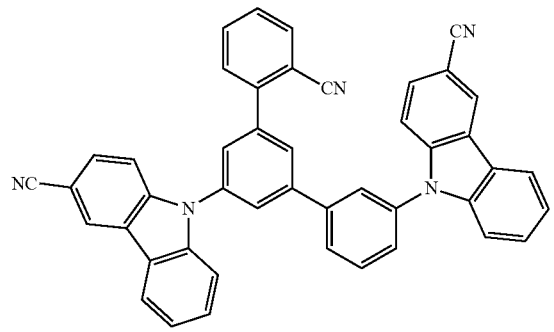
65
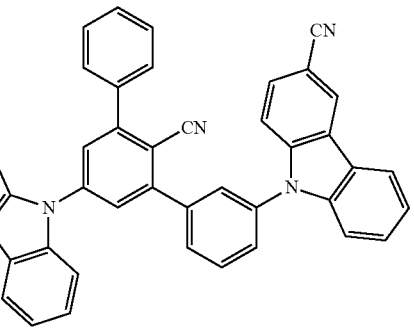
62
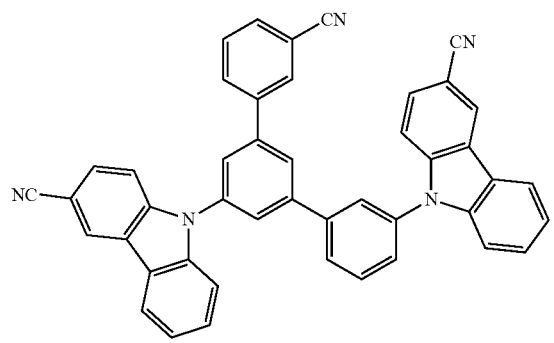
66
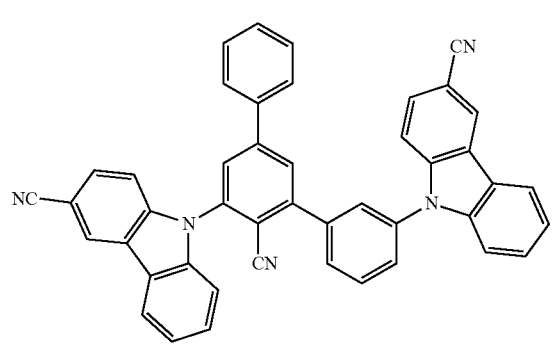
63
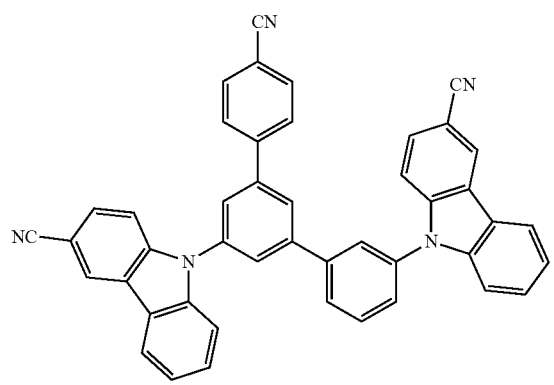
67
64
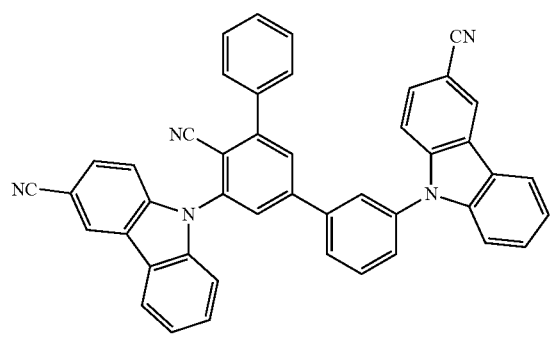
68
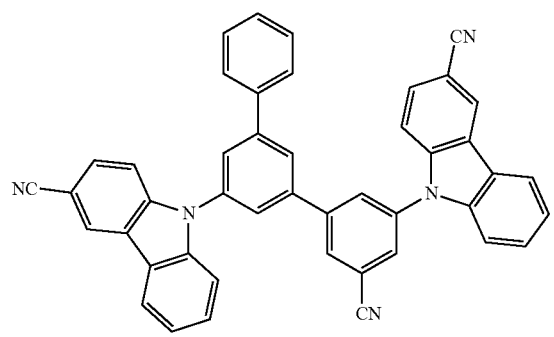

69
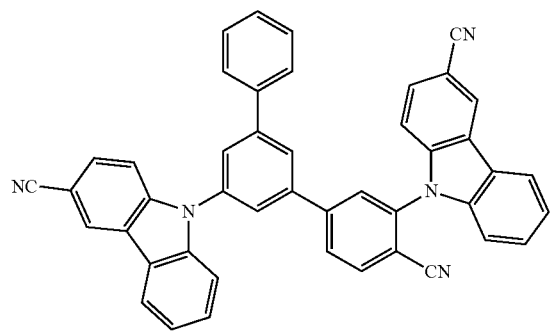
70
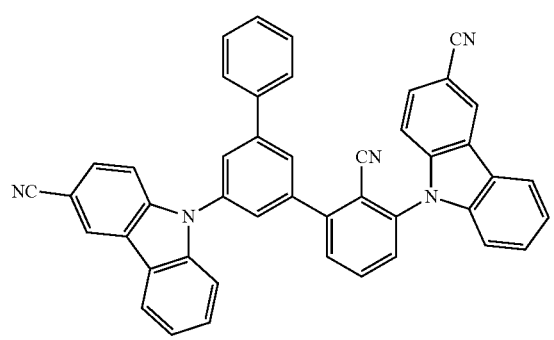
71
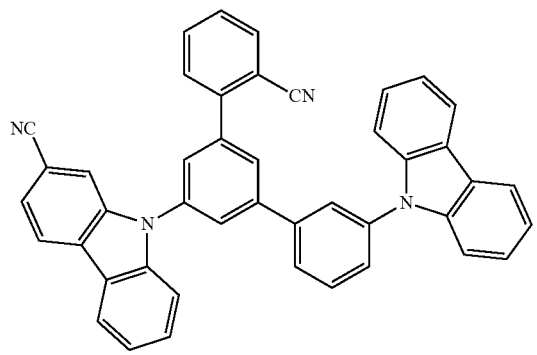
72
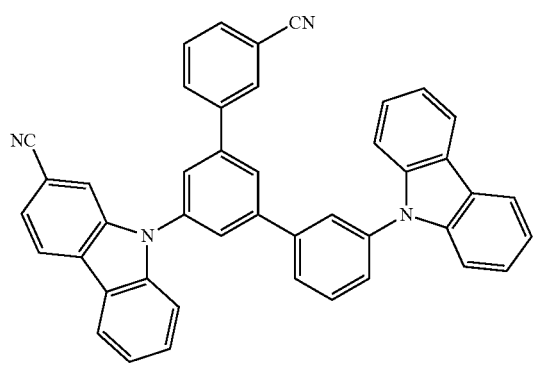
73
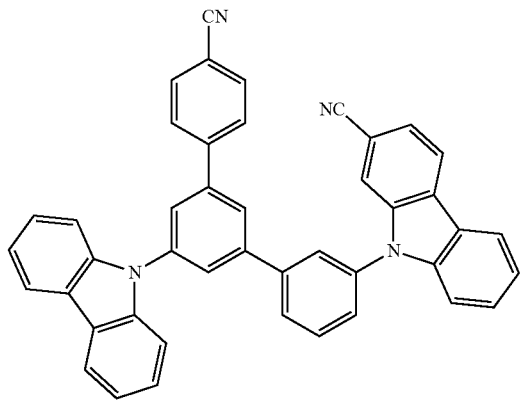
74
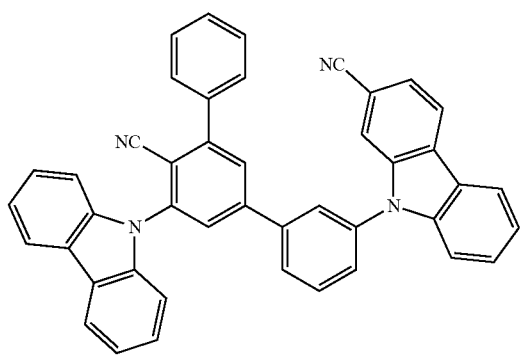
75
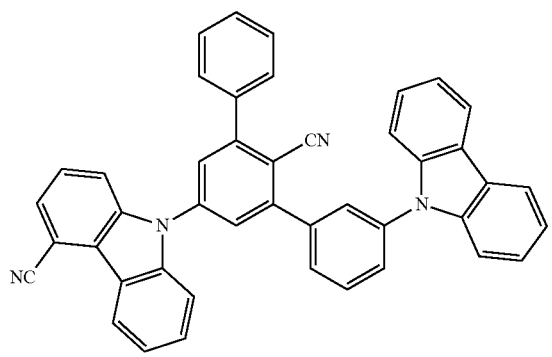
76
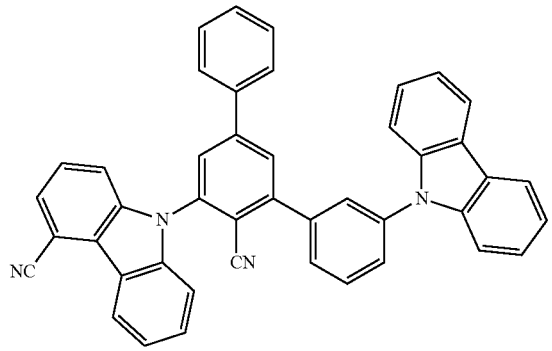

77
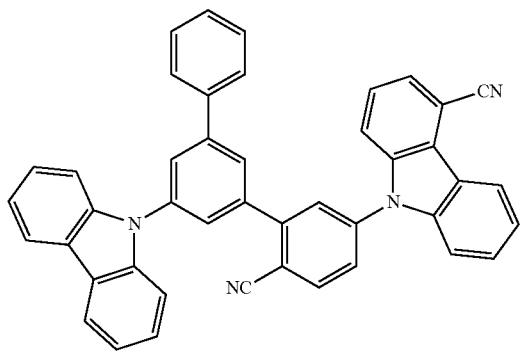
78
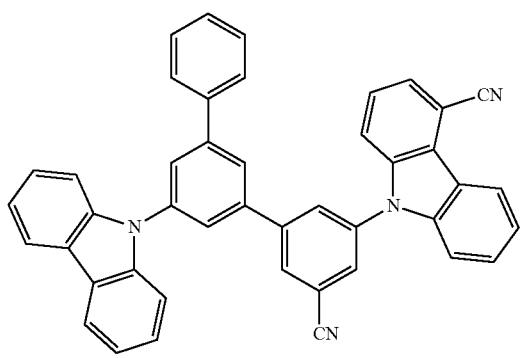
79
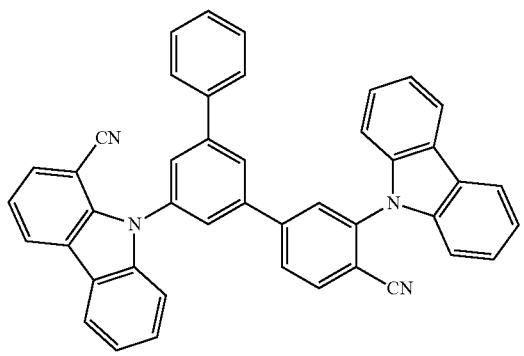
81
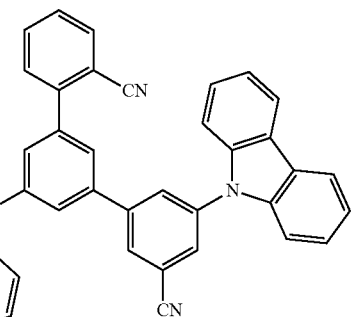
82
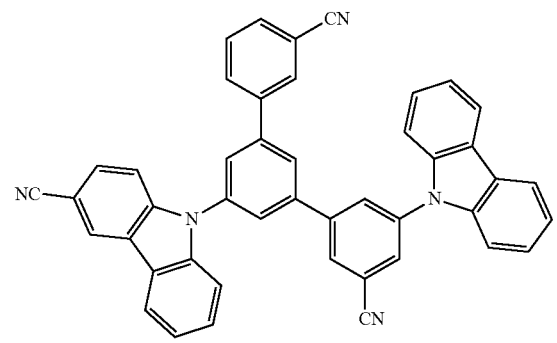
83
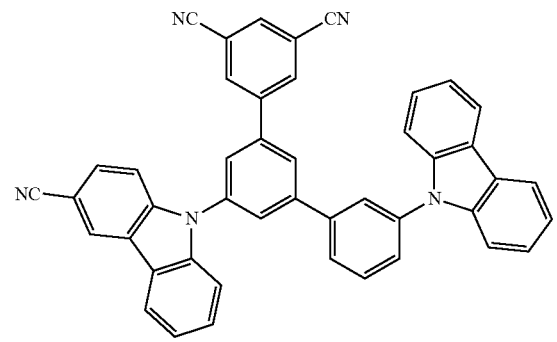
84
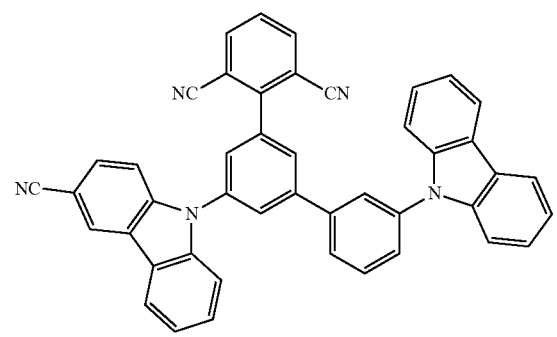
80

85
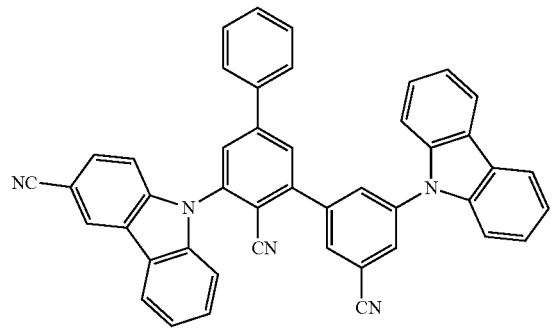
86
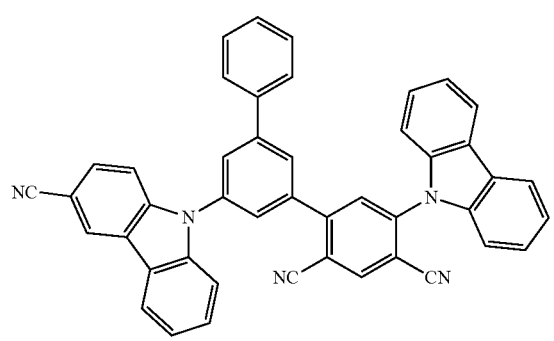
87
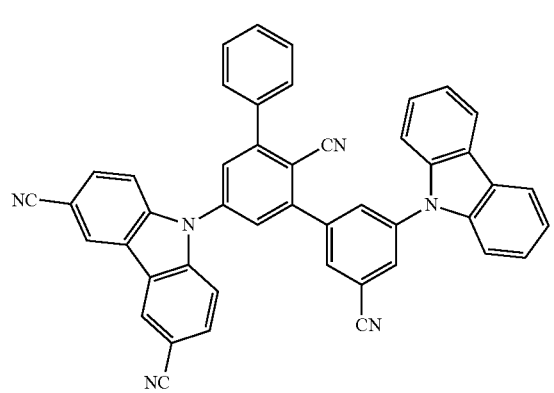
88
89
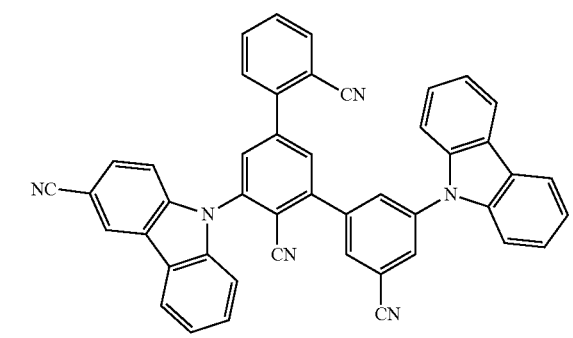
90
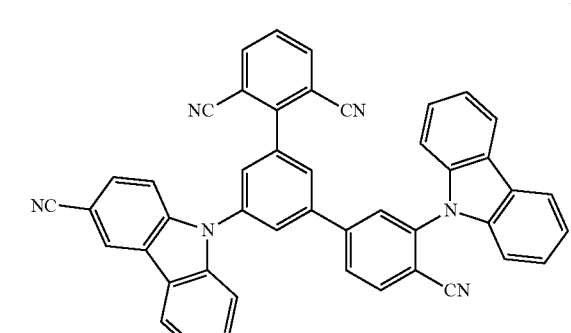
91
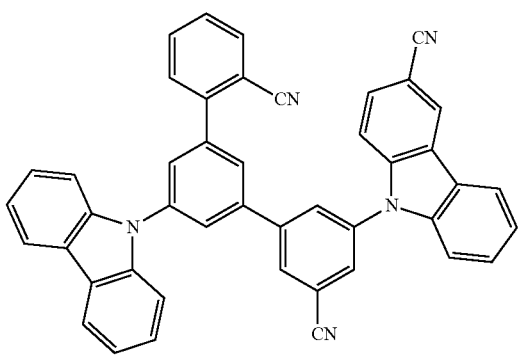
92
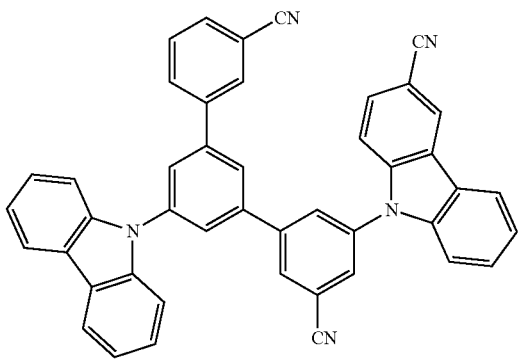

-continued
93
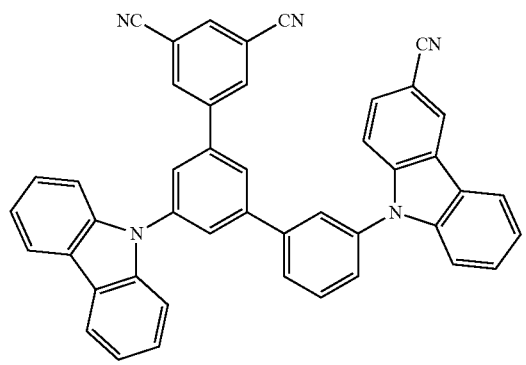
94
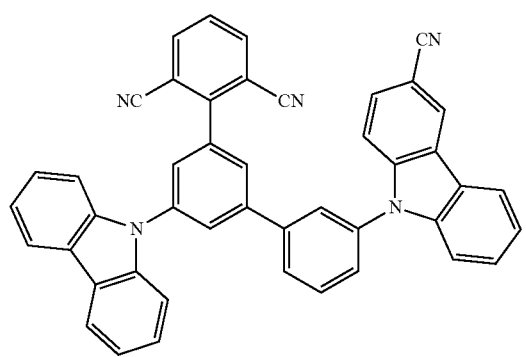
95
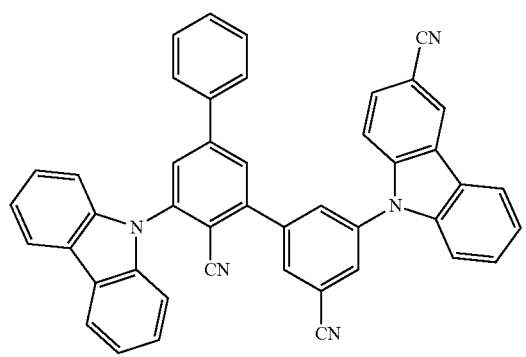
96
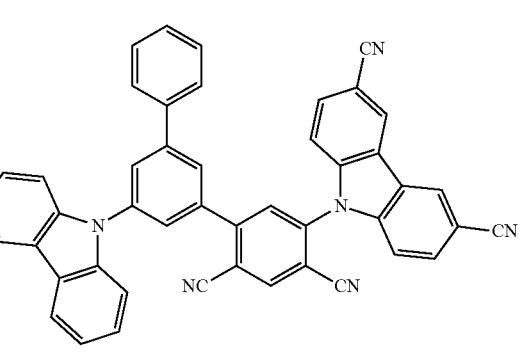
-continued
97
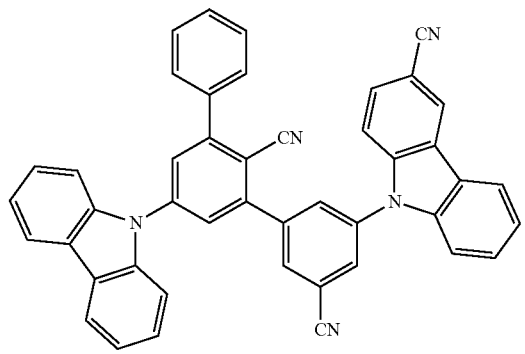
98
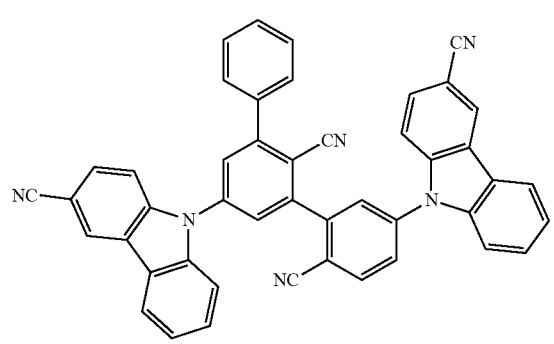
99
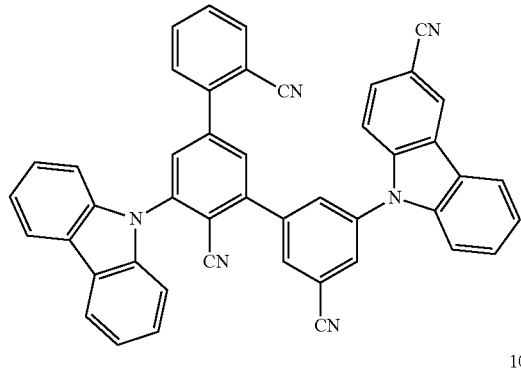
100
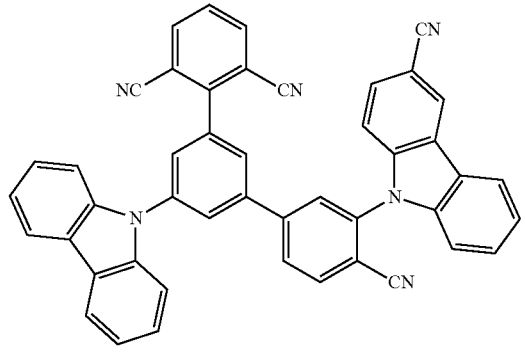

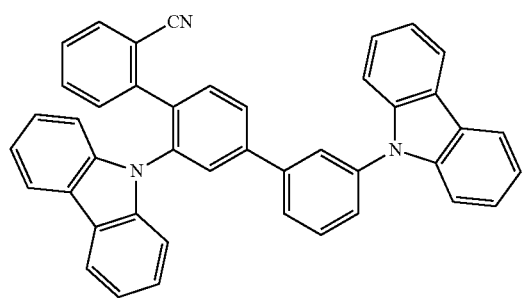
101
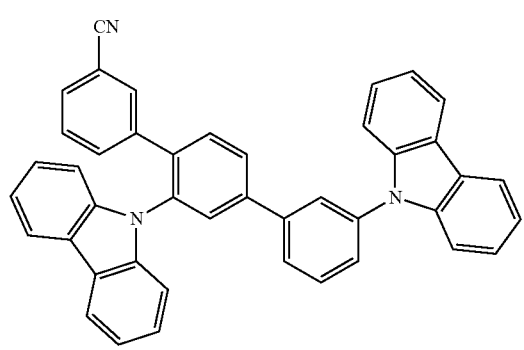
102
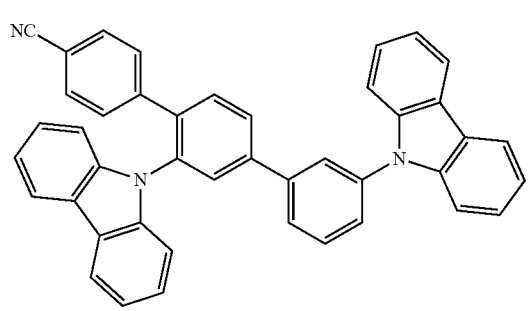
103
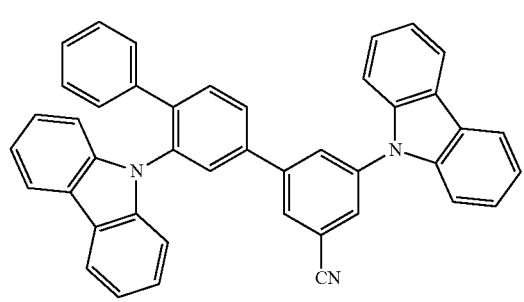
104
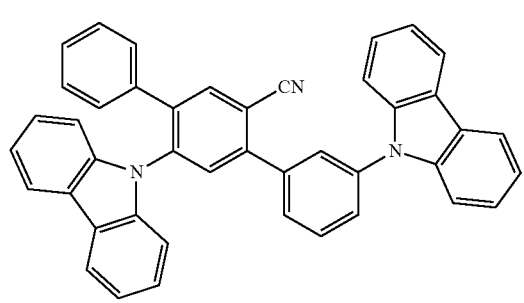
105
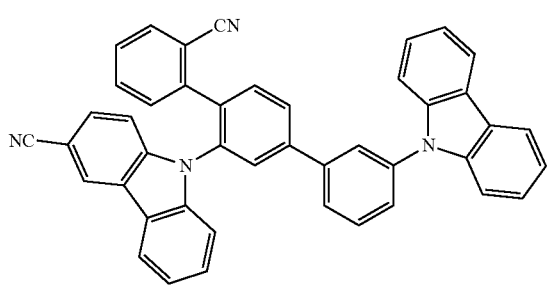
106
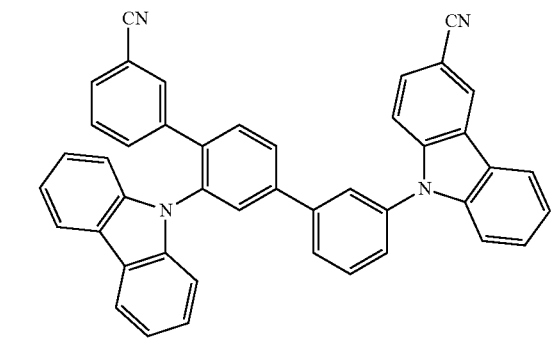
107
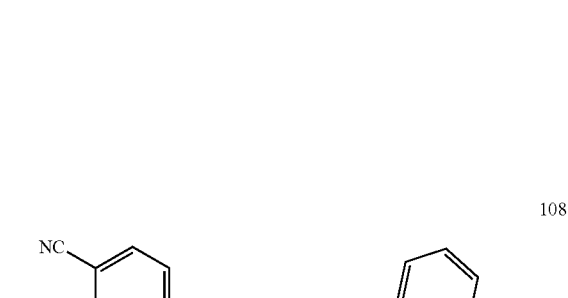
108
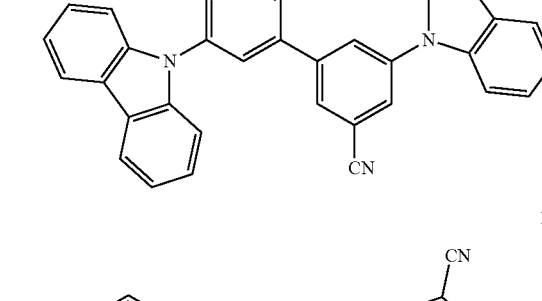
109
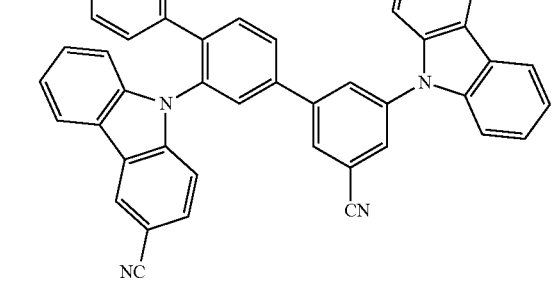

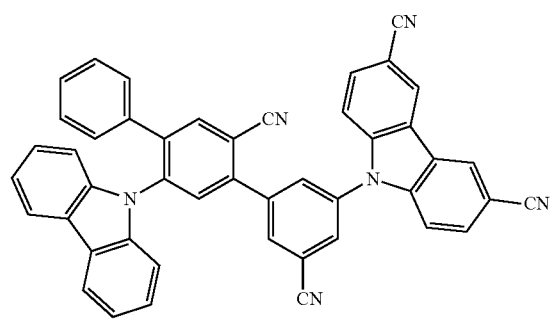
110
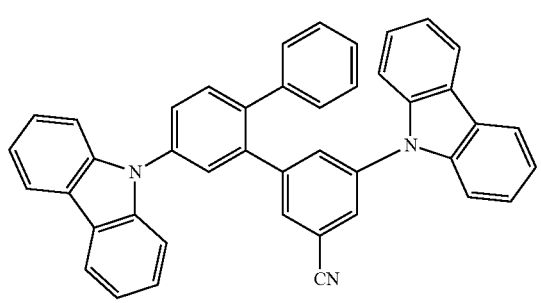
114
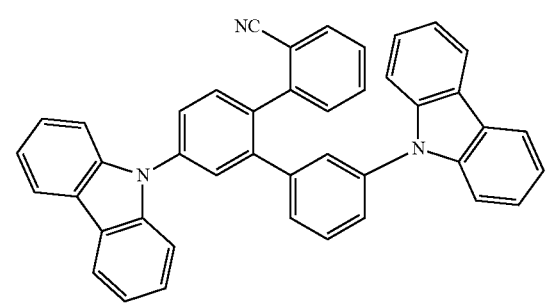
111
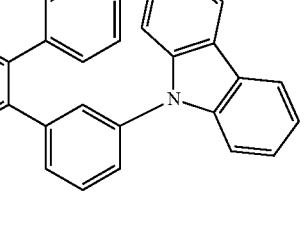
115
116
112
117
113
118
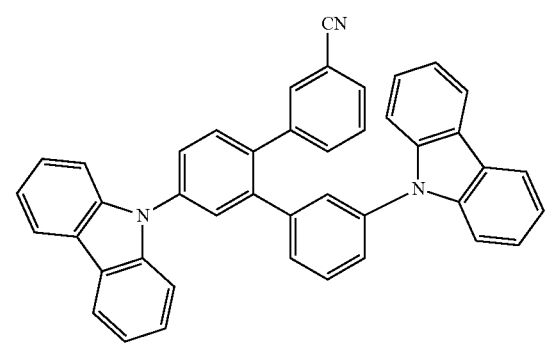
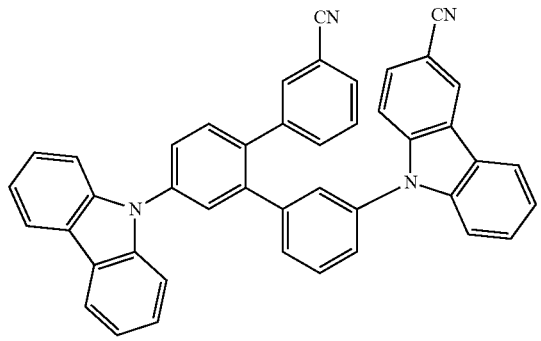
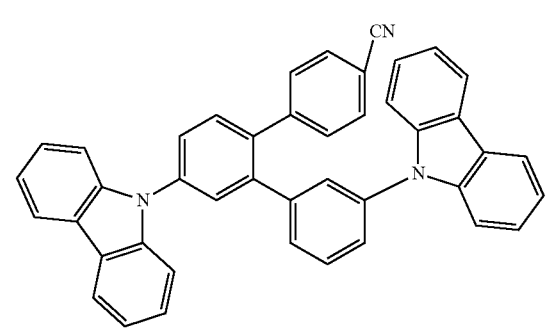

119
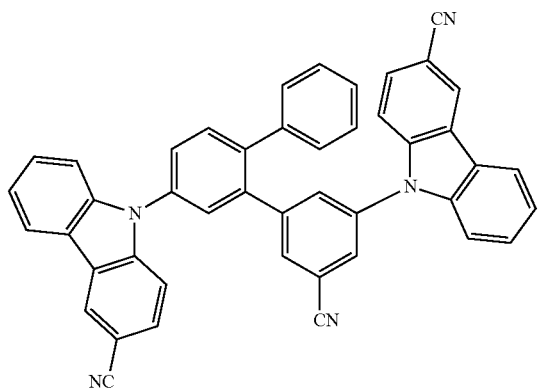
120
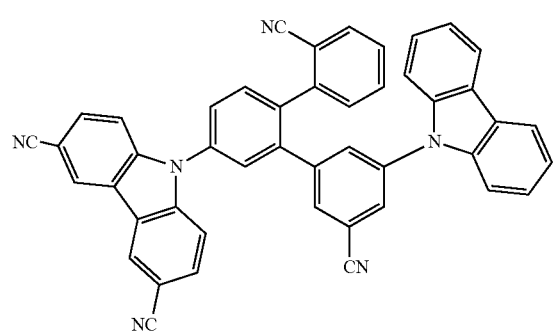
121
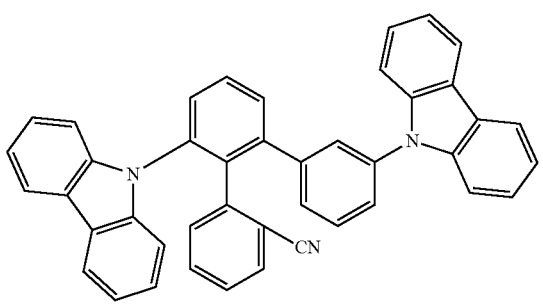
122
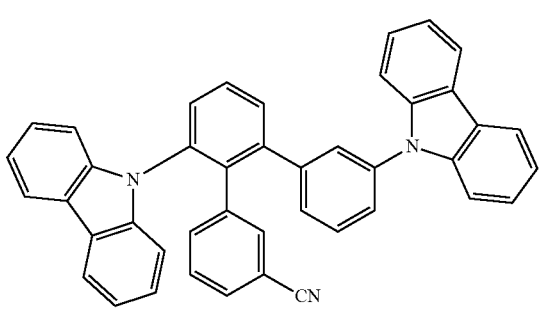
123
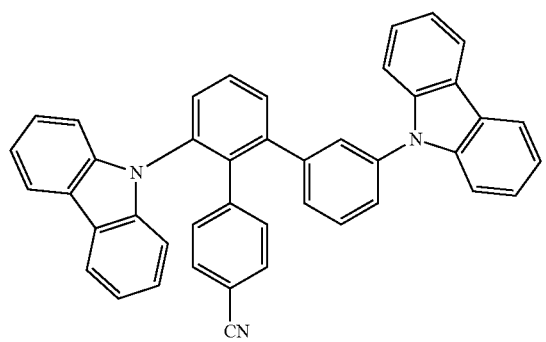
124
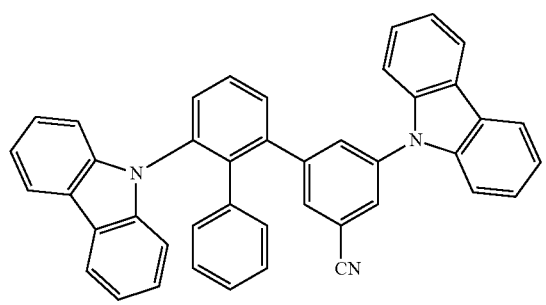
125
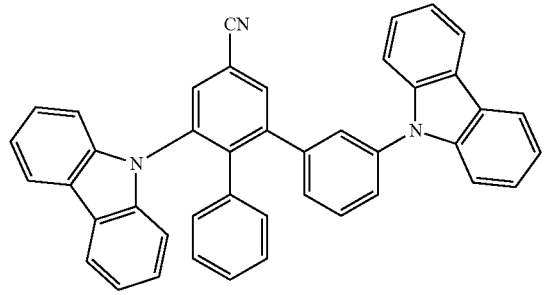
126
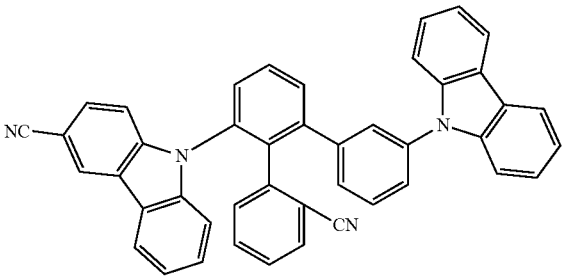

127
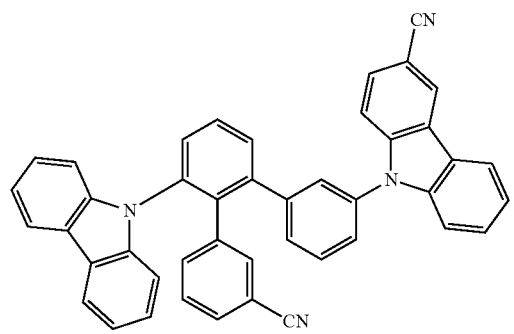
128
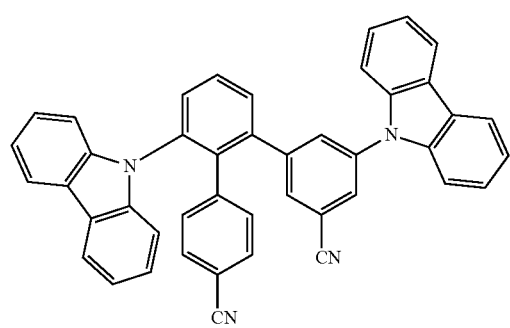
129
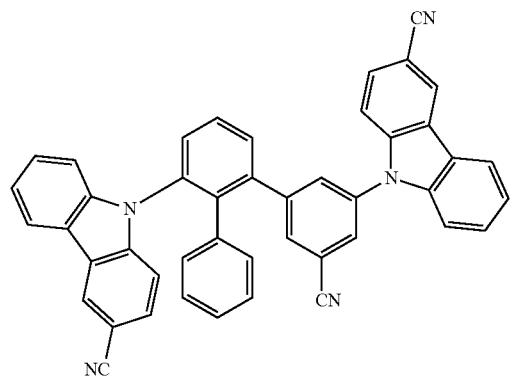
130
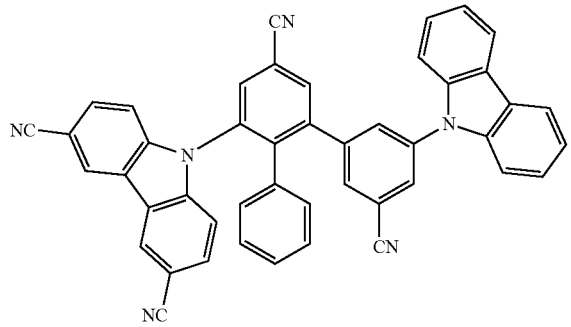
131
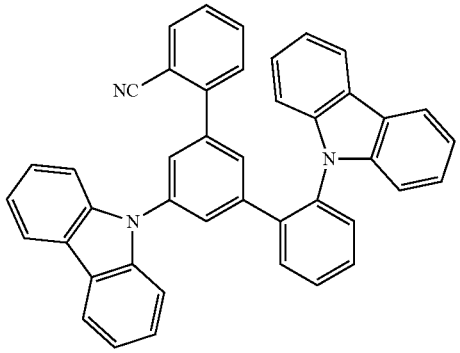
132
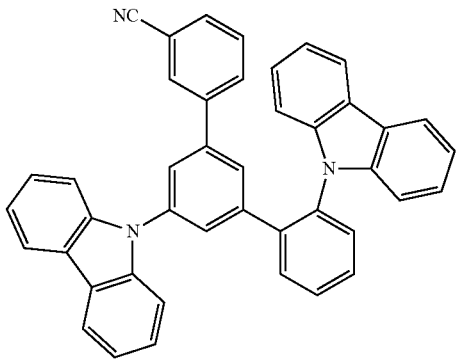
133
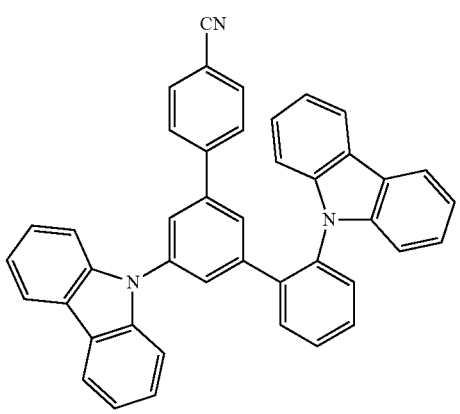
134
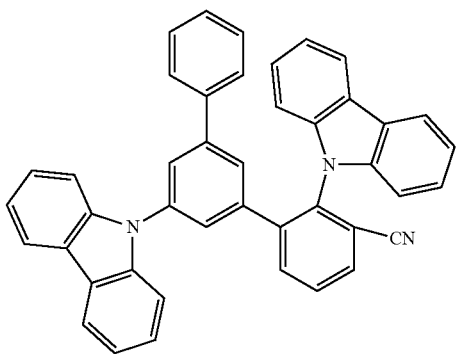

135 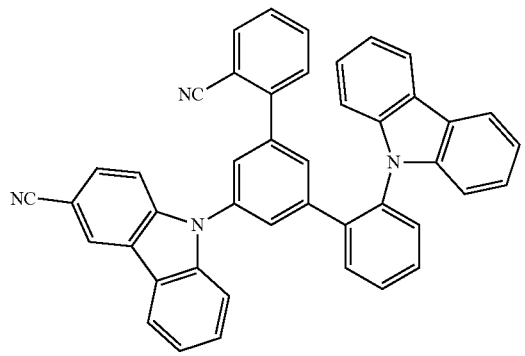
136 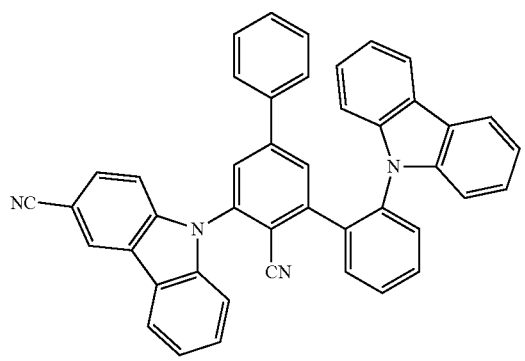
137 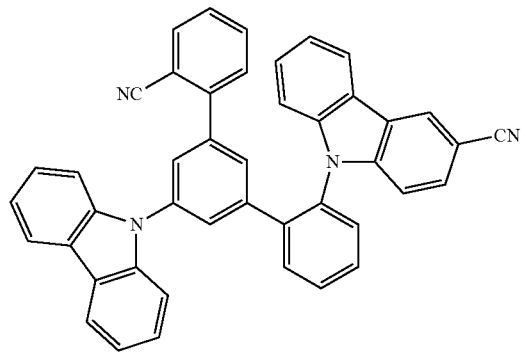
138 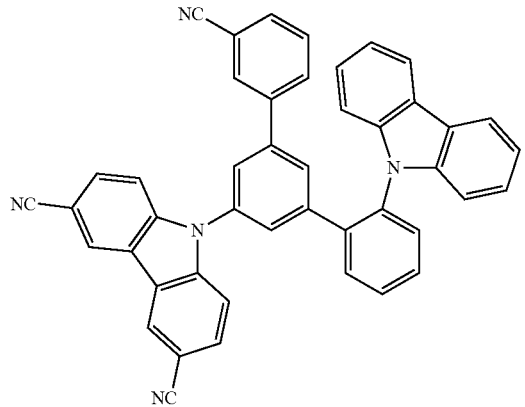
139 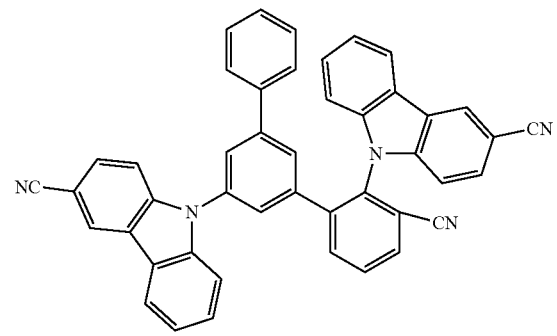
140 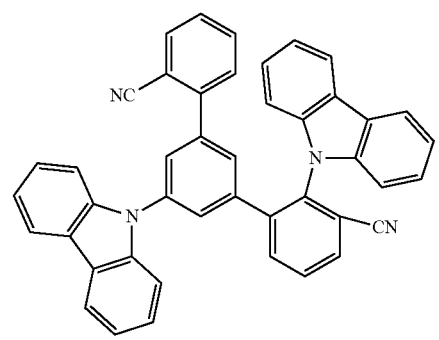
141 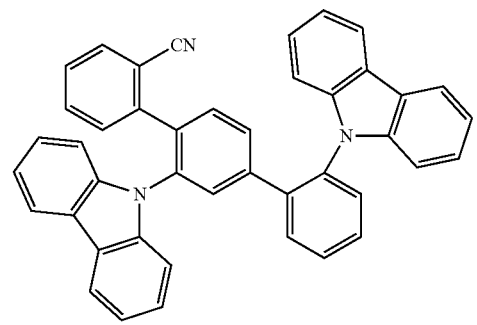
142 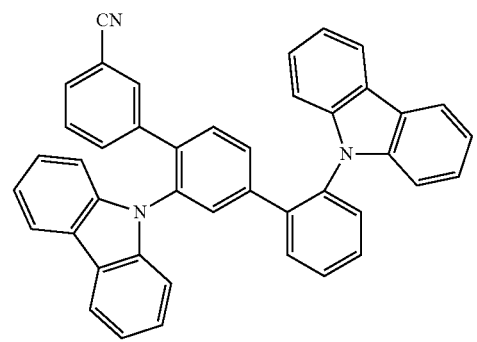

143
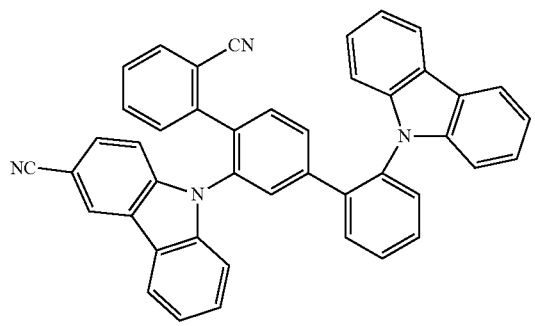
144
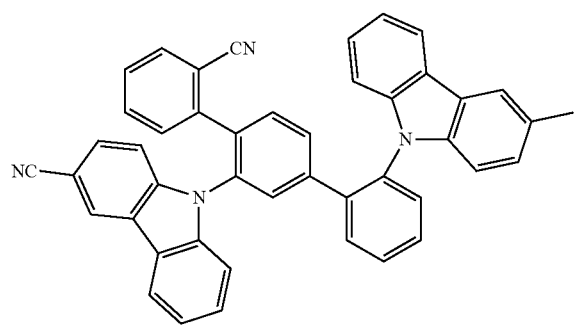
145
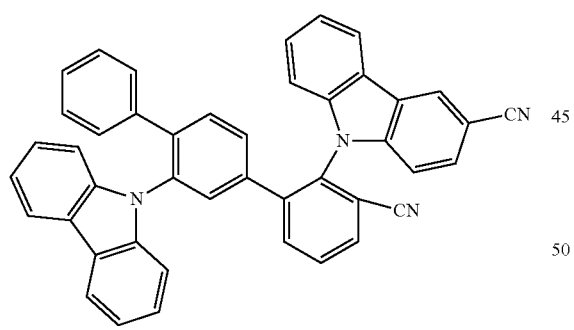
146
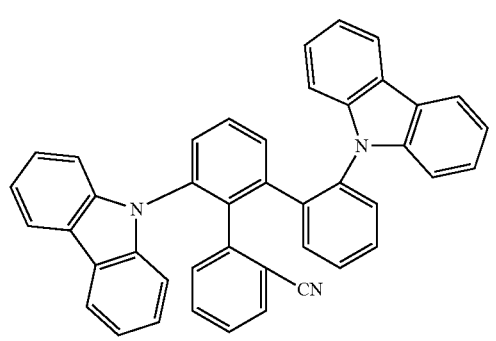
147
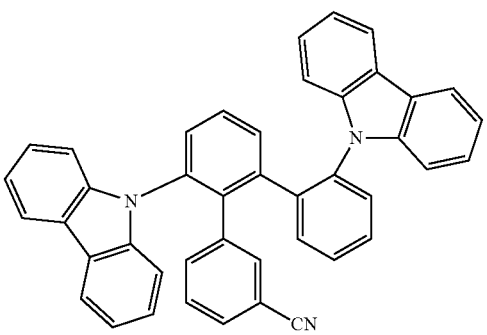
148
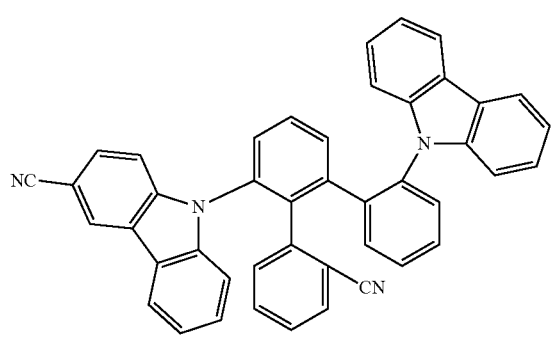
149
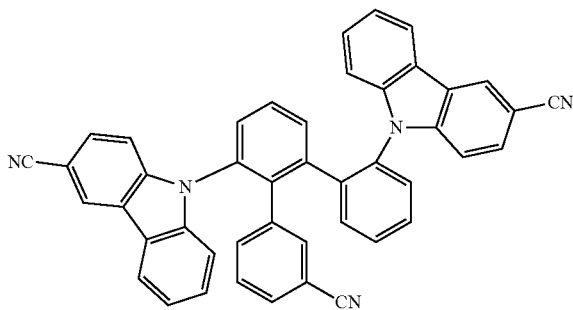
150
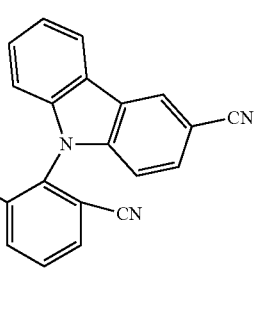

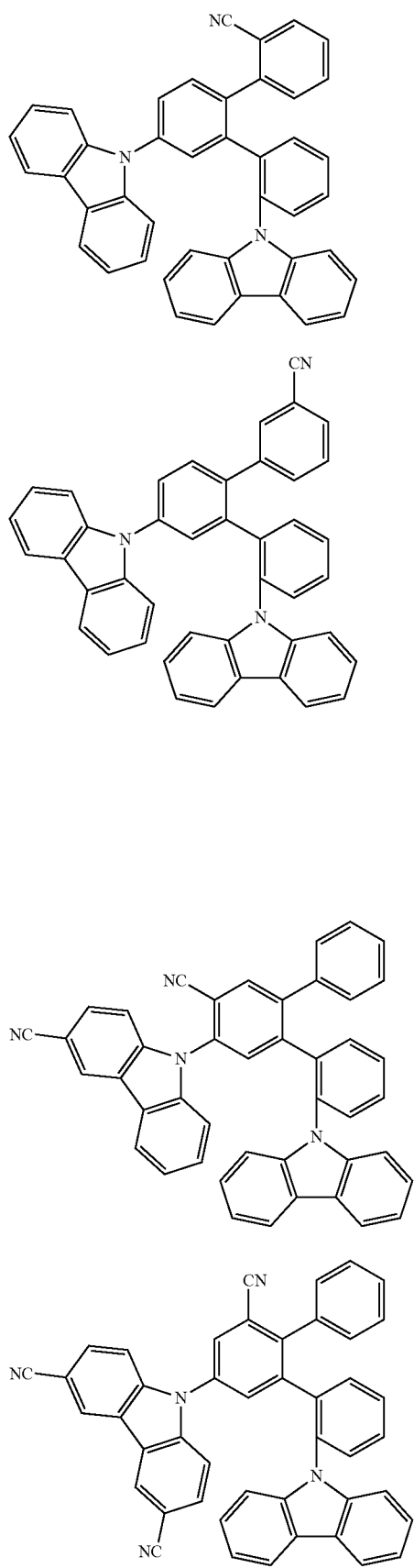
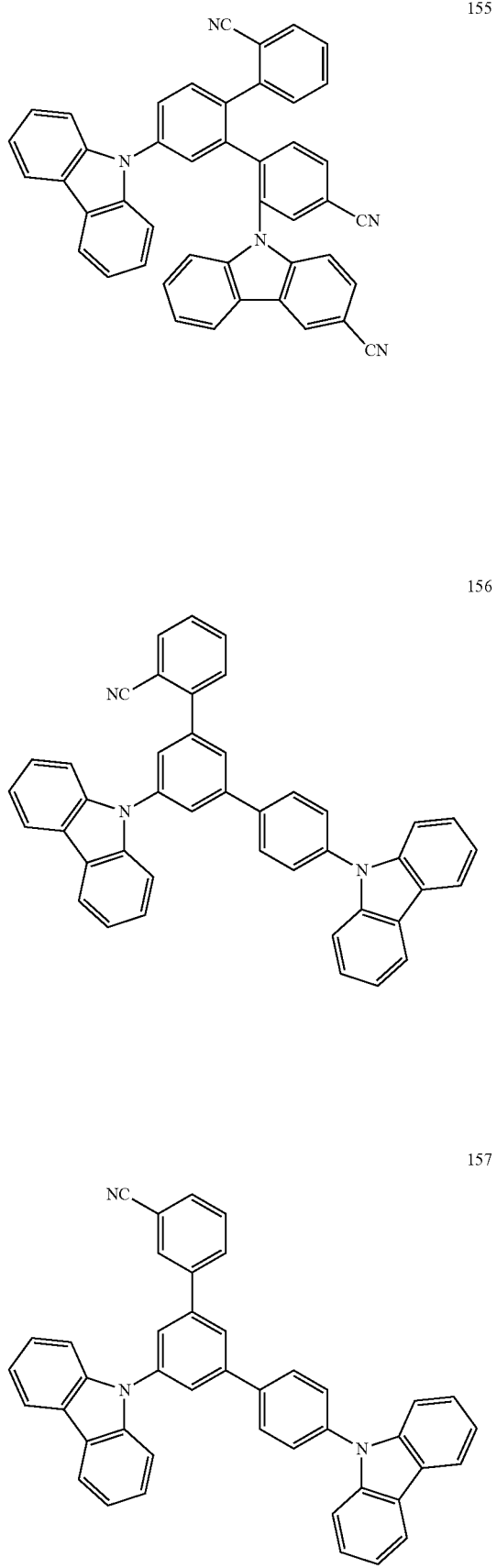

158
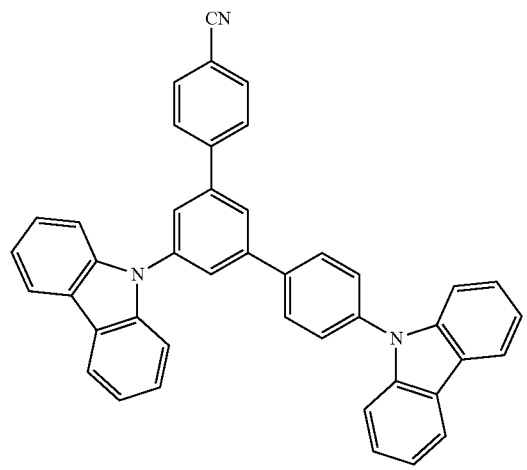
159
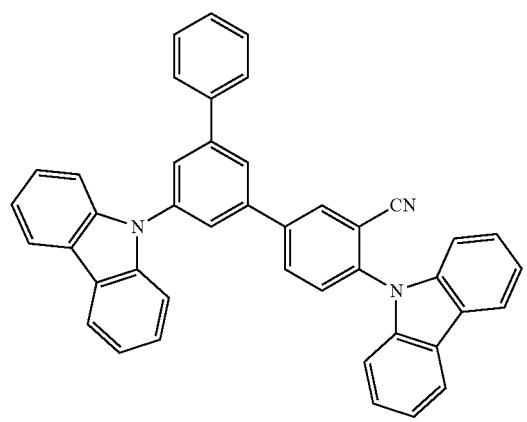
160
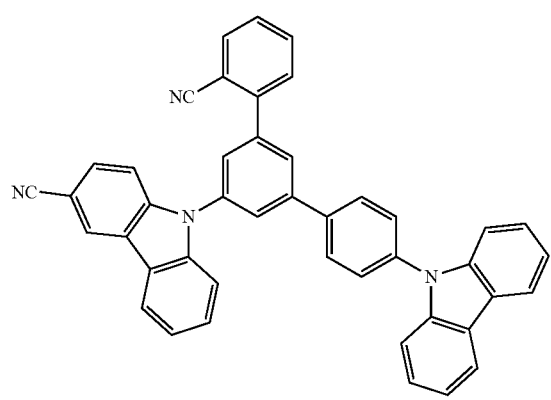
161
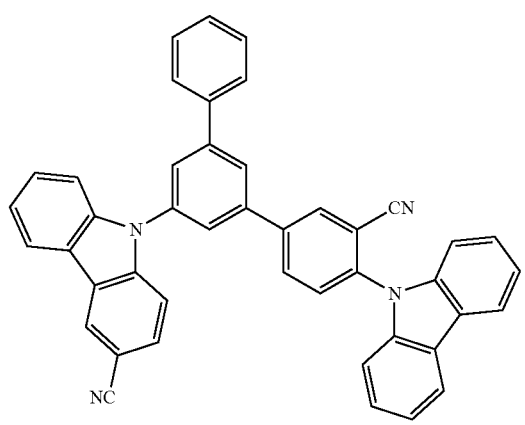
162
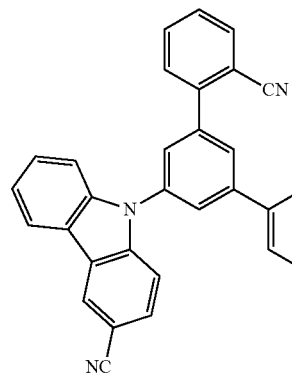
163
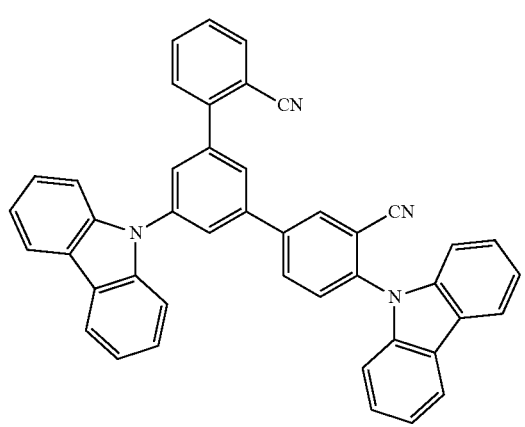

164
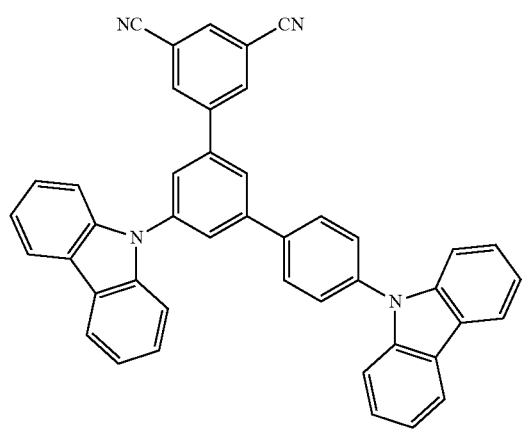
165
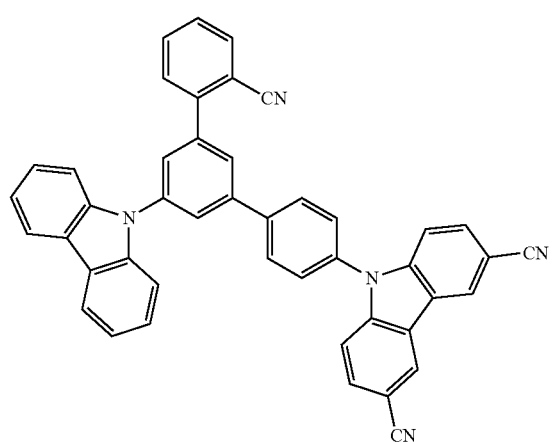
166
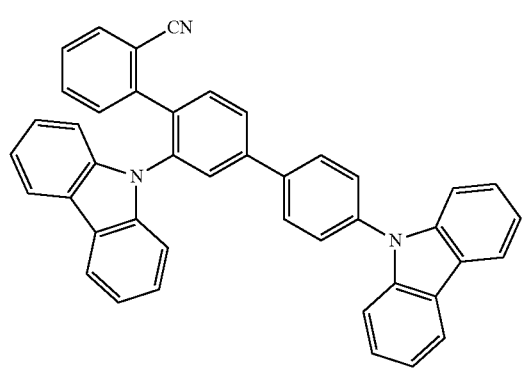
167
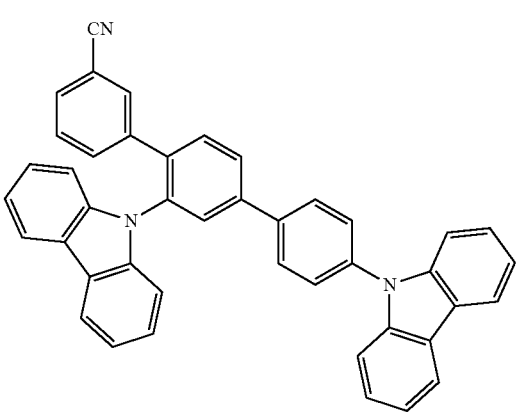
168
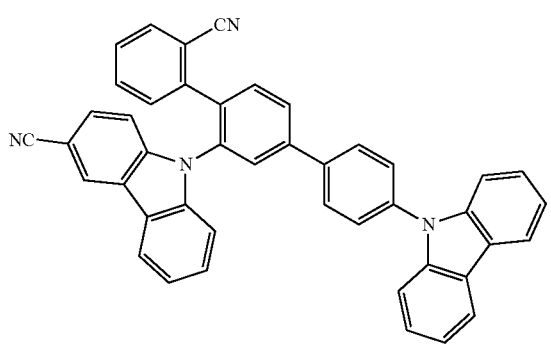
169
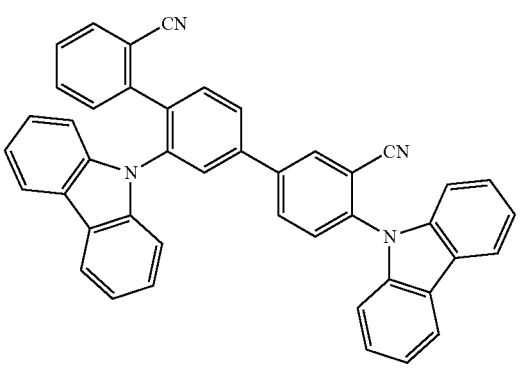
170
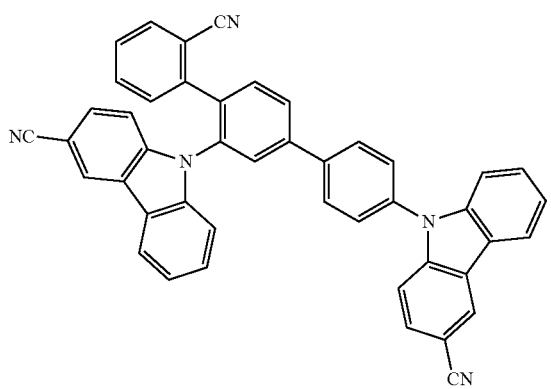

-continued
171
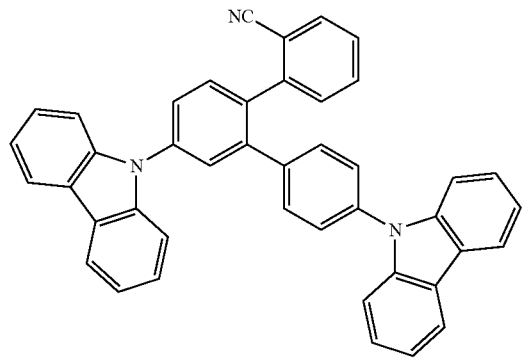
172
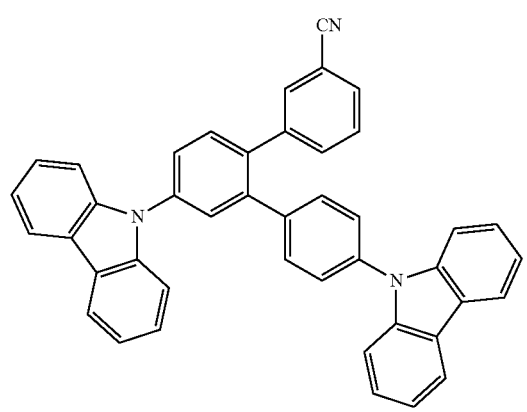
173
174
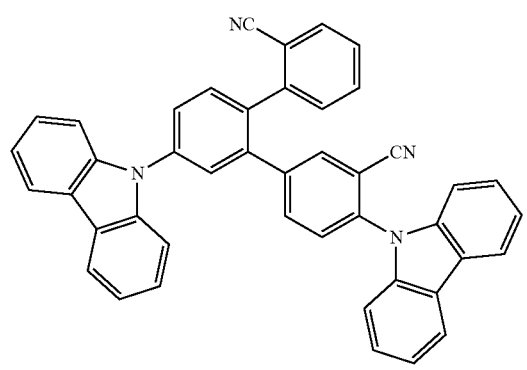
-continued
175
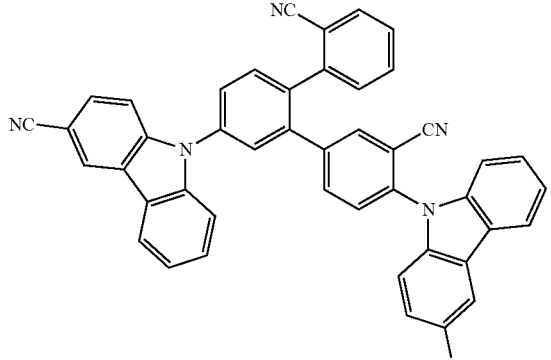
176
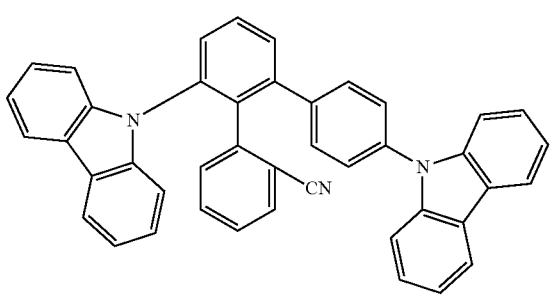
177
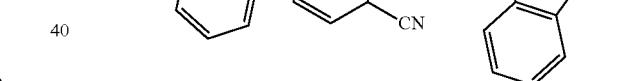
178
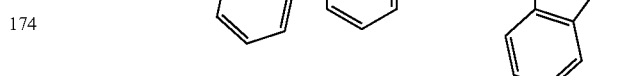
179
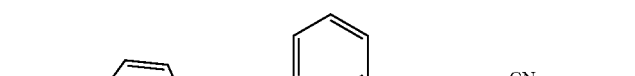

-continued
180
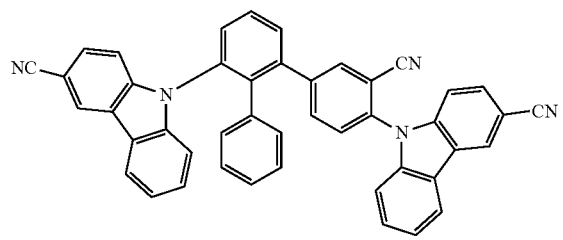
181
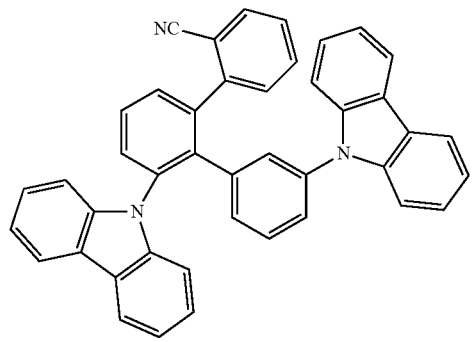
182
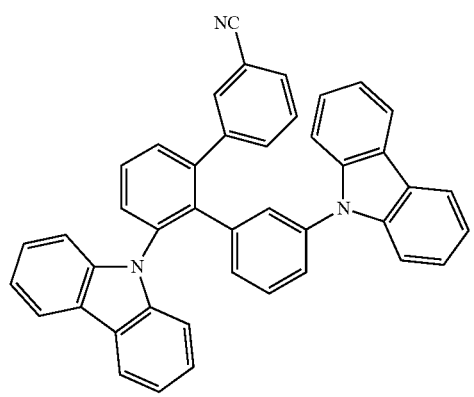
183
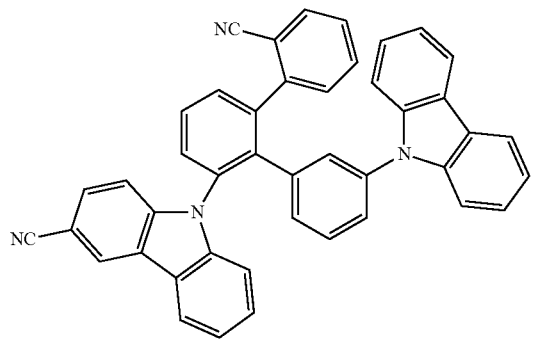
-continued
184
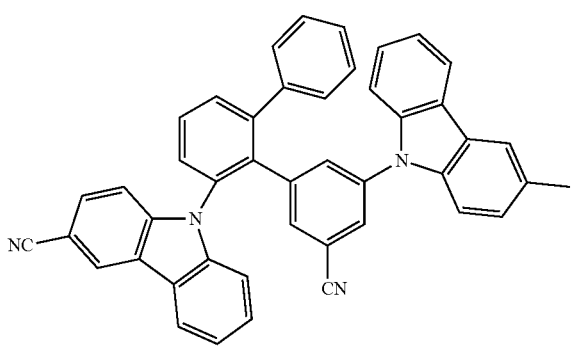
185
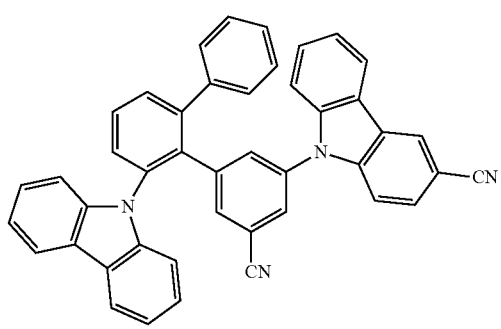
186
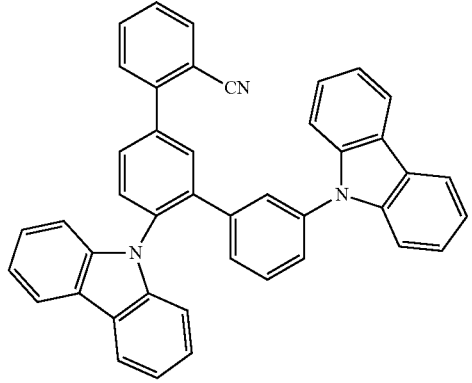
187
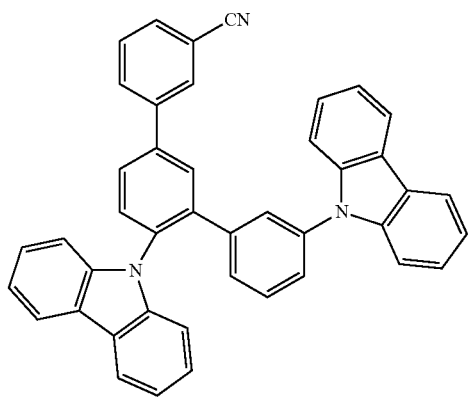

188
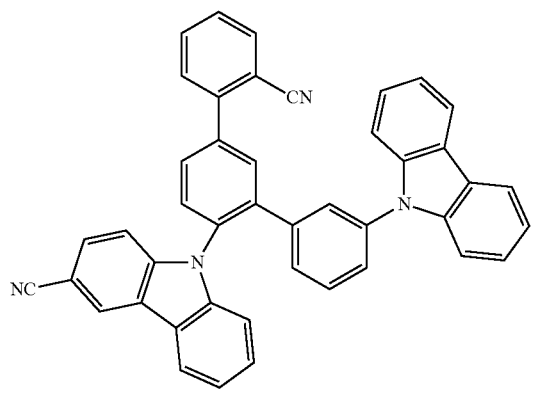
189
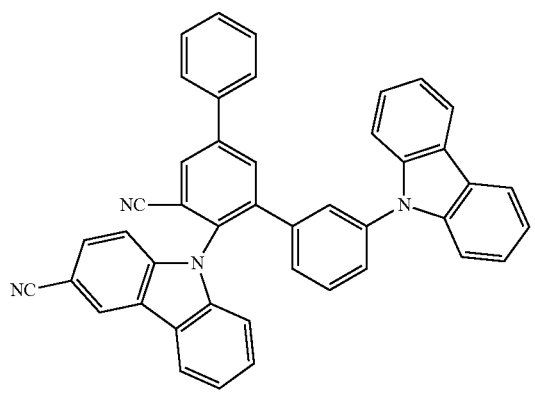
190
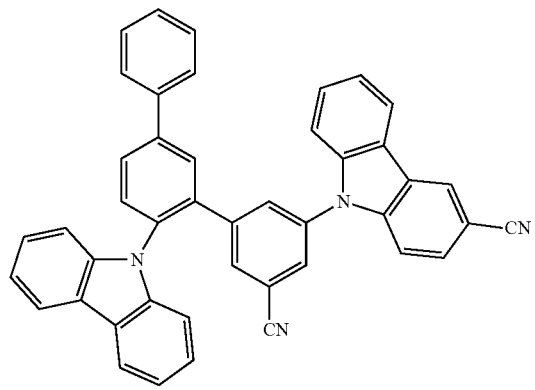
191
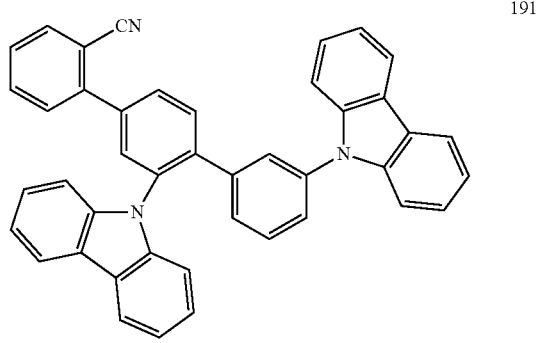
192
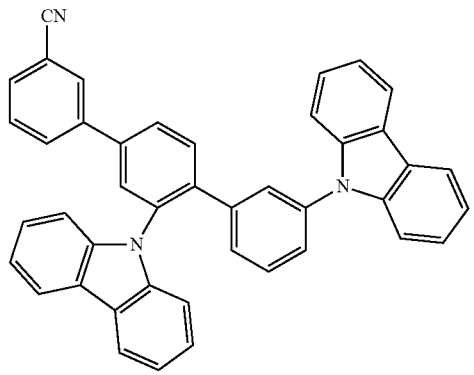
193
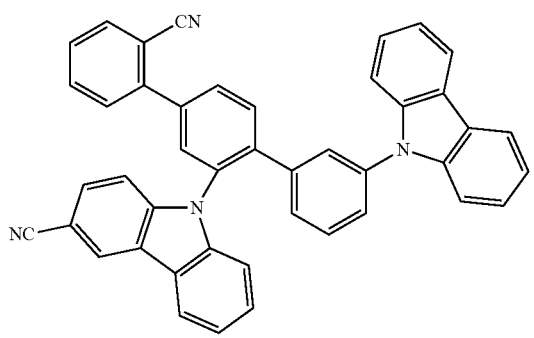
194
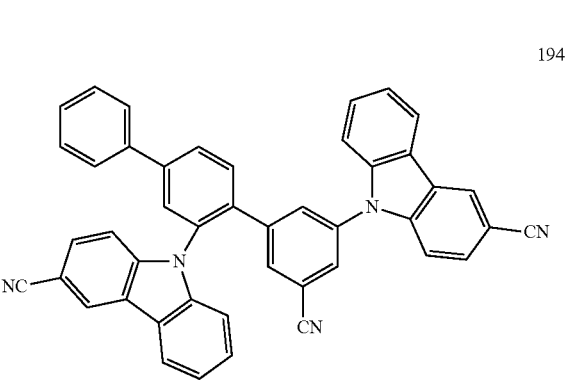
195
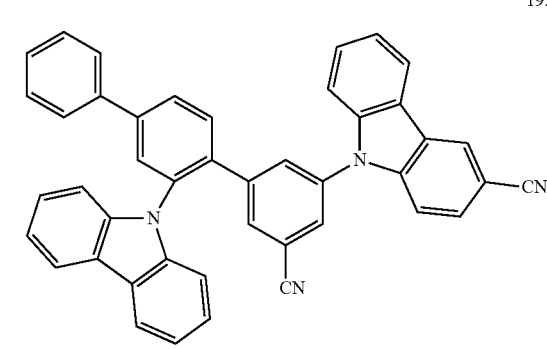

196
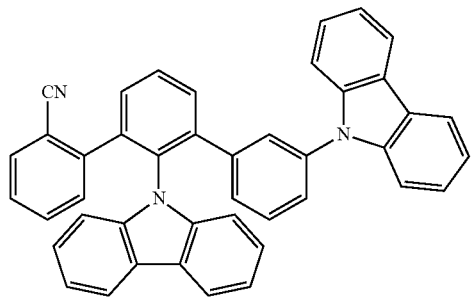
197
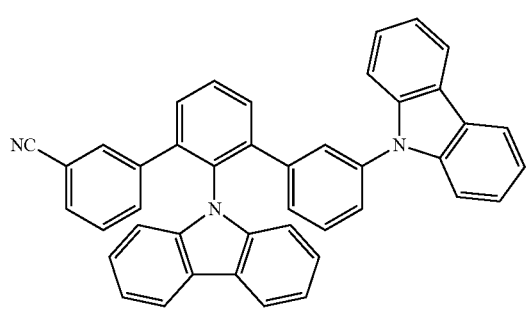
198
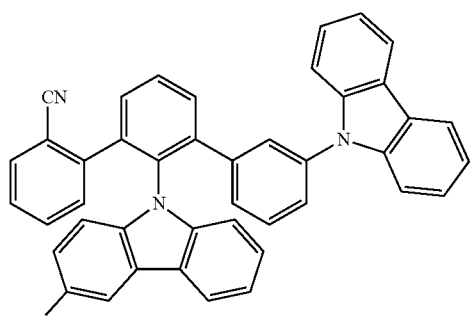
199
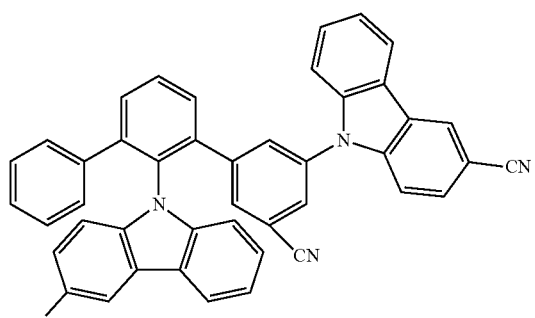
200
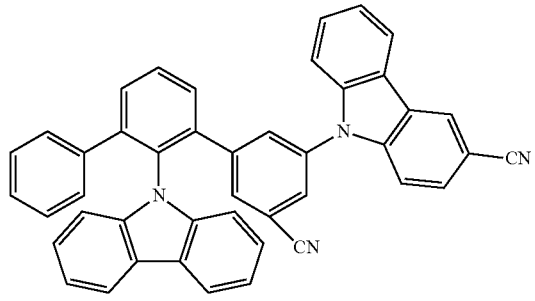
201
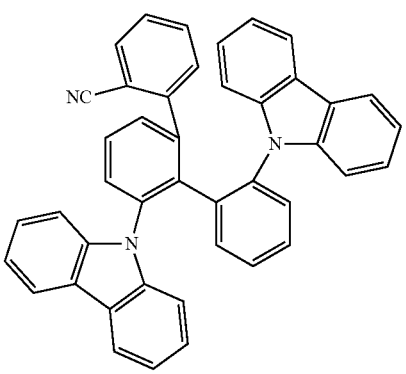
202
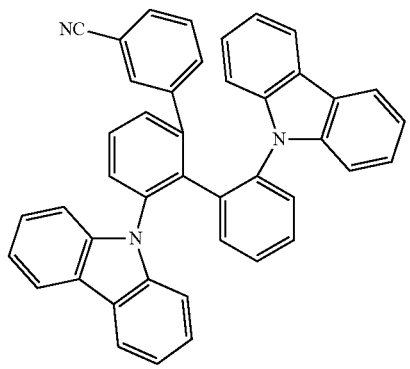
203
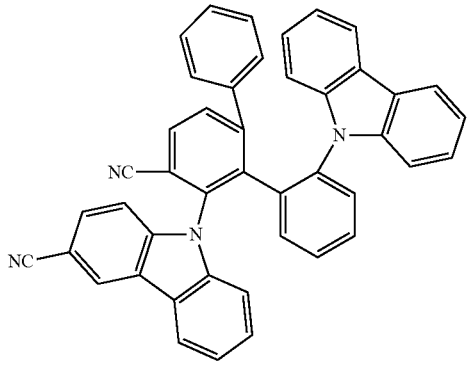
204
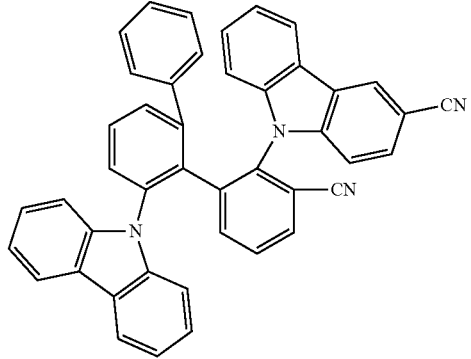

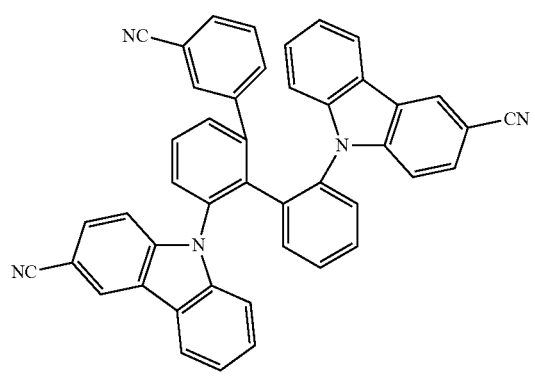
205
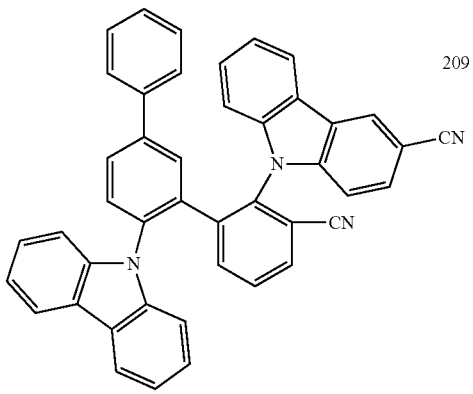 [SMILES: N#Cc1ccc2c(c1)c1ccccc1n2-c1c(C#N)cccc1-c1cc(-c2ccccc2)ccc1-n1c2ccccc2c2ccccc21]
209
206
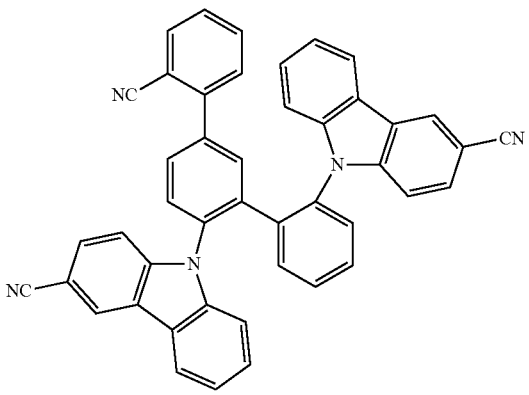
210
207
211
208
212
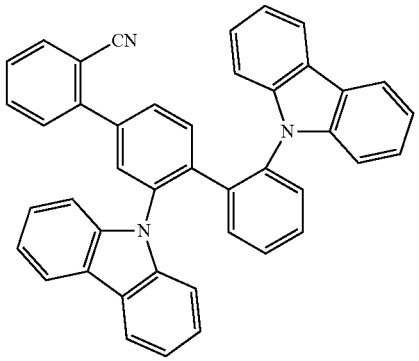
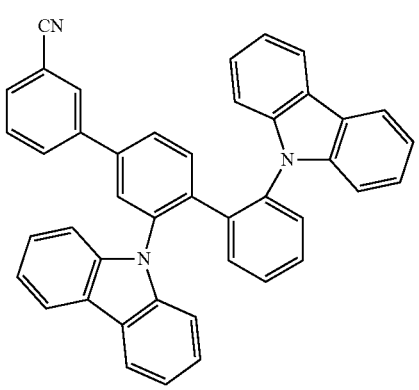

71
-continued
213
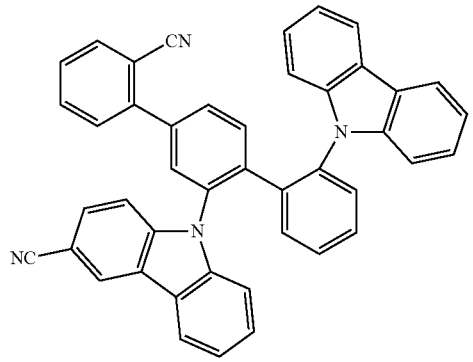
214
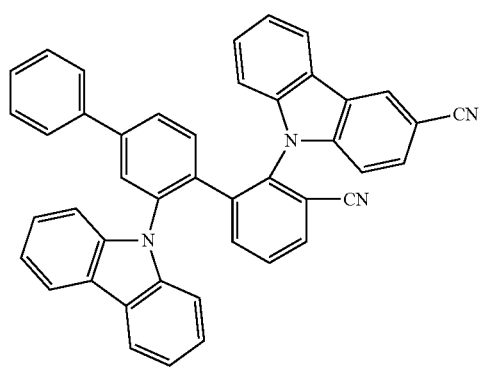
215
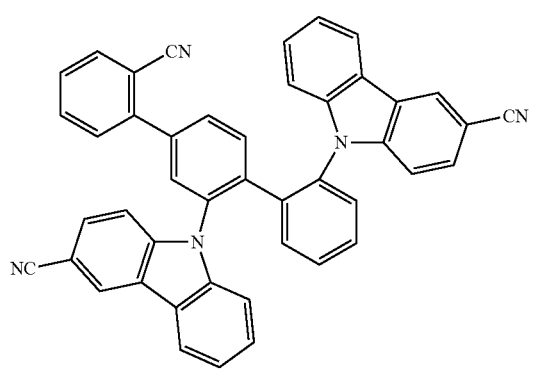
216
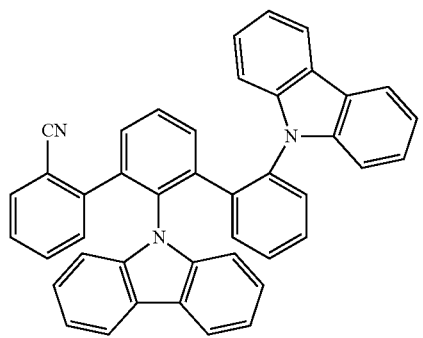
72
-continued
217
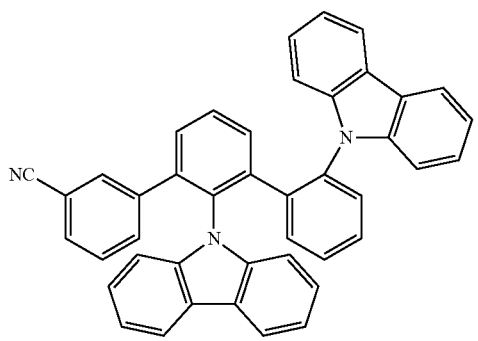
218
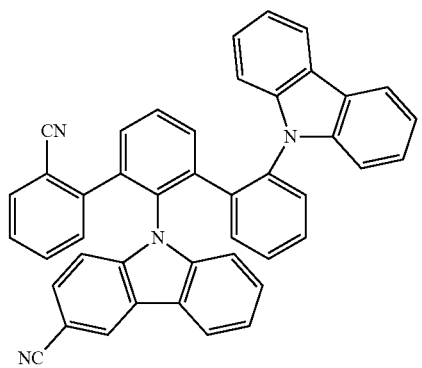
219
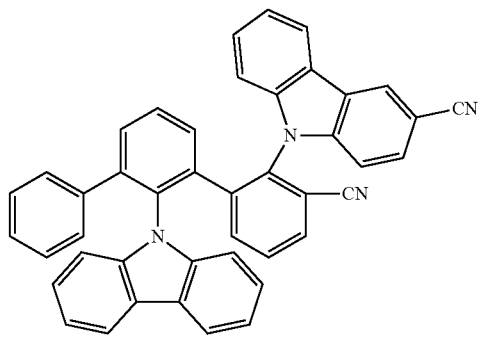
220
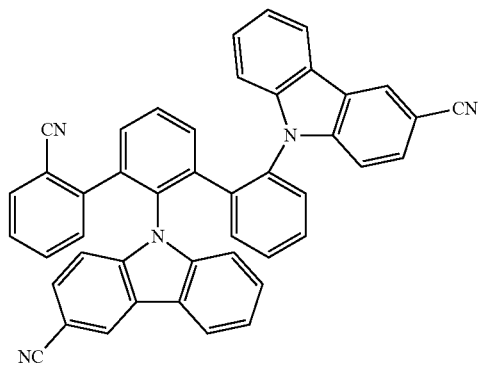

221
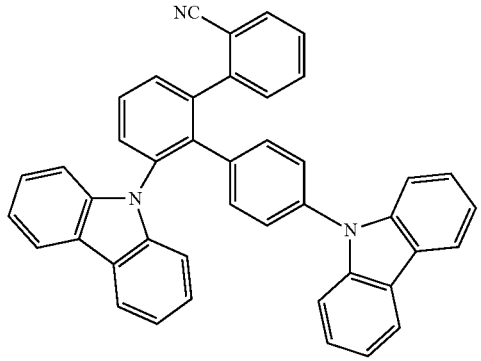
222
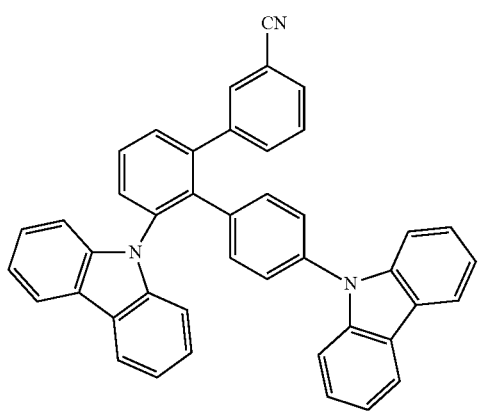
223
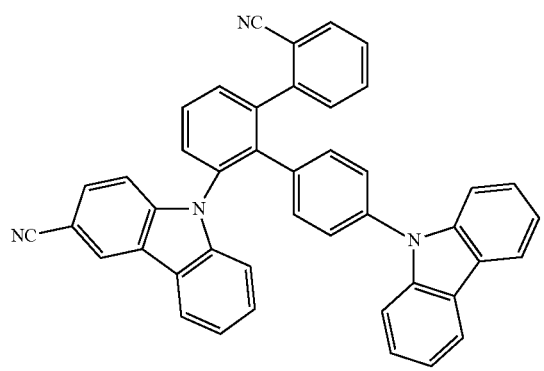
224
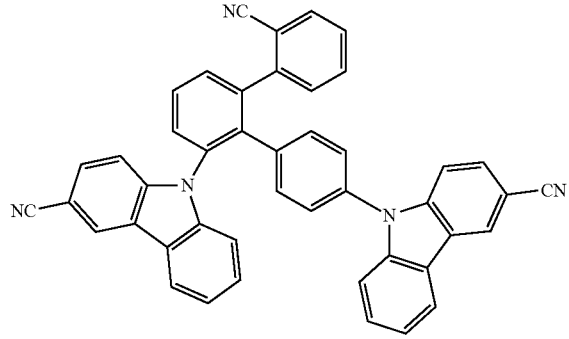
225
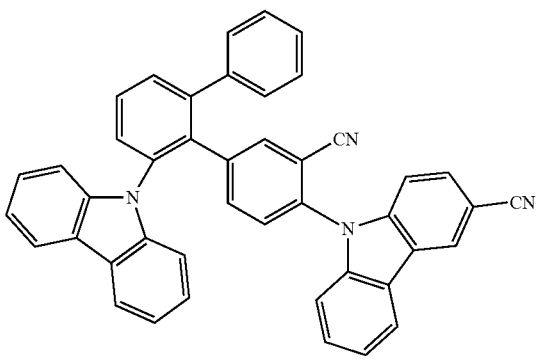
226
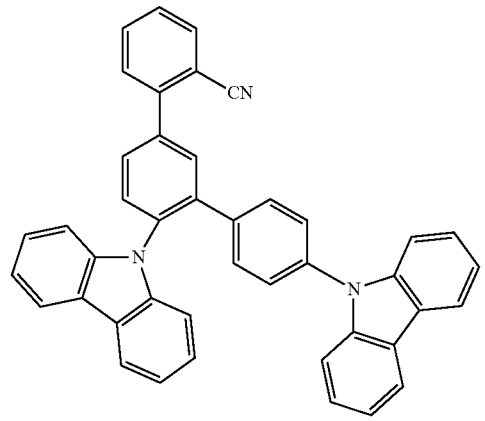
227
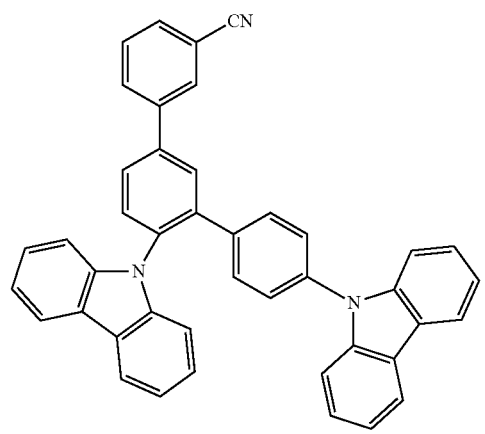

228
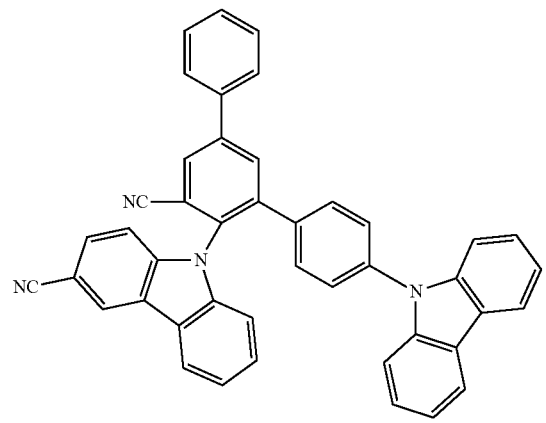
229
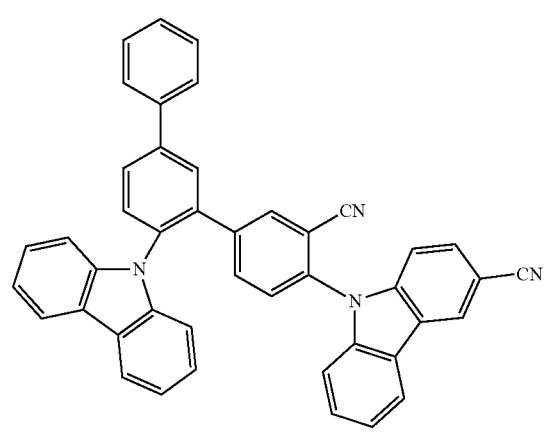
230
231
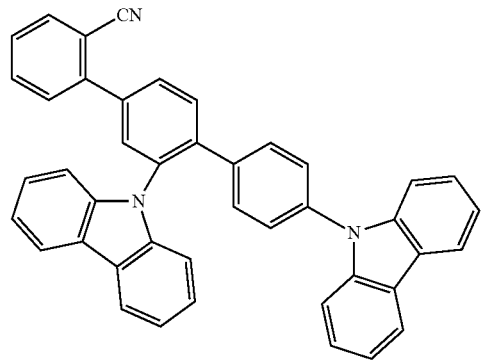
232
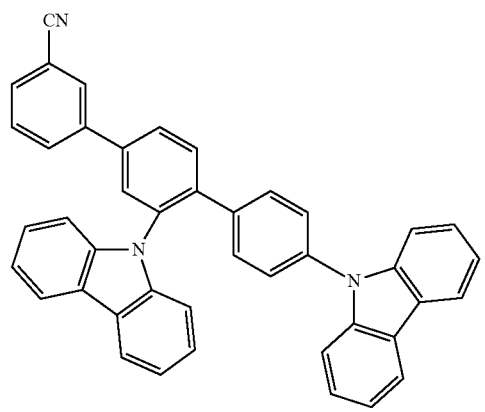
233
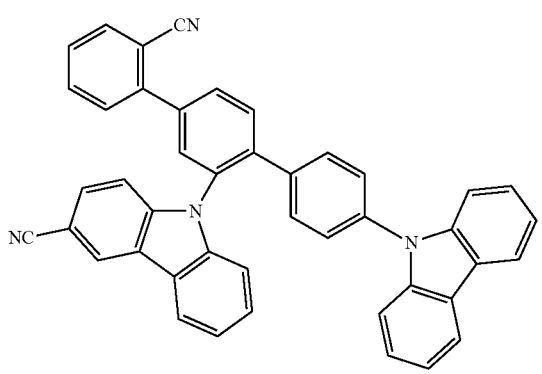
234
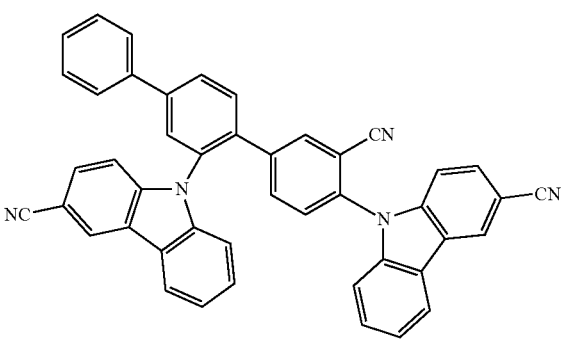

235
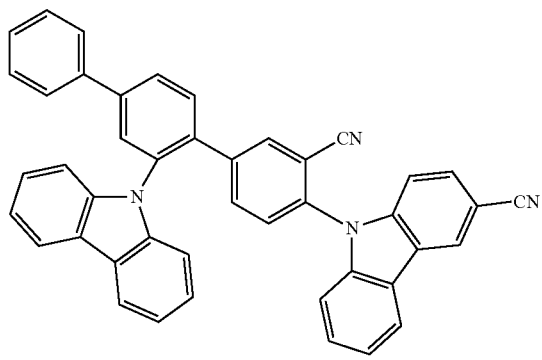
236
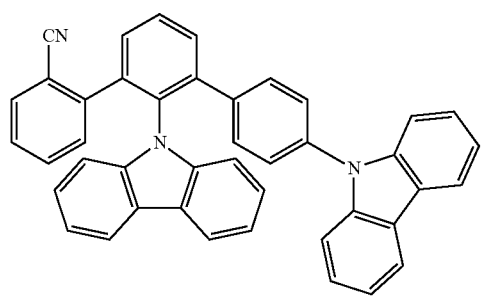
237
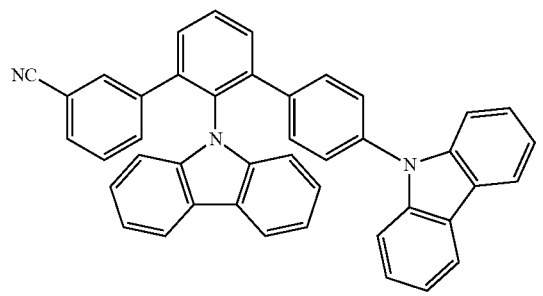
238
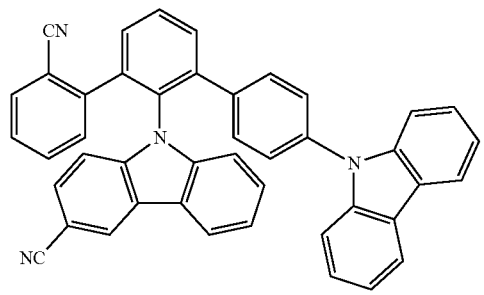
239
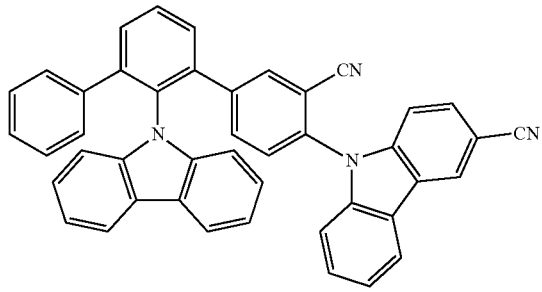
240
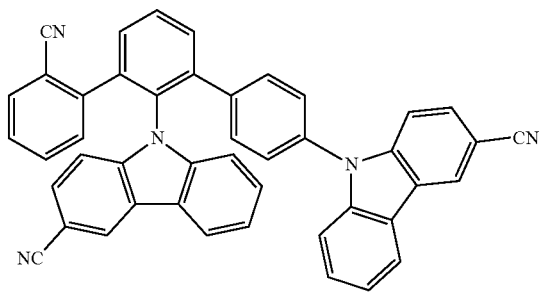
241
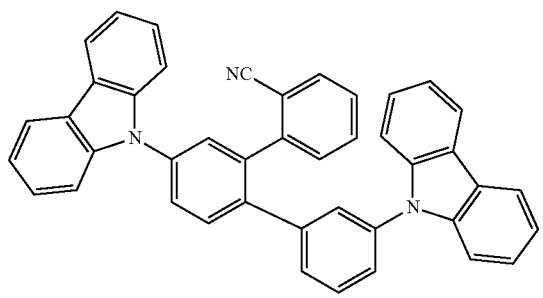
242
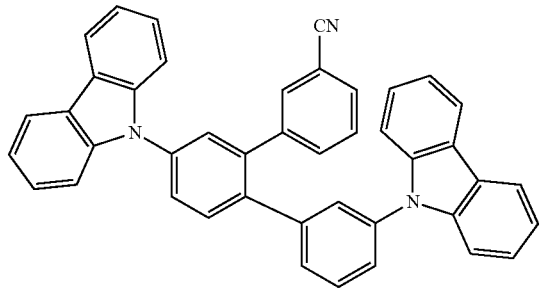
243
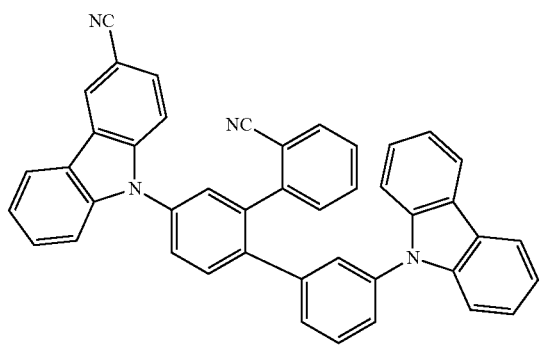

244
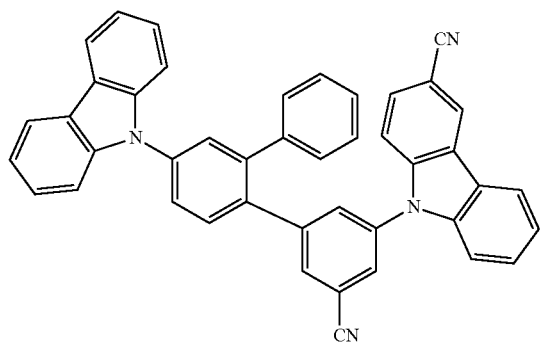
245
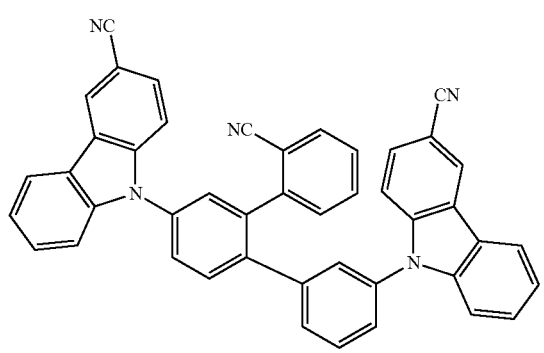
246
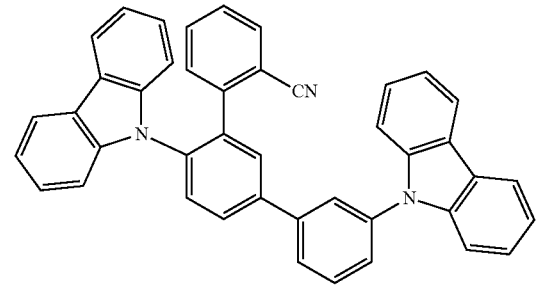
247
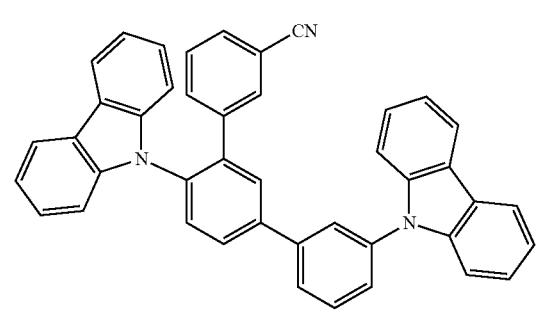
248
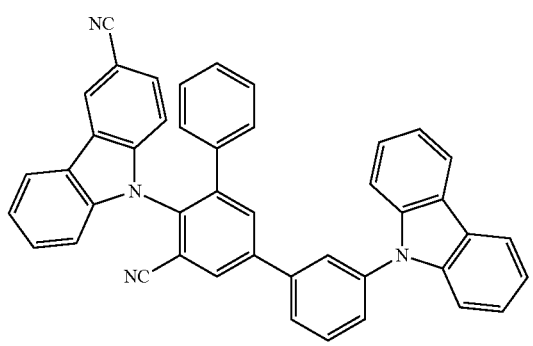
249
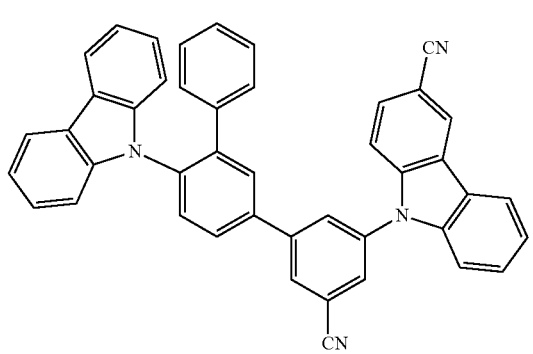
250
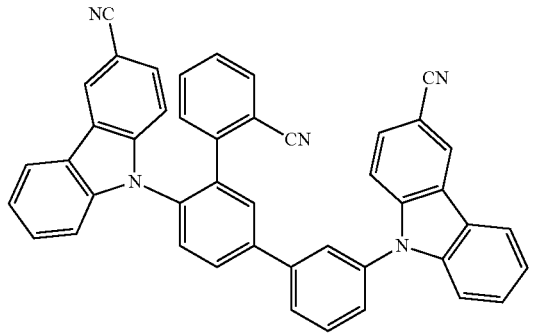
251
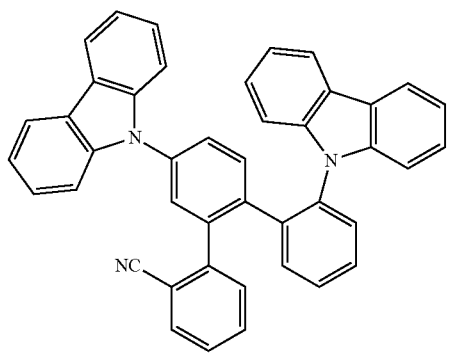

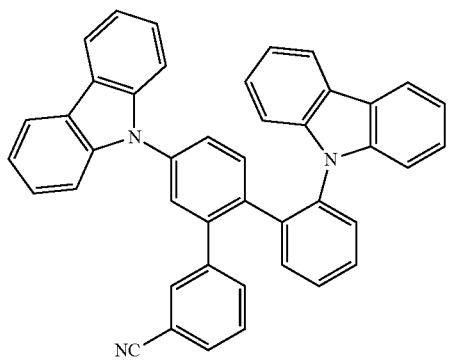
252
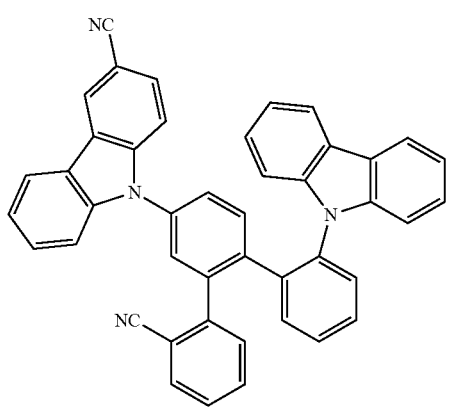
253
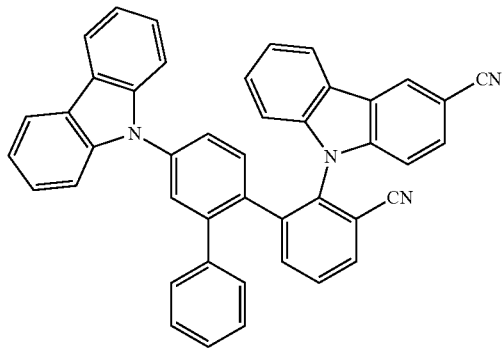
254
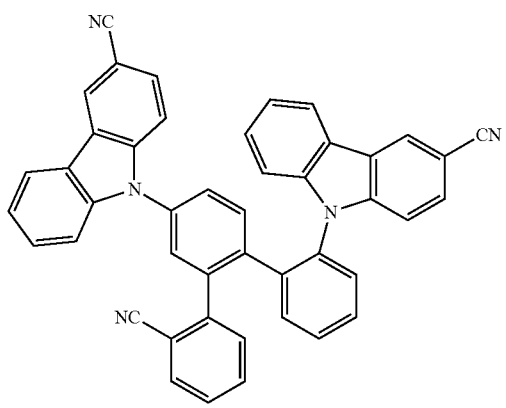
255
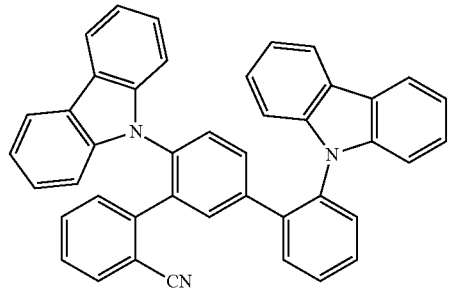
256
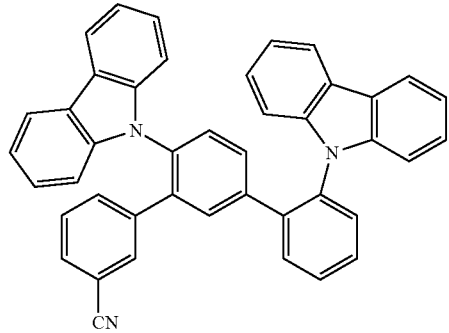
257
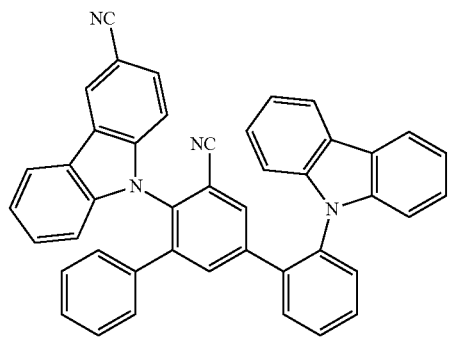
258
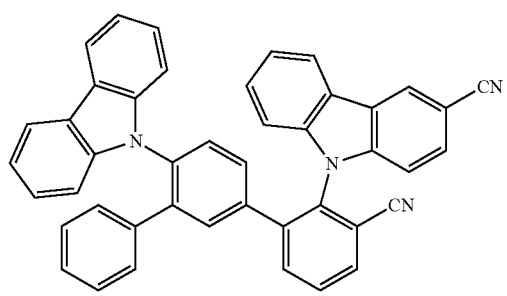
259

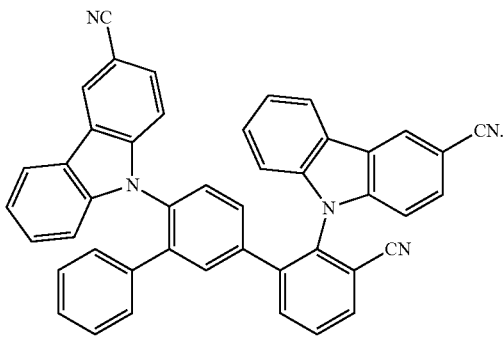

260

TABLE 1-continued

| Compound No. | HOMO (eV) | LUMO (eV) | T₁(eV) | S₁(eV) |
|---|---|---|---|---|
| 31 | −5.513 | −1.799 | 3.065 | 3.206 |
| 32 | −5.640 | −1.794 | 3.067 | 3.327 |
| 38 | −5.600 | −2.034 | 2.998 | 3.126 |
| 41 | −5.641 | −2.053 | 3.081 | 3.220 |
| 51 | −5.597 | −1.904 | 3.063 | 3.175 |
| 61 | −5.933 | −1.982 | 3.098 | 3.443 |
| 91 | −5.607 | −2.120 | 2.924 | 3.023 |
| 157 | −5.483 | −1.681 | 2.982 | 3.350 |
| 160 | −5.524 | −1.886 | 2.973 | 3.314 |
| A | −5.531 | −1.802 | 3.024 | 3.274 |
| B | −5.437 | −1.758 | 3.074 | 3.258 |
| C | −5.378 | −1.280 | 3.071 | 3.556 |

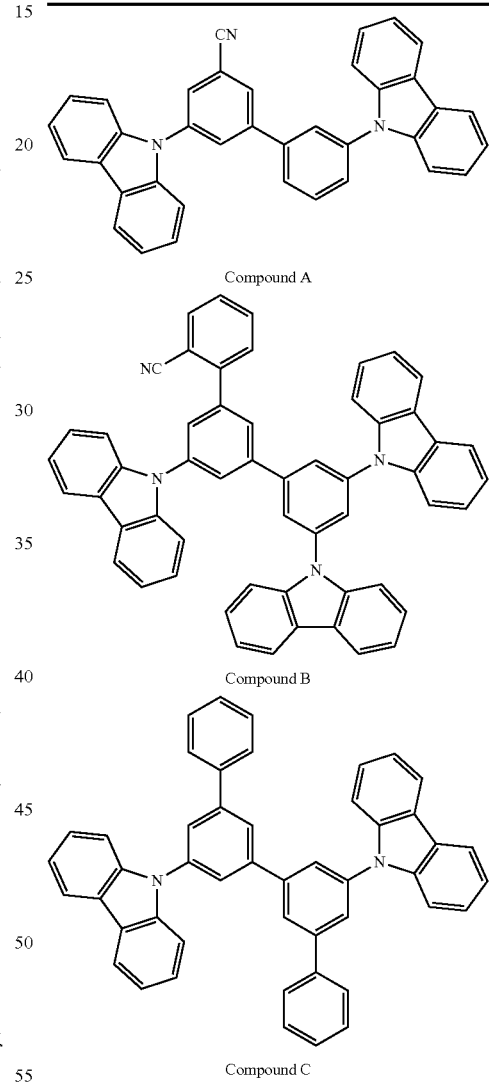

Compound A

Compound B

Compound C

In the condensed cyclic compound represented by Formula 1, $L_1$ may be selected from the group represented by Formula 4A, the group represented by Formula 4B, and the group represented by Formula 4C, and $L_2$ may be selected from the group represented by Formula 4D, the group represented by Formula 4E, and the group represented by Formula 4F, wherein a case in which $L_1$ is the group represented by Formula 4C and $L_2$ is the group represented by Formula 4F is excluded. That is, the group represented by *-$L_1$-$L_2$-*' in the condensed cyclic compound represented by Formula 1 necessarily includes a terphenylene group. In this regard, $Ar_1$ and $Ar_2$ necessarily include at least one ortho- or meta-connection, when respectively connected to $L_1$ and $L_2$, thereby providing a sufficiently high triple energy as to enable blue fluorescence. Excellent electron mobility effects of a terphenylene group may provide excellent charge transport characteristics.

The group represented by *-$L_1$-$L_2$-*' in Formula 1 may include one, two, three, or four cyano group(s), and the condensed cyclic compound represented by Formula 1 may include one, two, three, or four cyano group(s). Therefore, the condensed cyclic compound may have a relatively low lowest unoccupied molecular orbital (LUMO) energy level (that is, a relatively great LUMO energy absolute value), and excellent electron mobility characteristics. Due to these features, the condensed cyclic compound may have electric characteristics that are suitable for use as a material for forming an organic light-emitting device, for example, a material for forming a host in an emission layer. Accordingly, an organic light-emitting device including the condensed cyclic compound may have high efficiency and long lifespan.

The highest occupied molecular orbital (HOMO), LUMO, triplet ($T_1$) energy levels, and singlet ($S_1$) energy levels of Compounds 1 to 31 and Compounds A to C were evaluated by using a DFT method of Gaussian program in which structural optimizing is executed at the level of B3LYP/6-31G(d,p).

TABLE 1

| Compound No. | HOMO (eV) | LUMO (eV) | T₁(eV) | S₁(eV) |
|---|---|---|---|---|
| 1 | −5.403 | −1.681 | 3.066 | 3.224 |
| 2 | −5.458 | −1.674 | 3.082 | 3.383 |
| 8 | −5.509 | −1.790 | 3.010 | 3.260 |
| 11 | −5.514 | −1.897 | 2.990 | 3.119 |
| 12 | −5.668 | −1.948 | 2.984 | 3.201 |
| 21 | −5.540 | −1.875 | 3.094 | 3.301 |
| 22 | −5.551 | −1.859 | 3.076 | 3.307 |

Referring to Table 1, it was confirmed that the condensed cyclic compound represented by Formula 1 has excellent electric characteristics, for example, a high $T_1$ energy level.

A method of synthesizing the condensed cyclic compound represented by Formula 1 may be understood by referring to Synthesis Examples below.

As described above, the condensed cyclic compound represented by Formula 1 is suitable for an organic layer of an organic light-emitting device, for example, a host or emitter (for example, TADF emitter) of an emission layer in the organic layer.

Accordingly, another aspect of embodiments of the present disclosure provides an organic light-emitting device including:

a first electrode;

a second electrode; and an organic layer disposed between the first electrode and the second electrode, wherein the organic layer includes an emission layer, and wherein the organic layer includes at least one of the condensed cyclic compounds represented by Formula 1.

The organic light-emitting device may have, due to the inclusion of the organic layer including the condensed cyclic compound represented by Formula 1, low driving voltage, high efficiency, high brightness, high quantum emission efficiency, and a long lifespan.

For example, the condensed cyclic compound represented by Formula 1 may be included in the emission layer.

In an embodiment, the condensed cyclic compound represented by Formula 1 may be included in the emission layer, and the condensed cyclic compound represented by Formula 1 may be a delayed fluorescent material.

In an embodiment, the emission layer may include a host and a dopant (an amount of the host is greater than an amount of the dopant), and the host may include the condensed cyclic compound represented by Formula 1. The condensed cyclic compound acting as the host may transfer energy to the dopant based on a delayed fluorescent emission mechanism. The dopant may include at least one selected from a fluorescent dopant and a phosphorescent dopant. The dopant may be selected from any known dopants. The host may further include any host selected from known hosts.

In one or more embodiments, the emission layer may include a host and a dopant (an amount of the host is greater than an amount of the dopant), and the dopant may include the condensed cyclic compound represented by Formula 1. The condensed cyclic compound acting as the dopant may emit delayered fluorescence to the dopant based on a delayed fluorescent emission mechanism. The host may be selected from known dopants.

The emission layer may emit red, green, or blue light.

In an embodiment, the emission layer may be a blue emission layer including a phosphorescent dopant, but embodiments of the present disclosure are not limited thereto.

In an embodiment, the condensed cyclic compound represented by Formula 1 may be included in an electron transport region constituting the organic light-emitting device.

For example, the electron transport region of the organic light-emitting device may include at least one selected from a hole blocking layer and an electron transport layer, and at least one selected from an electron blocking layer and an electron transport layer may include the condensed cyclic compound represented by Formula 1.

In an embodiment, the electron transport region of the organic light-emitting device may include a hole blocking layer that includes the condensed cyclic compound represented by Formula 1. The hole blocking layer may directly contact the emission layer.

The expression that "(an organic layer) includes at least one of the condensed cyclic compounds" as used herein may include a case in which "(an organic layer) includes identical condensed cyclic compounds represented by Formula 1" and a case in which "(an organic layer) includes two or more different condensed cyclic compounds represented by Formula 1."

For example, the organic layer may include, as the condensed cyclic compound, only Compound 1. In this regard, Compound 1 may be included in an emission layer of the organic light-emitting device. In one or more embodiments, the organic layer may include, as the condensed cyclic compound, Compound 1 and Compound 2. In this regard, Compound 1 and Compound 2 may be included in either an identical layer (for example, Compound 1 and Compound 2 all may be included in an emission layer), or different layers.

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region may include at least one selected from a hole injection layer, a hole transport layer, and an electron blocking layer, and ii) an electron transport region that is disposed between the emission layer and the second electrode, wherein the electron transport region may include at least one selected from a hole blocking layer, an electron transport layer, and an electron injection layer.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), potassium (Ca), magnesium-indium (Mg—In), or magnesium-silver (Mg—Ag) may be used as the material for forming the first electrode.

The first electrode 11 may have a single-layered structure or a multi-layered structure including two or more layers.

For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (A/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

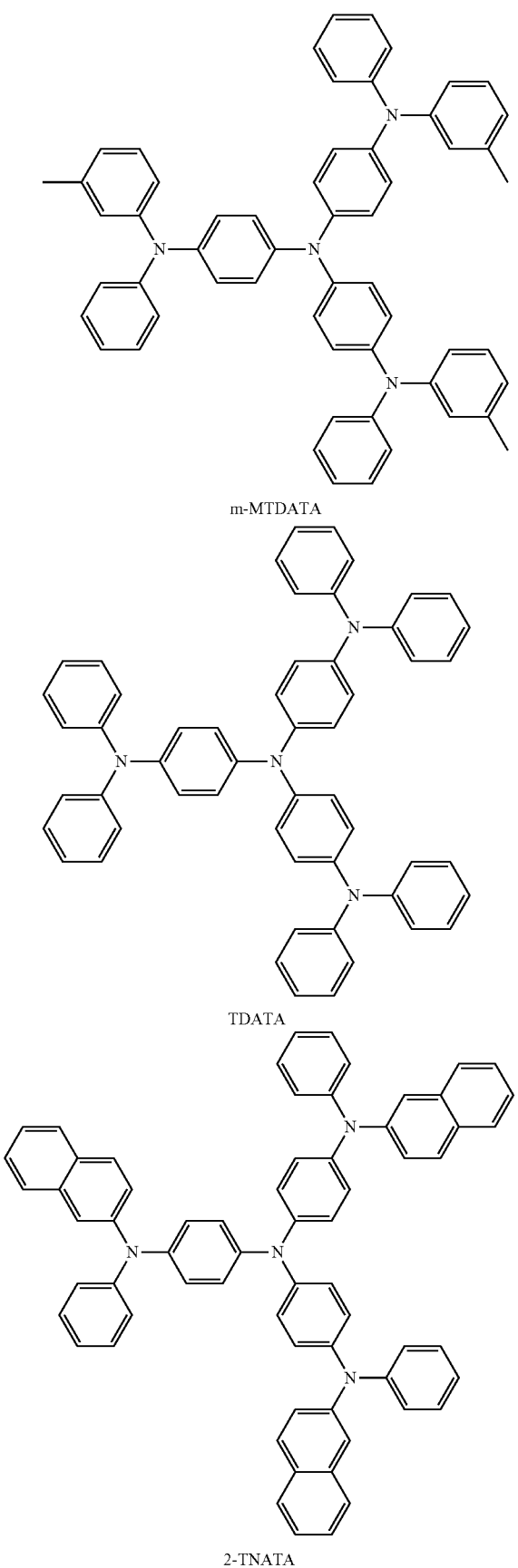

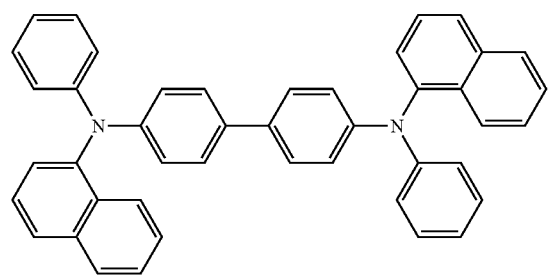
NPB
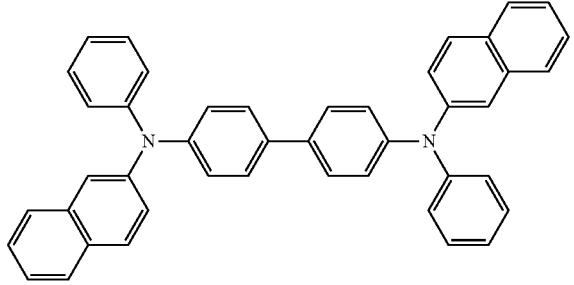
β-NPB
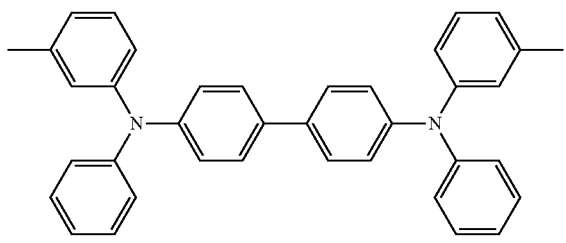
TPD
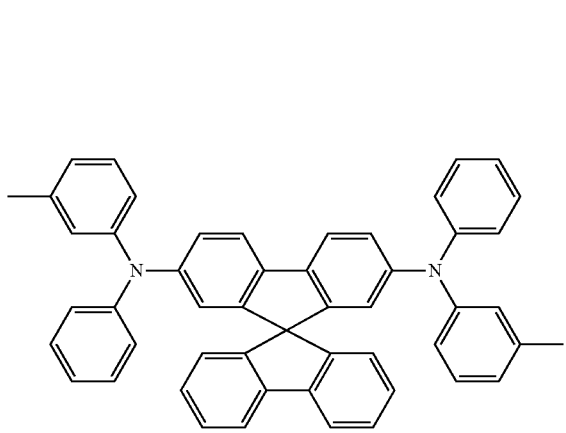
Spiro-TPD
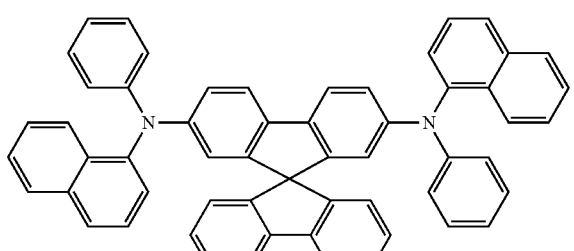
Spiro-NPB
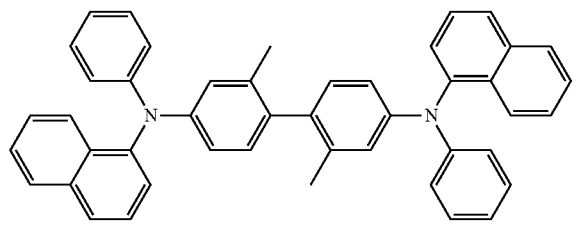
methylated NPB
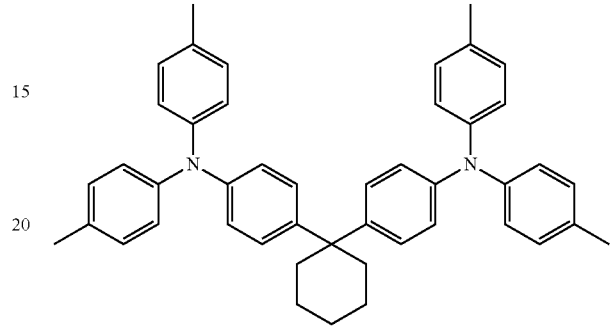
TAPC
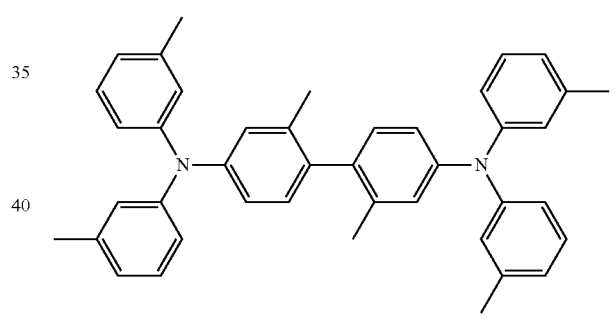
HMTPD
Formula 201
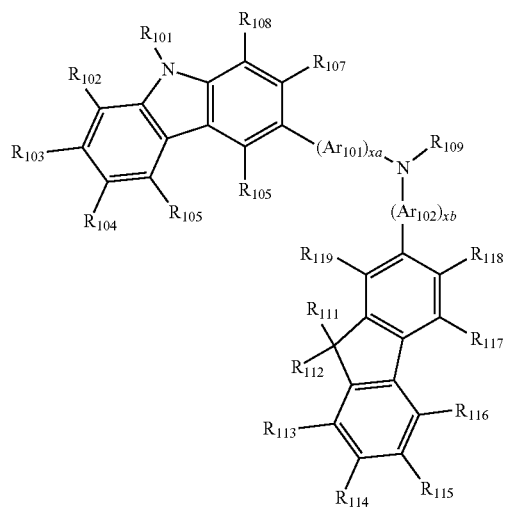

Formula 202

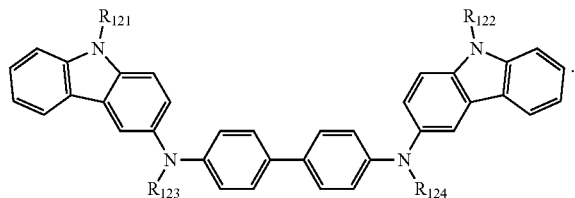

Ar₁₀₁ and Ar₁₀₂ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or 0, 1, or 2. For example, xa is 1 and xb is 0, but xa and xb are not limited thereto.

$R_{101}$ to $R_{108}$, $R_{111}$ to $R_{110}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

Formula 201A

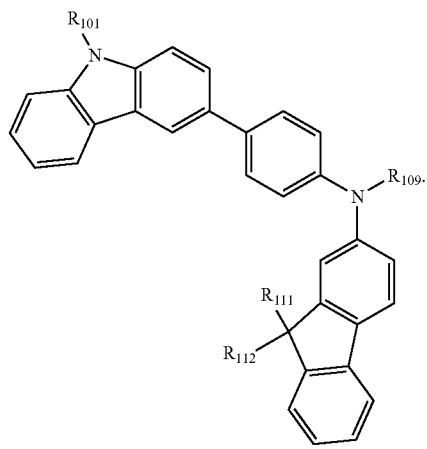

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto:

HT1
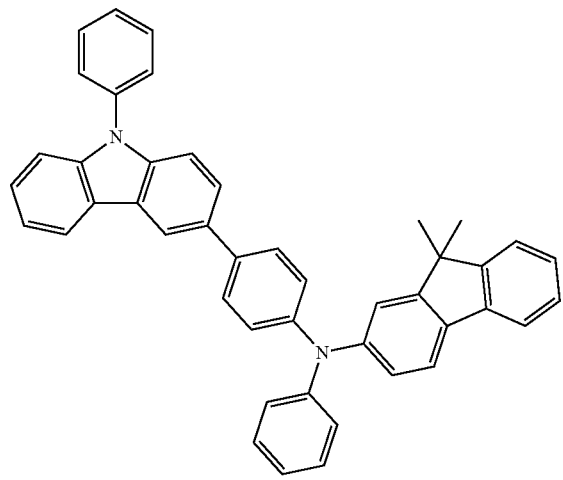
HT3
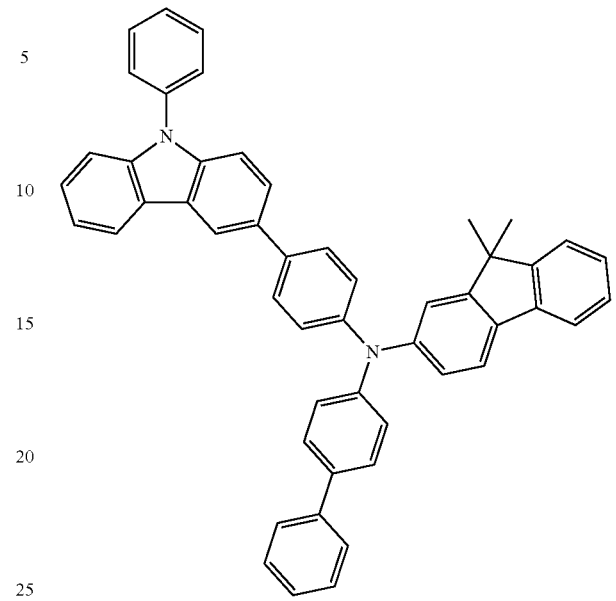
HT2
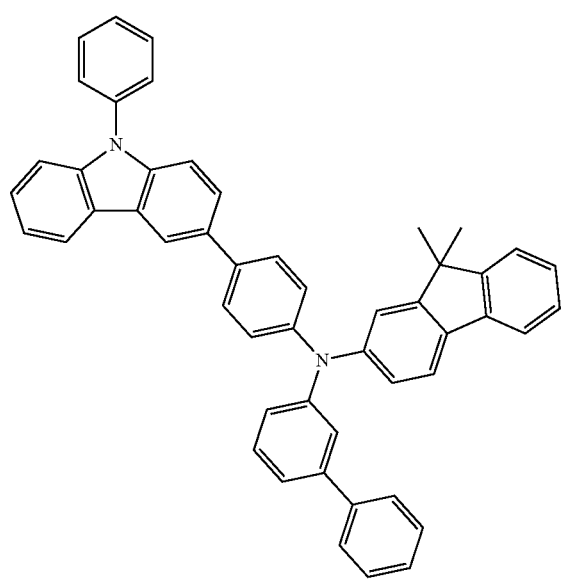
HT4
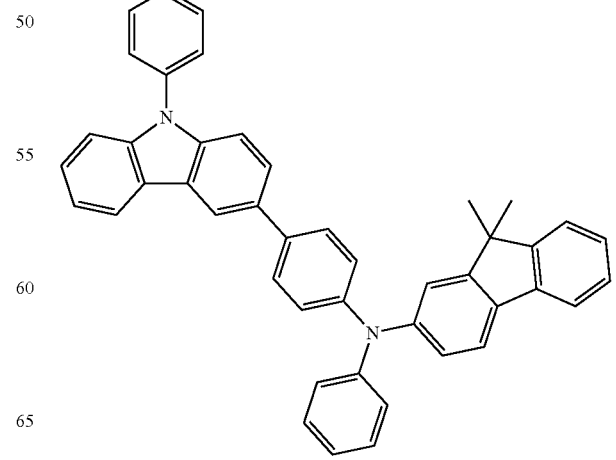

HT5
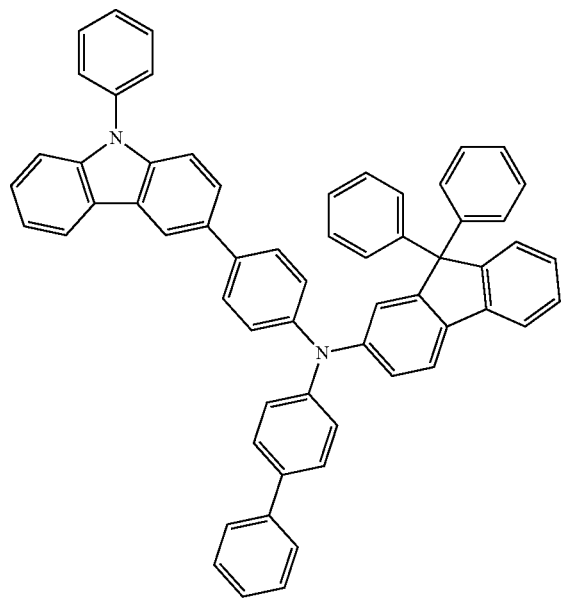
HT6
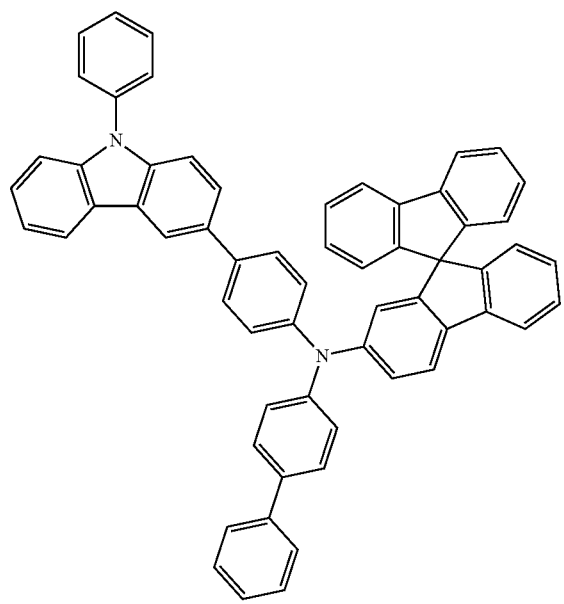
HT7
HT8
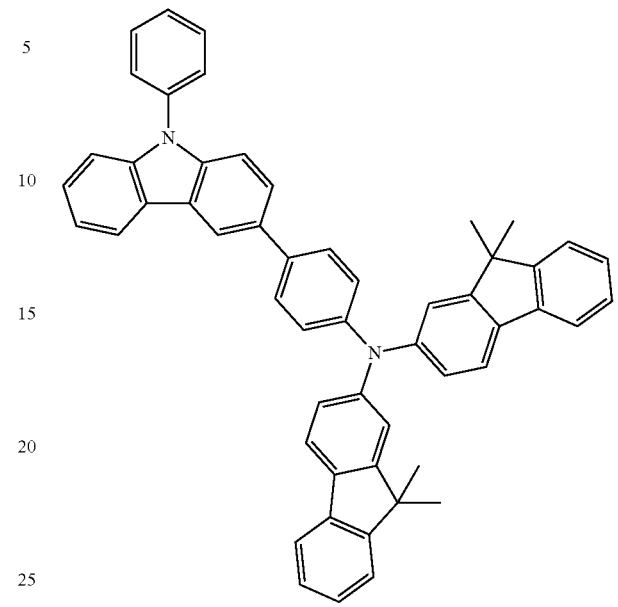
HT9
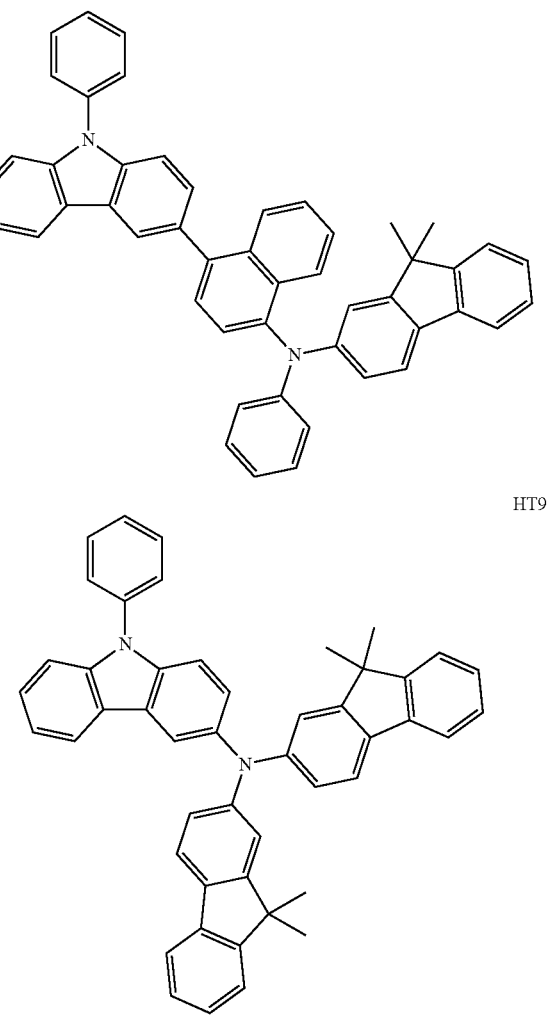

HT10
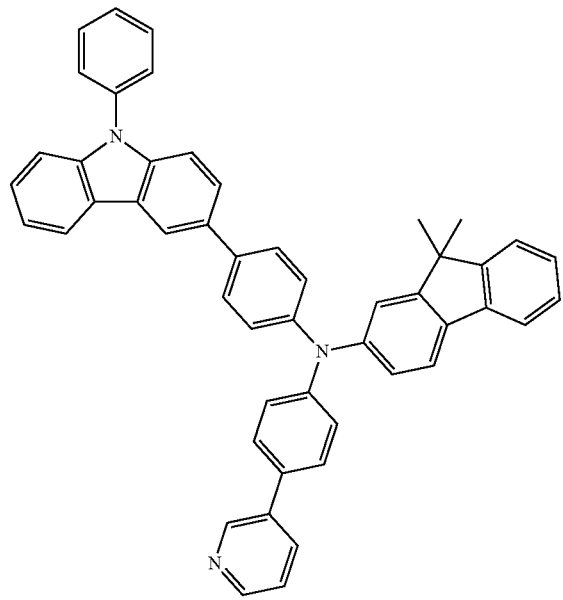
HT11
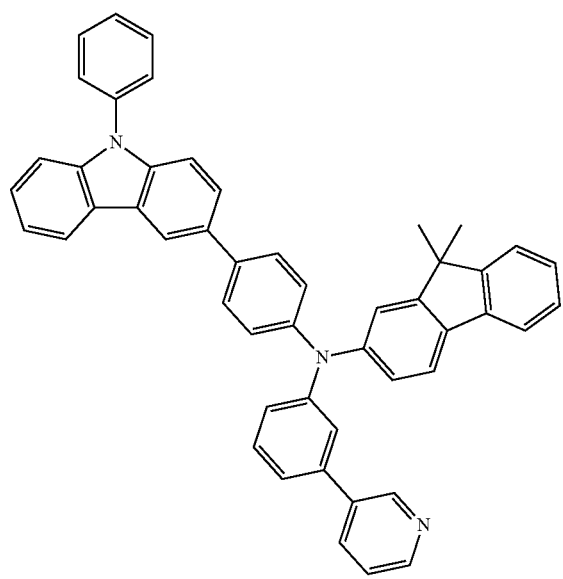
HT12
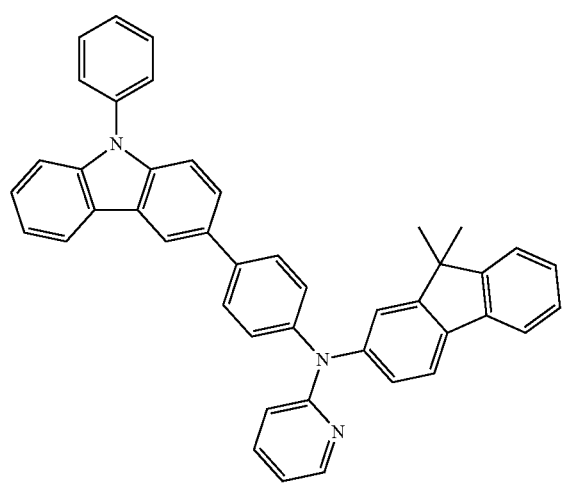
HT13
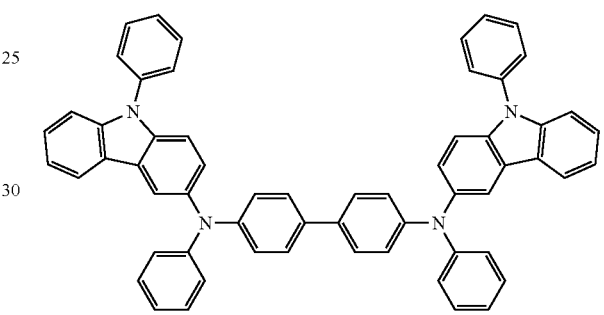
HT14
HT15
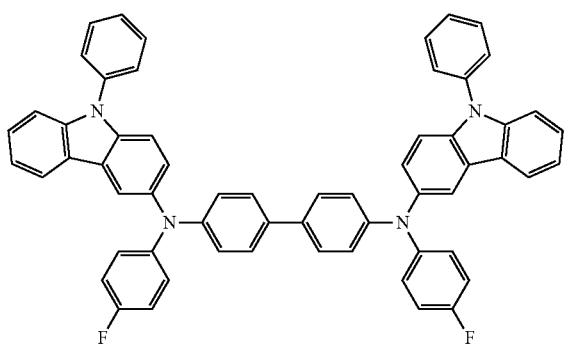

HT16

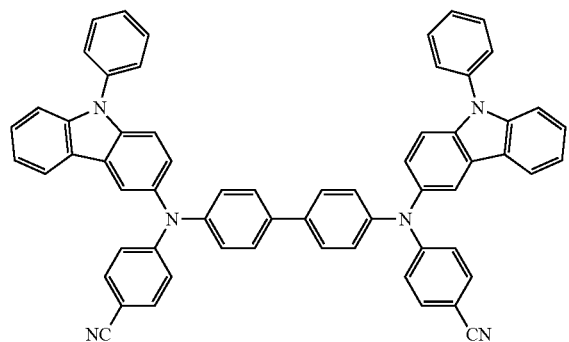

HT17

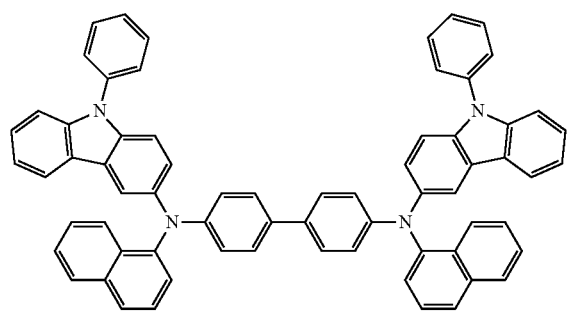

HT18

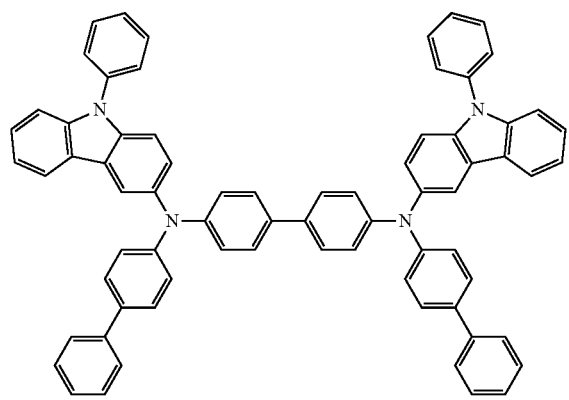

HT19

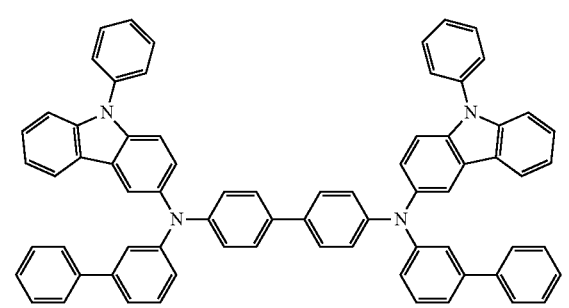

HT20

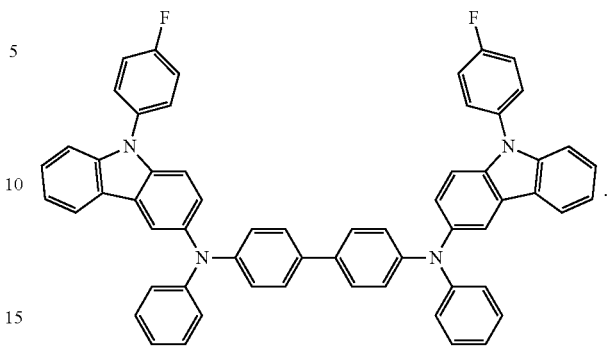

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or HP-1, but are not limited thereto.

Compound HT-D1

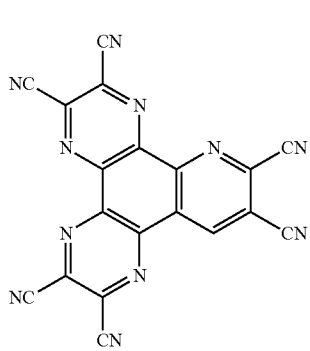

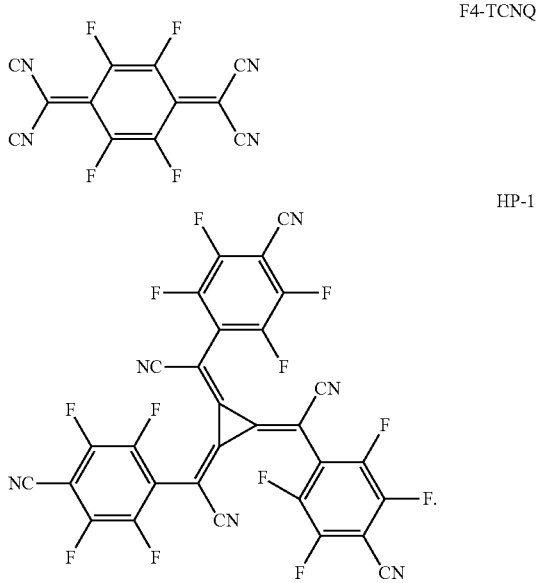

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary depending on the material that is used to form the emission layer.

The electron transport region may further include an electron blocking layer. The electron blocking layer may include, for example, mCP, but a material therefor is not limited thereto.

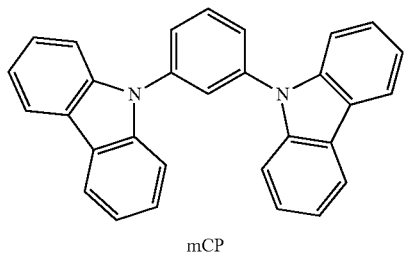 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. In one or more embodiments, due to a stack structure including a red emission layer, a green emission layer, and/or a blue emission layer, the emission layer may emit white light.

The emission layer may include the condensed cyclic compound represented by Formula 1. For example, the emission layer may include the compound represented by Formula 1 alone. In one or more embodiment, the emission layer may include a host and a dopant, and the host may include the condensed cyclic compound represented by Formula 1. In one or more embodiment, the emission layer may include a host and a dopant, and the dopant may include the condensed cyclic compound represented by Formula 1.

In one or more embodiment, the dopant in the emission layer may be a phosphorescent dopant, and the phosphorescent dopant may include an organometallic compound represented by Formula 81 below:

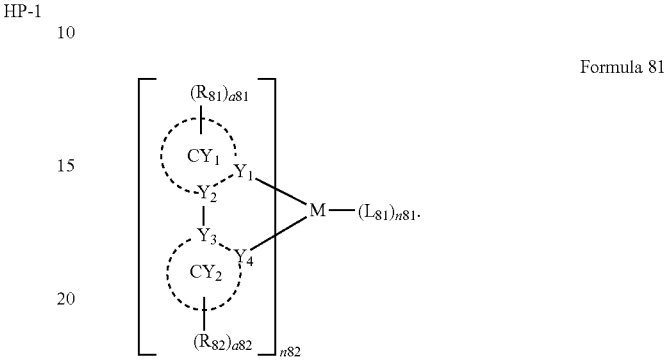

Formula 81

In Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may each independently be selected from carbon (C) and nitrogen (N);

$Y_1$ and $Y_2$ may be linked via a single bond or a double bond, and $Y_3$ and $Y_4$ are linked via a single bond or a double bond;

$CY_1$ and $CY_2$ may each independently be selected from a benzene group, a naphthalene group, a fluorene group, a spiro-fluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzooxazole group, a triazole group, a tetrazole group, an oxadiazole group, a triazine group, a dibenzofuran group, and a dibenzothiophene group, and $CY_1$ and $CY_2$ are optionally linked through a single bond or an organic linking group;

$R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$), a81 and a82 may each independently be an integer selected from 1 to 5, n81 may be an integer selected from 0 to 4, n82 may be 1, 2, or 3, and L$_{81}$ may be a monovalent organic ligand, a divalent organic ligand, or a trivalent organic ligand.

R$_{81}$ and R$_{82}$ may be the same as described in connection with Riot

The phosphorescent dopant may include at least one selected from Compounds PD1 to PD78 and FIr$_6$, but embodiments of the present disclosure are not limited thereto:

PD1
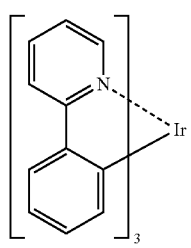

PD2
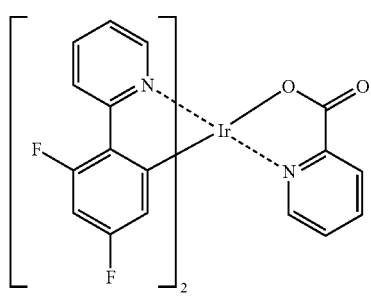

PD3
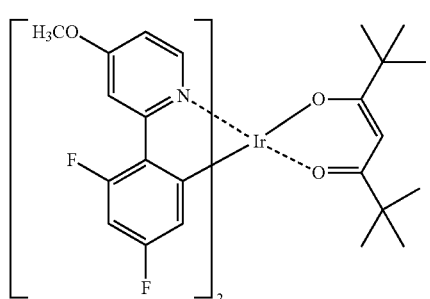

PD4
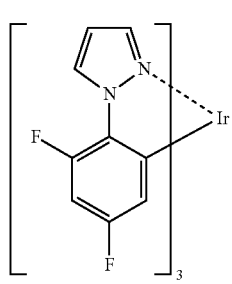

PD5
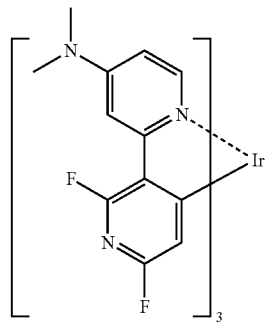

PD6
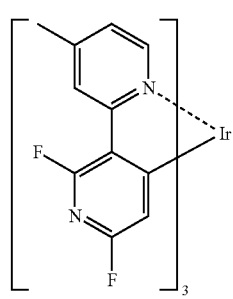

PD7
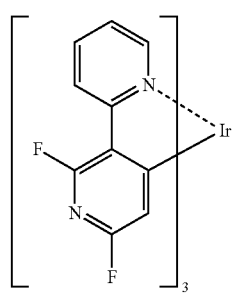

PD8
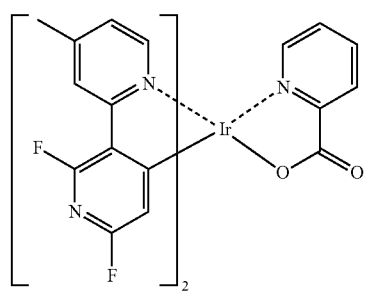

PD9
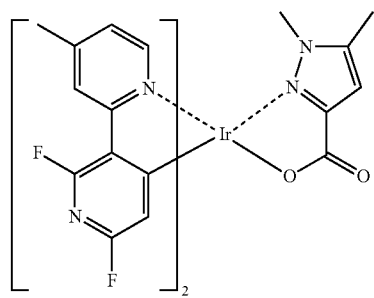

PD10
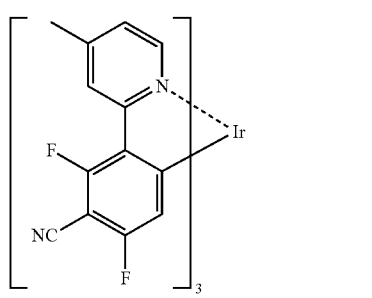
PD11
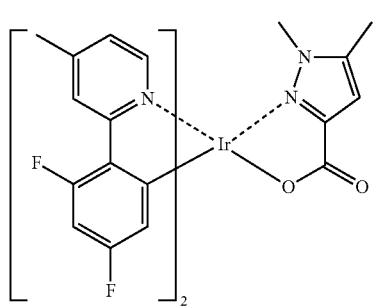
PD12
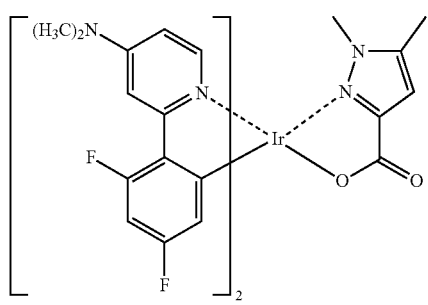
PD13
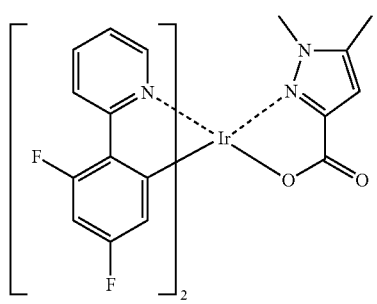
PD14
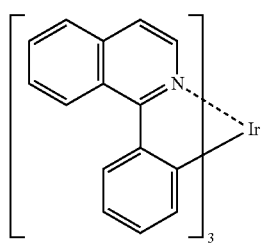
PD15
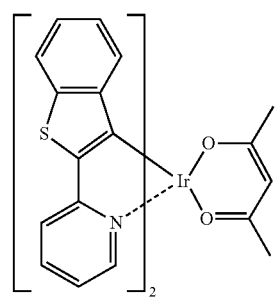
PD16
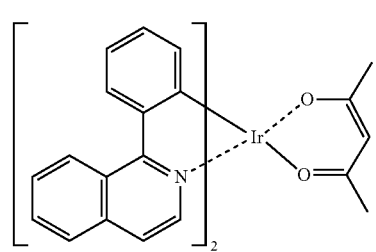
PD17
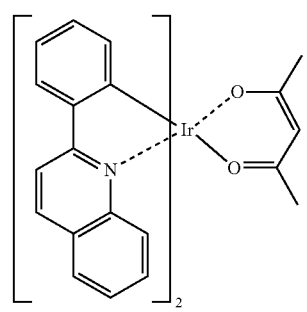
PD18
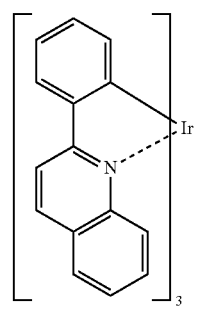
PD19
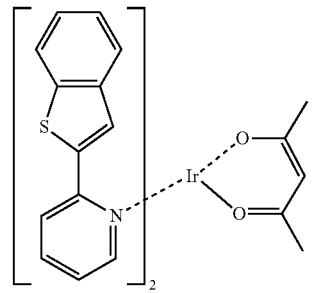

PD20
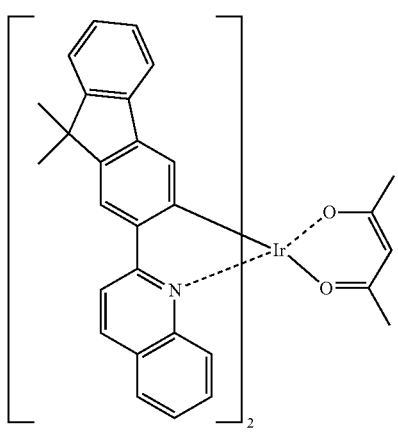
PD21
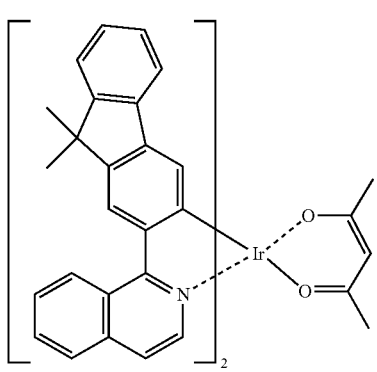
PD22
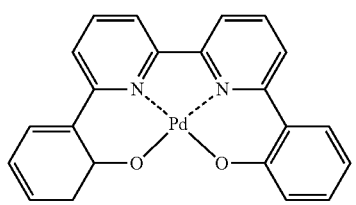
PD23
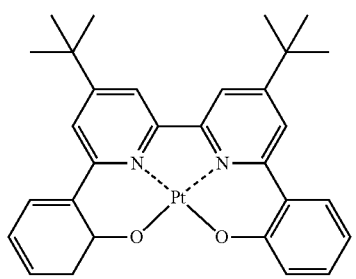
PD24
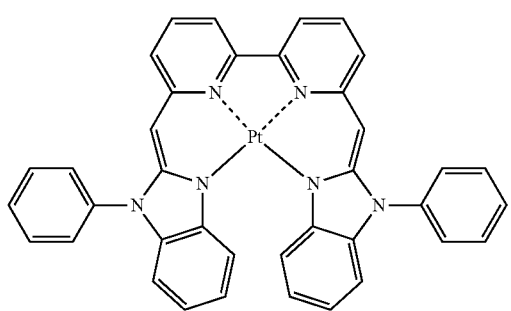
PD25
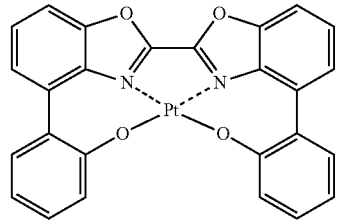
PD26
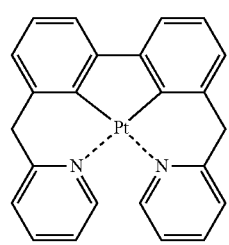
PD27
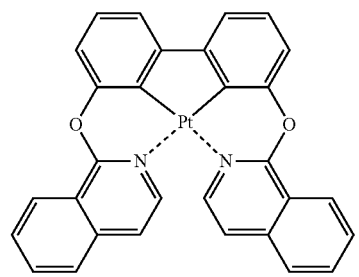
PD28
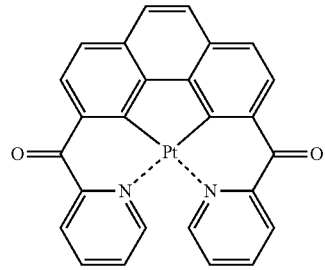
PD29
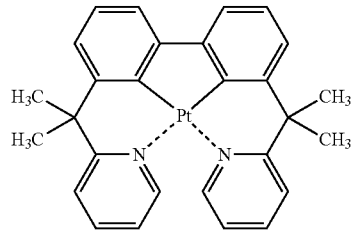
PD30
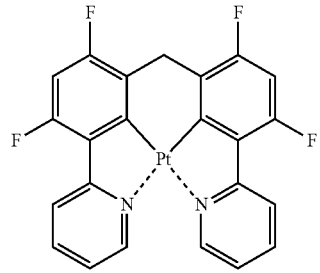

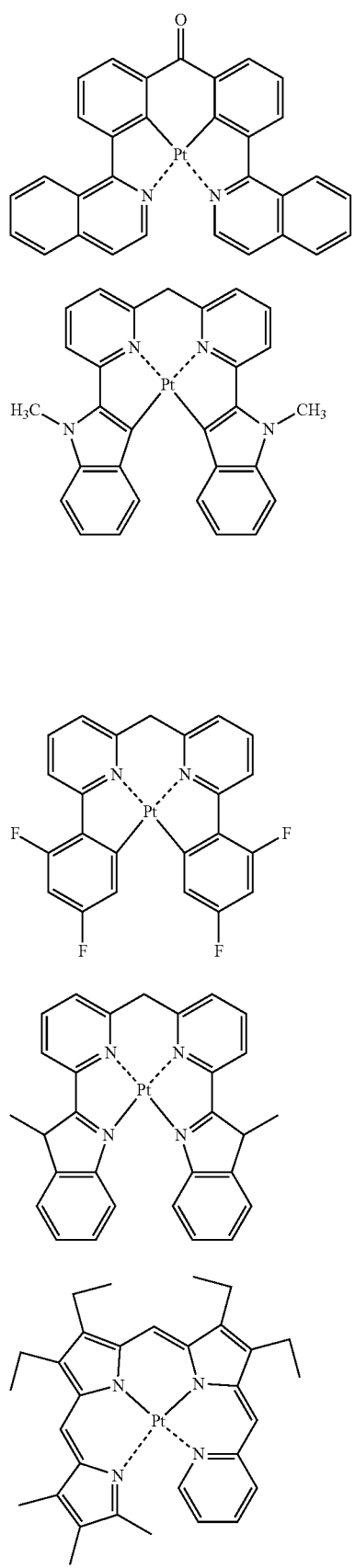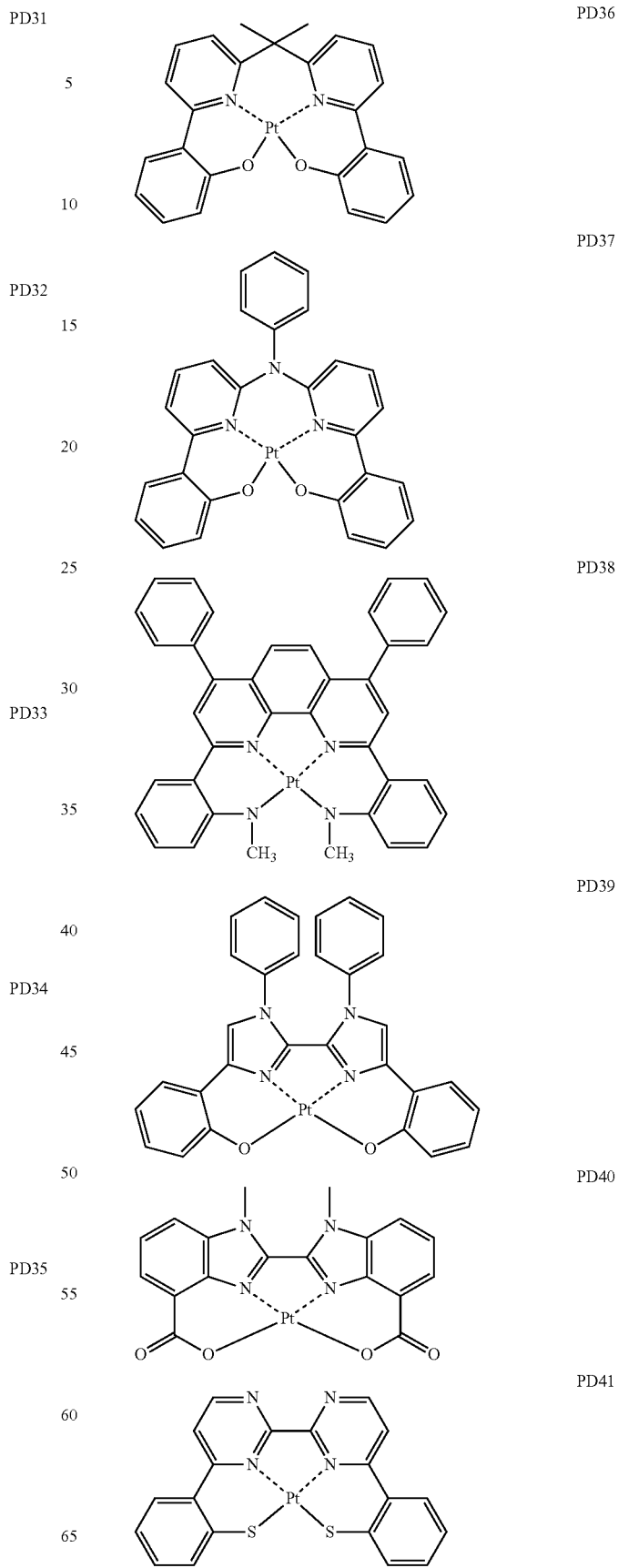

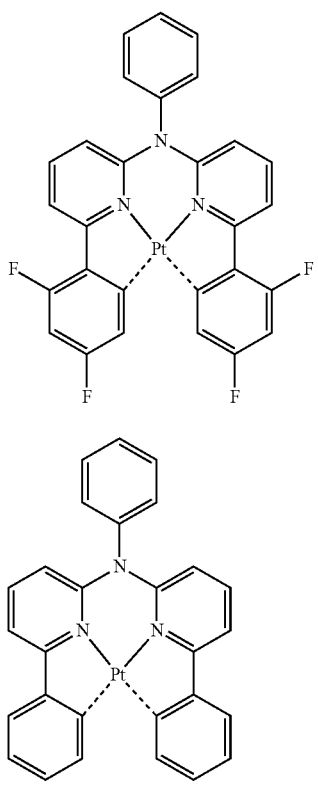
PD42
PD43
PD44
PD45
PD46
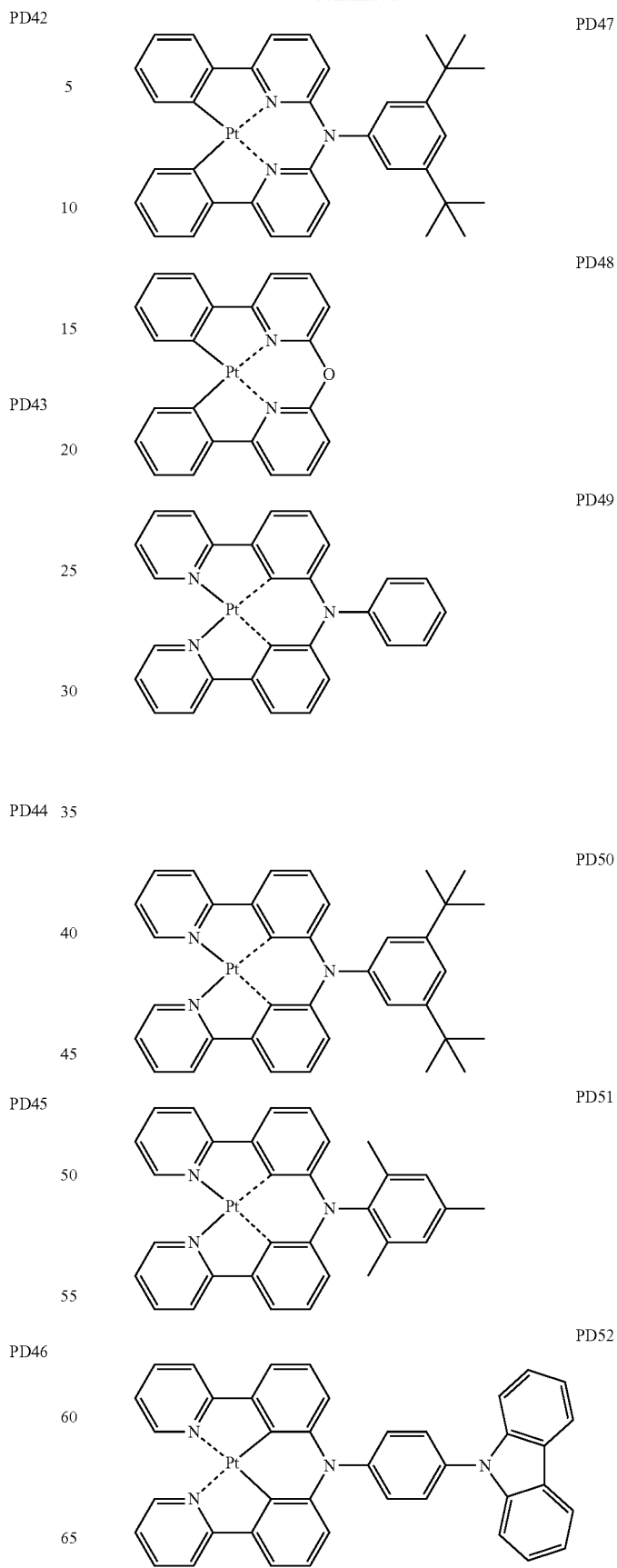
PD47
PD48
PD49
PD50
PD51
PD52

-continued
PD53
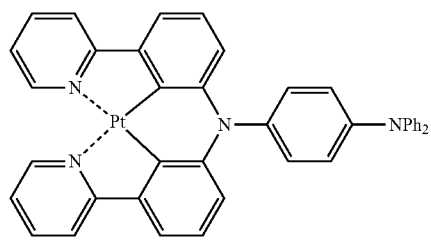
PD54
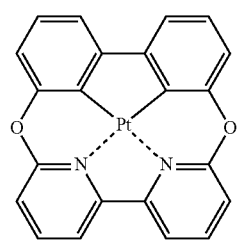
PD55
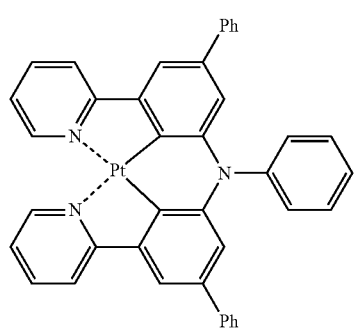
PD56
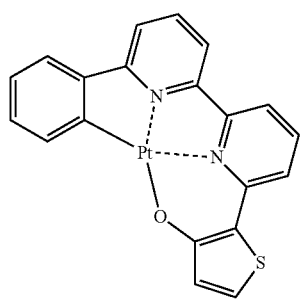
PD57
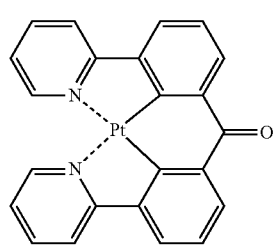
-continued
PD58
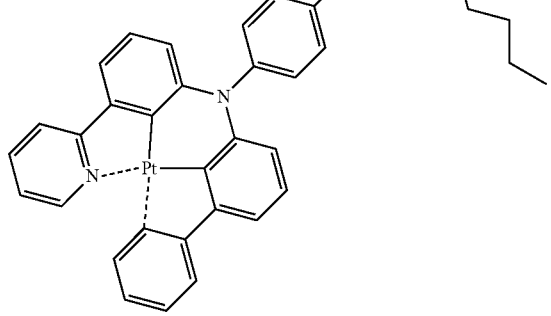
PD59
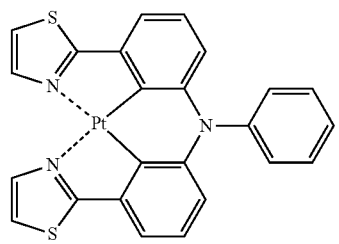
PD60
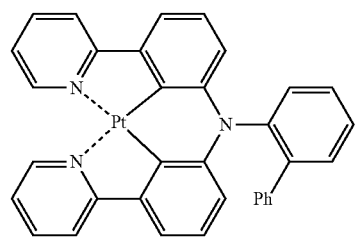
PD61
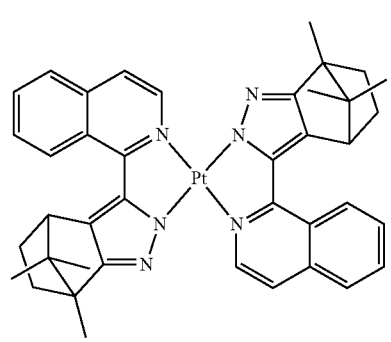
PD62
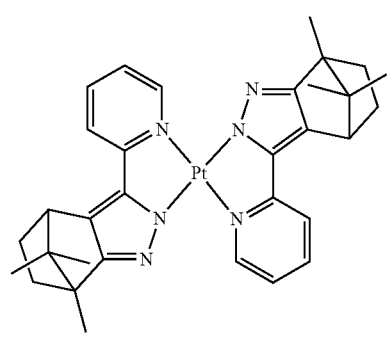

PD63 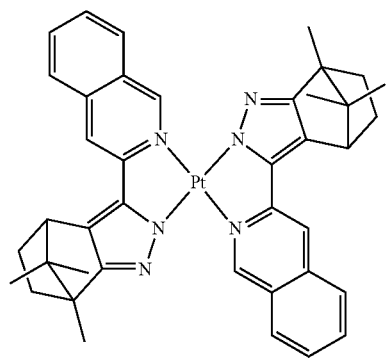
PD64 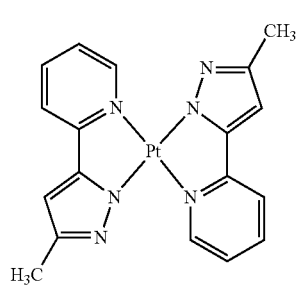
PD65 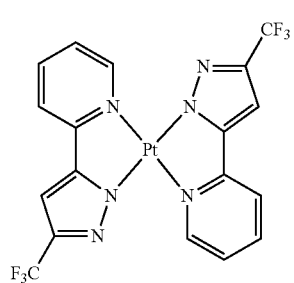
PD66 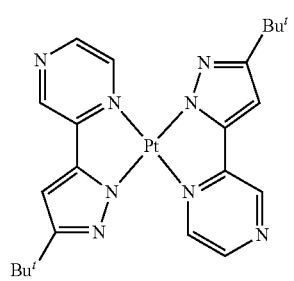
PD67 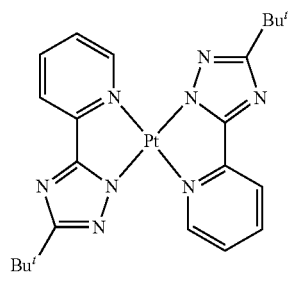
PD68 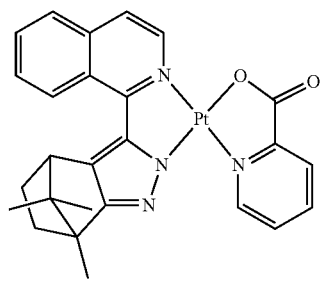
PD69 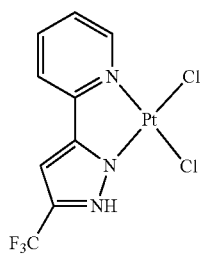
PD70 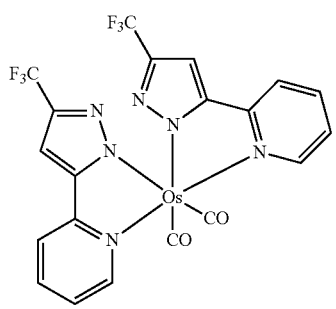
PD71 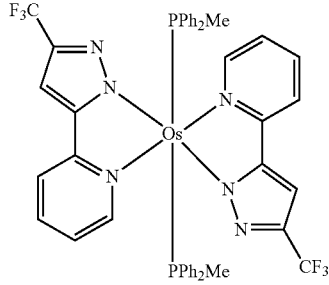
PD72 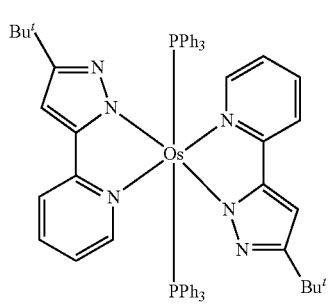

-continued

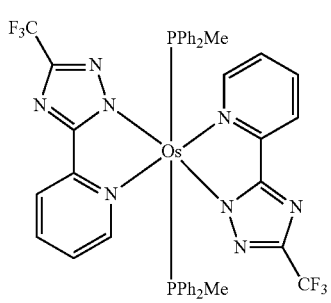
PD73

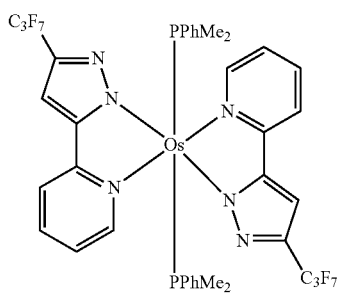
PD74

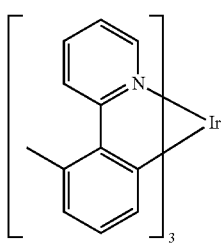
PD75

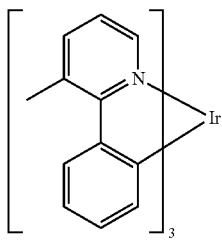
PD76

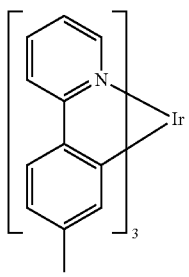
PD77

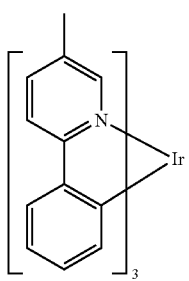
PD78

-continued

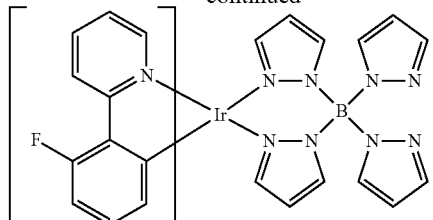
Flr6

In one or more embodiments, the phosphorescent dopant may include PtOEP:

PtOEP

When the emission layer includes a host and a dopant, an amount of the dopant may be in a range of about 0.01 to about 20 parts by weight based on about 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

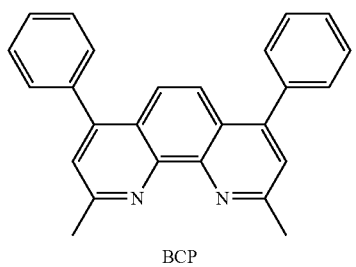

BCP

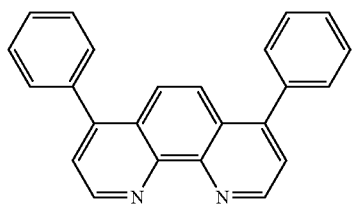

Bphen

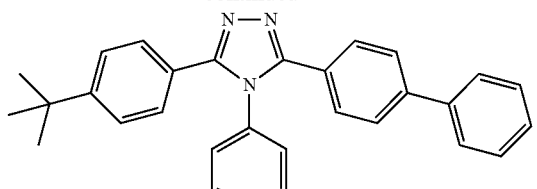

TAZ

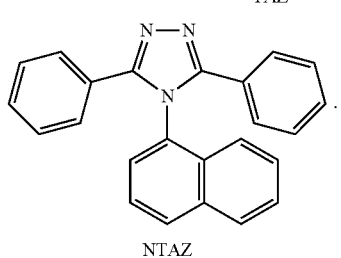

NTAZ

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq₃, BAlq, TAZ, and NTAZ:

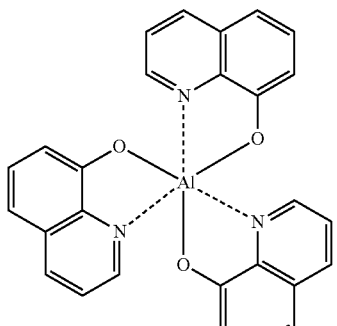

Alq₃

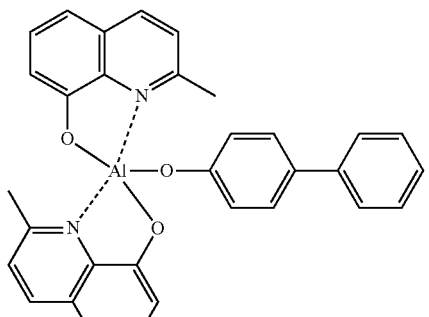

BAlq

In one or more embodiments, the electron transport layer may include at least one selected from Compounds ET1, ET2, and ET3, but embodiments are not limited thereto:

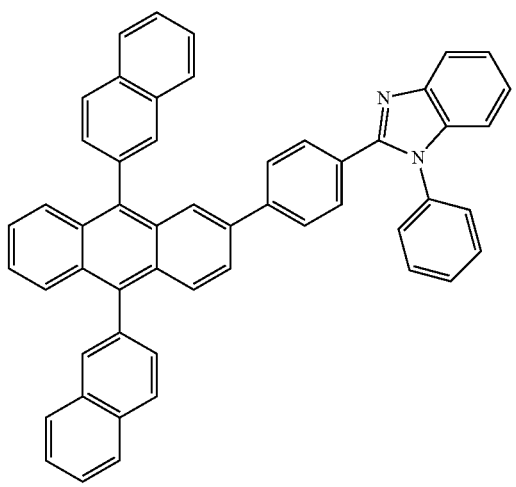

ET1

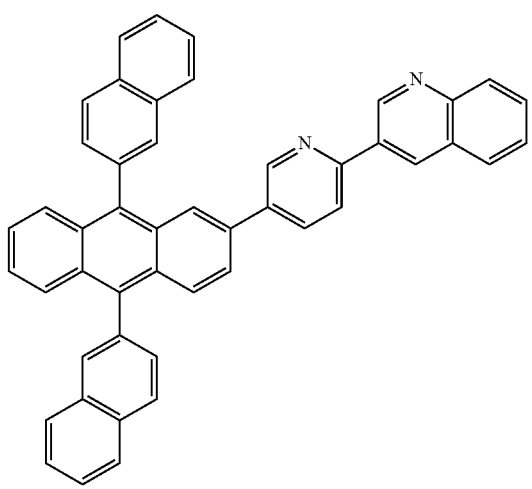

ET2

ET3

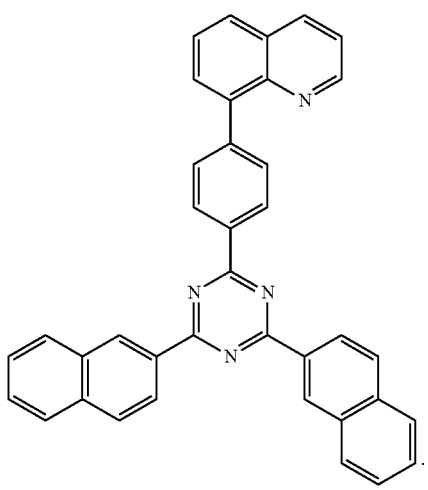

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

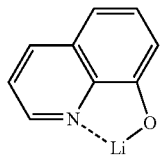

ET-D2

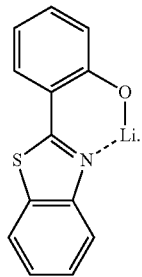

The electron transport region may include an electron injection layer (EIL) that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), potassium (Ca), magnesium-indium (Mg—In), or magnesium-silver (Mg—Ag) may be used as a material for forming the second electrode 19. In one or more embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{60}$ alkyl group" as used herein refers to a linear or branched saturated aliphatic hydrocarbon monovalent group having 1 to 60 carbon atoms. Non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by—$OA_{101}$ (wherein $A_{101}$ is the $C_1$-$C_{60}$ alkyl group). Non-limiting examples thereof include a methoxy group, an ethoxy group, and an iso-propyloxy (iso-propoxy) group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group. Examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms. Non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms. Non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof, and which is not aromatic. Non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Non-limiting examples of the $C_2$-$C_{10}$ heterocycloalkenyl group include a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, Si, and S as a ring-forming atom, and 1 to 60 carbon atoms. The term "$C_1$-$C_{60}$ heteroarylene group," as used herein refers to a divalent group having a heterocyclic aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group that has two or more rings condensed to each other, only carbon atoms (for example, the number of carbon atoms may be in a range of 8 to 60) as a ring-forming atom, and which is non-aromatic in the entire molecular structure. Non-limiting examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group that has two or more rings condensed to each other, has a heteroatom selected from N, O, P, Si, and S, other than carbon atoms (for example, the number of carbon atoms may be in a range of 2 to 60), as a ring-forming atom, and which is non-aromatic in the entire molecular structure. Non-limiting examples of the monovalent non-aromatic condensed heteropolycyclic group include a carbazolyl group. The term "divalent non-aromatic condensed heteropolycyclic group," used herein, refers to a divalent group having the same structure as the monovalent non-aromatic condensed heteropolycyclic group.

At least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group and a monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "a biphenyl group" as used herein refers to a monovalent group in which two benzenes are linked via a single bond.

The term "a terphenyl group" as used herein refers to a monovalent group in which three benzenes are linked via a single bond. The term "terphenylene group" as used herein refers to a divalent group having the same structure as that of the terphenyl group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1

Synthesis of Compound 1

Compound 1 was synthesized according to Reaction Scheme 1:

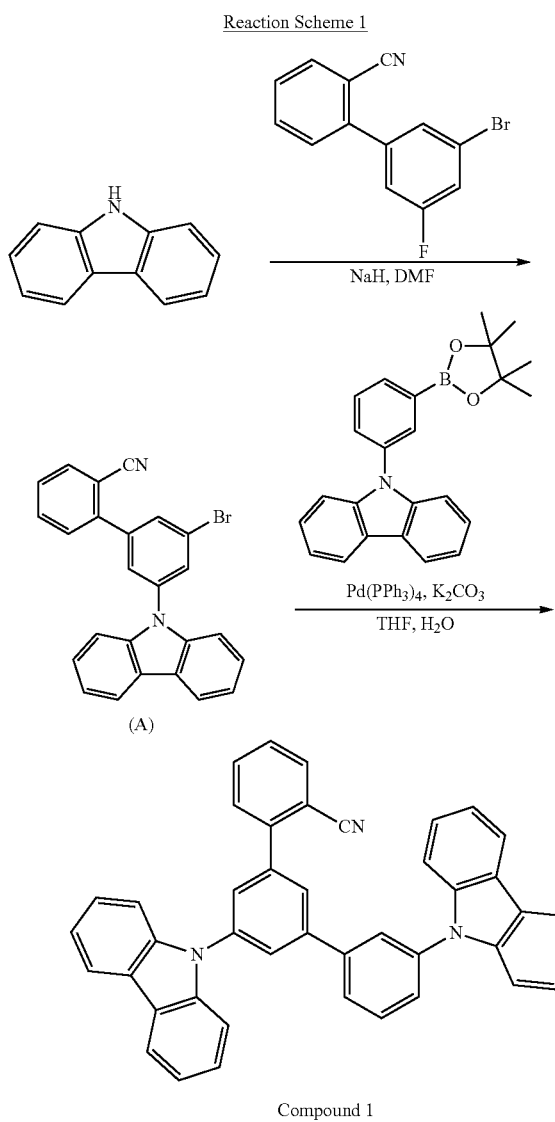

Reaction Scheme 1

(A)

Compound 1

Synthesis of Intermediate (A)

15.0 grams (g) (89.7 millimoles, mmol) of carbazole was dissolved in 200 milliliters (mL) of DMF, and cooled to a temperature of 0° C. 3.77 g (94.19 mmol) of hydrogenated sodium (NaH, 60% dispersion in mineral oil) was slowly added thereto, and the resultant was stirred for 30 minutes at a temperature of 0° C. To the reaction mixture, 27.2 g (98.7 mmol) of 3'-bromo-5'-fluoro-[1,1'-biphenyl]-2-carbonitrile that had been diluted in 100 mL of DMF was slowly added for 10 minutes. The reaction temperature was raised to 150° C., and the resultant was stirred for 18 hours. Once the reaction was completed, the reaction product was cooled to room temperature, a saturated ammonium chloride (NH$_4$Cl) aqueous solution was added thereto, and an organic layer was extracted and isolated therefrom by using dichloromethane (DCM). Water was removed therefrom by using anhydrous magnesium sulfate (MgSO$_4$), and the resultant was filtered and concentrated under reduced pressure. The product was separated by silica gel column chromatography, thereby completing the preparation of 24.3 g (yield of 64%) of Intermediate (A), which is the target compound.

LC-Mass (calculated: 422.04 grams per mole (g/mol), found: [M+1]$^+$=423 g/mol).

3'-bromo-5'-fluoro-[1,1'-biphenyl]-2-carbonitrile was synthesized by using the synthesis method disclosed by WO 2002/074773 and WO 2003/006464.

Synthesis of Compound 1

10.0 g (23.6 mmol) of Intermediate (A), 10.5 g (28.4 mmol) of 9-(3-(4,4,5,5-tetramethyl-1,3,2-dioxaborolan-2-yl)phenyl)-9H-carbazole, 1.37 g (1.18 mmol) of tetrakistriphenylphosphine palladium(0) (Pd(PPh$_3$)$_4$), and 8.16 g (59.1 mmol) of potassium carbonate were added to a mixed solution including 50 mL of THF and 25 mL of water, and the mixture was stirred under reflux. Once the reaction was completed, the reaction solution was cooled to room temperature, an aqueous solution layer was removed by extraction, and the remaining product was filtered through silica gel under reduced pressure. The product was separated therefrom by silica gel column chromatography, thereby completing the preparation of 11.6 g (yield of 84%) of Compound 1, which is the target compound.

LC-Mass (calculated: 585.22 g/mol, found: [M+1]$^+$=586 g/mol).

Synthesis Example 2

Synthesis of Compound 2

Compound 2 was synthesized according to Reaction Scheme 2:

Reaction Scheme 2

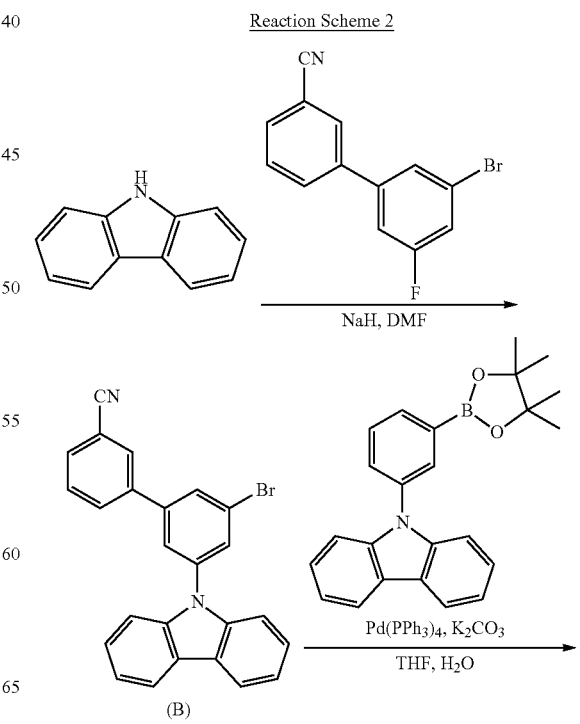

(B)

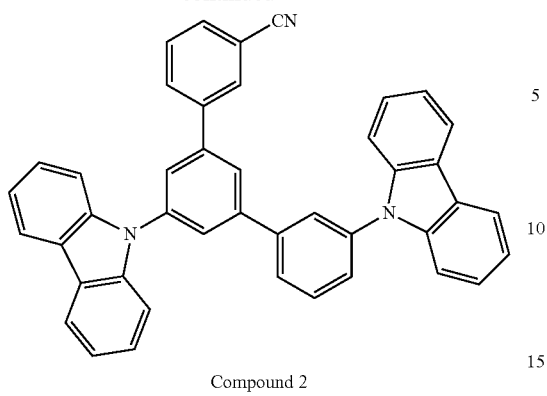

Compound 2

Synthesis of Intermediate (B)

26.2 g (yield of 69%) of Intermediate (B), which is the target compound, was prepared in the same manner as Intermediate (A), except that 27.2 g (98.7 mmol) of 3'-bromo-5'-fluoro-[1,1'-biphenyl]-3-carbonitrile was used instead of 3'-bromo-5'-fluoro-[1,1'-biphenyl]-2-carbonitrile.

LC-Mass (calculated: 422.04 g/mol, found: [M+1]$^+$=423 g/mol).

3'-bromo-5'-fluoro-[1,1'-biphenyl]-3-carbonitrile was synthesized by using the synthesis method disclosed by WO 2002/074773 and WO 2003/006464.

Synthesis of Compound 2

11.2 g (yield of 81%) of Compound 2, which is the target compound, was prepared in the same manner as Compound 1, except that 10.0 g (23.6 mmol) of Intermediate (B) was used instead of Intermediate (A).

LC-Mass (calculated: 585.22 g/mol, found: [M+1]$^+$=586 g/mol).

Synthesis Example 3

Synthesis of Compound 8

Compound 8 was synthesized according to Reaction Scheme 3:

Reaction Scheme 3

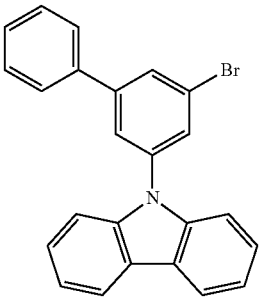

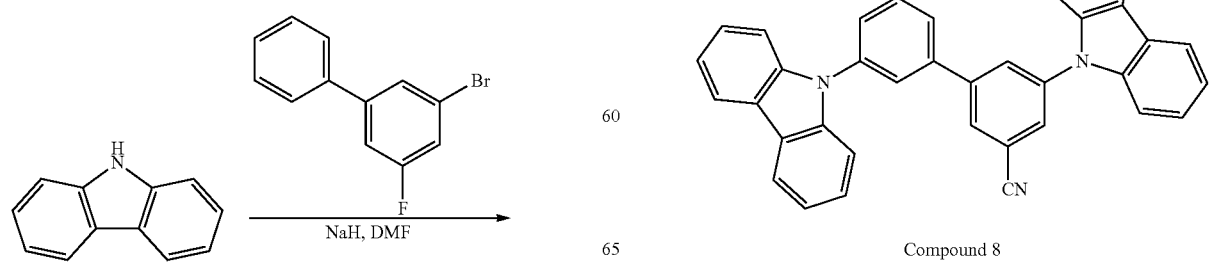

Compound 8

Synthesis of Intermediate (C)

28.9 g (yield of 81%) of Intermediate (C), which is the target compound, was prepared in the same manner as Intermediate (A), except that 24.8 g (98.7 mmol) of 3-bromo-5-fluoro-1,1'-biphenyl was used instead of 3'-bromo-5'-fluoro-[1,1'-biphenyl]-2-carbonitrile.

LC-Mass (calculated: 397.05 g/mol, found: [M+1]⁺=398 g/mol).

Synthesis of Intermediate (D)

19.9 g (yield of 64%) of Intermediate (D), which is the target compound, was prepared in the same manner as Intermediate (A), except that 19.7 g (98.7 mmol) of 3-bromo-5-fluorobenzonitrile was used instead of 3'-bromo-5'-fluoro-[1,1'-biphenyl]-2-carbonitrile.

LC-Mass (calculated: 346.01 g/mol, found: [M+1]⁺=347 g/mol).

Synthesis of Intermediate (E)

15.0 g (43.2 mmol) of Intermediate (D), 13.2 g (51.8 mmol) of bis(pinacolato)diboron, 1.76 g (2.16 mmol) of PdC₂(dppf).CH₂Cl₂, and 12.7 g (130 mmol) of potassium acetate were dissolved in 145 mL of DMF, and the mixture was stirred for 20 hours at a temperature of 100° C. Once the reaction was completed, the reaction solution was cooled to room temperature, and was filtered through silica gel under reduced pressure. The filtrate was concentrated under reduced pressure. The product was separated therefrom by silica gel column chromatography. The product was re-crystallized by using dichloromethane (DCM)/n-hexane thereby completing the preparation of 11.9 g (yield of 70%) of Intermediate (E), which is the target compound.

LC-Mass (calculated: 394.19 g/mol, found: [M+1]⁺=395 g/mol).

Synthesis of Compound 8

10.9 g (yield of 74%) of Compound 8, which is the target compound, was prepared in the same manner as Compound 1, except that 10.0 g (25.1 mmol) of Intermediate (C) was used instead of Intermediate (A) and 11.9 g (30.1 mmol) of Intermediate (E) was used instead of 9-(3-(4,4,5,5-tetramethyl-1,3,2-dioxaborolan-2-yl)phenyl)-9H-carbazole.

LC-Mass (calculated: 585.22 g/mol, found: [M+1]⁺=586 g/mol).

Synthesis Example 4

Synthesis of Compound 11

Compound 11 was synthesized according to Reaction Scheme 4:

Reaction Scheme 4

(A) + (E) $\xrightarrow{\text{Pd(PPh}_3)_4, \text{K}_2\text{CO}_3}{\text{THF, H}_2\text{O}}$

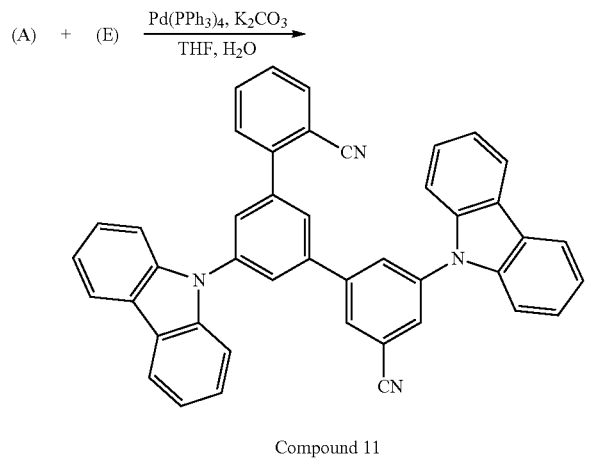

Compound 11

Synthesis of Compound 11

9.95 g (yield of 69%) of Compound 11, which is the target compound, was prepared in the same manner as Compound 1, except that 11.2 g (28.4 mmol) of Intermediate (E) was used instead of 9-(3-(4,4,5,5-tetramethyl-1,3,2-dioxaborolan-2-yl)phenyl)-9H-carbazole.

LC-Mass (calculated: 610.22 g/mol, found: [M+1]⁺=611 g/mol).

Synthesis Example 5

Synthesis of Compound 12

Compound 12 was synthesized according to Reaction Scheme 5:

Reaction Scheme 5

(B) + (E) $\xrightarrow{\text{Pd(PPh}_3)_4, \text{K}_2\text{CO}_3}{\text{THF, H}_2\text{O}}$

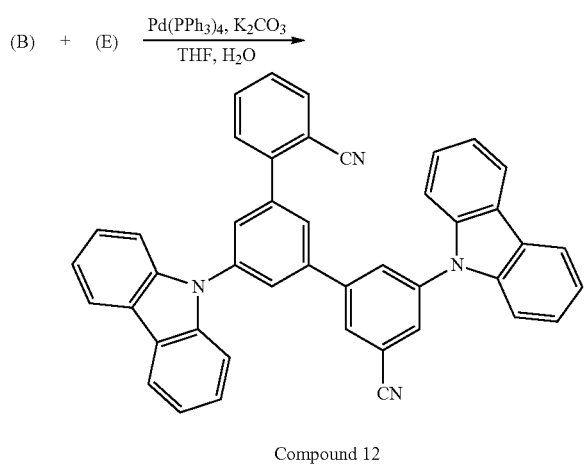

Compound 12

Synthesis of Compound 12

9.38 g (yield of 65%) of Compound 12, which is the target compound, was prepared in the same manner as Compound 1, except that 10.0 g (23.6 mmol) of Intermediate (B) was used instead of Intermediate (A) and 11.2 g (28.4 mmol) of Intermediate (E) was used instead of 9-(3-(4,4,5,5-tetramethyl-1,3,2-dioxaborolan-2-yl)phenyl)-9H-carbazole.

LC-Mass (calculated: 610.22 g/mol, found: [M+1]⁺=611 g/mol).

Synthesis Example 6

Synthesis of Compound 21

Compound 21 was synthesized according to Reaction Scheme 6:

Reaction Scheme 6

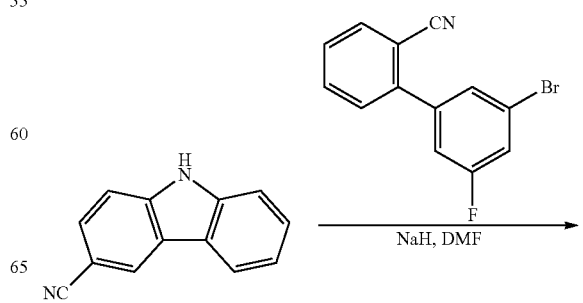

Synthesis Example 7

Synthesis of Compound 22

Compound 22 was synthesized according to Reaction Scheme 7:

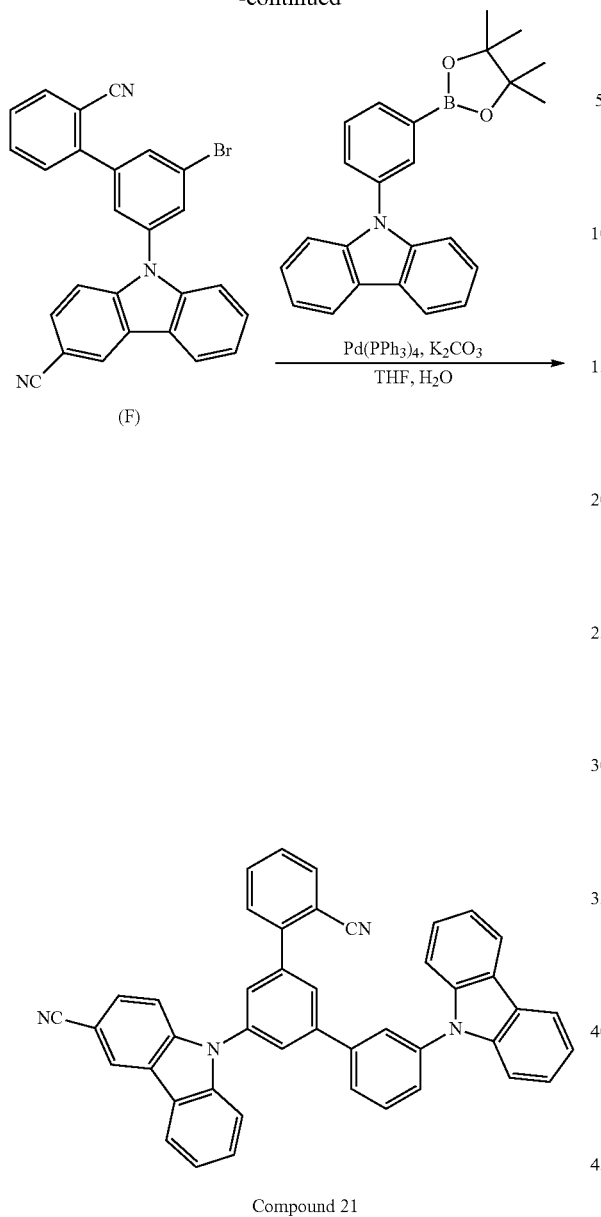

Compound 21

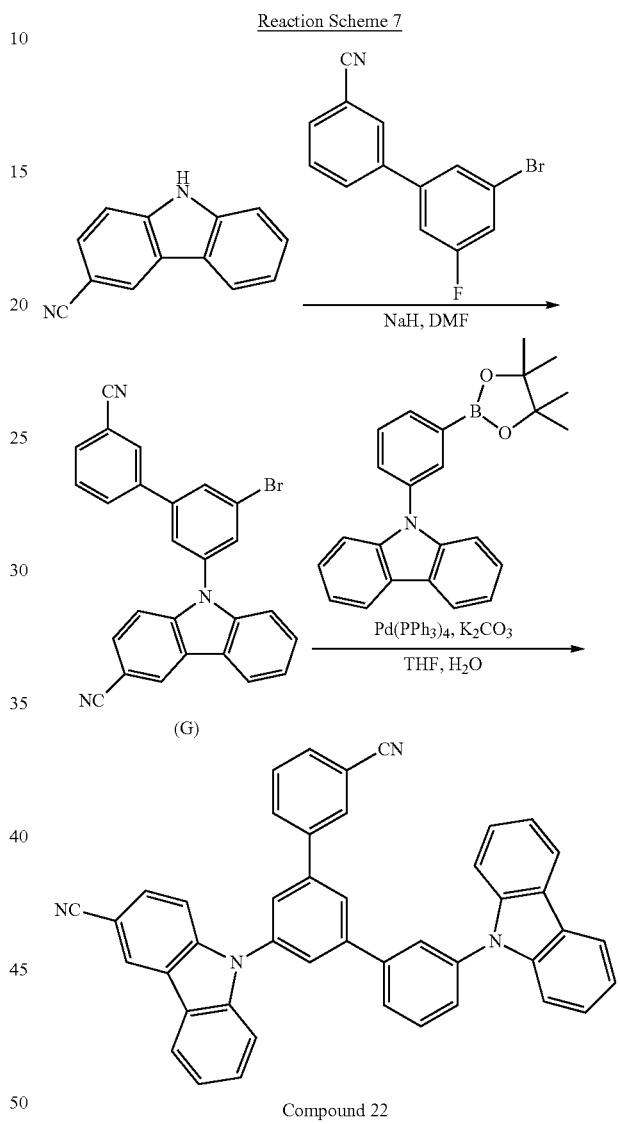

Compound 22

Synthesis of Intermediate (F)

20.3 g (yield of 58%) of Intermediate (F), which is the target compound, was prepared in the same manner as Intermediate (A), except that 15.0 g (78.0 mmol) of 9H-carbazole-3-carbonitrile was used instead of carbazole.

LC-Mass (calculated: 447.04 g/mol, found: [M+1]$^+$=448 g/mol).

Synthesis of Compound 21

8.85 g (yield of 65%) of Compound 21, which is the target compound, was prepared in the same manner as Compound 1, except that 10.0 g (22.3 mmol) of Intermediate (F) was used instead of Intermediate (A).

LC-Mass (calculated: 610.22 g/mol, found: [M+1]$^+$=611 g/mol).

Synthesis of Intermediate (G)

22.7 g (yield of 65%) of Intermediate (G), which is the target compound, was prepared in the same manner as Intermediate (B), except that 15.0 g (78.0 mmol) of 9H-carbazole-3-carbonitrile was used instead of carbazole.

LC-Mass (calculated: 447.04 g/mol, found: [M+1]$^+$=448 g/mol).

Synthesis of Compound 22

9.67 g (yield of 71%) of Compound 22, which is the target compound, was prepared in the same manner as Compound 1, except that 10.0 g (22.3 mmol) of Intermediate (G) was used instead of Intermediate (A).

LC-Mass (calculated: 610.22 g/mol, found: [M+1]$^+$=611 g/mol).

Synthesis Example 8

Synthesis of Compound 31

Compound 31 was synthesized according to Reaction Scheme 8:

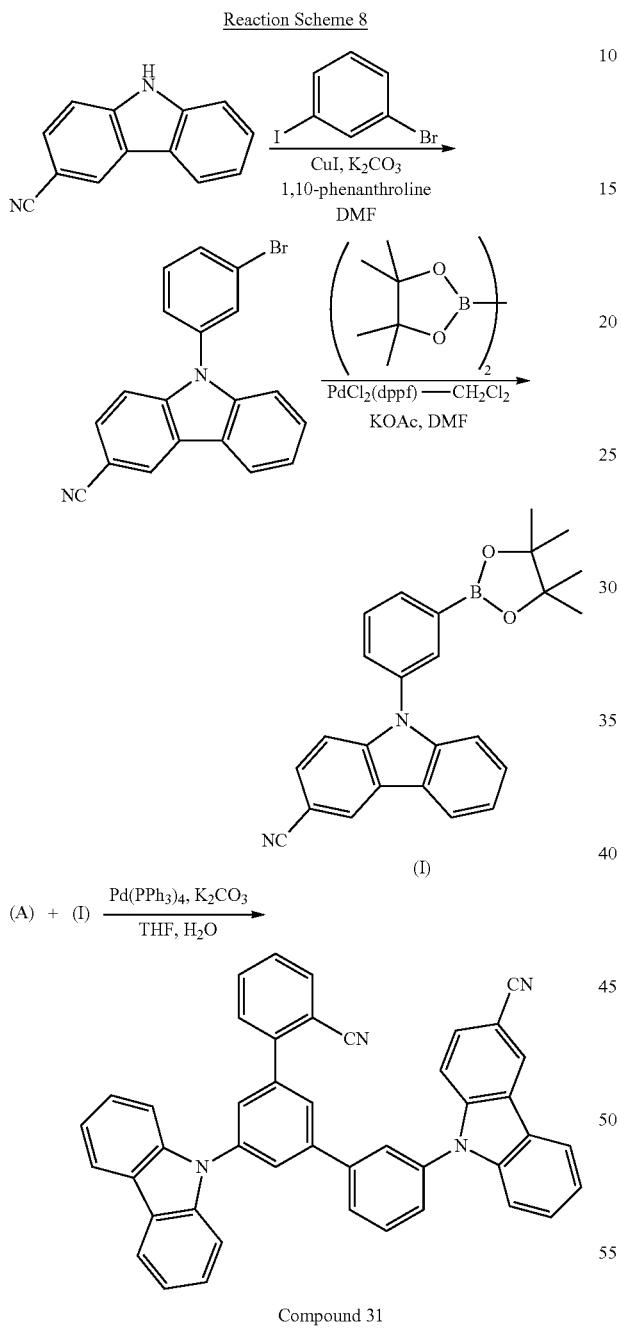

Compound 31

Synthesis of Intermediate H 10.0 g (52.0 mmol) of 9H-carbazole-3-carbonitrile, 22.1 g (78.0 mmol) of 1-bromo-3-iodobenzene, 1.98 g (10.4 mmol) of copper iodide (CuI), 28.8 g (208 mmol) of potassium carbonate ($K_2CO_3$), and 3.75 g (20.8 mmol) of 1,10-phenanthroline were dissolved in 175 mL of DMF, and the mixture was stirred under reflux for 24 hours. Once the reaction was completed, the reaction product was cooled to room temperature, and filtered through silica gel under reduced pressure. The filtrate was concentrated under reduced pressure. The product was separated by silica gel column chromatography, thereby completing the preparation of 13.4 g (yield of 74%) of Intermediate (H), which is the target compound.

LC-Mass (calculated: 346.01 g/mol, found: $[M+1]^+=347$ g/mol).

Synthesis of Intermediate (I)

8.29 g (yield of 73%) of Intermediate (I), which is the target compound, was prepared in the same manner as Intermediate (E), except that 10.0 g (28.8 mmol) of Intermediate (H) was used instead of Intermediate (D).

LC-Mass (calculated: 394.19 g/mol, found: $[M+1]^+=395$ g/mol).

Synthesis of Compound 31

Compound 31 6.67 g (yield of 66%), which is the target compound, was prepared in the same manner as Compound 1, except that 7.82 g (19.8 mmol) of Intermediate (I) was used instead of 9-(3-(4,4,5,5-tetramethyl-1,3,2-dioxaborolan-2-yl)phenyl)-9H-carbazole.

LC-Mass (calculated: 610.22 g/mol, found: $[M+1]^+=611$ g/mol).

Synthesis Example 9

Synthesis of Compound 32

Compound 32 was synthesized according to Reaction Scheme 9:

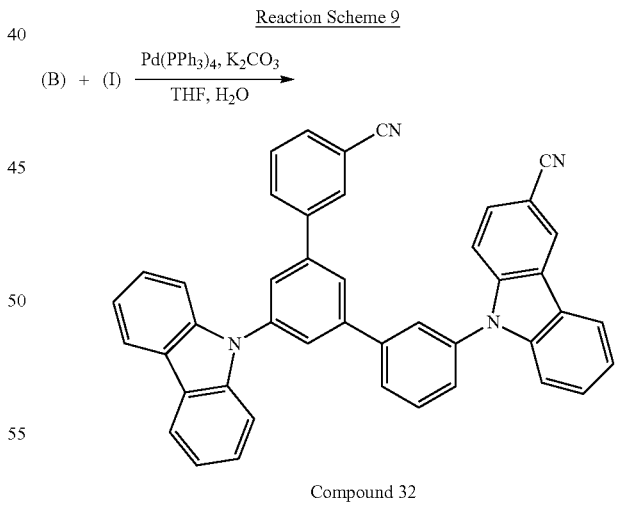

Compound 32

Synthesis of Compound 32

7.07 g (yield of 70%) of Compound 32, which is the target compound, was prepared in the same manner as Compound 31, except that 7.00 g (16.5 mmol) of Intermediate (B) was used instead of Intermediate (A).

LC-Mass (calculated: 610.22 g/mol, found: $[M+1]^+=611$ g/mol).

Synthesis Example 10

Synthesis of Compound 38

Compound 38 was synthesized according to Reaction Scheme 10:

Reaction Scheme 10

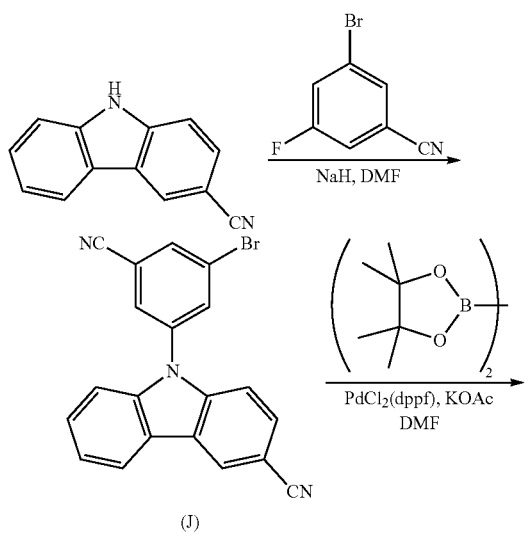

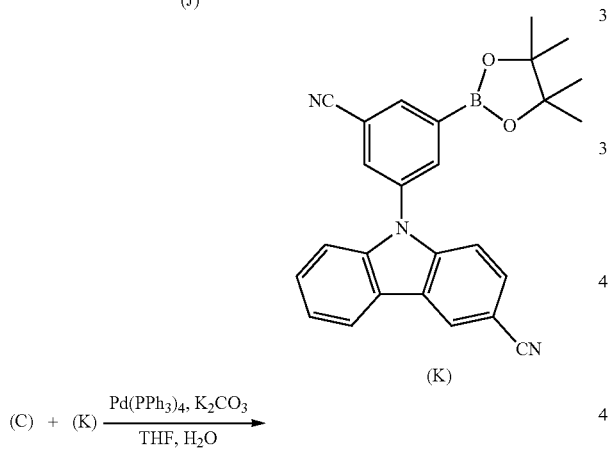

Compound 38

Synthesis of Intermediate J 16.0 g (yield of 55%) of Intermediate (J), which is the target compound, was prepared in the same manner as Intermediate (D), except that 15.0 g (78.0 mmol) of 9H-carbazole-3-carbonitrile was used instead of carbazole.

LC-Mass (calculated: 371.01 g/mol, found: [M+1]$^+$=372 g/mol).

Synthesis of Intermediate (K)

7.64 g (yield of 72%) of Intermediate (K), which is the target compound, was prepared in the same manner as Intermediate (E), except that 7.48 g (17.8 mmol) of Intermediate (J) was used instead of Intermediate (D).

LC-Mass (calculated: 419.18 g/mol, found: [M+1]$^+$=420 g/mol).

Synthesis of Compound 38

6.16 g (yield of 73%) of Compound 38, which is the target compound, was prepared in the same manner as Compound 8, except that 6.95 g (16.6 mmol) of Intermediate (K) was used instead of Intermediate (E).

LC-Mass (calculated: 610.22 g/mol, found: [M+1]$^+$=611 g/mol).

Synthesis Example 11

Synthesis of Compound 41

Compound 41 was synthesized according to Reaction Scheme 11:

Reaction Scheme 11

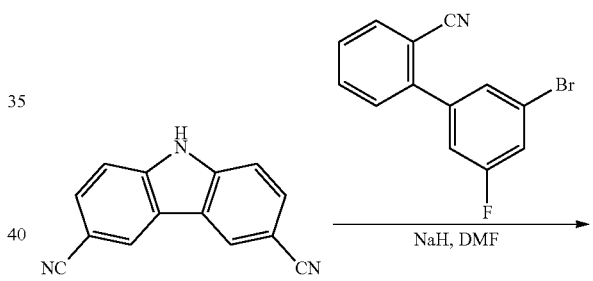

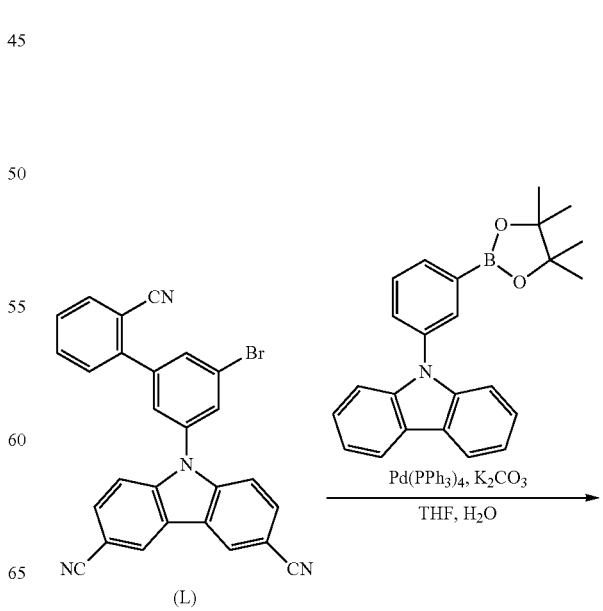

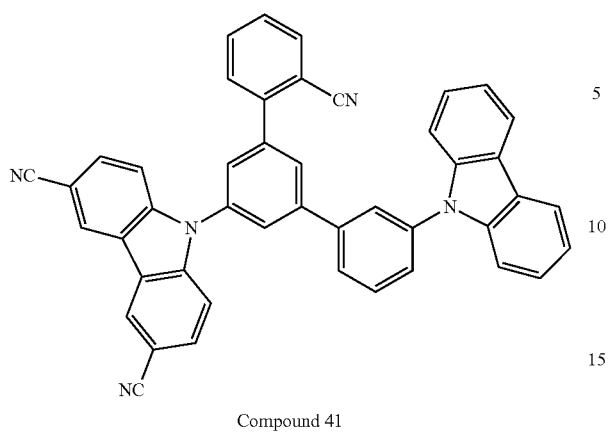

Compound 41

Synthesis of Intermediate (L)

8.22 g (yield of 32%) of Intermediate (L), which is the target compound, was prepared in the same manner as Intermediate (A), except that 15.0 g (69.1 mmol) of 9H-carbazole-3,6-dicarbonitrile was used instead of carbazole.

LC-Mass (calculated: 472.03 g/mol, found: [M+1]$^+$=473 g/mol).

Synthesis of Compound 41

5.16 g (yield of 48%) of Compound 41, which is the target compound, was prepared in the same manner as Compound 1, except that 8.00 g (16.9 mmol) of Intermediate (L) was used instead of Intermediate (A).

LC-Mass (calculated: 635.21 g/mol, found: [M+1]$^+$=636 g/mol).

Synthesis Example 12

Synthesis of Compound 51

Compound 51 was synthesized according to Reaction Scheme 12:

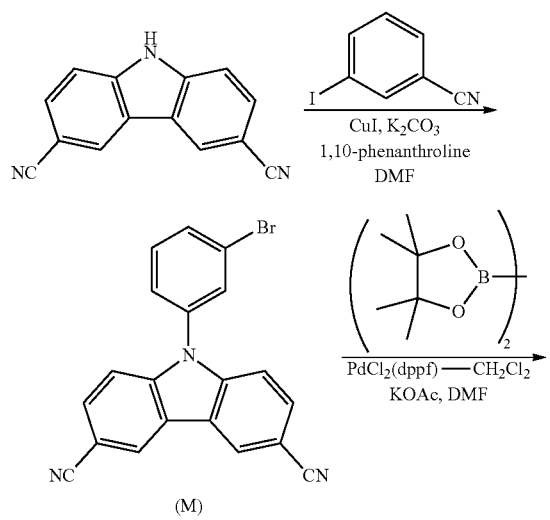

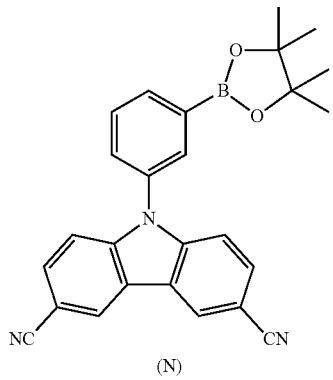

(N)

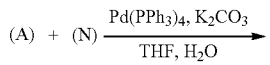

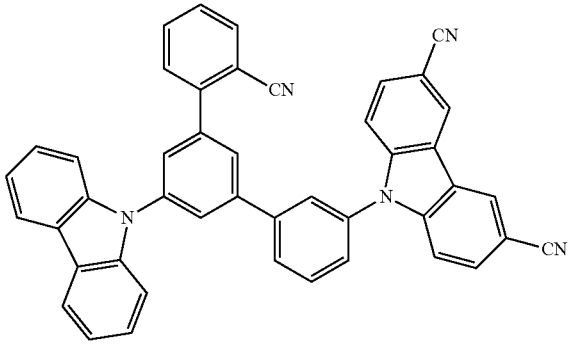

Compound 51

Synthesis of Intermediate (M)

9.00 g (yield of 35%) of Intermediate (M), which is the target compound, was prepared in the same manner as Intermediate (H), except that 15.0 g (69.1 mmol) of 9H-carbazole-3,6-dicarbonitrile was used instead of 9H-carbazole-3-carbonitrile.

LC-Mass (calculated: 371.01 g/mol, found: [M+1]$^+$=372 g/mol).

Synthesis of Intermediate (N)

5.47 g (yield of 54%) of Intermediate (N), which is the target compound, was prepared in the same manner as Intermediate (E), except that 9.00 g (24.2 mmol) of Intermediate (M) was used instead of Intermediate (D).

LC-Mass (calculated: 419.18 g/mol, found: [M+1]$^+$=420 g/mol).

Synthesis of Compound 51

3.99 g (yield of 59%) of Compound 51, which is the target compound, was prepared in the same manner as Compound 1, except that 5.35 g (12.8 mmol) of Intermediate (N) was used instead of 9-(3-(4,4,5,5-tetramethyl-1,3,2-dioxaborolan-2-yl)phenyl)-9H-carbazole.

LC-Mass (calculated: 635.21 g/mol, found: [M+1]$^+$=636 g/mol).

Synthesis Example 13

Synthesis of Compound 61

Compound 61 was synthesized according to Reaction Scheme 13:

Reaction Scheme 13

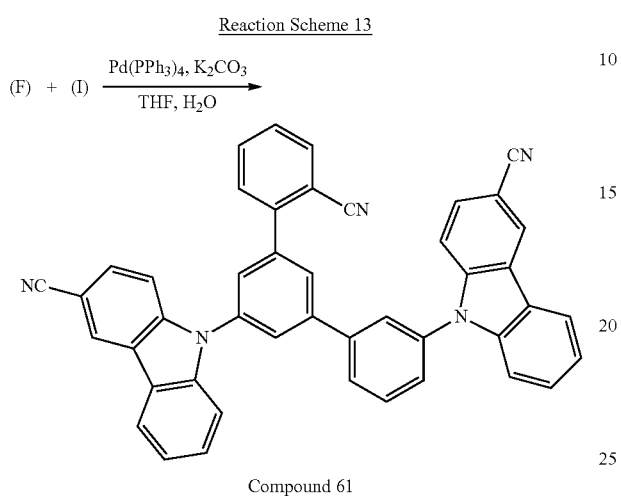

Compound 61

Synthesis of Compound 61

4.67 g (yield of 47%) of Compound 61, which is the target compound, was prepared in the same manner as Compound 21, except that 7.39 g (18.7 mmol) of Intermediate (I) was used instead of 9-(3-(4,4,5,5-tetramethyl-1,3,2-dioxaborolan-2-yl)phenyl)-9H-carbazole.

LC-Mass (calculated: 635.21 g/mol, found: $[M+1]^+$=636 g/mol).

Synthesis Example 14

Synthesis of Compound 91

Compound 91 was synthesized according to Reaction Scheme 14:

Reaction Scheme 14

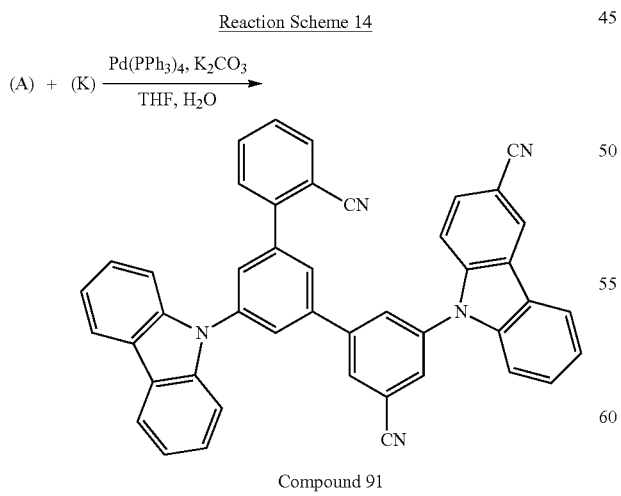

Compound 91

Synthesis of Compound 91

6.73 g (yield of 64%) of Compound 91, which is the target compound, was prepared in the same manner as Compound 1, except that 8.32 g (19.8 mmol) of Intermediate (K) was used instead of 9-(3-(4,4,5,5-tetramethyl-1,3,2-dioxaborolan-2-yl)phenyl)-9H-carbazole.

LC-Mass (calculated: 635.21 g/mol, found: $[M+1]^+$=636 g/mol).

Synthesis Example 15

Synthesis of Compound 157

Compound 157 was synthesized according to Reaction Scheme 15:

Reaction Scheme 15

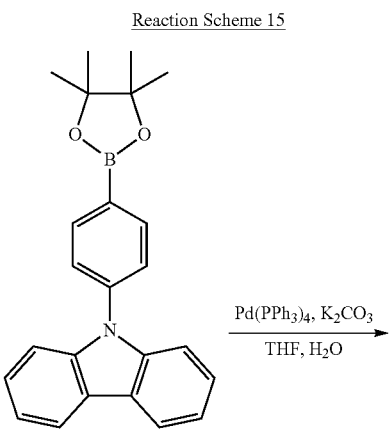

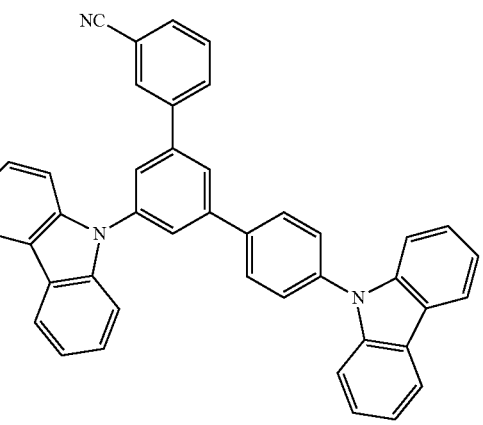

Compound 157

Synthesis of Compound 157

11.2 g (yield of 81%) of Compound 157, which is the target compound, was prepared in the same manner as Compound 2, except that 10.5 g (28.4 mmol) of 9-(4-(4,4,5,5-tetramethyl-1,3,2-dioxaborolan-2-yl)phenyl)-9H-carbazole was used instead of 9-(3-(4,4,5,5-tetramethyl-1,3,2-dioxaborolan-2-yl)phenyl)-9H-carbazole.

LC-Mass (calculated: 585.22 g/mol, found: $[M+1]^+$=586 g/mol).

Synthesis Example 16

Synthesis of Compound 160

Compound 160 was synthesized according to Reaction Scheme 16:

Reaction Scheme 16

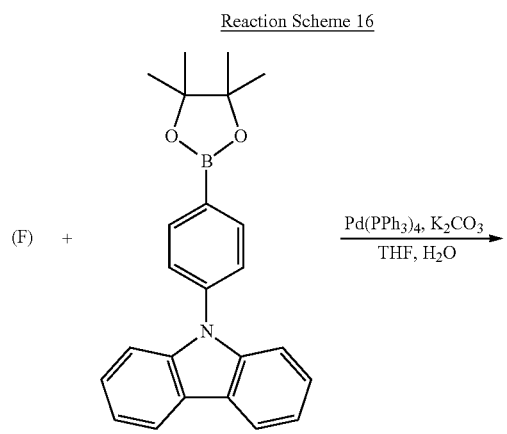

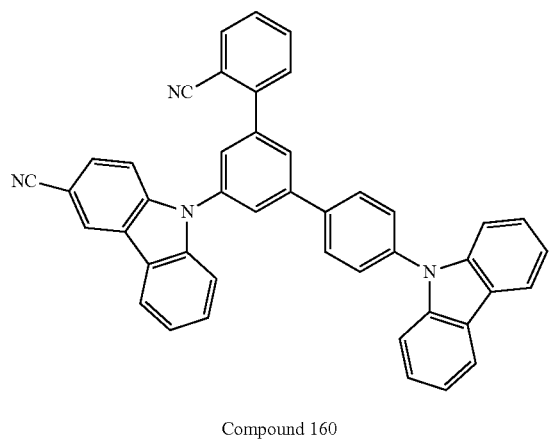

Compound 160

Synthesis of Compound 160

9.26 g (yield of 68%) of Compound 160, which is the target compound, was prepared in the same manner as Compound 21, except that 9.88 g (26.8 mmol) of 9-(4-(4,4,5,5-tetramethyl-1,3,2-dioxaborolan-2-yl)phenyl)-9H-carbazole was used instead of 9-(3-(4,4,5,5-tetramethyl-1,3,2-dioxaborolan-2-yl)phenyl)-9H-carbazole.

LC-Mass (calculated: 610.22 g/mol, found: [M+1]$^+$=611 g/mol).

Synthesis Example 17

Synthesis of Compound A

Compound A was synthesized according to Reaction Scheme 17:

Reaction Scheme 17

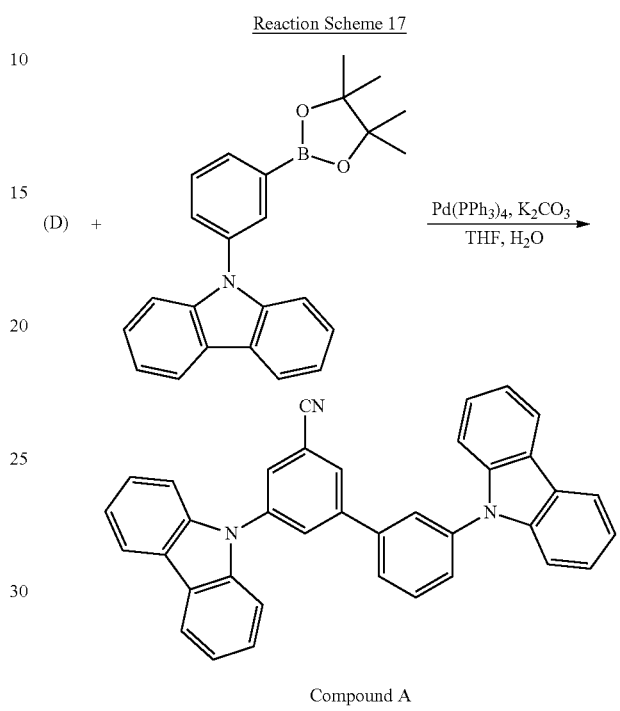

Compound A

Synthesis of Compound A 12.8 g (yield of 87%) of Compound A, which is the target compound, was prepared in the same manner as Compound 1, except that 10.0 g (28.8 mmol) of Intermediate (D) was used instead of Intermediate (A).

LC-Mass (calculated: 509.19 g/mol, found: [M+1]$^+$=510 g/mol).

Synthesis Example 18

Synthesis of Compound B

Compound B was synthesized according to Reaction Scheme 18:

Reaction Scheme 18

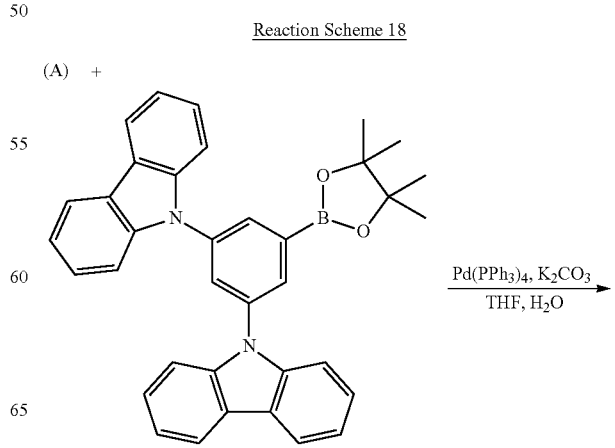

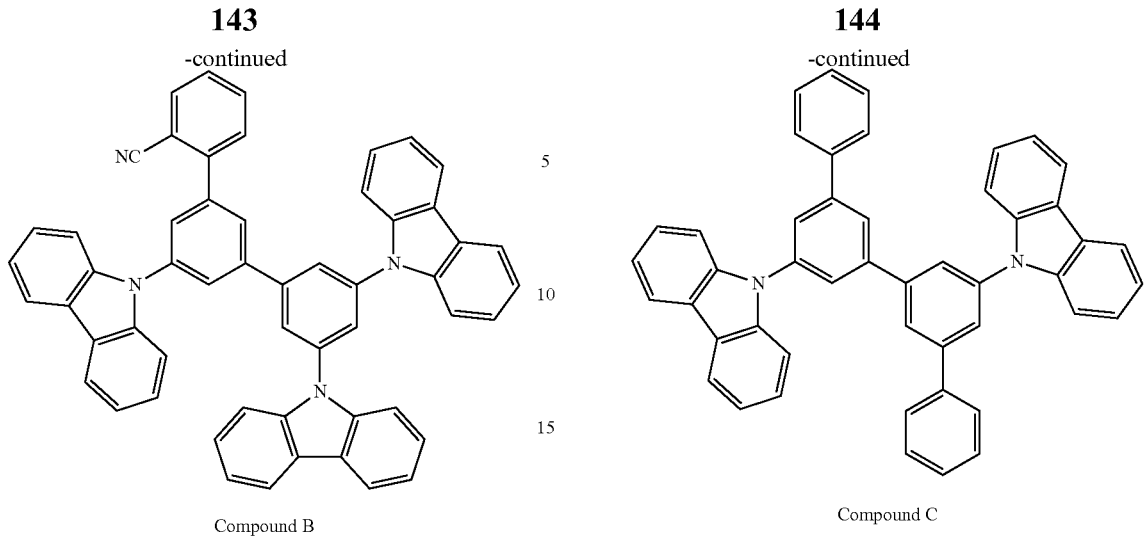

Compound B

Synthesis of Compound B 12.4 g (yield of 70%) of Compound B, which is the target compound, was prepared in the same manner as Compound 1, except that 15.2 g (28.4 mmol) of 9,9'-(5-(4,4,5,5-tetramethyl-1,3,2-dioxaborolan-2-yl)-1,3-phenylene)bis(9H-carbazole) was used instead of 9-(3-(4,4,5,5-tetramethyl-1,3,2-dioxaborolan-2-yl)phenyl)-9H-carbazole.

LC-Mass (calculated: 750.28 g/mol, found: $[M+1]^+$=751 g/mol).

Synthesis Example 19

Synthesis of Compound C

Compound C was synthesized according to Reaction Scheme 19:

Reaction Scheme 19

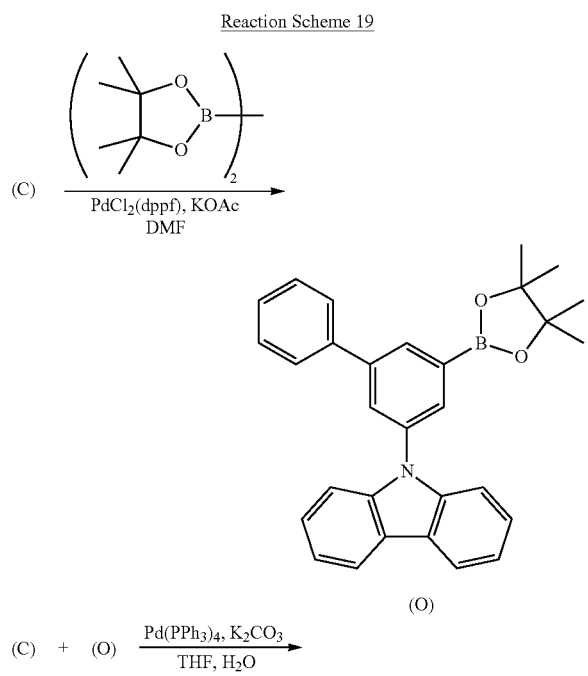

Synthesis of Intermediate (O)

12.1 g (yield of 72%) of Intermediate (O), which is the target compound, was prepared in the same manner as Intermediate (E), except that 15.0 g (37.7 mmol) of Intermediate (C) was used instead of Intermediate (D).

Synthesis of Compound C 8.70 g (yield of 68%) of Compound C, which is the target compound, was prepared in the same manner as Compound 8, except that 10.7 g (24.1 mmol) of Intermediate (O) was used instead of Intermediate (E).

LC-Mass (calculated: 636.26 g/mol, found: $[M+1]^+$=637 g/mol).

Evaluation Example 1

Thermal Characteristics Evaluation

Compounds 38 and A were thermally analyzed by thermo gravimetric analysis (TGA) and differential scanning calorimetry (DSC) ($N_2$ atmosphere, a temperature range: from room temperature to 600° C. (10 degrees Centigrade per minute, ° C./min)-TGA, from room temperature to 400° C.-DSC, and Pan Type: Pt Pan in disposable Al pan (TGA), disposable Al pan(DSC)). Results thereof are shown in Table 2. Referring to Table 2, it was confirmed that Compound 38 has excellent thermal stability compared to Compound A.

TABLE 2

| Compound No. | Tg (° C.) | Td (° C.) (0.1%) |
|---|---|---|
| Compound 38 | 153 | 387 |
| Compound A | 114 | 347 |

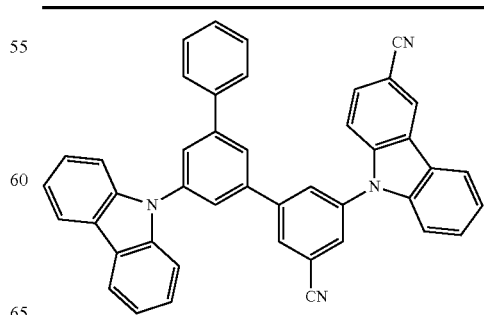

38

TABLE 2-continued

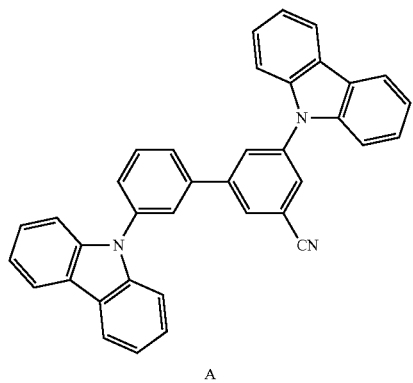

A

Example 1

A glass substrate with a 1,500 Angstrom (A)-thick indium tin oxide (ITO) electrode (first electrode, anode) thereon was sonicated in distilled water. When the sonication with distilled water was completed, the resultant was sonicated using a solvent, such as iso-propyl alcohol, acetone, or methanol. The obtained resultant was dried and transferred to a plasma washer, washed with oxygen plasma for 5 minutes therein, and transferred to a vacuum depositing device.

Compound HT3 and Compound HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby completing the formation of a hole transport region.

Compound 1 (host) and FIr6 (dopant, 10 percent by weight, wt %) were co-deposited on the hole transport region to form an emission layer having a thickness of 400 Å.

BCP was vacuum-deposited on the emission layer to form a hole blocking layer having a thickness of 100 Å, Compound ET3 and Liq were vacuum-codeposited on the hole blocking layer to form an electron transport layer having a thickness of 300 Å, Liq was deposited on the electron transport layer to form an electron injection layer having a thickness of 10 Å, and Al was deposited on the electron injection layer to form a second electrode (cathode) having a thickness of 1,200 Å, thereby completing manufacture of an organic light-emitting device.

Examples 2 to 16 and Comparative Examples 1 to 3

Organic light-emitting devices were manufactured in the same manner as in Example 1, except that, in forming the emission layer, as a host, Compounds shown in Table 3 were used instead of Compound 1.

Evaluation Example 2

Evaluation on Characteristics of Organic Light-emitting Devices

A current-density change according to voltage, a luminescent change, and luminescent efficiency of the organic light-emitting devices of Examples 1 to 16 and Comparative Examples 1 to 3 were measured. Measurement methods used herein are described below, and results thereof are shown in Table 3.

(1) Change in Current Density According to Voltage

Regarding an organic light-emitting device, current flowing in a unit device was measured by using a current-voltage meter (Keithley 2400) while a voltage was raised from 0 volts (V) to 10 V, and the measured current was divided by an area.

(2) Change in Luminance According to Voltage

The luminance of an organic light-emitting device was measured by using a luminance meter (Minolta Cs-1000A) while a voltage was raised from 0 V to 10 V.

(3) Luminance Efficiency Measurement

Current efficiency (candelas per ampere, cd/A) at the same current density (10 milliamperes per square centimeter, $mA/cm^2$) was calculated by using the current density and the luminance, respectively obtained in (1) and (2).

(4) Durability Measurement

A time that had lapsed when the initial luminance of 100% was reduced to 95% thereof was evaluated.

TABLE 3

| | Host | Driving voltage (relative value) | Current efficiency (relative value) | Durability (relative value) | Color |
|---|---|---|---|---|---|
| Example 1 | Compound 1 | 94% | 115% | 108% | Blue |
| Example 2 | Compound 2 | 93% | 120% | 106% | Blue |
| Example 3 | Compound 8 | 91% | 118% | 112% | Blue |
| Example 4 | Compound 11 | 84% | 130% | 131% | Blue |
| Example 5 | Compound 12 | 86% | 127% | 125% | Blue |
| Example 6 | Compound 21 | 84% | 131% | 124% | Blue |
| Example 7 | Compound 22 | 86% | 121% | 119% | Blue |
| Example 8 | Compound 31 | 89% | 117% | 121% | Blue |
| Example 9 | Compound 32 | 86% | 120% | 118% | Blue |
| Example 10 | Compound 38 | 81% | 135% | 143% | Blue |
| Example 11 | Compound 41 | 92% | 108% | 110% | Blue |
| Example 12 | Compound 51 | 93% | 104% | 115% | Blue |
| Example 13 | Compound 61 | 89% | 110% | 114% | Blue |
| Example 14 | Compound 91 | 87% | 115% | 121% | Blue |
| Example 15 | Compound 157 | 96% | 108% | 104% | Blue |
| Example 16 | Compound 160 | 88% | 110% | 118% | Blue |

TABLE 3-continued

| | Host | Driving voltage (relative value) | Current efficiency (relative value) | Durability (relative value) | Color |
|---|---|---|---|---|---|
| Comparative Example 1 | Compound A | 100% | 100% | 100% | Blue |
| Comparative Example 2 | Compound B | 135% | 64% | 26% | Blue |
| Comparative Example 3 | Compound C | 141% | 32% | 15% | Blue |

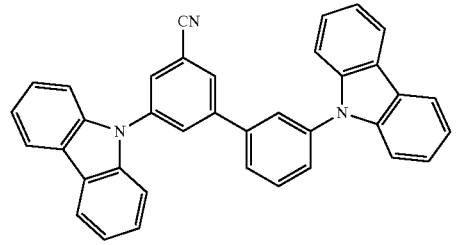

Compound A

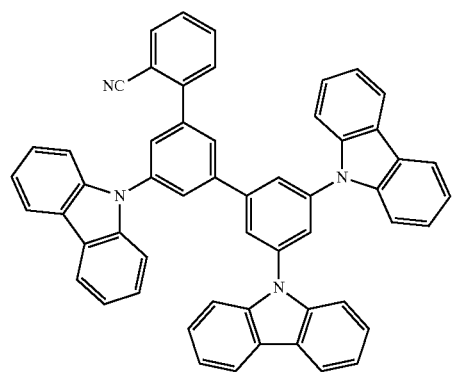

Compound B

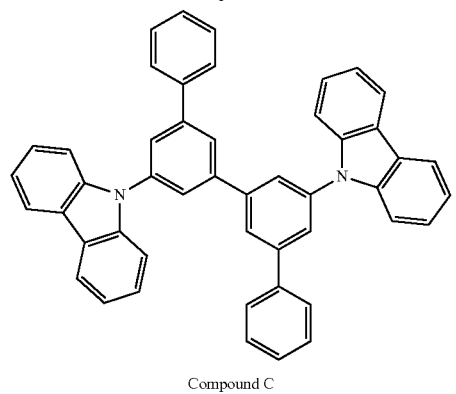

Compound C

The condensed cyclic based compound according to embodiments has excellent electric characteristics and thermal stability. Accordingly, an organic light-emitting device including the condensed cyclic based compound may have a low driving voltage, high efficiency, high power, high quantum luminescent efficiency, and a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

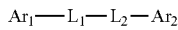

Formula 1

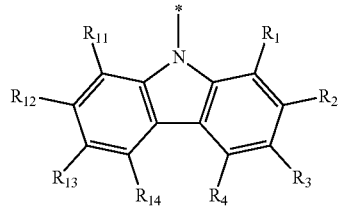

Formula 2

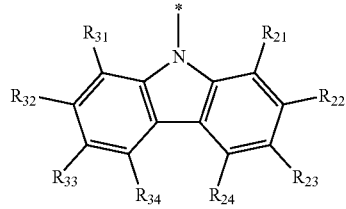

Formula 3

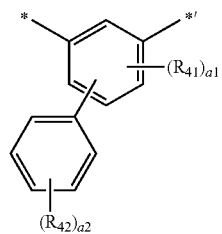

Formula 4A

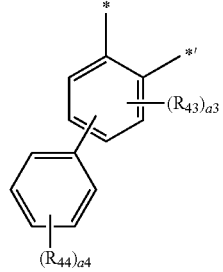

Formula 4B

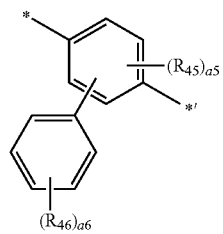

Formula 4C

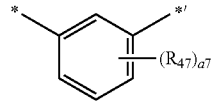

Formula 4D

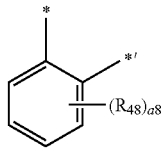

Formula 4E

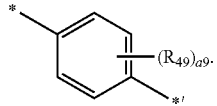

Formula 4F wherein, in Formula 1, $Ar_1$ is a group represented by Formula 2, $Ar_2$ is a group represented by Formula 3, $L_1$ is selected from a group represented by Formula 4A, a group represented by Formula 4B, and a group represented by Formula 4C, $L_2$ is selected from a group represented by Formula 4D, a group represented by Formula 4E, and a group represented by Formula 4F, wherein a case in which $L_1$ is the group represented by Formula 4C and $L_2$ is the group represented by Formula 4F is excluded, $R_1$ to $R_4$, $R_{11}$ to $R_{14}$, $R_{21}$ to $R_{24}$, $R_{31}$ to $R_{34}$, and $R_{41}$ to $R_{49}$ are each independently selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group (provided that the substituted or unsubstituted monovalent non-aromatic condensed heteropolycyclic group is not a substituted or unsubstituted carbazolyl group), —N(Q₄)(Q₅), and —B(Q₆)(Q₇), the number of cyano group(s) (CN) in a group represented by *-$L_1$-$L_2$-*' in Formula 1 is 1, 2, 3, or 4, a1 to a9 are each independently an integer selected from 0 to 5,

* and *' each indicate a binding site to a neighboring atom, at least one of substituents of the substituted carbazolyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from deuterium, —CD₃, —CD₂H, —CDH₂, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group (provided that the non-aromatic condensed heteropolycyclic group is not a carbazolyl group);

a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group (provided that the non-aromatic condensed heteropolycyclic group is not a carbazolyl group), each substituted with at least one selected from deuterium,—$CD_3$, —$CD_2H$, —$CDH_2$, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group (provided that the non-aromatic condensed heteropolycyclic group is not a carbazolyl group), —$N(Q_{24})(Q_{25})$, and —$B(Q_{26})(Q_{27})$; and —$N(Q_{34})(Q_{35})$ and —$B(Q_{36})(Q_{37})$, wherein $Q_4$ to $Q_7$, $Q_{24}$ to $Q_{27}$ and $Q_{34}$ to $Q_{37}$ are each independently selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (provided that the substituted or unsubstituted monovalent non-aromatic condensed heteropolycyclic group is not a substituted or unsubstituted carbazolyl group).

2. The condensed cyclic compound of claim 1, wherein $R_1$ to $R_4$, $R_{11}$ to $R_{14}$, $R_{21}$ to $R_{24}$, $R_{31}$ to $R_{34}$, and $R_{41}$ to $R_{49}$ are each independently selected from:

hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzooxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzooxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N(Q$_{34}$)(Q$_{35}$), and —B(Q$_{36}$)(Q$_{37}$); and —N(Q$_4$)(Q$_5$) and —B(Q$_6$)(Q$_7$), wherein Q$_4$ to Q$_7$ and Q$_{34}$ to Q$_{37}$ are each independently selected from hydrogen, C$_1$-C$_{20}$ alkyl group, a C$_1$-C$_{20}$ alkoxy group, a phenyl group, a biphenyl group, a terphenyl group, a naphthyl group, a fluorenyl group, a dibenzofuranyl group, and a dibenzothiophenyl group.

3. The condensed cyclic compound of claim 1, wherein R$_1$ to R$_4$, R$_{11}$ to R$_{14}$, R$_{21}$ to R$_{24}$, R$_{31}$ to R$_{34}$, and R$_{41}$ to R$_{49}$ are each independently selected from:

hydrogen, deuterium, and a cyano group (CN);

a phenyl group, a biphenyl group, a terphenyl group, a naphthyl group, a fluorenyl group, a dibenzofuranyl group and a dibenzothiophenyl group; and a phenyl group, a biphenyl group, a terphenyl group, a naphthyl group, a fluorenyl group, a dibenzofuranyl group, and a dibenzothiophenyl group, each substituted with at least one selected from deuterium, a cyano group, a phenyl group, a biphenyl group, a terphenyl group, and a naphthyl group.

4. The condensed cyclic compound of claim 1, wherein at least one selected from R$_3$, R$_{13}$, R$_{23}$, and R$_{33}$ in Formulae 2 and 3 is a cyano group.

5. The condensed cyclic compound of claim 1, wherein a1 to a9 in Formulae 4A to 4F are each independently 0, 1, or 2.

6. The condensed cyclic compound of claim 1, wherein one, two, three, or four substituents of *-L$_1$-L$_2$-*' in Formula 1 are each independently selected from:

hydrogen, deuterium, and a cyano group;

a phenyl group, a biphenyl group, a terphenyl group, a naphthyl group, a fluorenyl group, a dibenzofuranyl group, and a dibenzothiophenyl group;

a phenyl group, a biphenyl group, a terphenyl group, a naphthyl group, a fluorenyl group, a dibenzofuranyl group, and a dibenzothiophenyl group, each substituted with at least one selected from deuterium, a cyano group, a phenyl group, a biphenyl group, a terphenyl group, and a naphthyl group.

7. The condensed cyclic compound of claim 1, wherein one, two, three, or four substituents of *-L$_1$-L$_2$-*' in Formula 1 are each independently selected from:

a cyano group; and a phenyl group, a biphenyl group, and a terphenyl group, each substituted with at least one cyano group.

8. The condensed cyclic compound of claim 1, wherein the number of cyano group(s) in the condensed cyclic compound represented by Formula 1 is 1, 2, 3, or 4.

9. The condensed cyclic compound of claim 1, wherein the number of carbazole ring systems in the condensed cyclic compound represented by Formula 1 is 2.

10. The condensed cyclic compound of claim 1, wherein the condensed cyclic compound is represented by one of Formulae 1-1 to 1-28:

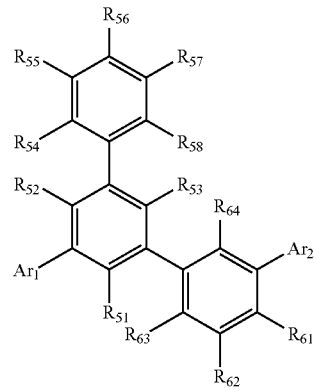

Formula 1-1

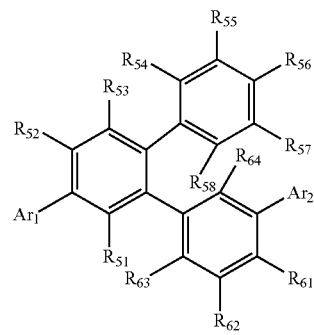

Formula 1-2

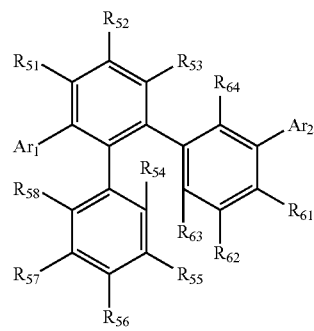

Formula 1-3

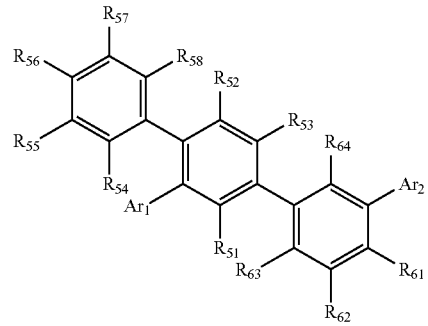

Formula 1-4

-continued
Formula 1-5
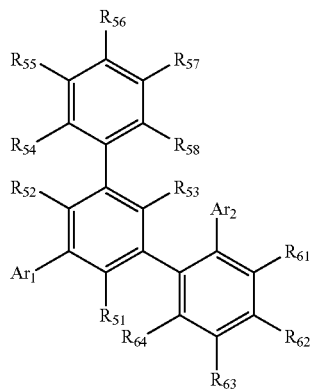
Formula 1-6
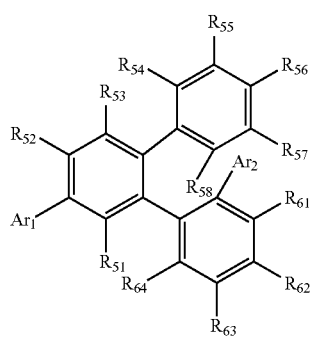
Formula 1-7
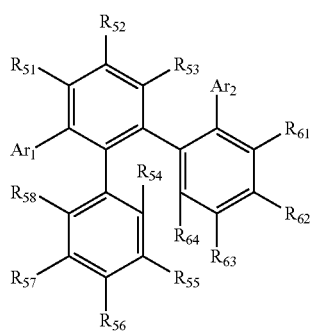
Formula 1-8
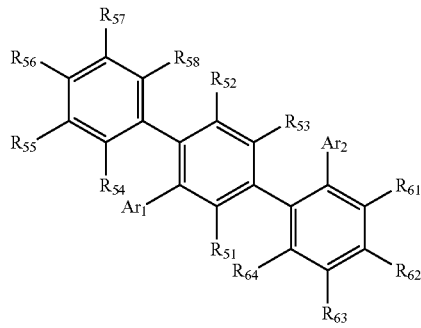
Formula 1-9
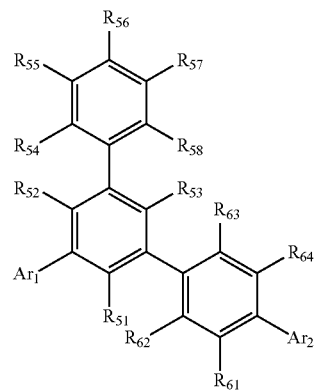
Formula 1-10
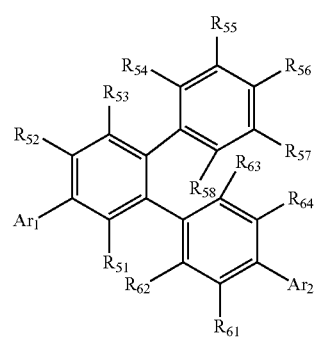
Formula 1-11
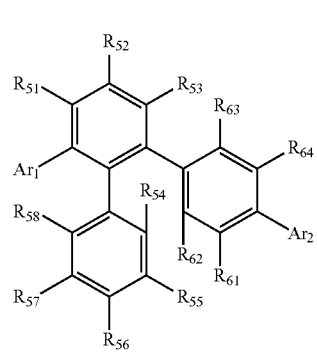
Formula 1-12
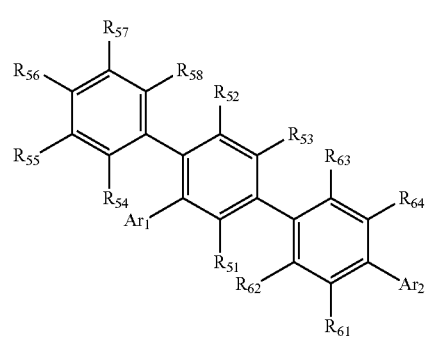

-continued
Formula 1-13
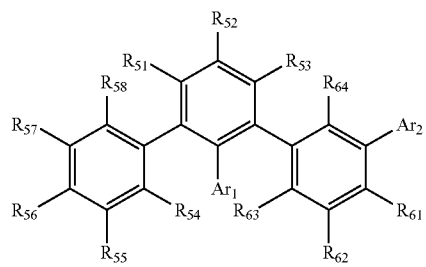
Formula 1-14
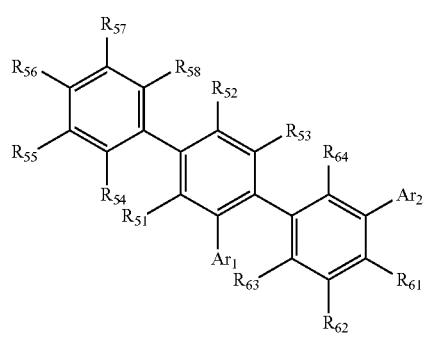
Formula 1-15
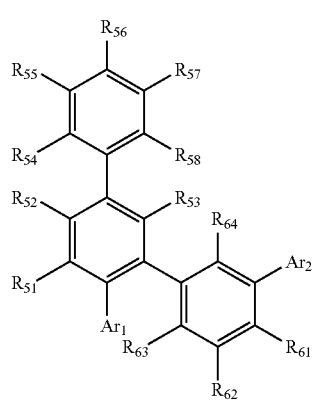
Formula 1-16
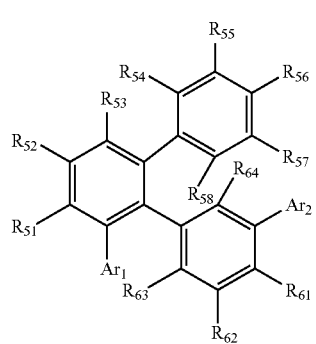
Formula 1-17
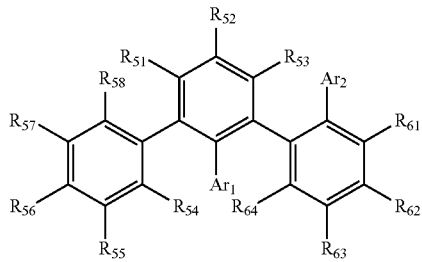
Formula 1-18
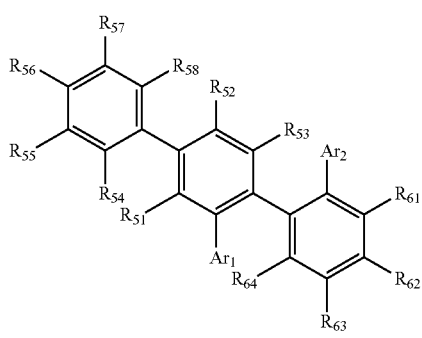
Formula 1-19
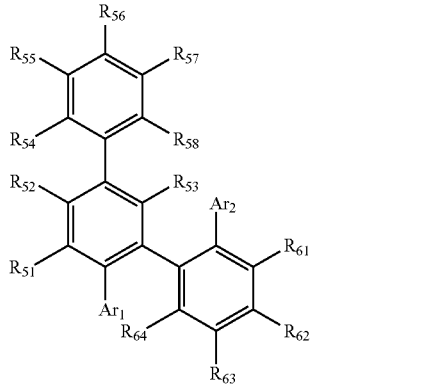
Formula 1-20
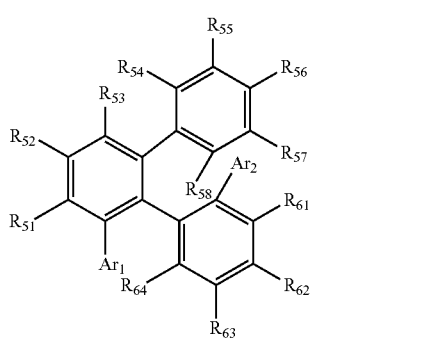
Formula 1-21
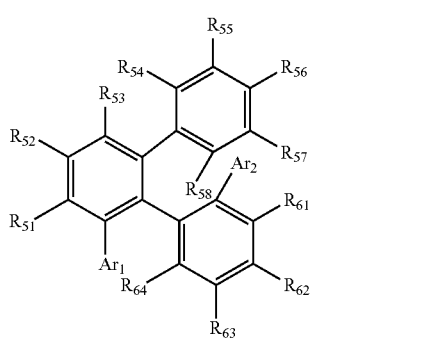

Formula 1-22

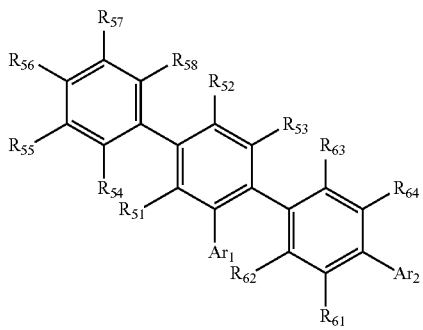

Formula 1-23

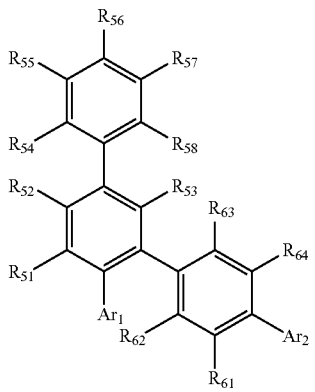

Formula 1-24

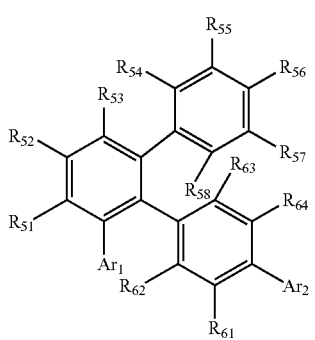

Formula 1-25

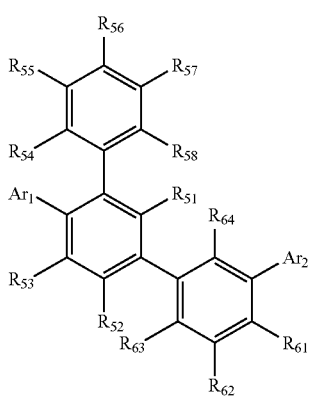

Formula 1-26

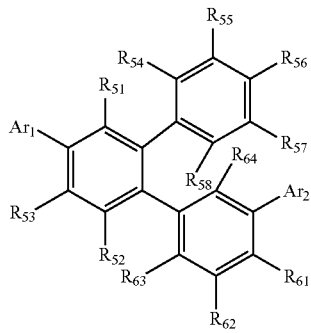

Formula 1-27

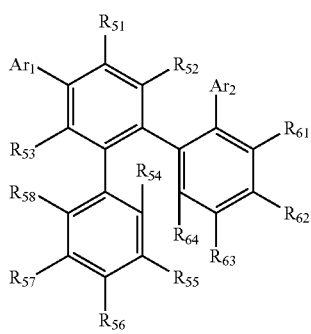

Formula 1-28

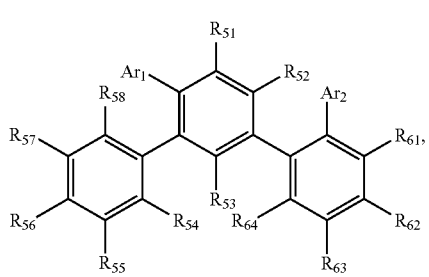

wherein, in Formulae 1-1 to 1-28, $Ar_1$ and $Ar_2$ are the same as described in claim 1, $R_{51}$ to $R_{58}$ and $R_{61}$ to $R_{64}$ are each independently the same as described in connection with $R_{41}$ in claim 1, and the number of cyano group(s) in $R_{51}$ to $R_{58}$ and $R_{61}$ to $R_{64}$ is 1, 2, 3, or 4.

11. The condensed cyclic compound of claim 10, wherein $R_{51}$ to $R_{58}$ and $R_{61}$ to $R_{64}$ are each independently selected from:

hydrogen, deuterium, and a cyano group;

a phenyl group, a biphenyl group, a terphenyl group, a naphthyl group, a fluorenyl group, a dibenzofuranyl group, and a dibenzothiophenyl group; and a phenyl group, a biphenyl group, a terphenyl group, a naphthyl group, a fluorenyl group, a dibenzofuranyl group, and a dibenzothiophenyl group, each substituted with at least one selected from deuterium, a cyano group, a phenyl group, a biphenyl group, a terphenyl group, and a naphthyl group.

12. The condensed cyclic compound of claim 10, wherein one, two, three, or four selected from $R_{51}$ to $R_{58}$ and $R_{61}$ to $R_{64}$ are each independently selected from:

a cyano group; and a phenyl group, a biphenyl group, and a terphenyl group, each substituted with at least one cyano group.

13. The condensed cyclic compound of claim 10, wherein one, two, three, or four selected from $R_{51}$ to $R_{58}$ and $R_{61}$ to $R_{64}$ are a cyano group.
14. A condensed cyclic compound selected from Compounds 1 to 260:
1
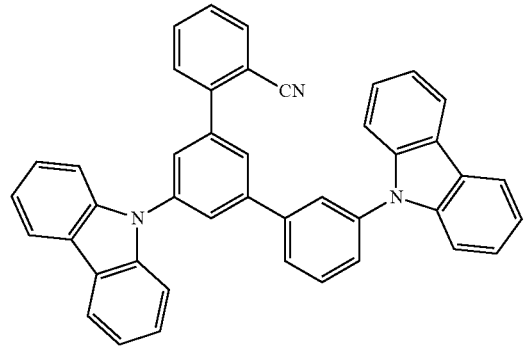
2
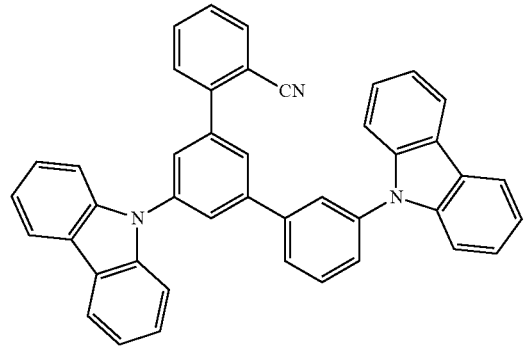
3
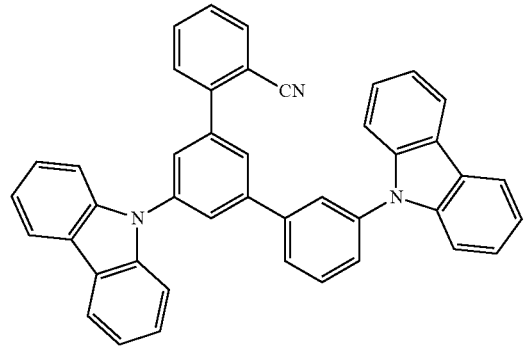
4
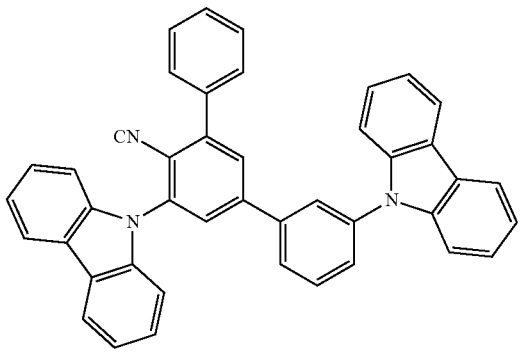
5
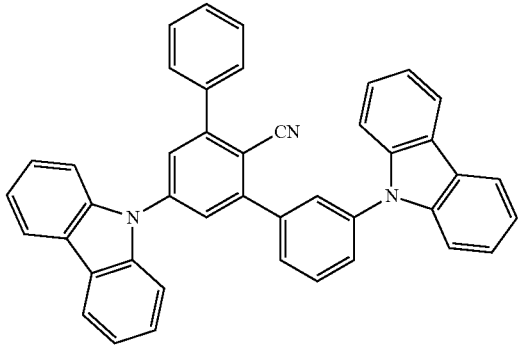
6
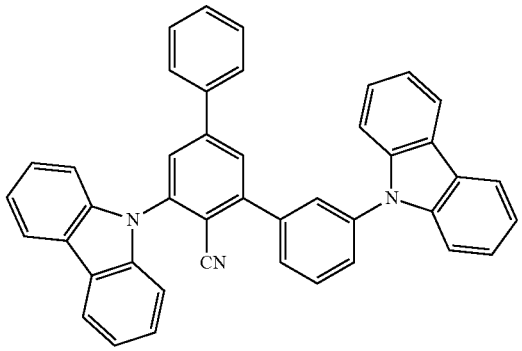
7
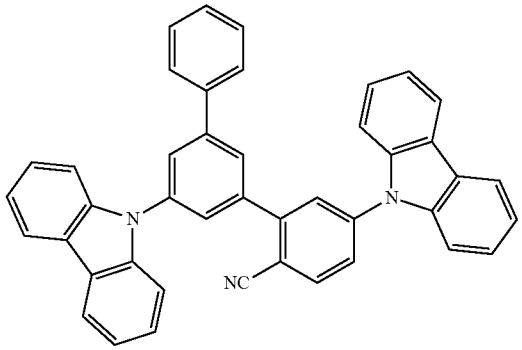

8
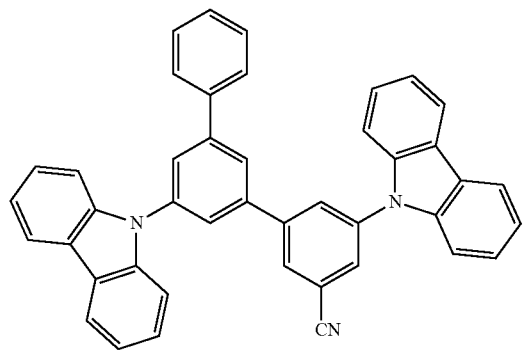
9
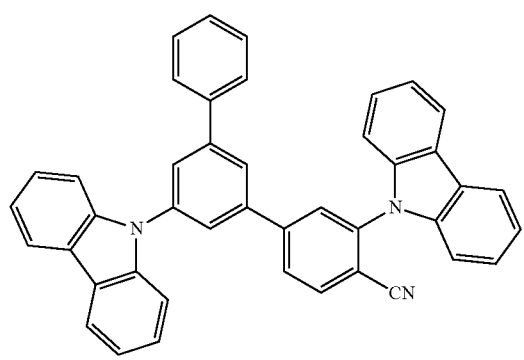
10
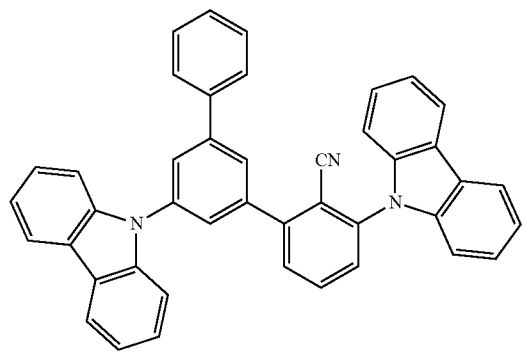
11
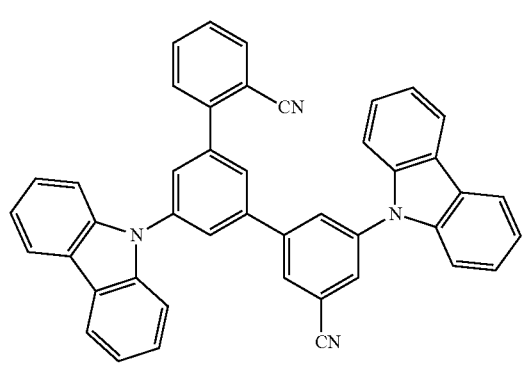
12
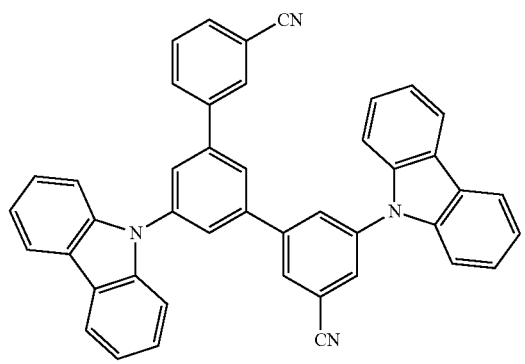
13
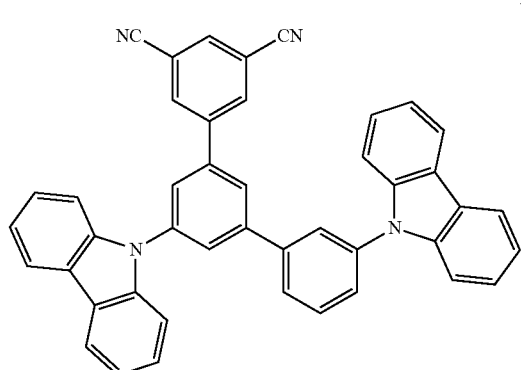
14
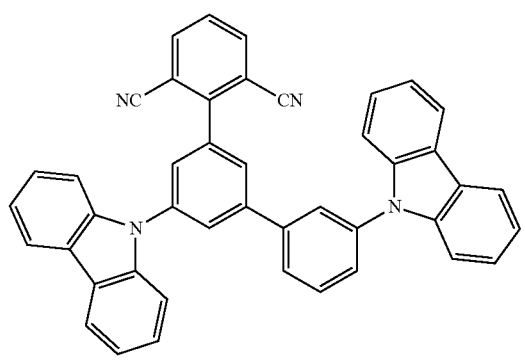
15
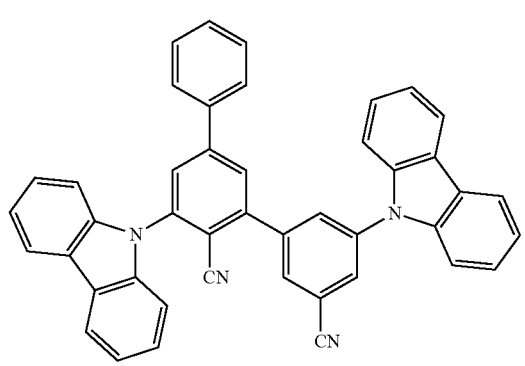

16
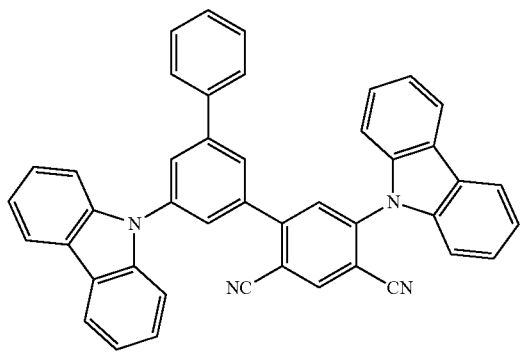
17
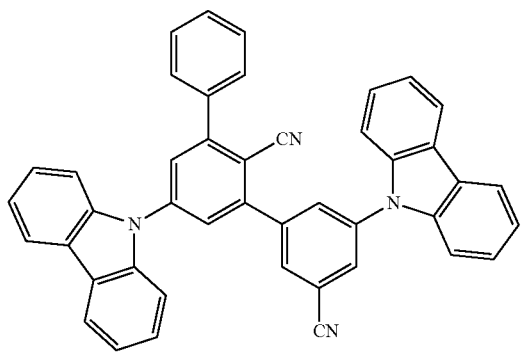
18
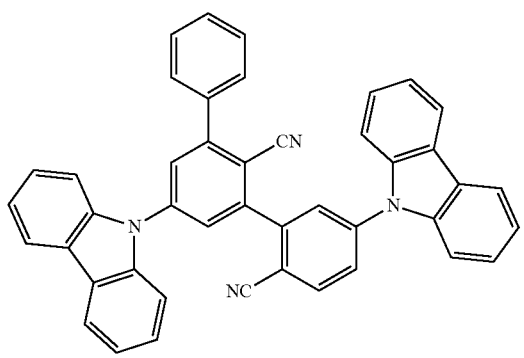
19
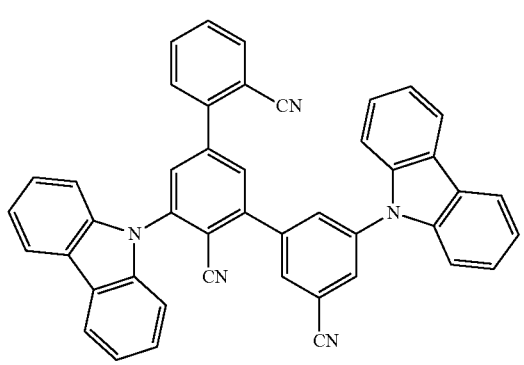
20
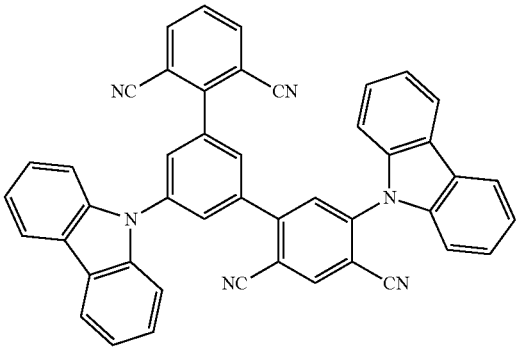
21
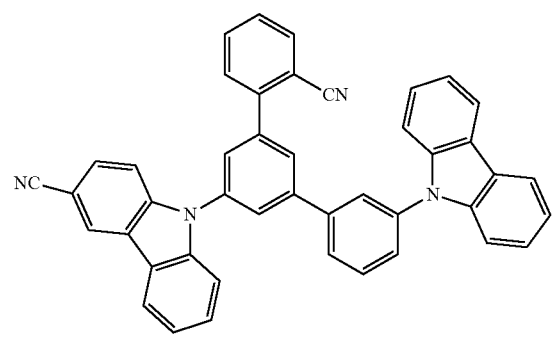
22
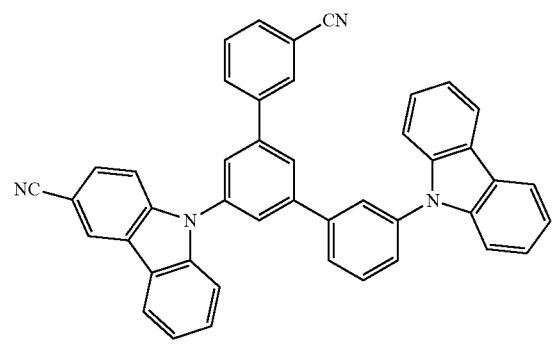
23
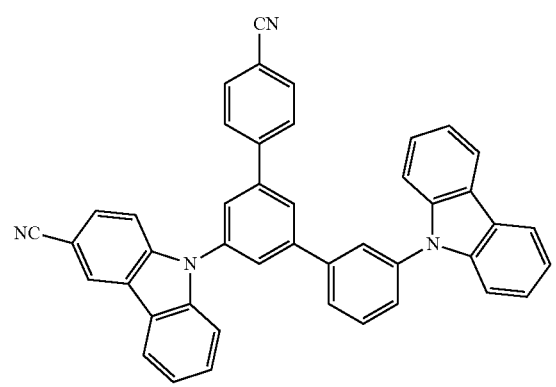

24
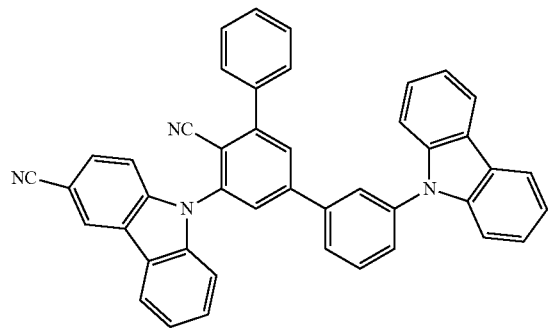
25
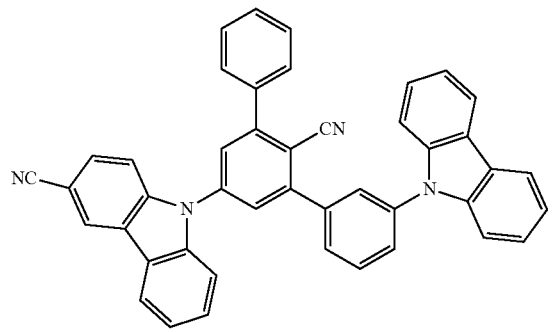
26
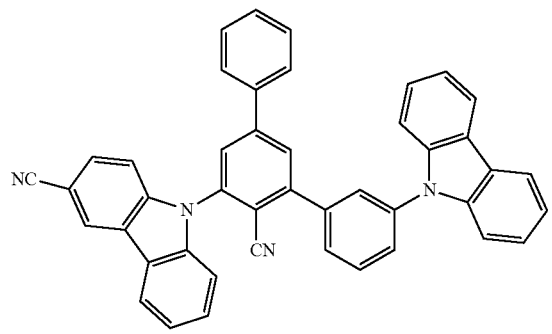
27
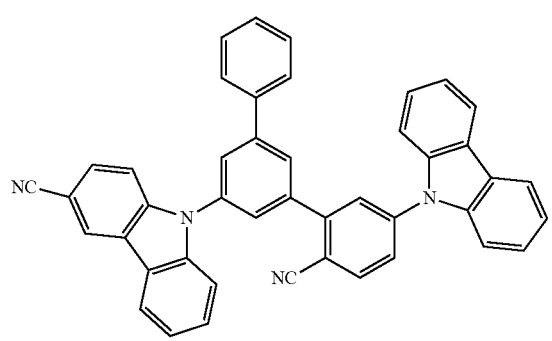
28
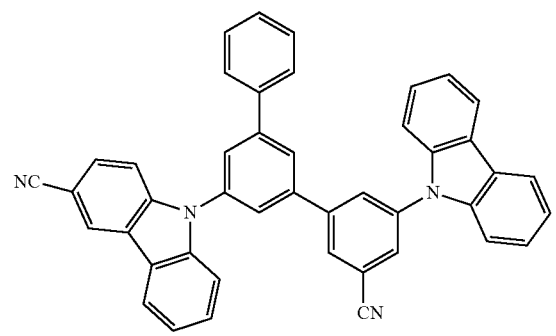
29
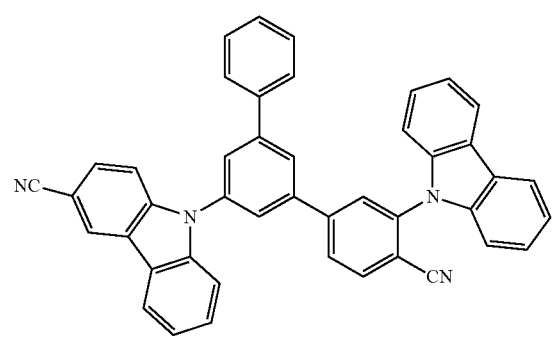
30
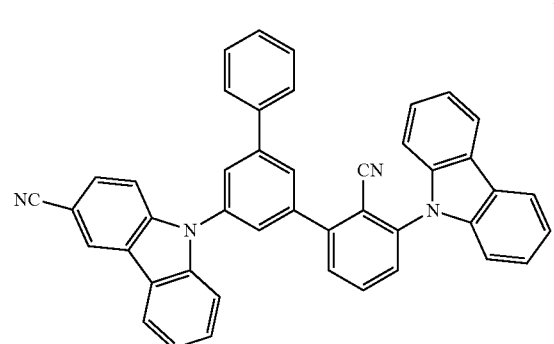
31
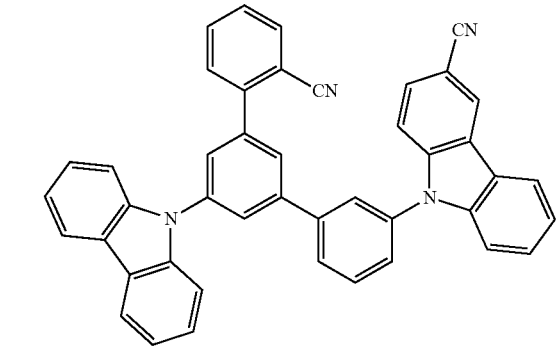

32
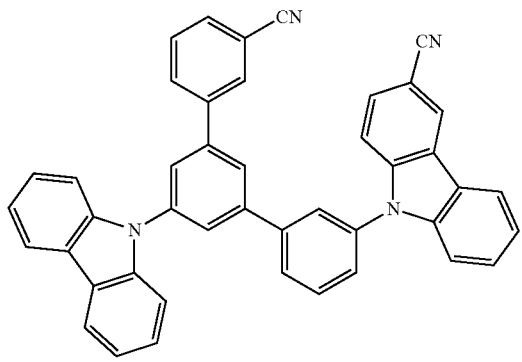
33
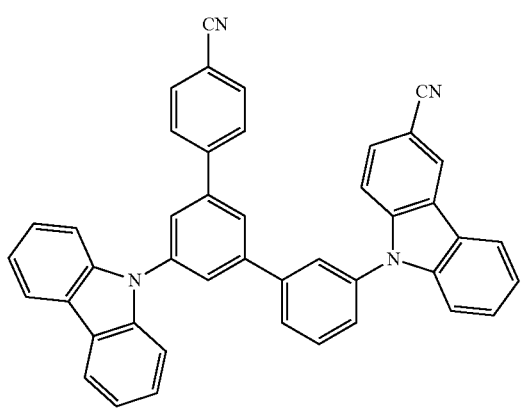
34
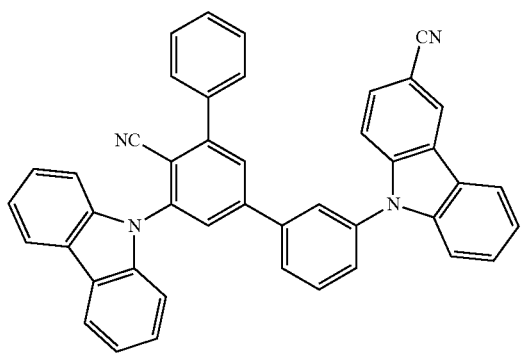
35
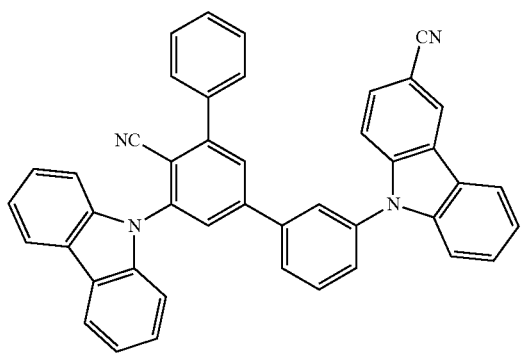
36
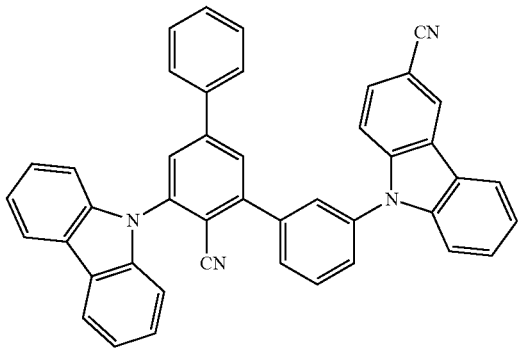
37
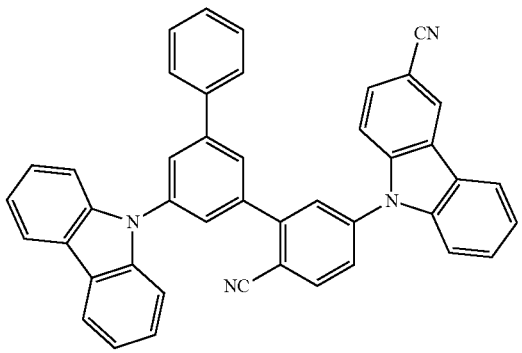
38
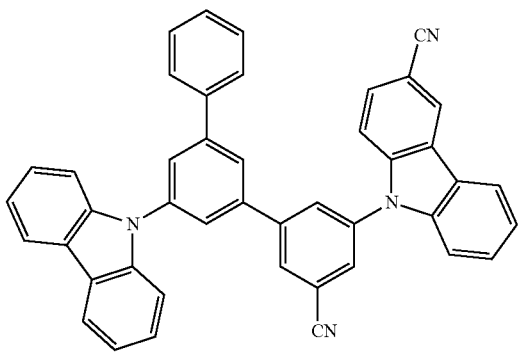
39
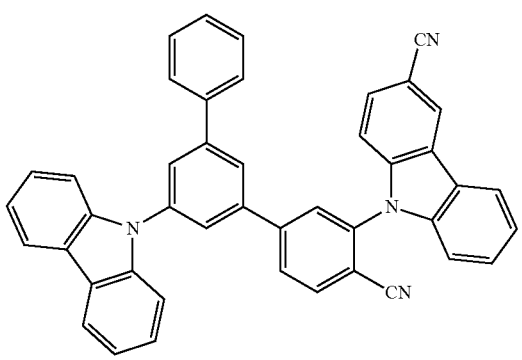

40
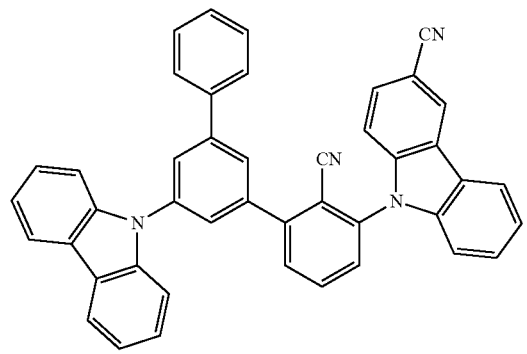
41
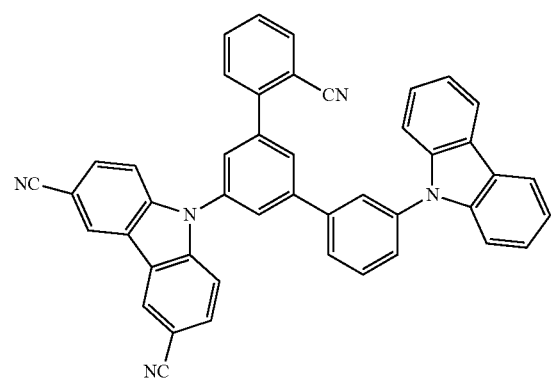
42
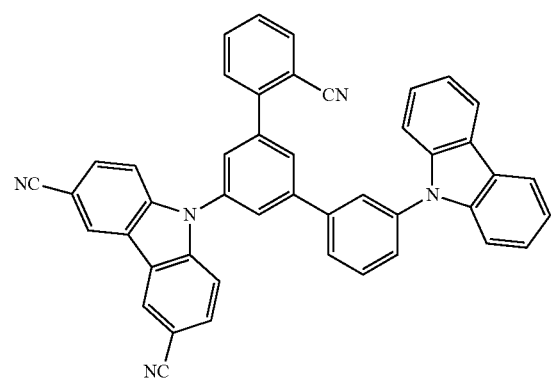
43
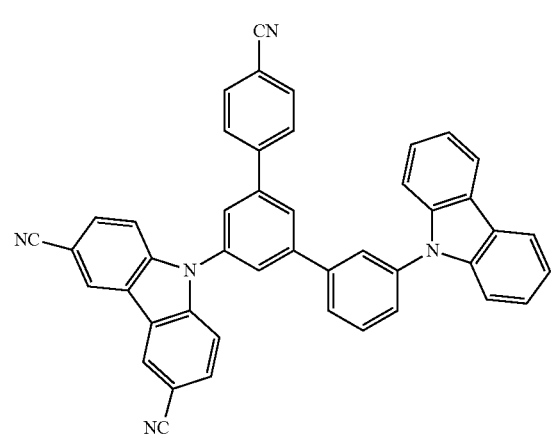
44
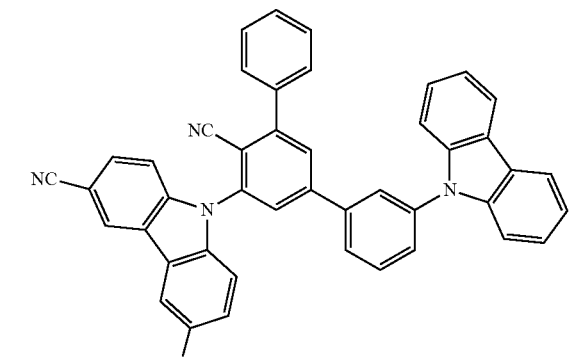
45
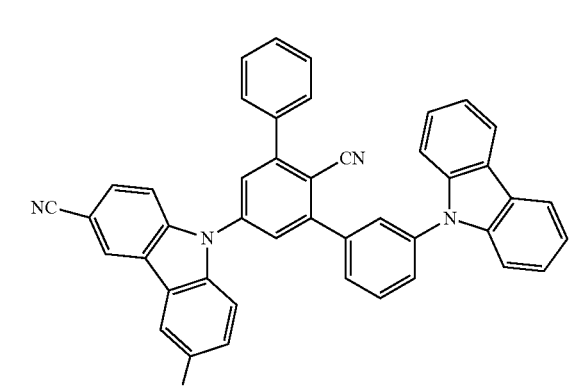
46
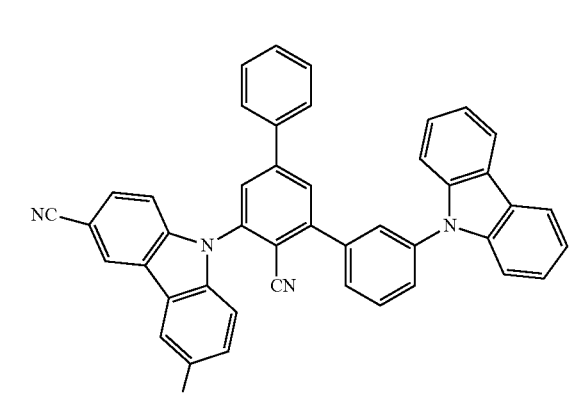
47
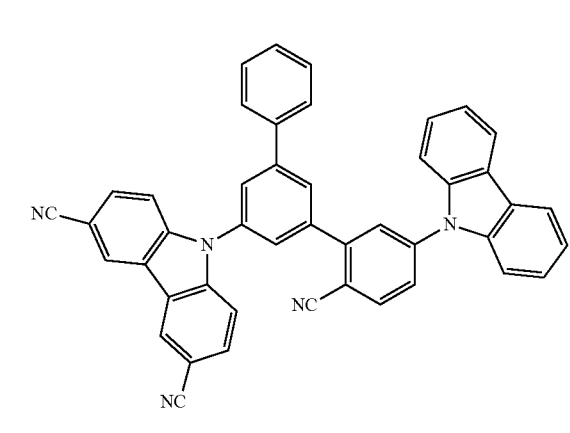

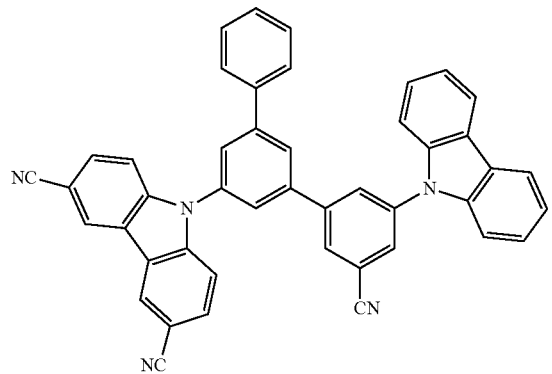
48
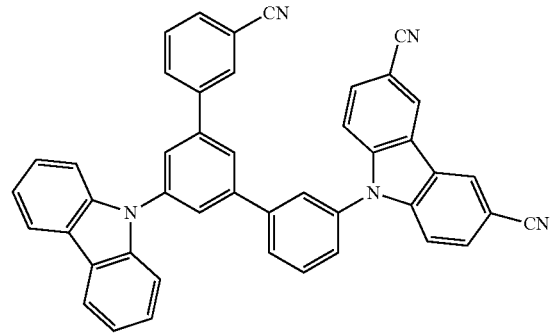
52
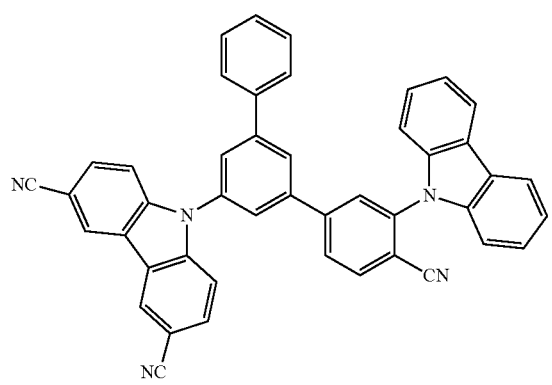
49
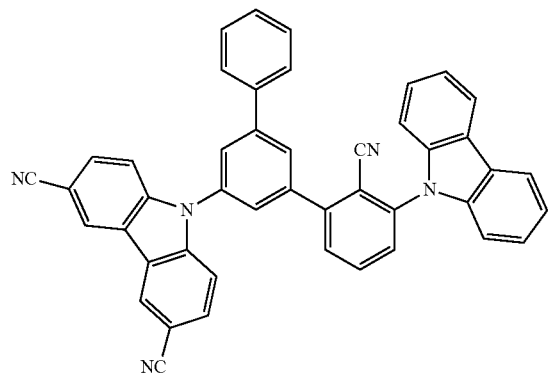
50
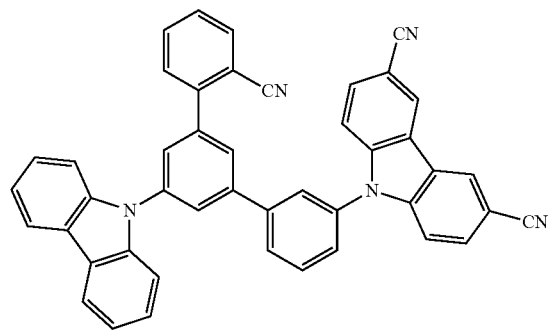
51
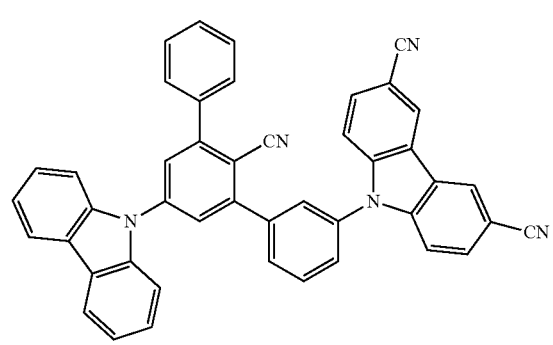
55

56
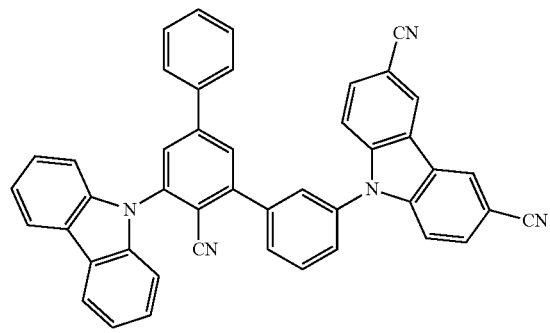
57
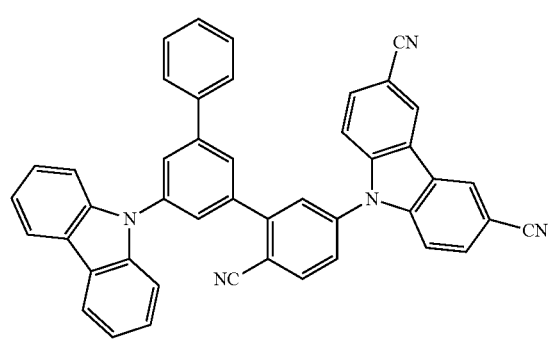
58
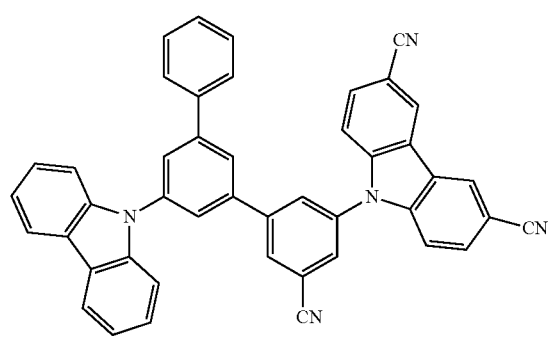
59
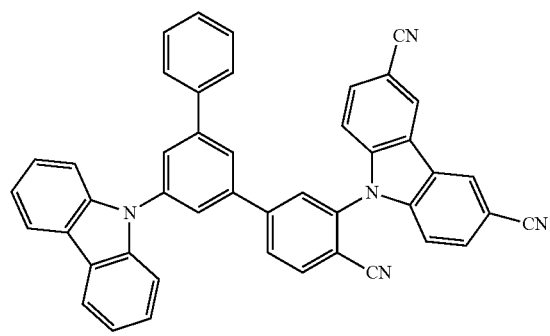
60
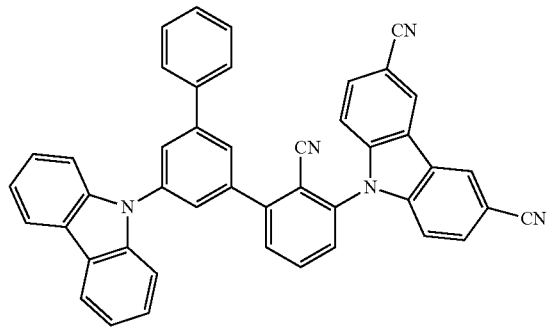
61
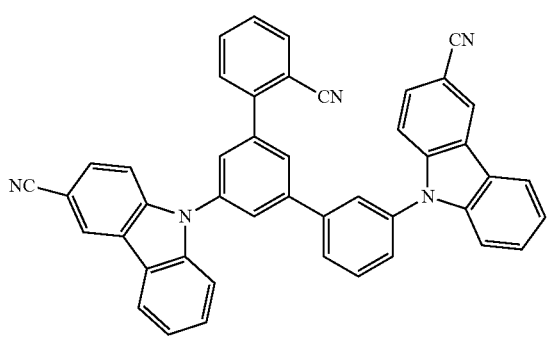
62
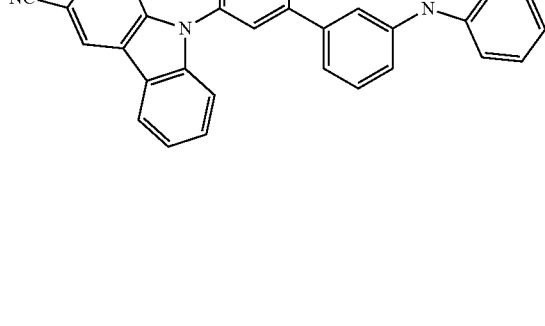
63
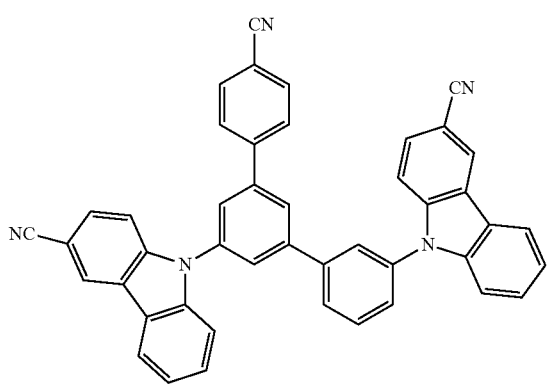

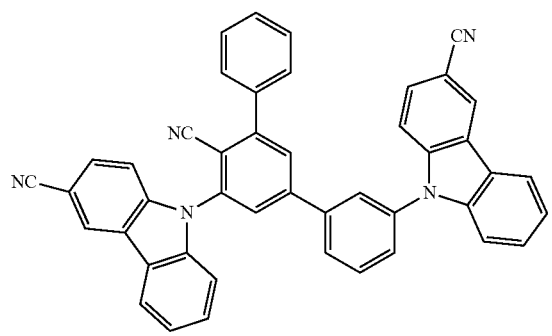
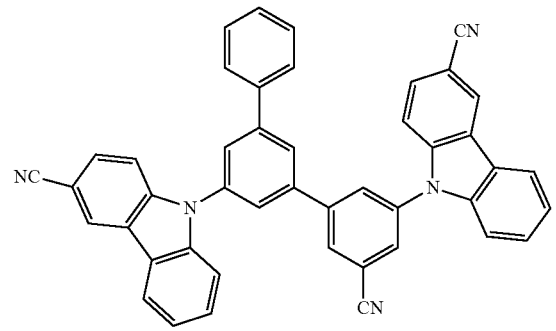
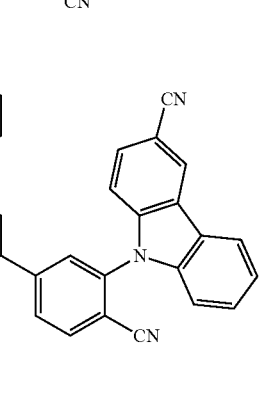
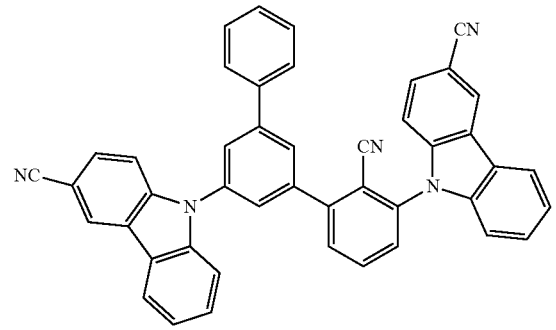
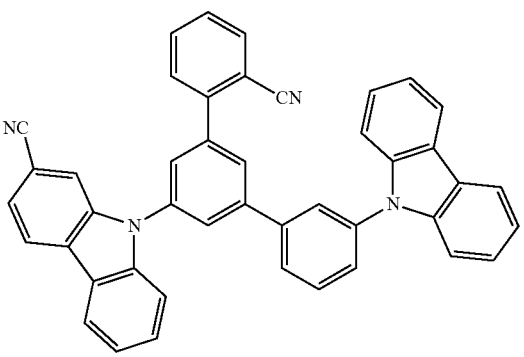

-continued
72
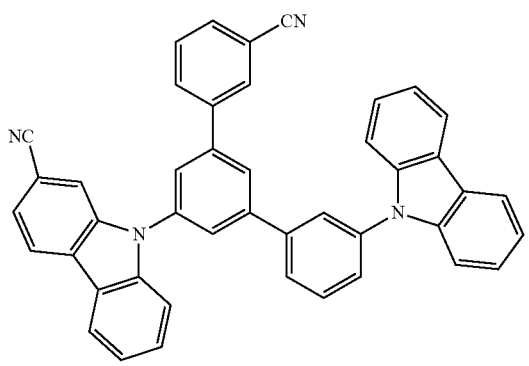
73
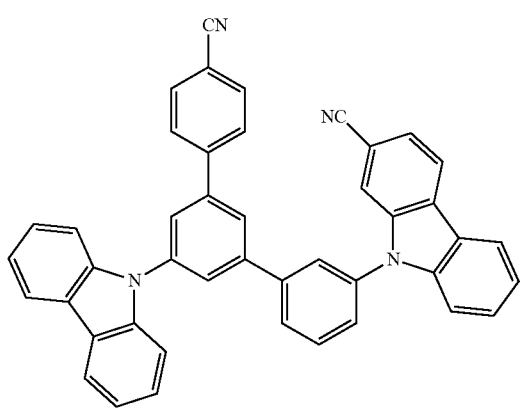
74
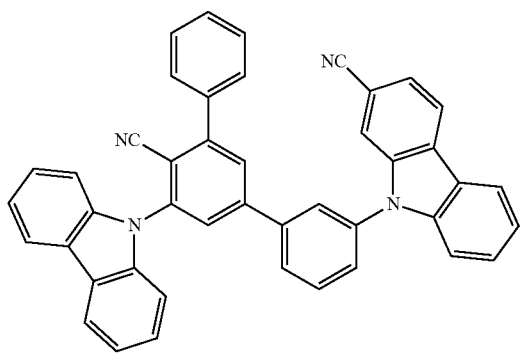
75
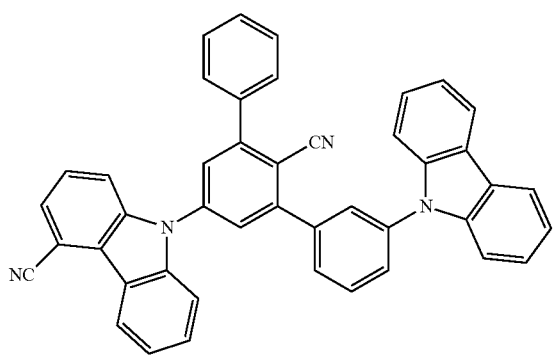
-continued
76
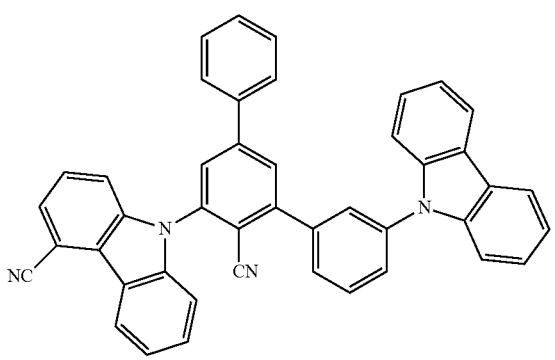
77
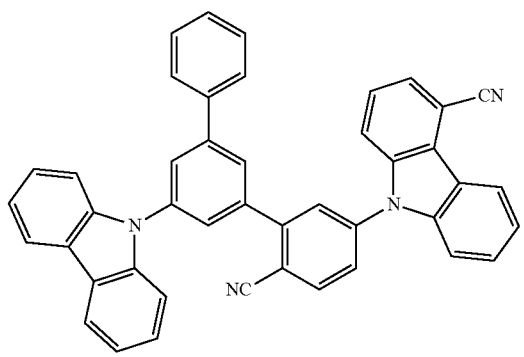
78
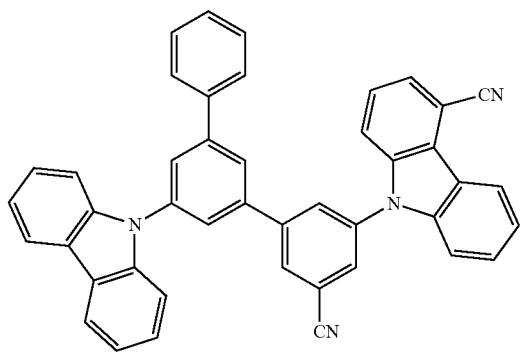
79
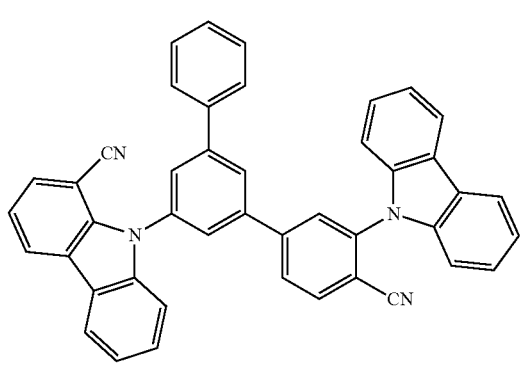

80
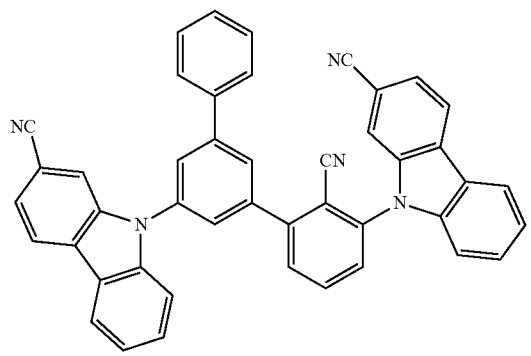
81
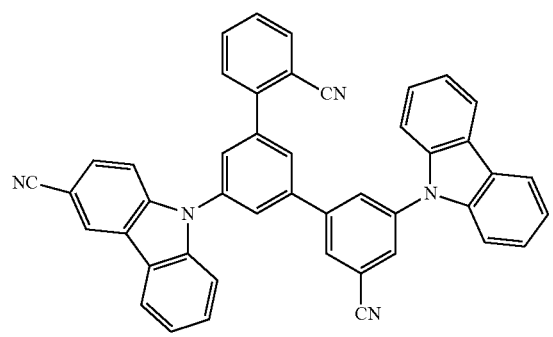
82
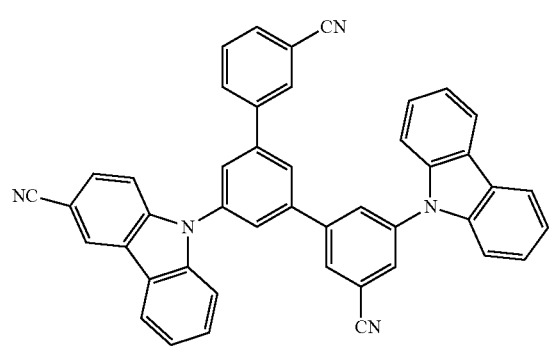
83
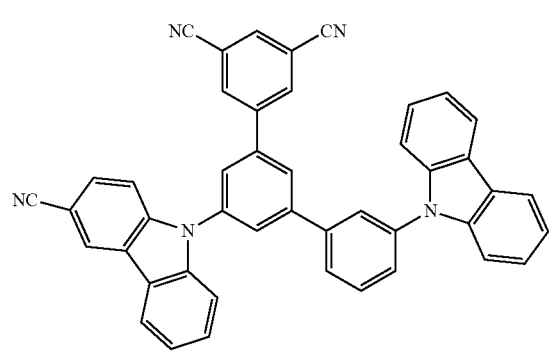
84
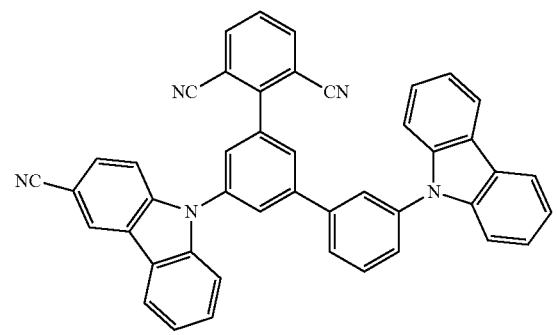
85
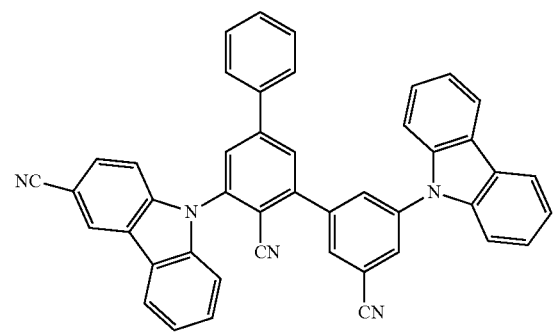
86
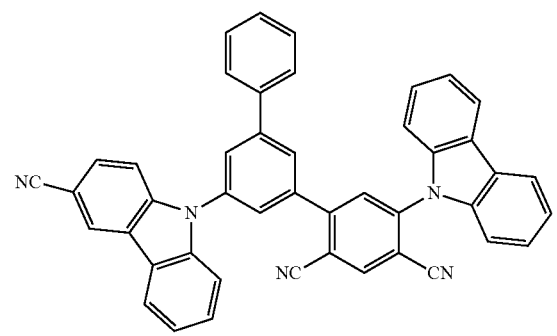
87
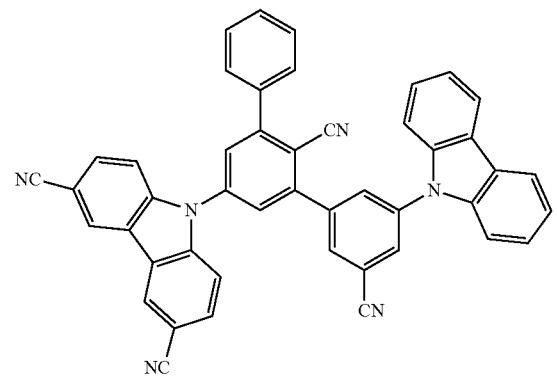

88
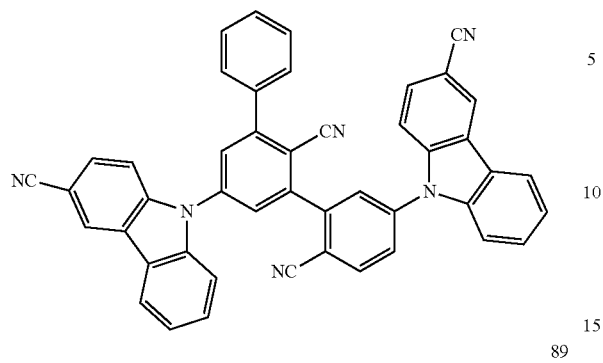
89
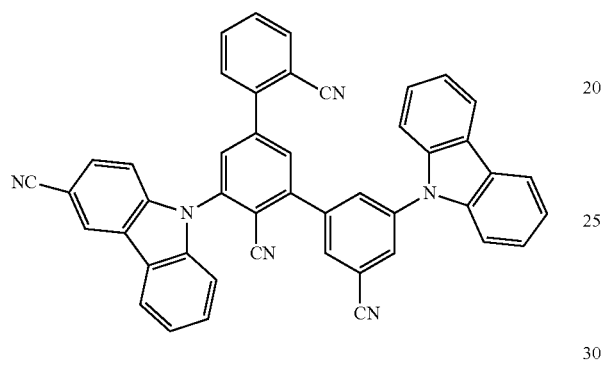
90
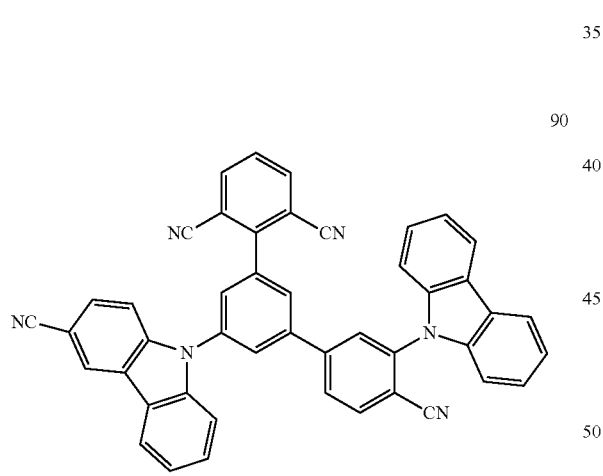
91
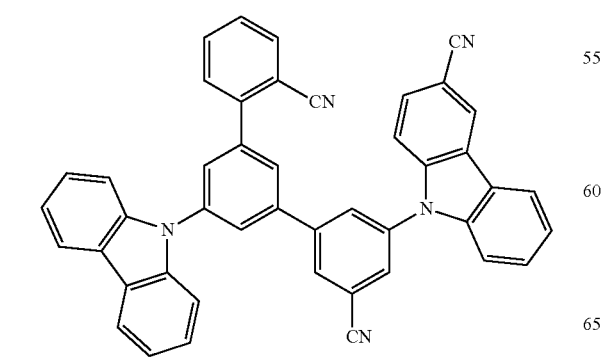
92
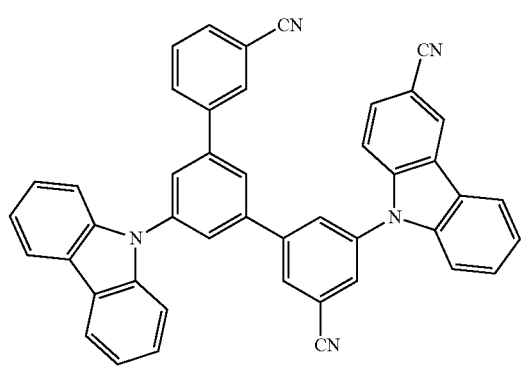
93
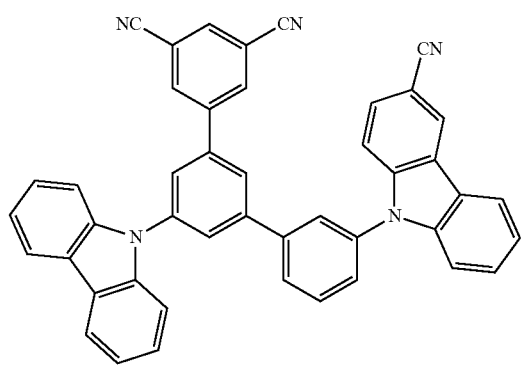
94
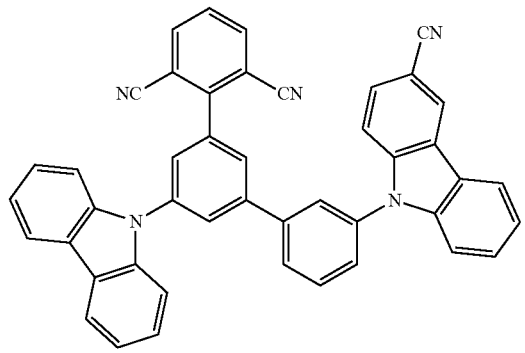
95
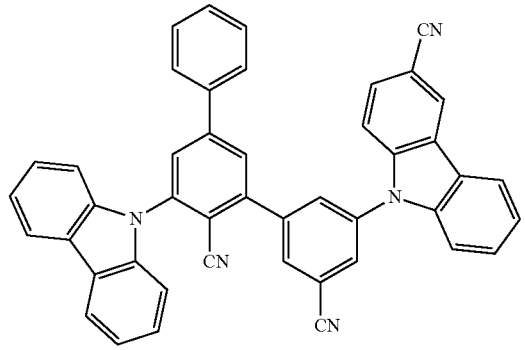

-continued
96
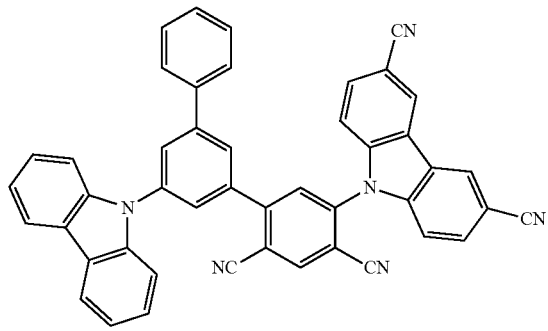
97
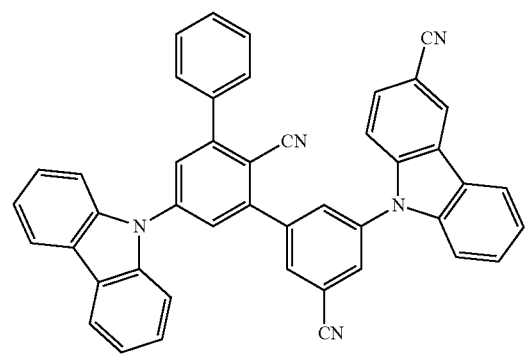
98
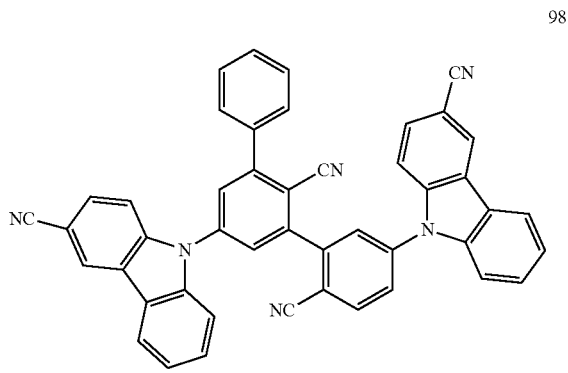
99
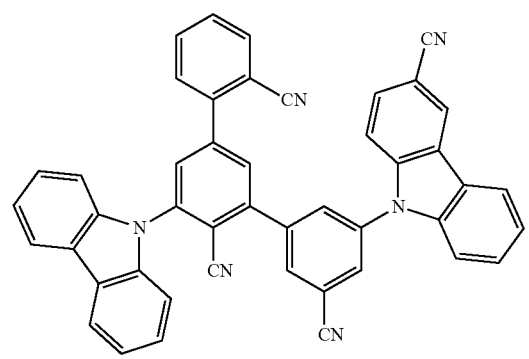
-continued
100
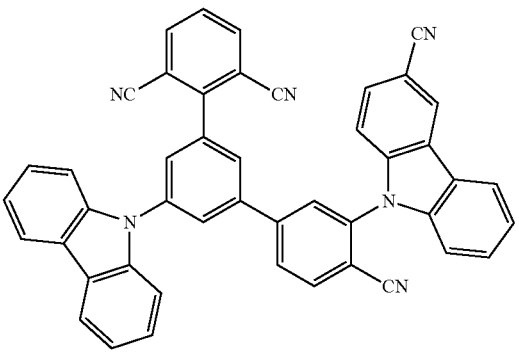
101
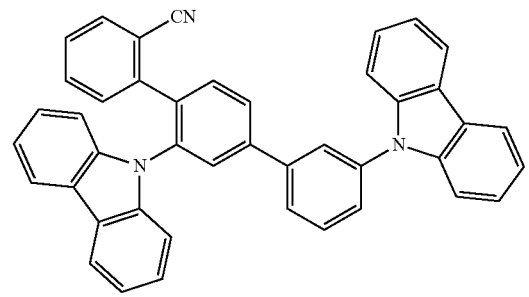
102
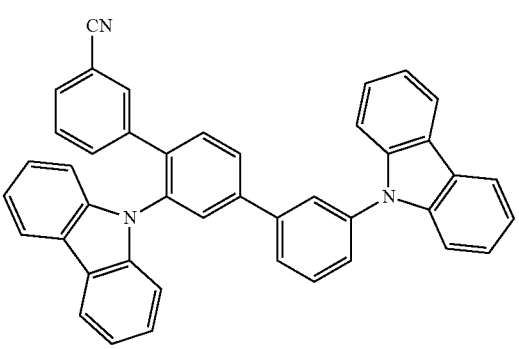
103

-continued
104
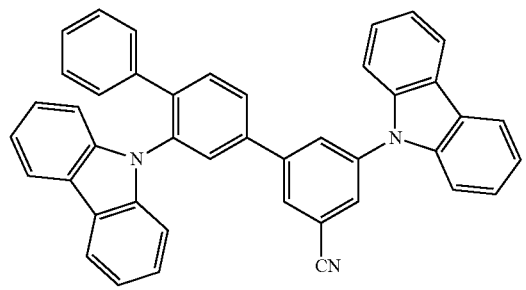
105
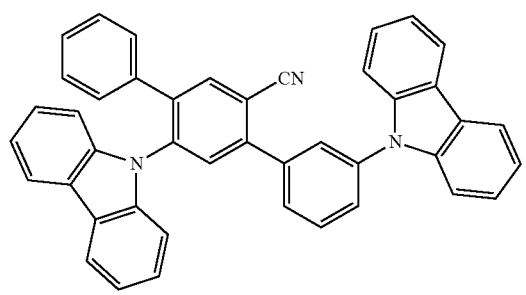
106
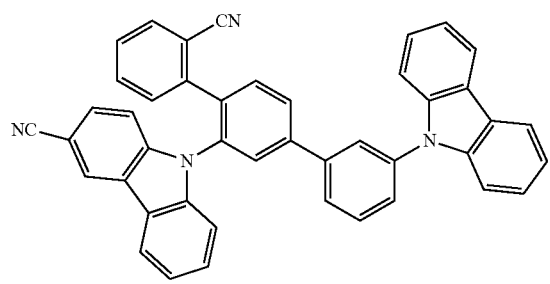
107
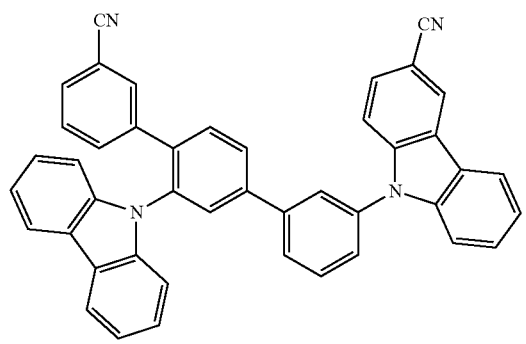
108
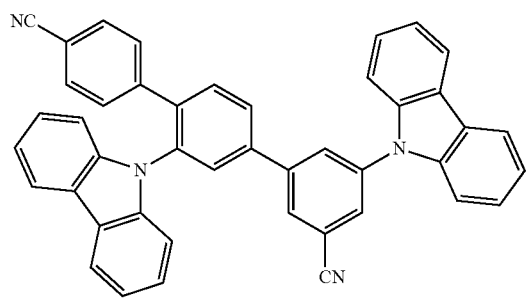
-continued
109
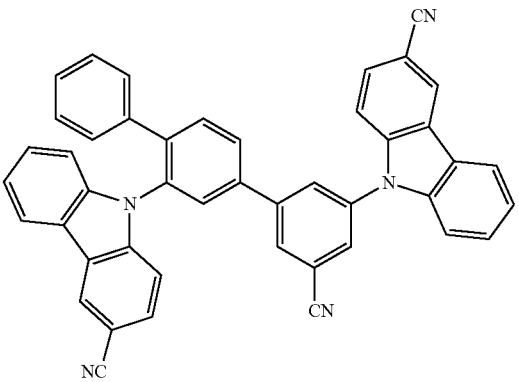
110
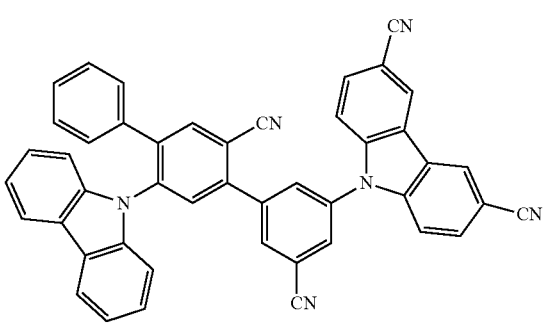
111
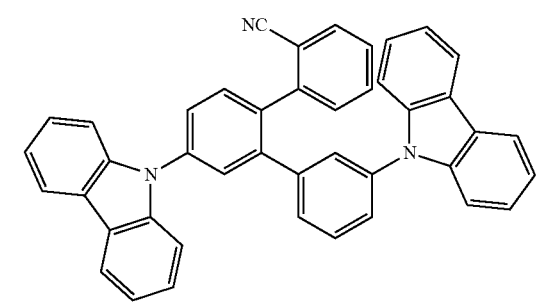
112
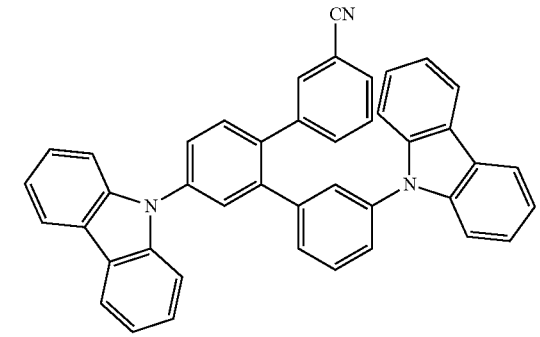

-continued
113
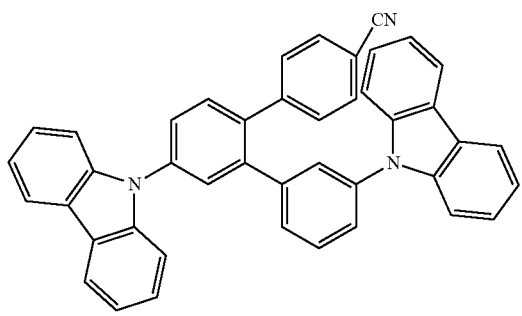
114
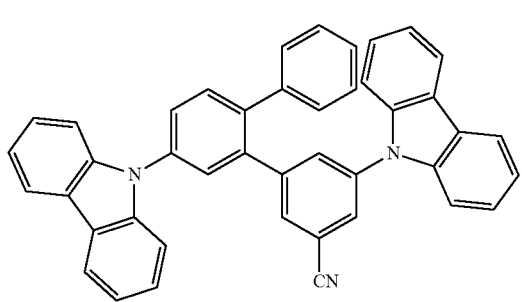
115
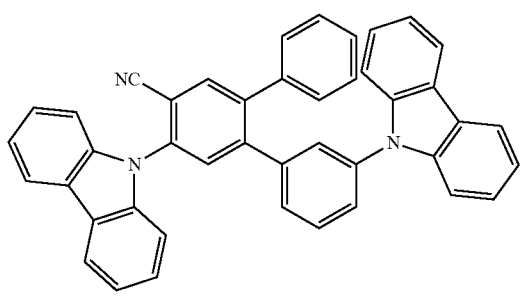
116
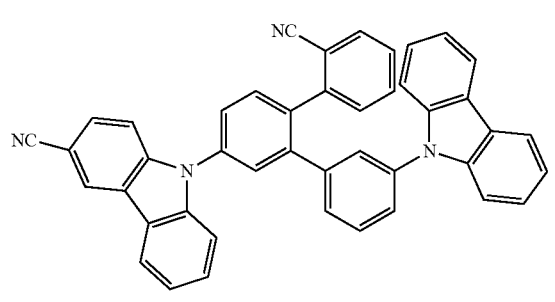
117
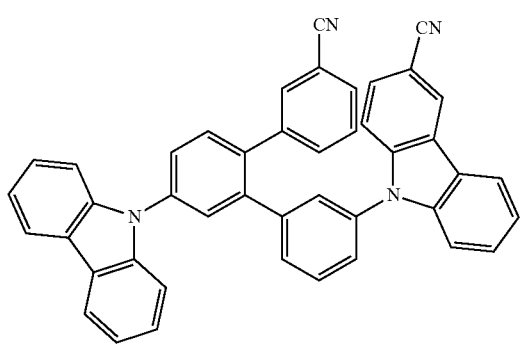
-continued
118
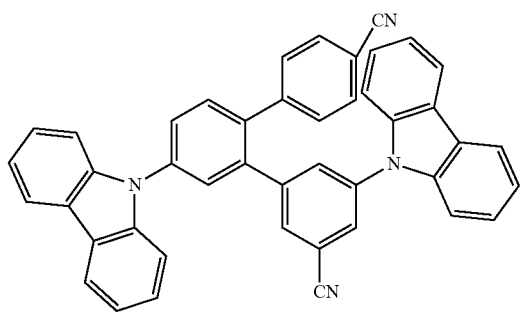
119
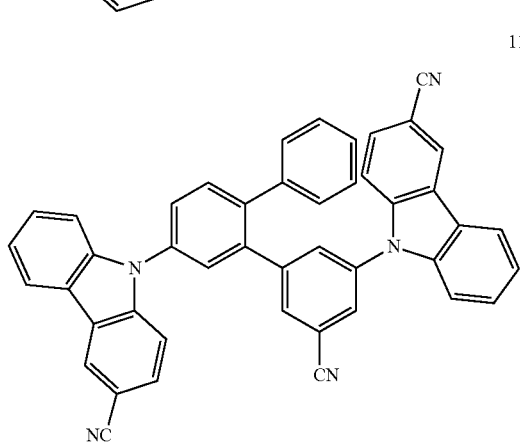
120
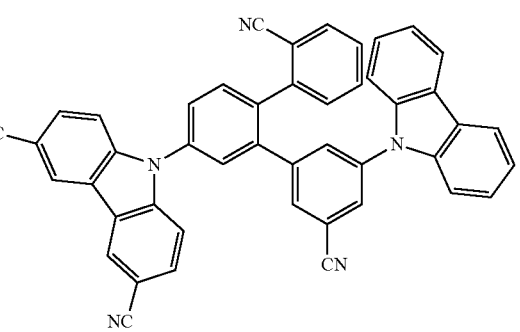
121
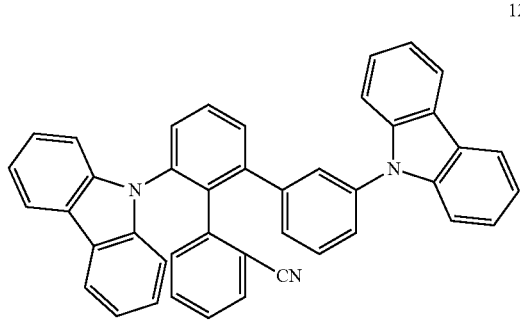

122
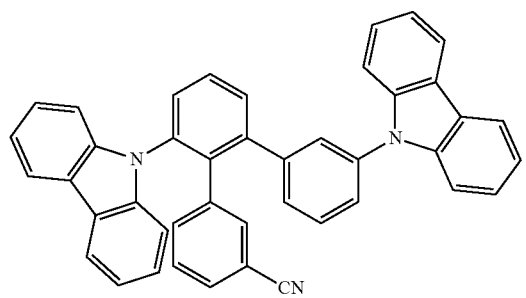
123
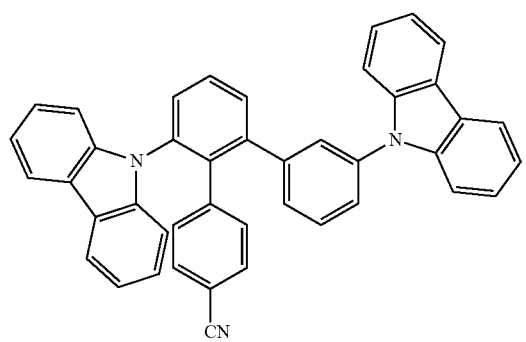
124
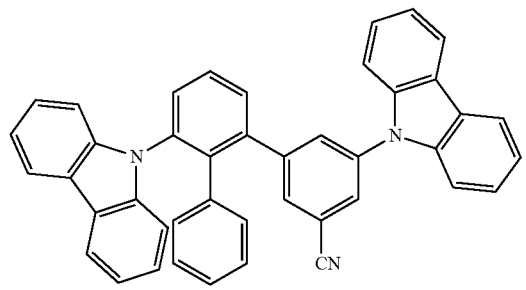
125
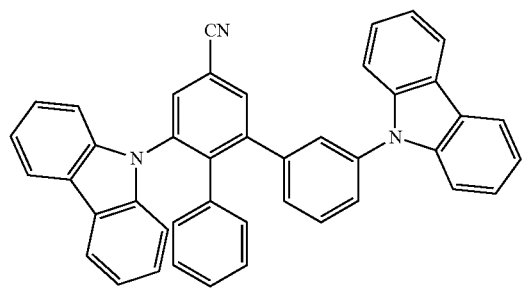
126
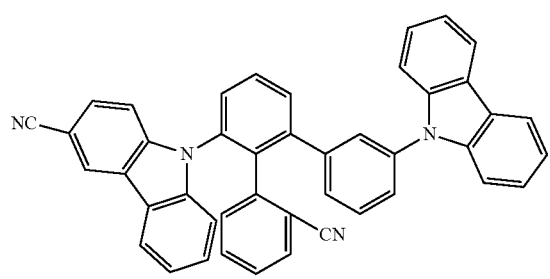
127
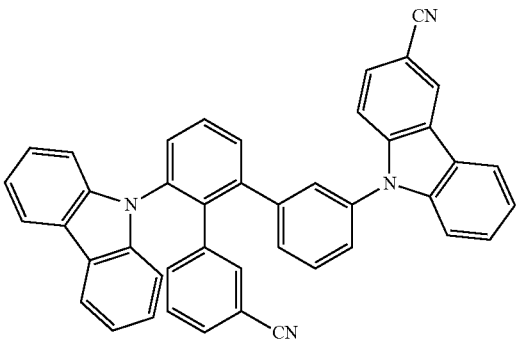
128
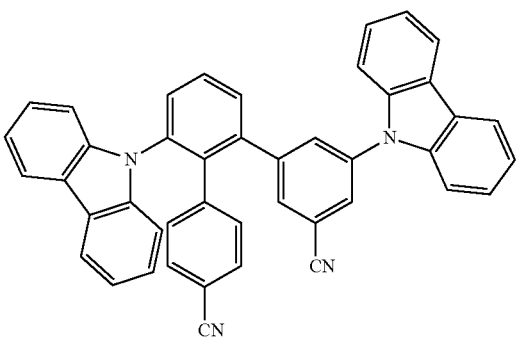
129
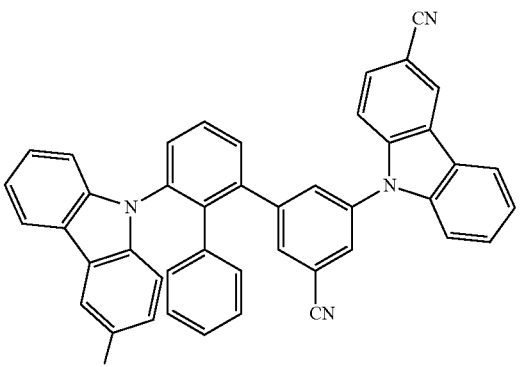
130
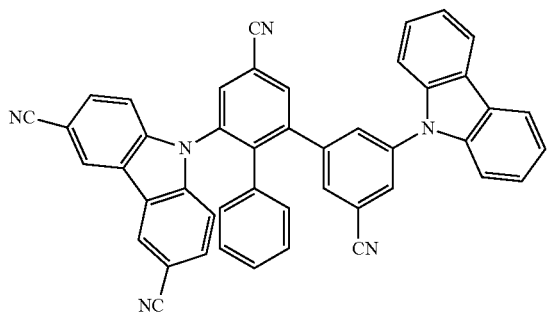

-continued
131
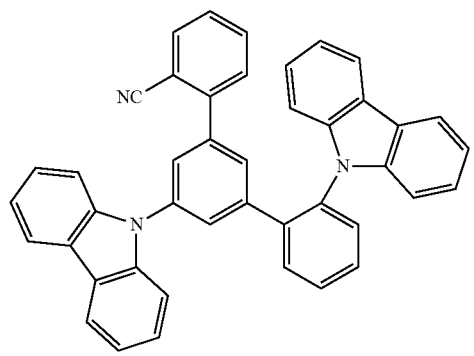
132
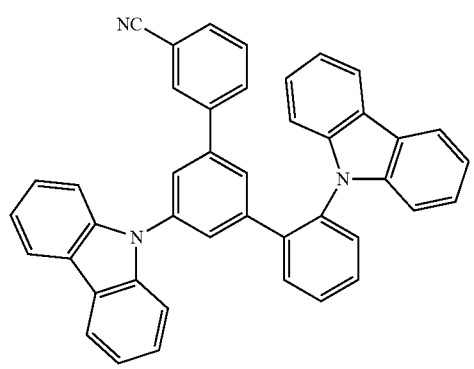
133
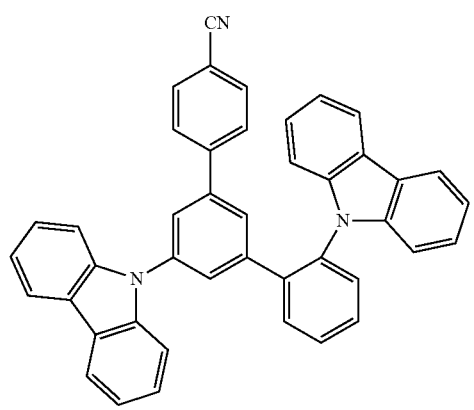
134
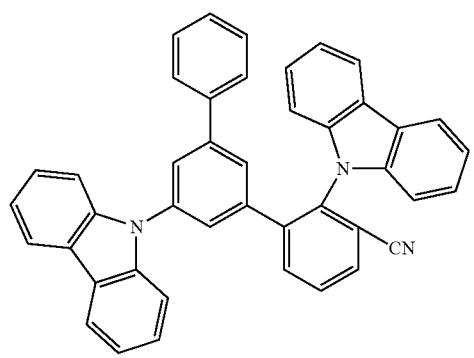
-continued
135
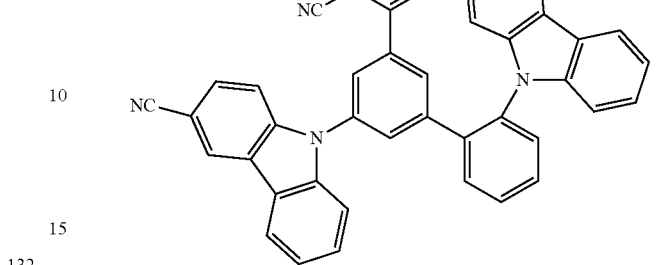
136
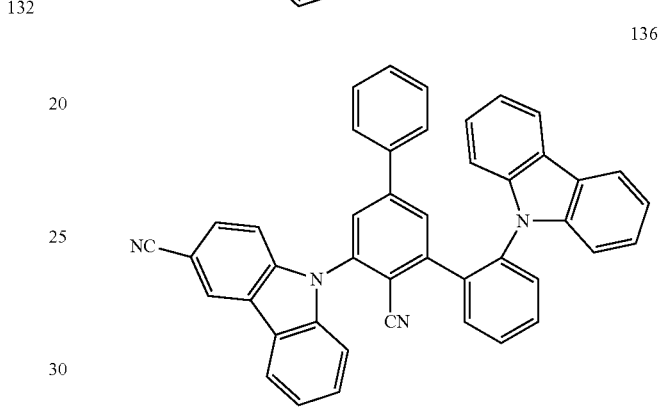
137
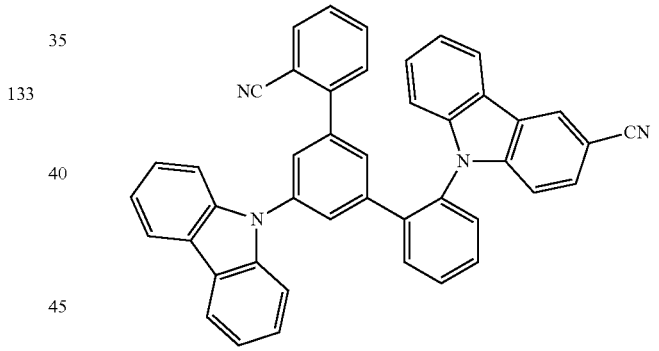
138
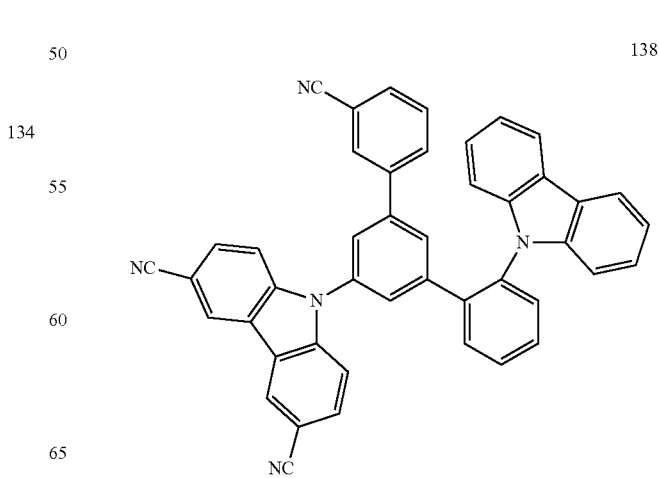

139
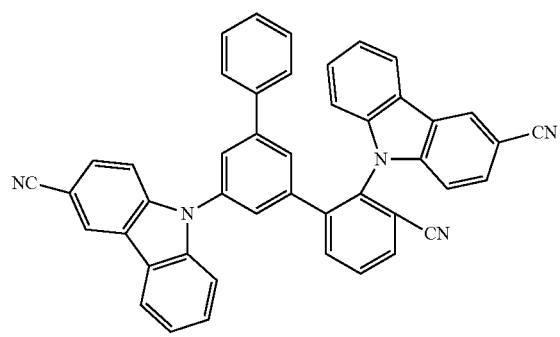
140
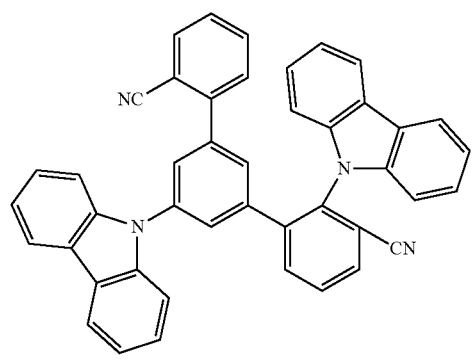
141
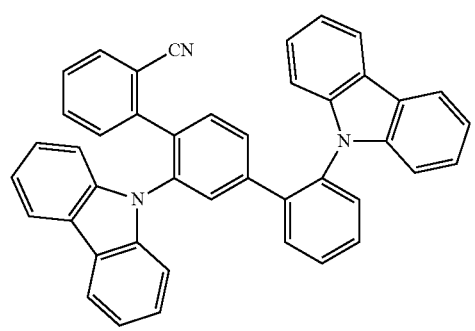
142
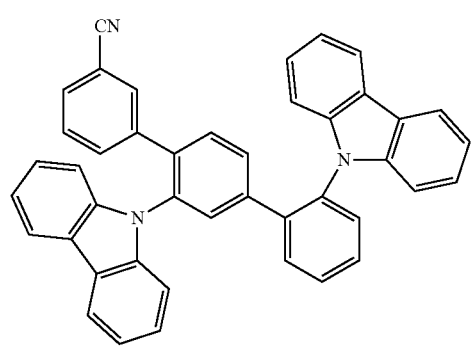
143
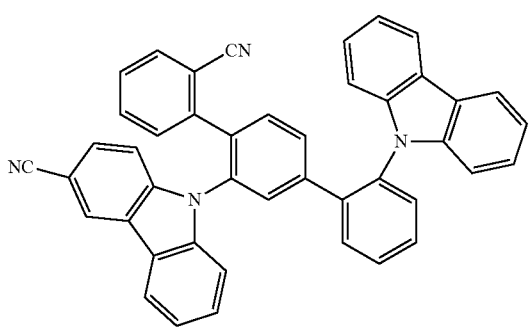
144
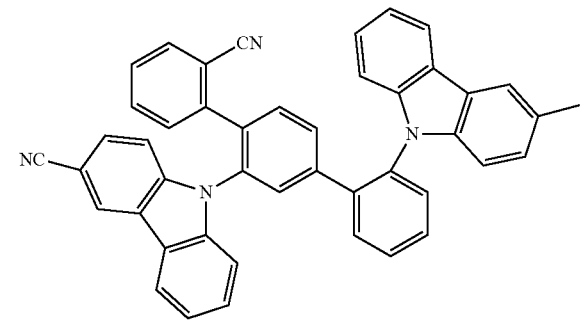
145
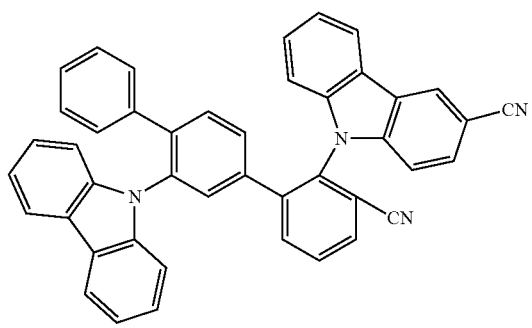
146
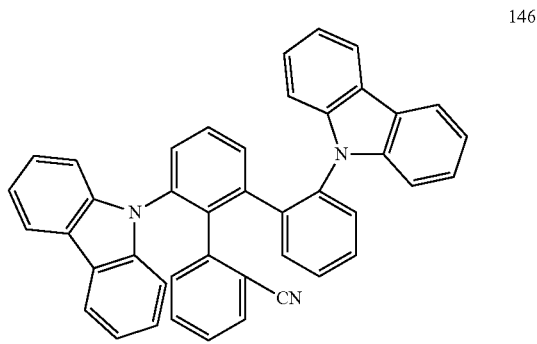

-continued
147
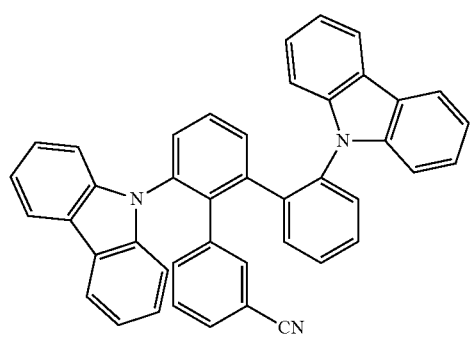
148
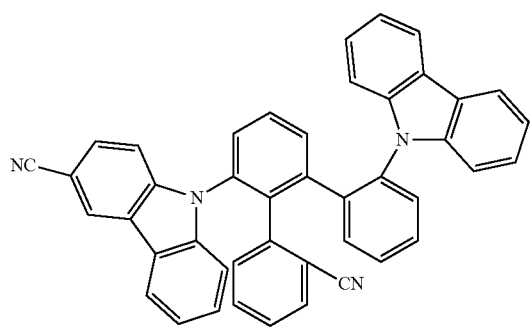
149
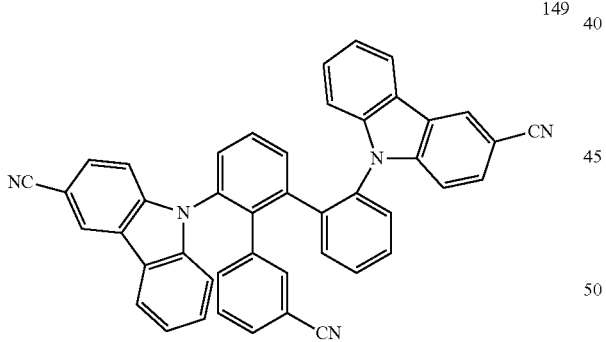
150
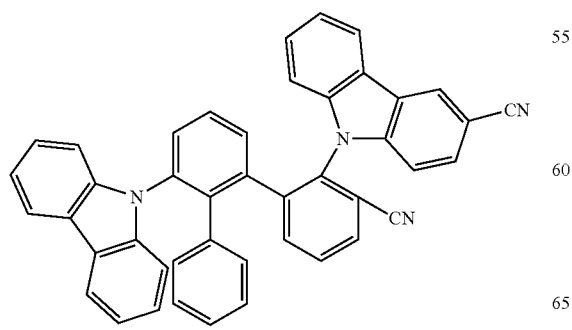
-continued
151
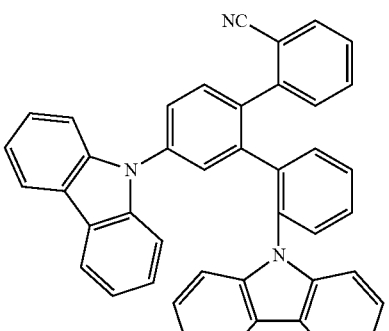
152
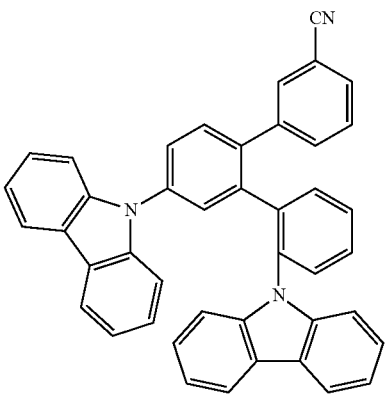
153
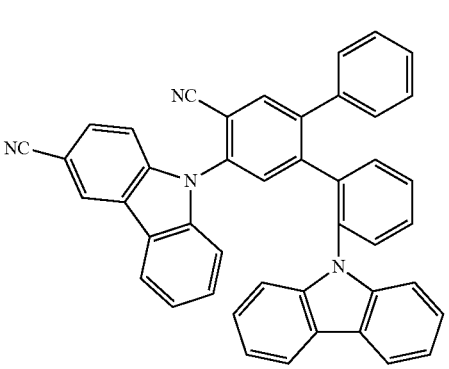
154
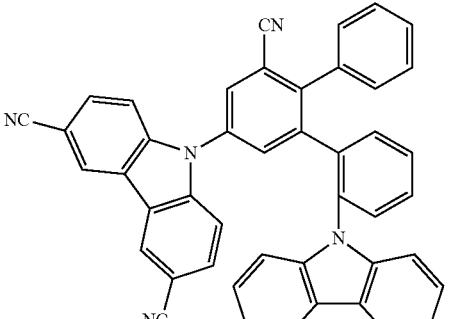

-continued
155
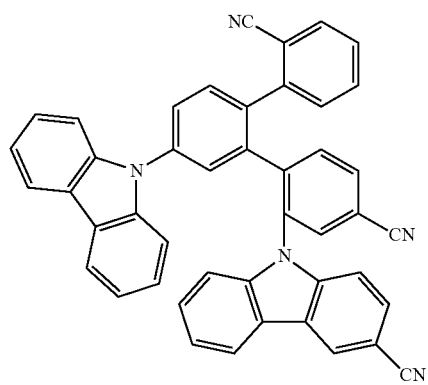
156
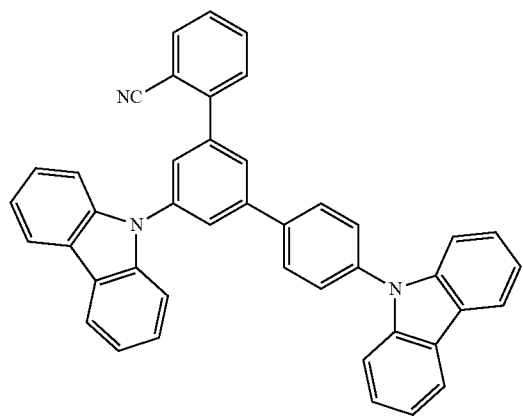
157
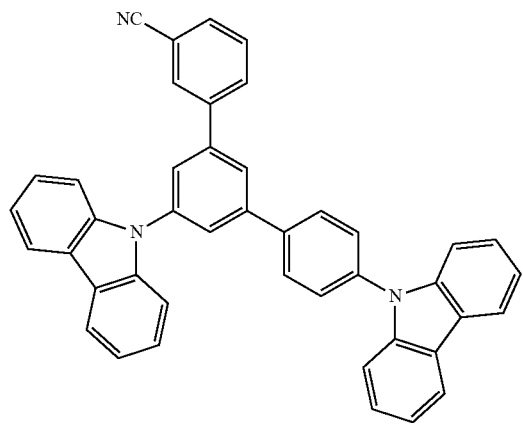
-continued
158
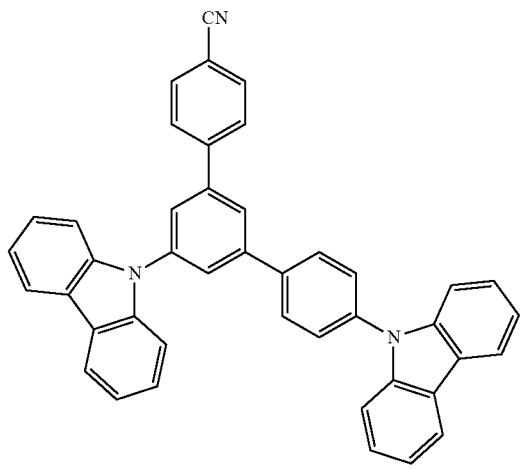
159
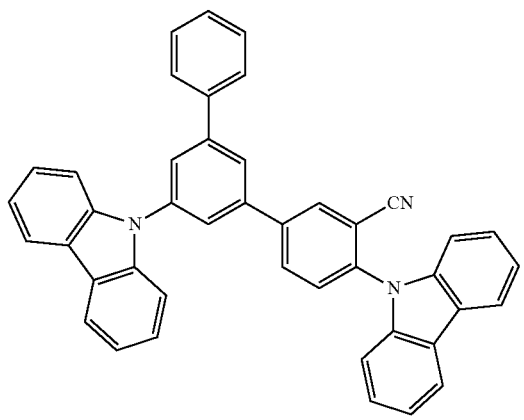
160
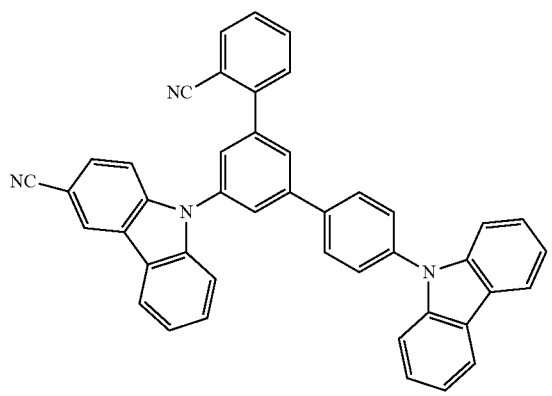

201
-continued
161
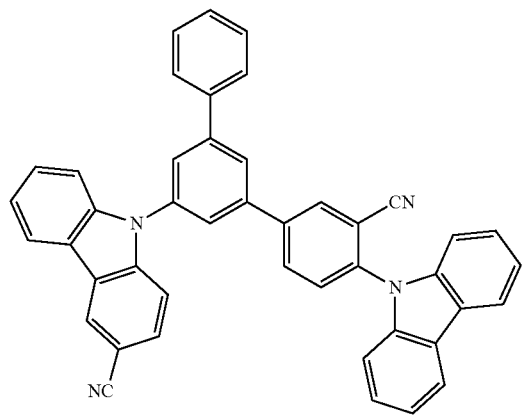
162
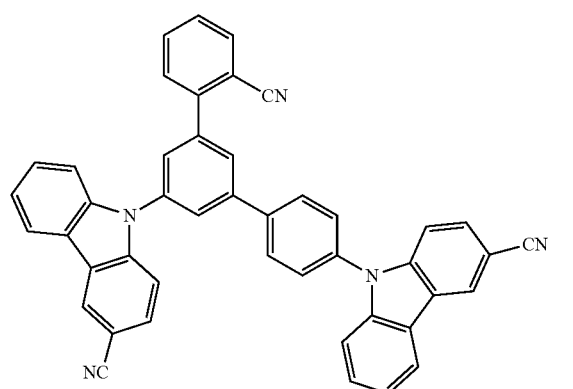
163
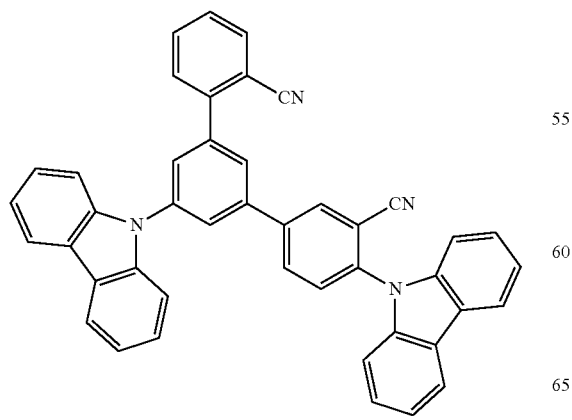
202
-continued
164
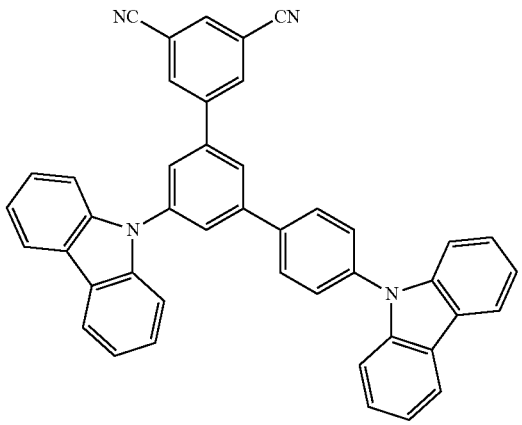
165
166

167
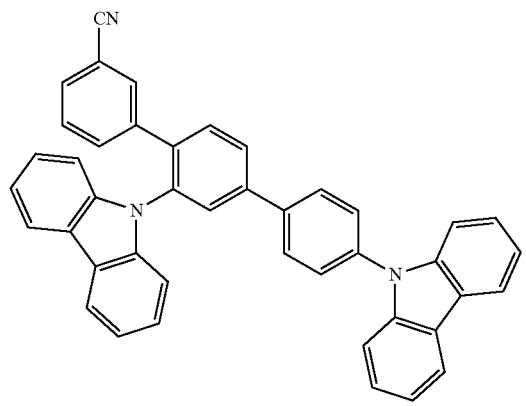
168
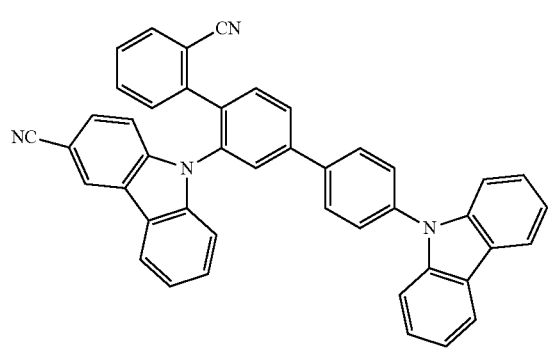
169
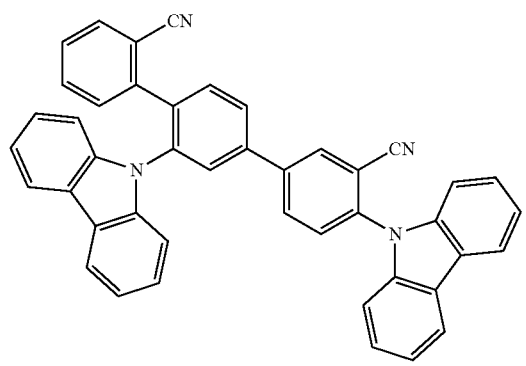
170
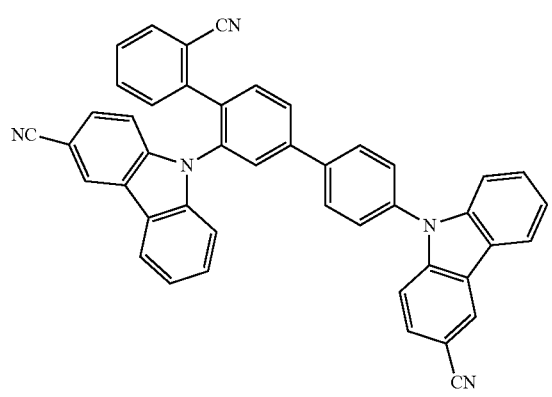
171
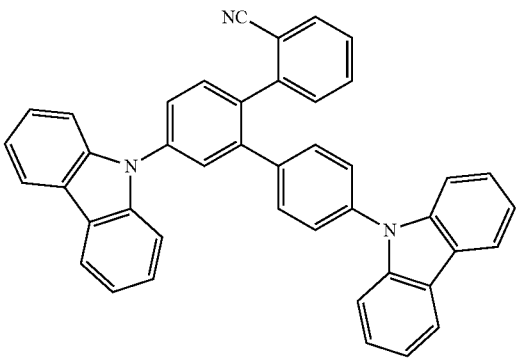
172
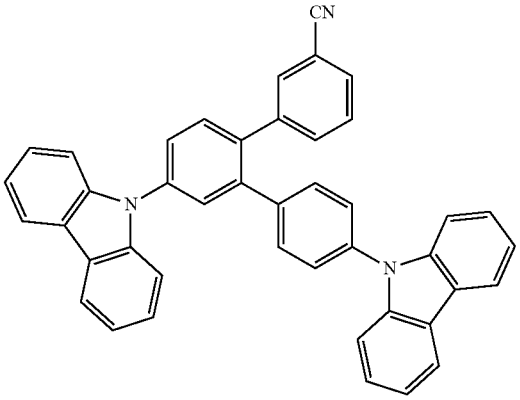
173
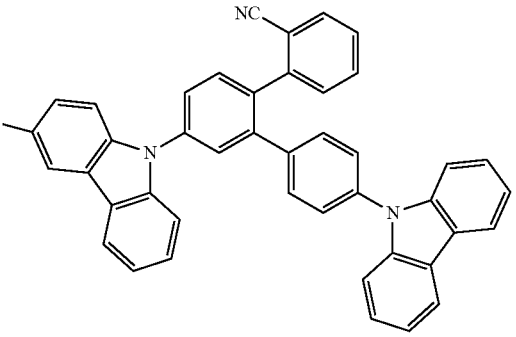
174
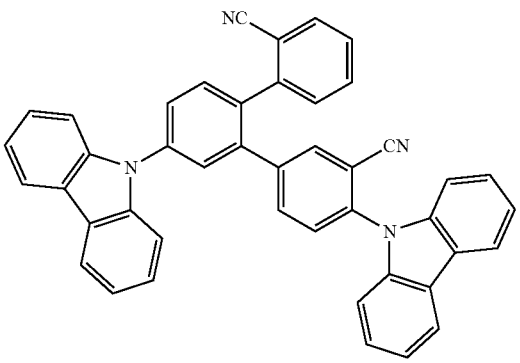

175
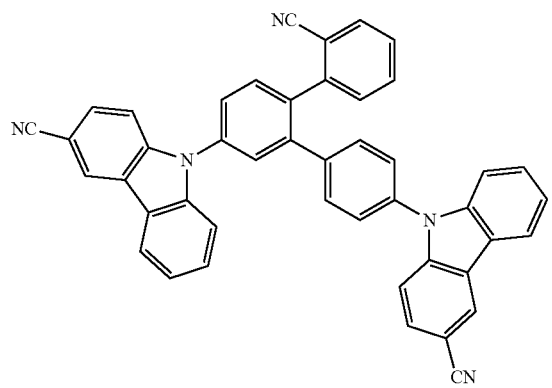
176
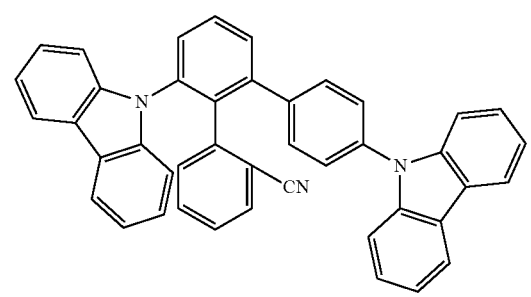
177
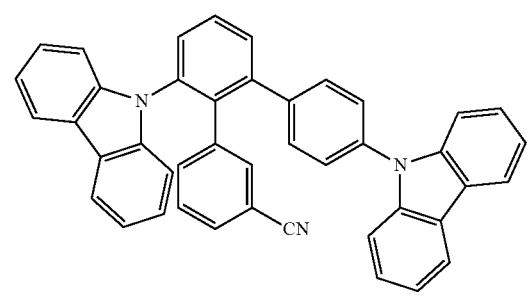
178
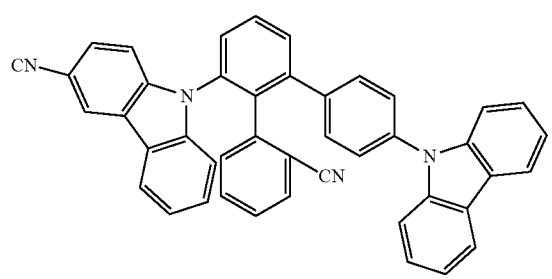
179
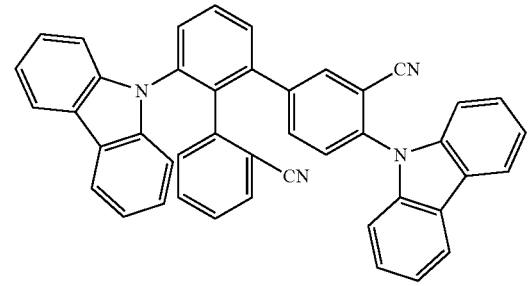
180
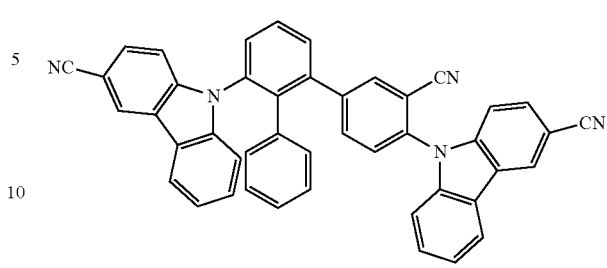
181
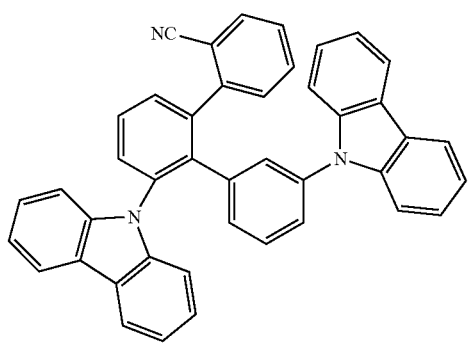
182
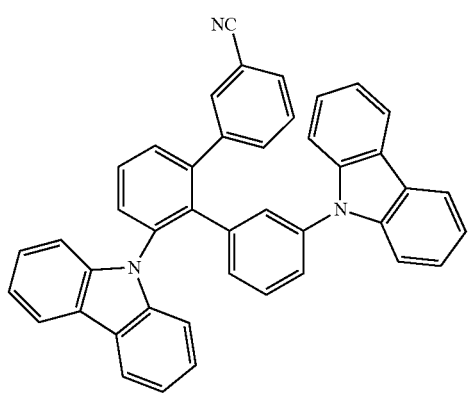
183
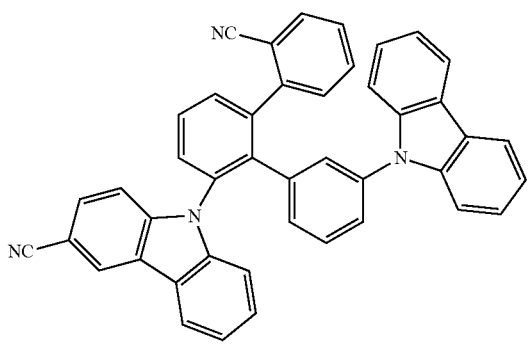

184
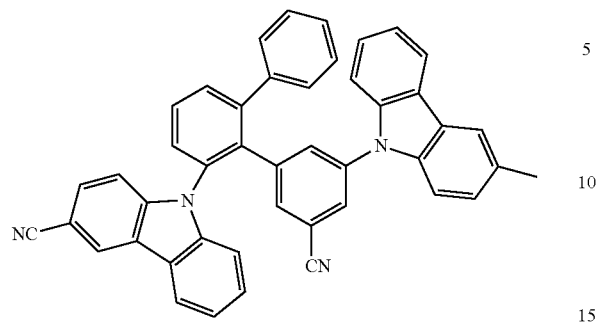
185
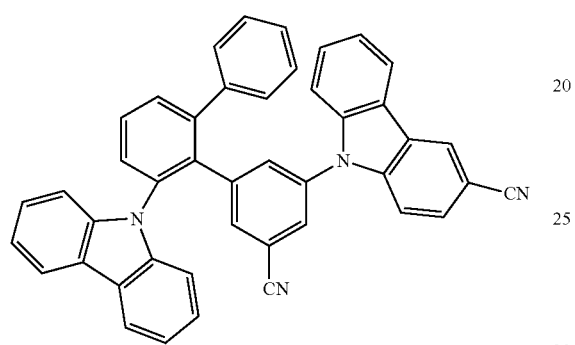
186
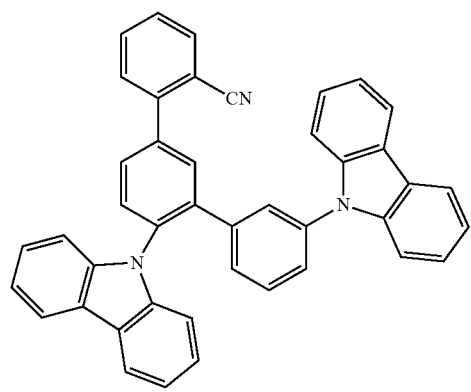
187
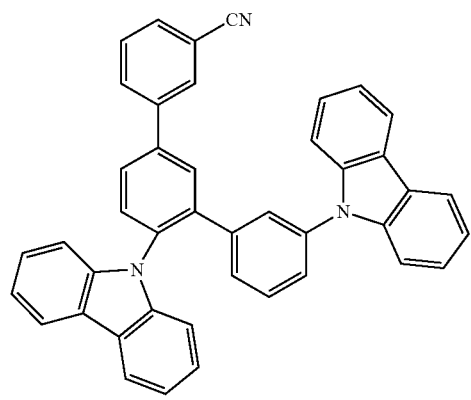
188
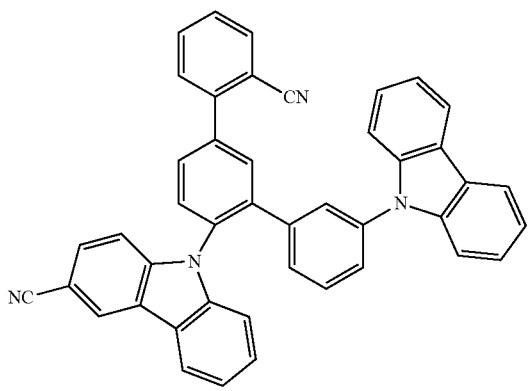
189
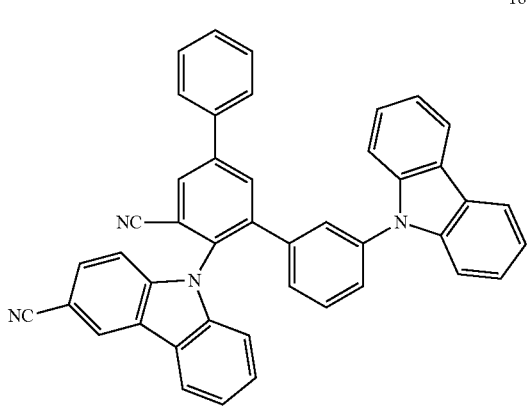
190
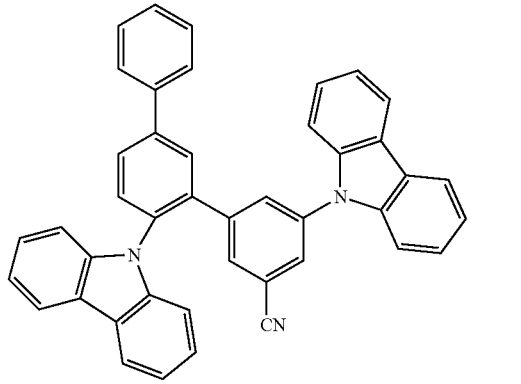
191
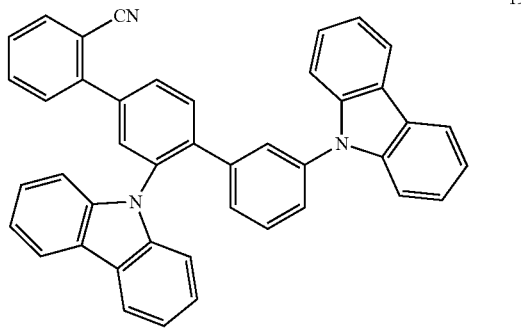

192
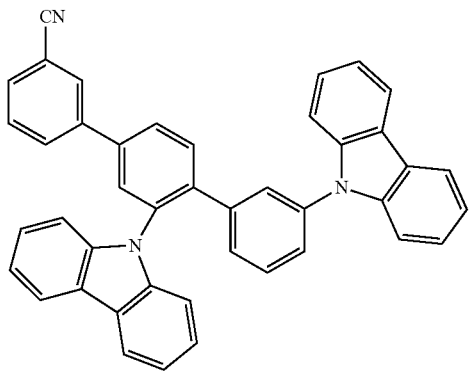
193
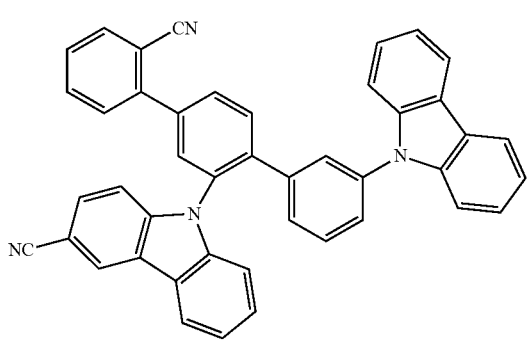
194
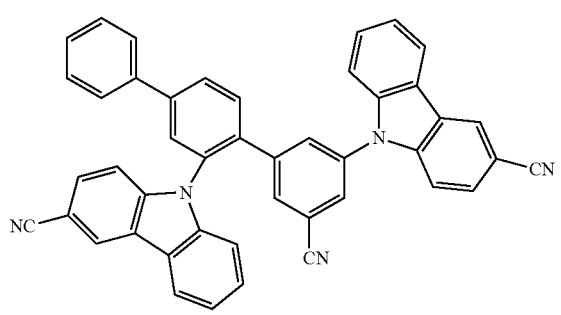
195
196
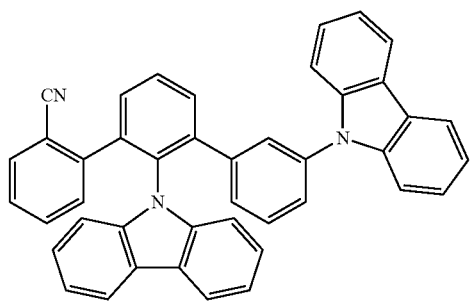
197
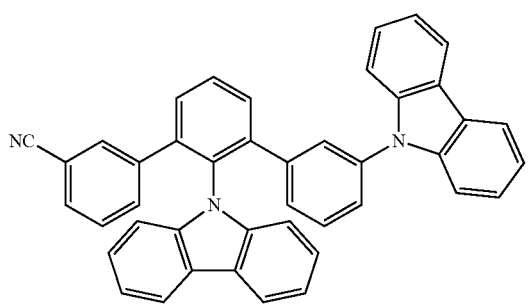
198
199
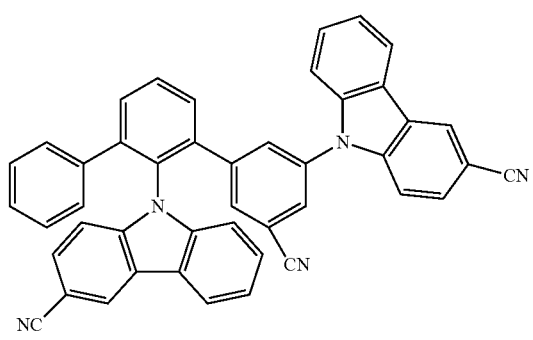
200
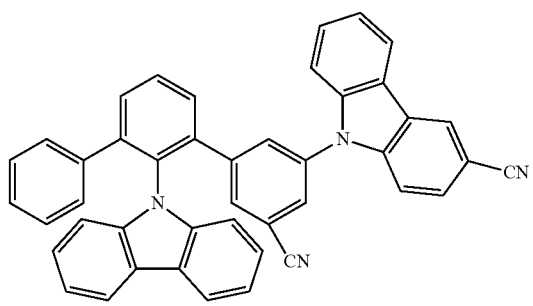

-continued
201
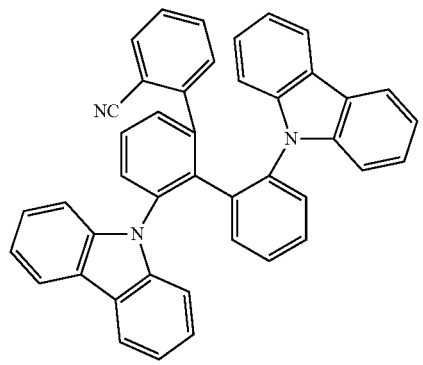
202
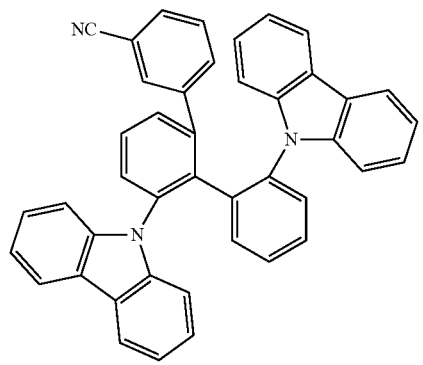
203
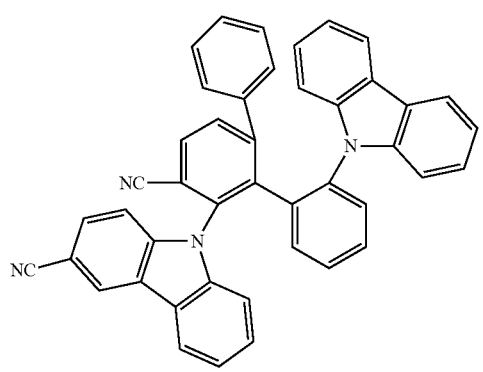
204
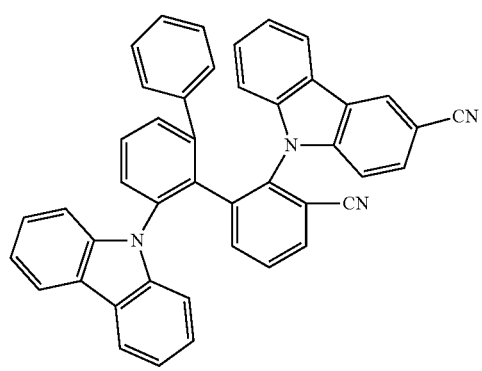
-continued
205
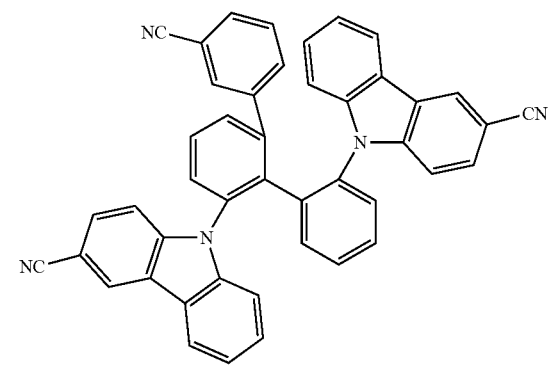
206
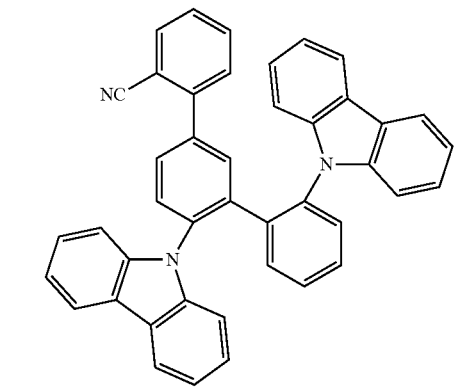
207
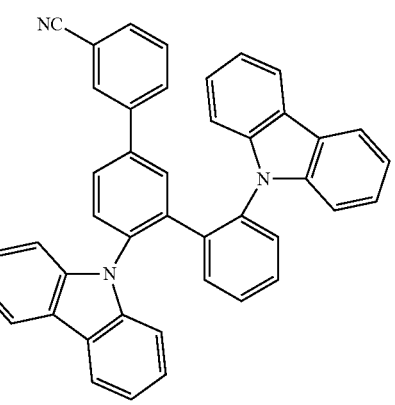
208
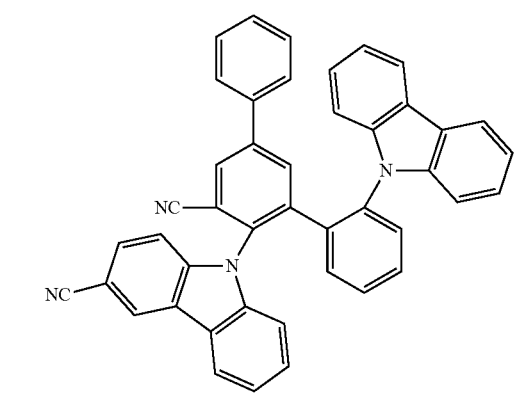

209
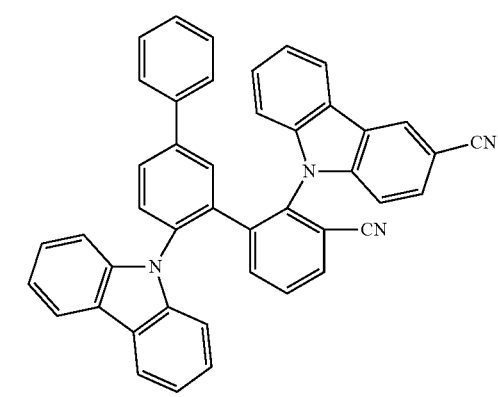
210
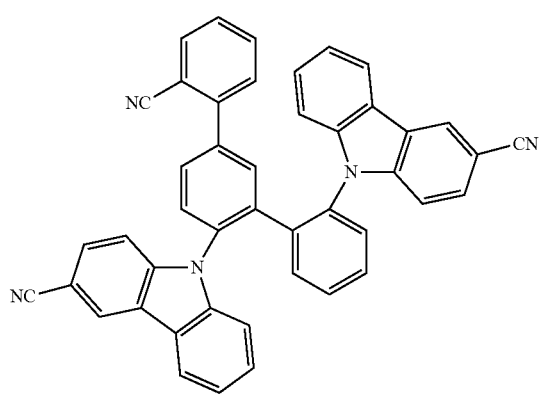
211
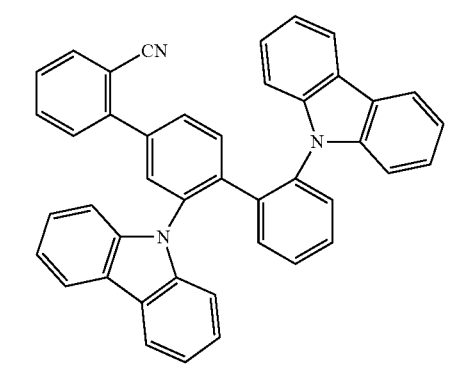
212
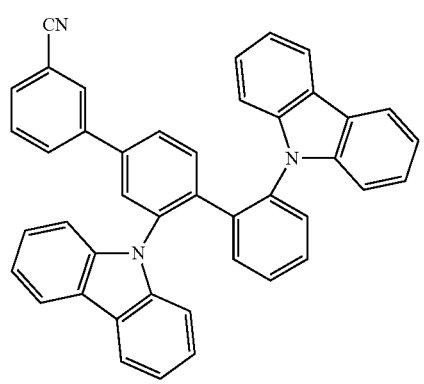
213
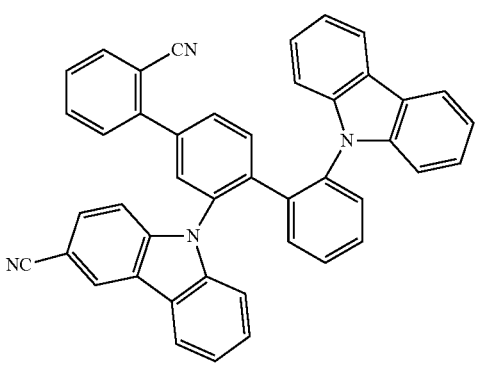
214
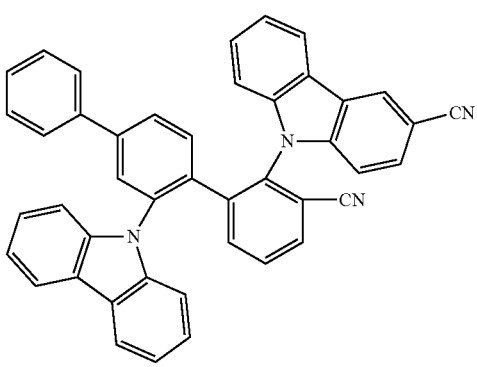
215
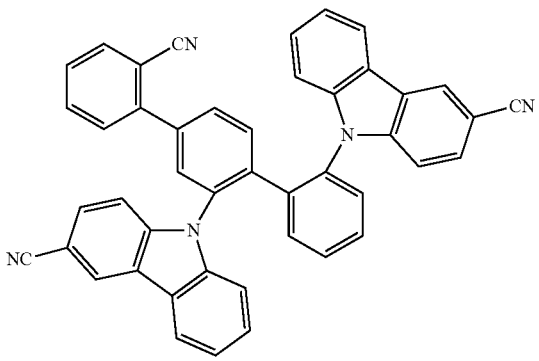
216
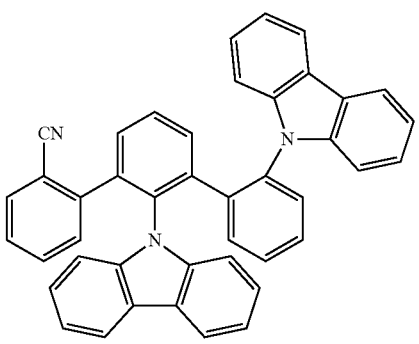

215
-continued
217
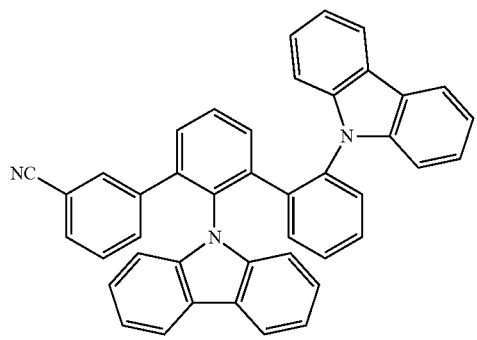
218
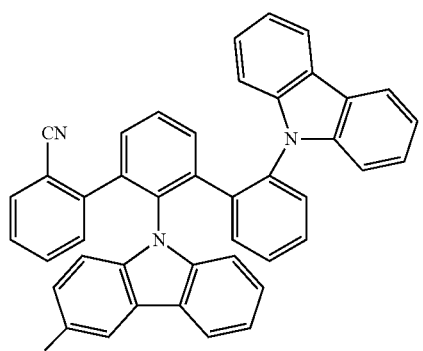
219
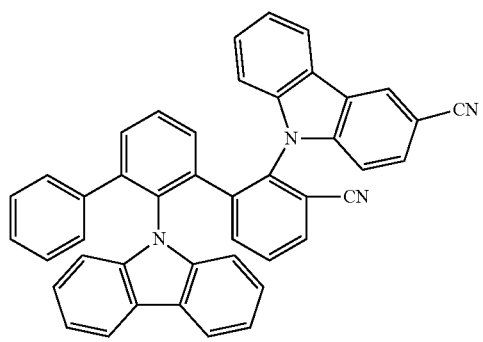
220
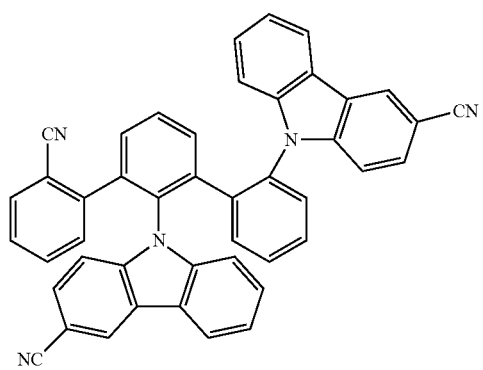
216
-continued
221
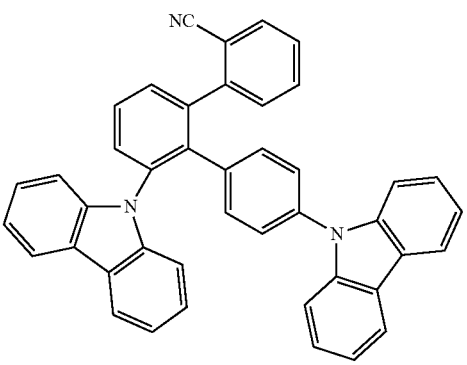
222
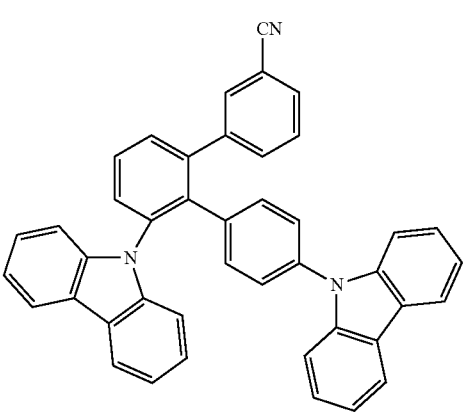
223
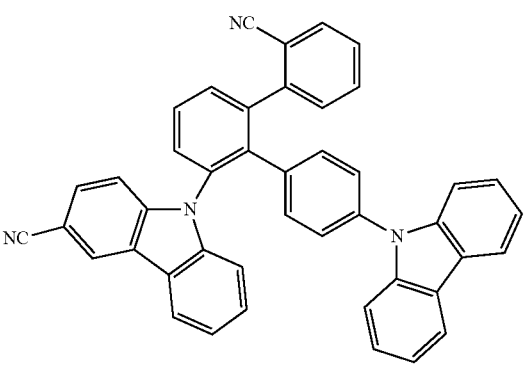
224
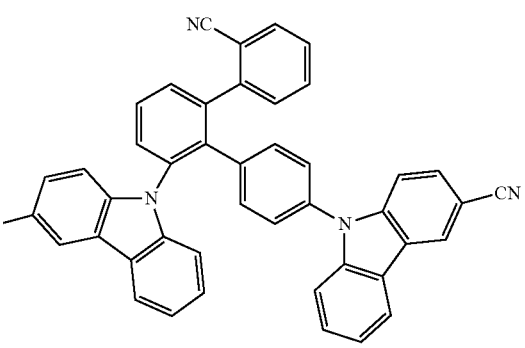

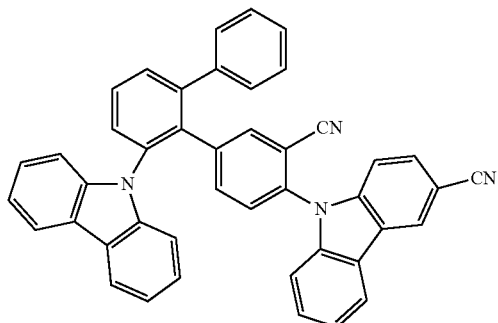
225
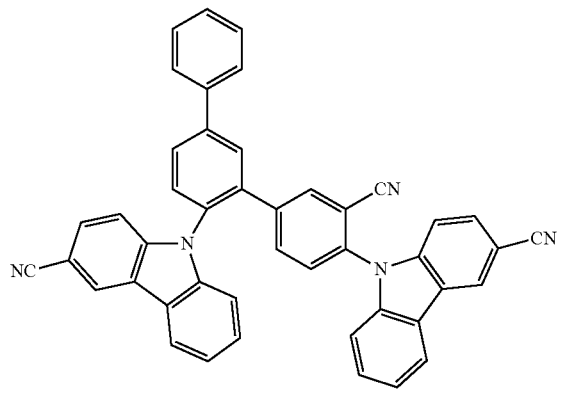
229
226
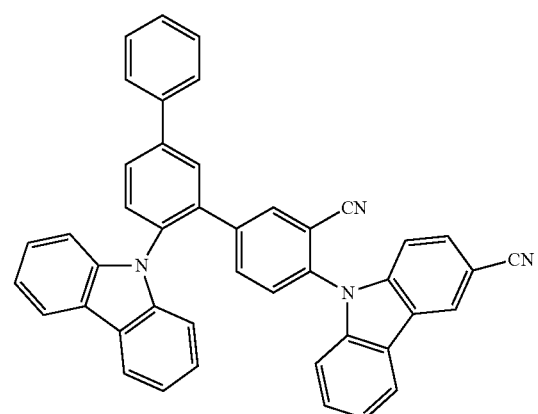
230
227
231
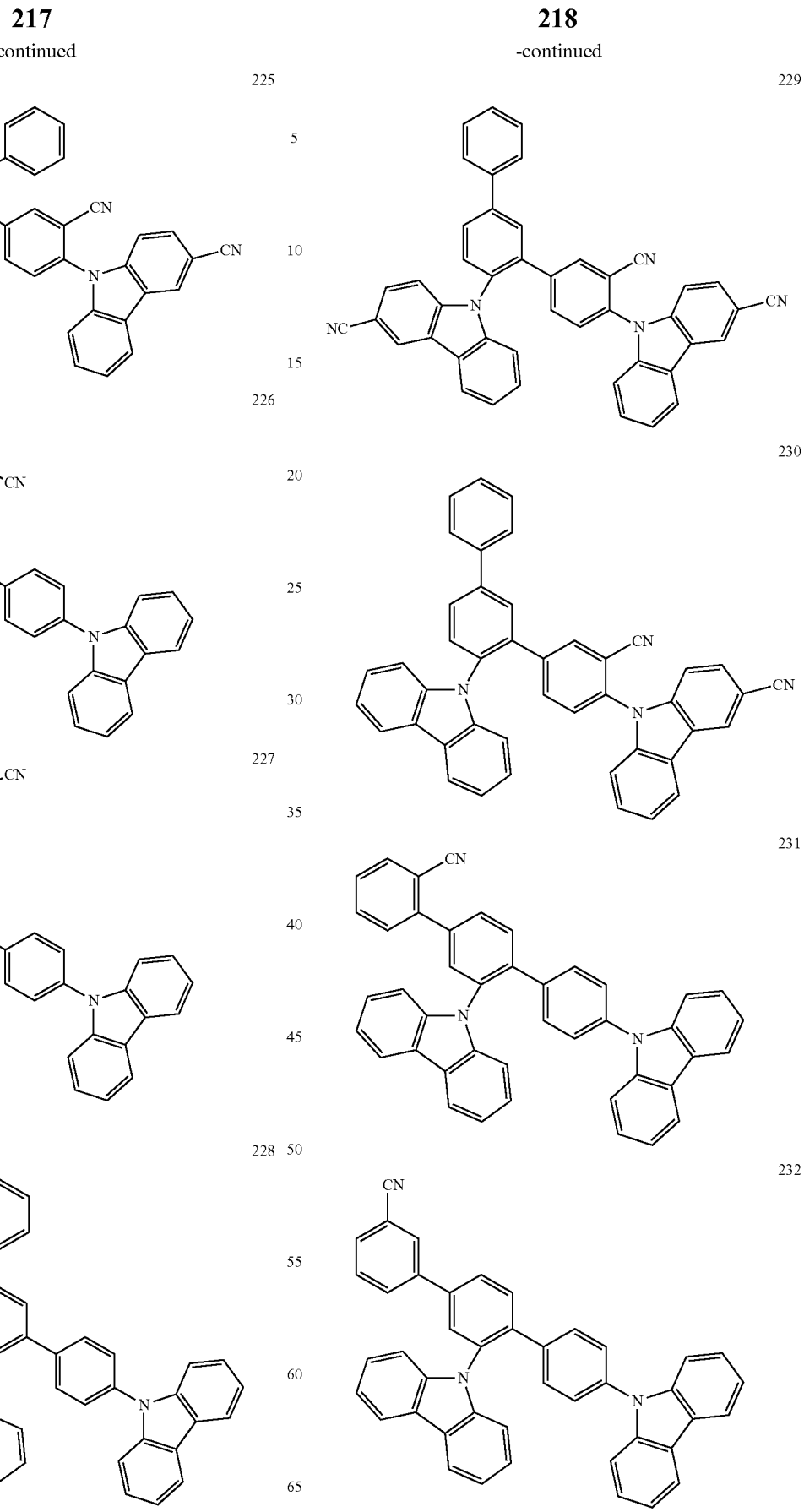
228
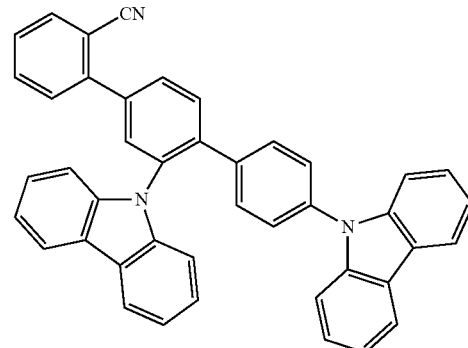
232
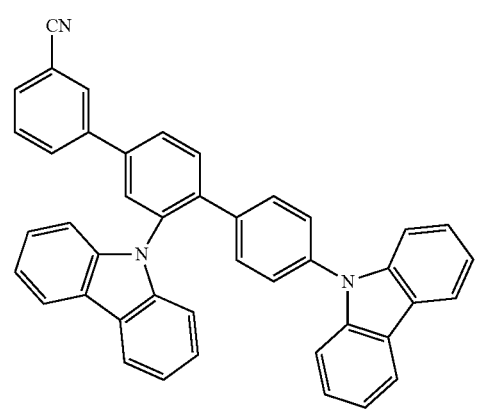

233
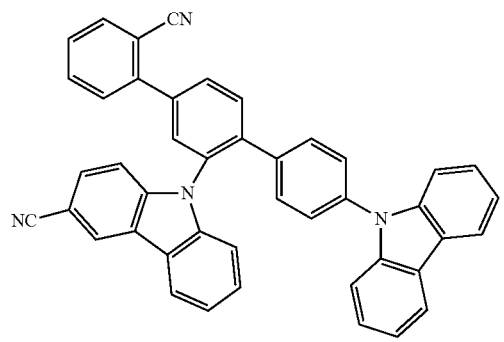
234
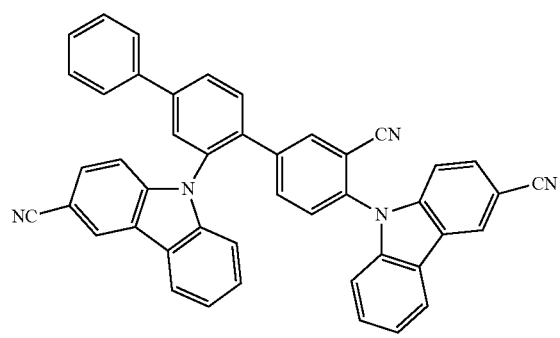
235
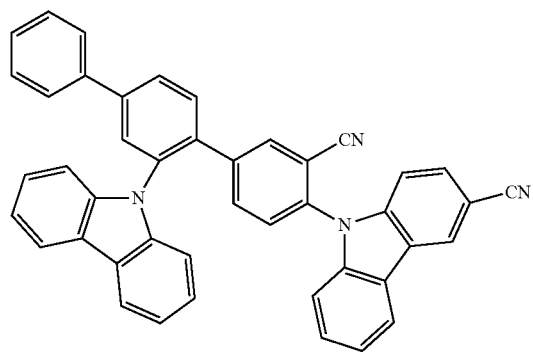
236
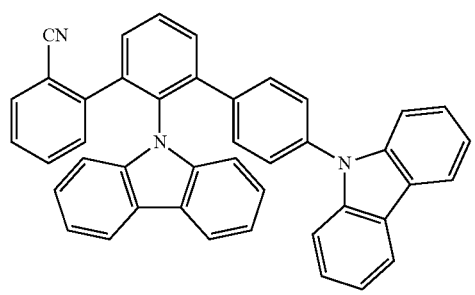
237
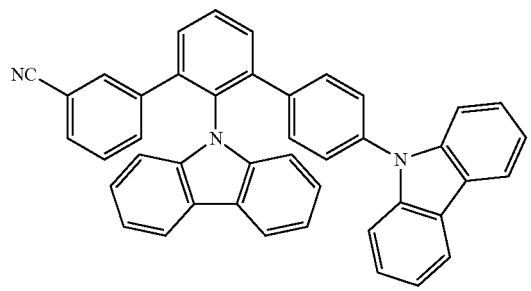
238
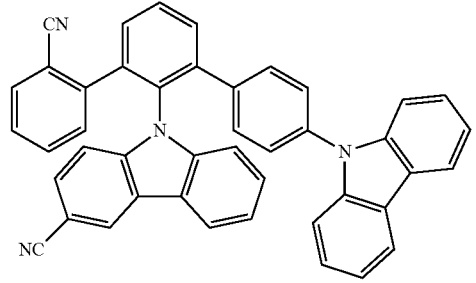
239
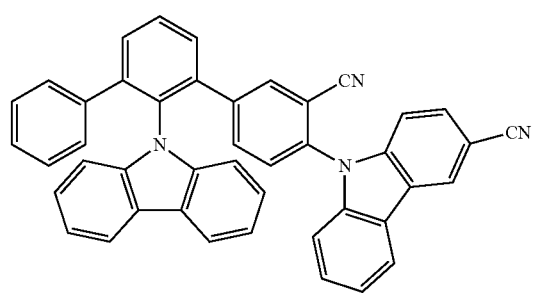
240
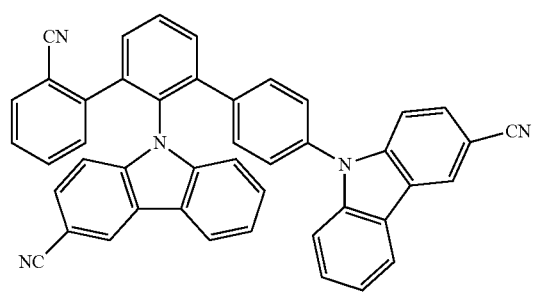
241
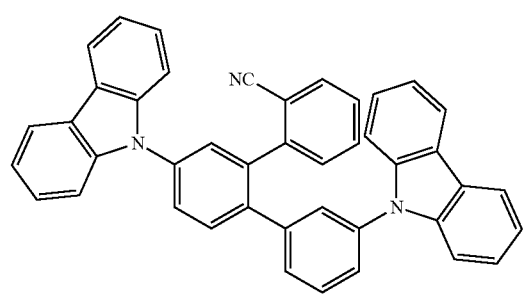

242
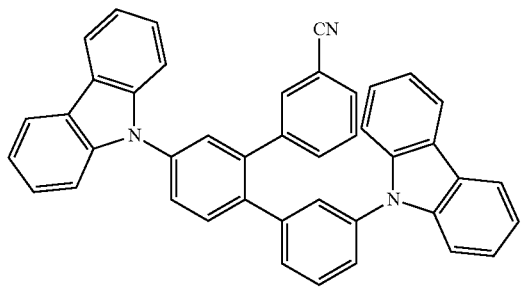
243
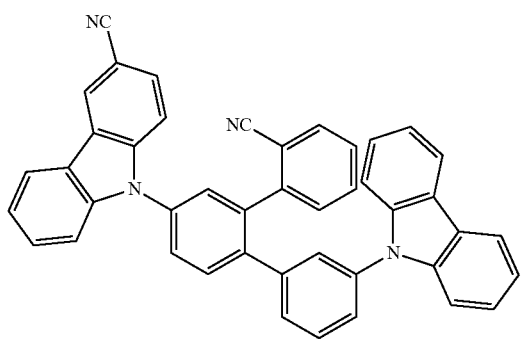
244
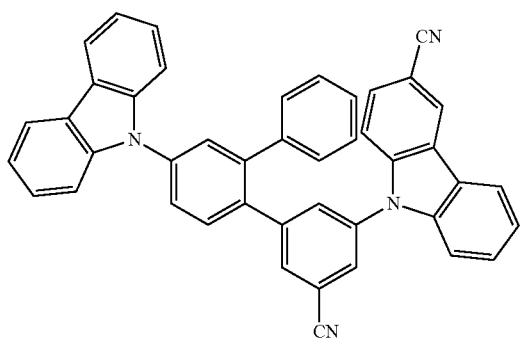
245
246
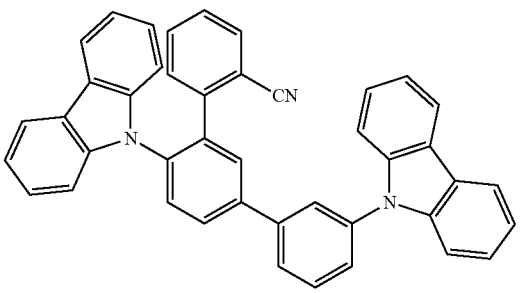
247
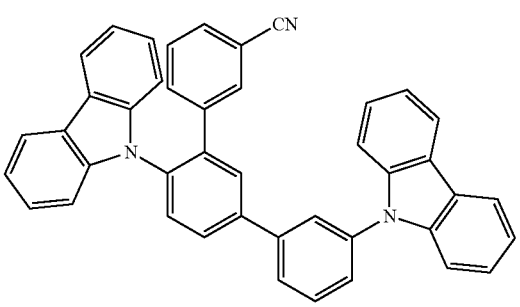
248
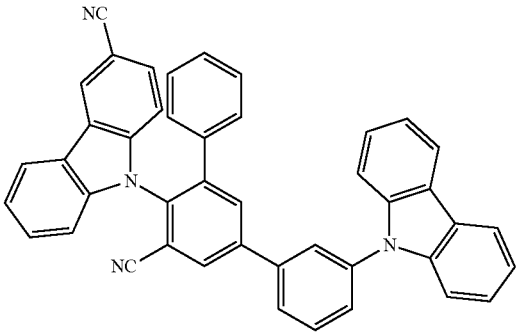
249
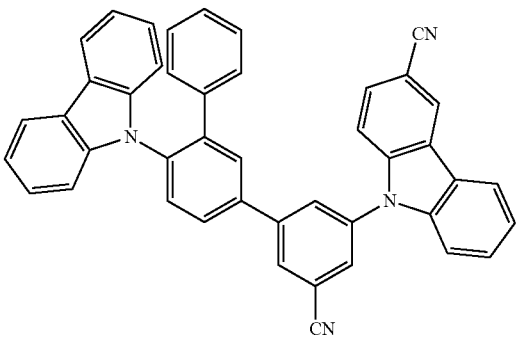

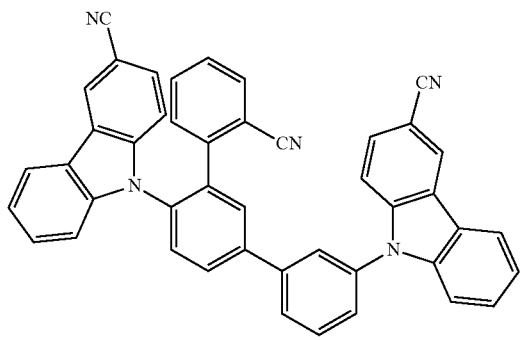
250
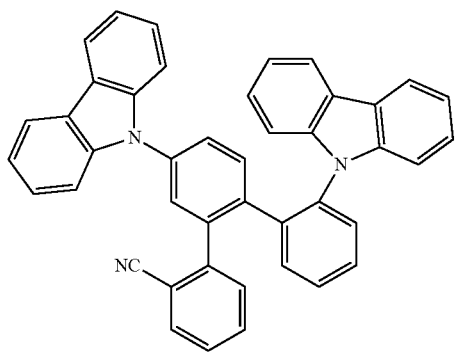
251
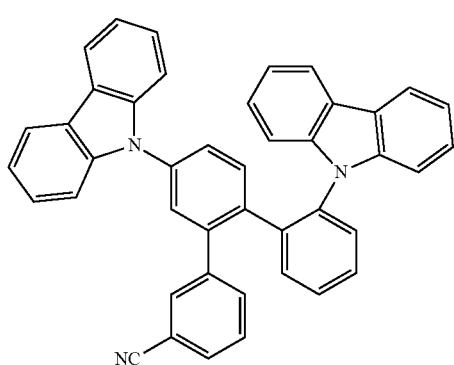
252
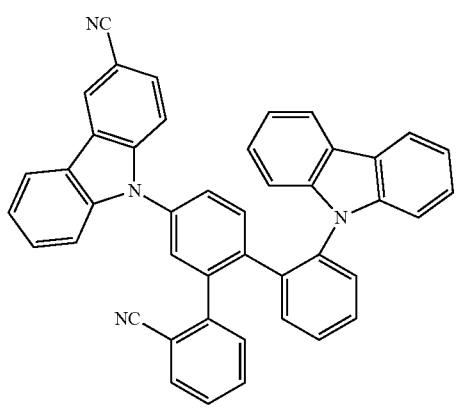
253
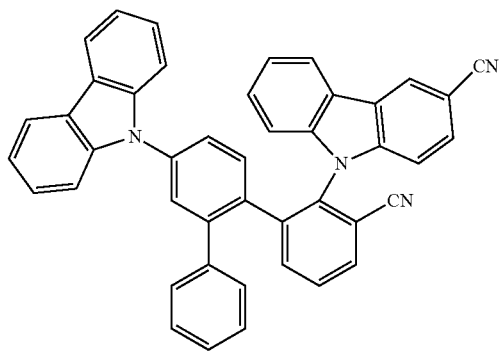
254
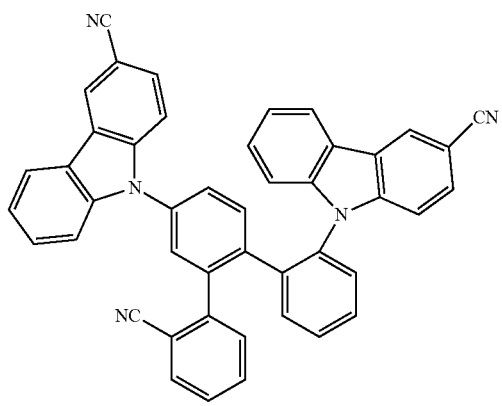
255
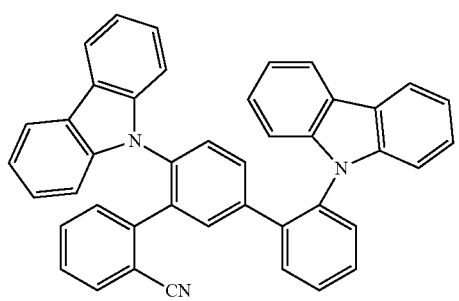
256
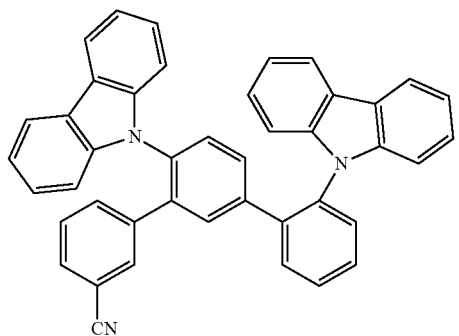
257

-continued

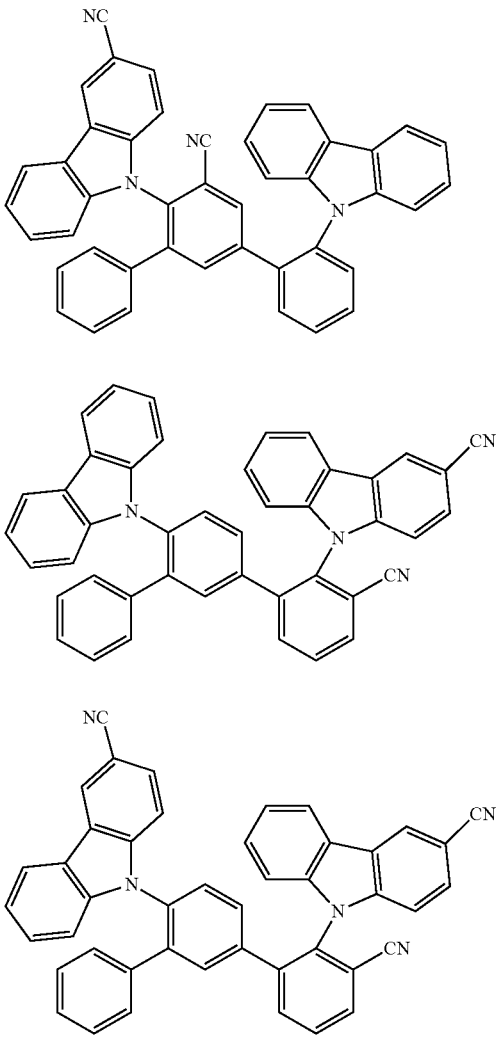

258

259

260

15. An organic light-emitting device, comprising
a first electrode;
a second electrode; and
an organic layer disposed between the first electrode and the second electrode,
wherein the organic layer comprises an emission layer, and
wherein the organic layer comprises at least one of the condensed cyclic compounds represented by Formula 1 of claim 1.

16. The organic light-emitting device of claim 15, wherein the first electrode is an anode,
the second electrode is a cathode, and
the organic layer comprises a hole transport region disposed between the first electrode and the emission layer and an electron transport region disposed between the emission layer and the second electrode,
wherein the hole transport region comprises at least one selected from a hole injection layer, a hole transport layer, and an electron blocking layer, and
wherein the electron transport region comprises at least one selected from a hole blocking layer, an electron transport layer, and an electron injection layer.

17. The organic light-emitting device of claim 15, wherein the emission layer comprises the condensed cyclic compound represented by Formula 1.

18. The organic light-emitting device of claim 15, wherein the emission layer comprises a host and a dopant,
the host comprises the condensed cyclic compound represented by Formula 1, and
an amount of the host is greater than an amount of the dopant.

19. The organic light-emitting device of claim 18, wherein the emission layer is a layer that emits blue light.

20. The organic light-emitting device of claim 16, wherein the electron transport region comprises the hole blocking layer, and the hole blocking layer comprises the condensed cyclic compound represented by Formula 1.

* * * * *